US010233432B2

(12) United States Patent
Garg et al.

(10) Patent No.: US 10,233,432 B2
(45) Date of Patent: Mar. 19, 2019

(54) MATERIALS AND METHODS FOR CHARACTERIZING AND USING A 3-KETOACYL-ACYL CARRIER PROTEIN (ACP) SYNTHASE III (KASIII) FOR PRODUCTION OF BI-FUNCTIONAL FATTY ACIDS

(71) Applicant: IOWA STATE UNIVERSITY RESEARCH FOUNDATION, INC., Ames, IA (US)

(72) Inventors: Shivani Garg, Houston, TX (US); Huanan Jin, Wuhan (CN); Marna Yandeau-Nelson, Ames, IA (US); Basil J. Nikolau, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/721,514

(22) Filed: Sep. 29, 2017

(65) Prior Publication Data

US 2018/0051263 A1 Feb. 22, 2018

Related U.S. Application Data

(62) Division of application No. 14/762,791, filed as application No. PCT/US2014/012616 on Jan. 22, 2014, now Pat. No. 9,809,804.

(60) Provisional application No. 61/755,946, filed on Jan. 23, 2013.

(51) Int. Cl.

*C12N 9/10* (2006.01)
*C12P 7/64* (2006.01)
*C12Q 1/48* (2006.01)

(52) U.S. Cl.

CPC .......... *C12N 9/1029* (2013.01); *C12P 7/6409* (2013.01); *C12Q 1/48* (2013.01); *C12Y 203/0118* (2013.01); *G01N 2333/91057* (2013.01)

(58) Field of Classification Search

None

See application file for complete search history.

(56) References Cited

U.S. PATENT DOCUMENTS

| | | | |
|---|---|---|---|
| 5,302,670 | A | 4/1994 | Frische et al. |
| 6,475,751 | B2 | 11/2002 | Reynolds et al. |
| 6,706,950 | B2 | 3/2004 | Dehesh |
| 6,770,465 | B1 | 8/2004 | Dehesh et al. |
| 7,301,070 | B2 | 11/2007 | Dehesh |
| 7,371,924 | B2 | 5/2008 | Dehesh |
| 7,601,522 | B2 | 10/2009 | Weaver et al. |
| 7,759,548 | B2 | 7/2010 | Metz et al. |
| 7,812,220 | B2 | 10/2010 | Dehesh et al. |
| 2003/0145350 | A1 | 7/2003 | Spener et al. |
| 2004/0216185 | A1 | 10/2004 | Dehesh et al. |
| 2008/0233628 | A1 | 9/2008 | Austin et al. |
| 2009/0075249 | A1 | 3/2009 | Dehesh et al. |
| 2011/0055970 | A1 | 3/2011 | Ghulam Kadir |
| 2012/0122193 | A1 | 5/2012 | Berry et al. |
| 2012/0164700 | A1 | 6/2012 | Watts et al. |

FOREIGN PATENT DOCUMENTS

| | | |
|---|---|---|
| WO | WO 2001/051925 | 7/2001 |
| WO | WO 2012/071439 | 5/2012 |

OTHER PUBLICATIONS

Bays et al., "A Simplified Scintillation Proximity Assay for Fatty Acid Synthase Activity: Development and Comparison With Other FAS Activity Assays," *Journal of Biomolecular Screening*, 6: 636-642 (2009).
Choi et al., "Identification and Substrate Specificity of β-Ketoacyl (Acyl Carrier Protein) Synthase III (mtFabH) from *Mycobacterium tuberculosis**," *J. Biol. Chem.*, 275(36): 28201-28207 (2000).
Choi et al., "β-Ketoacyl-Acyl Carrier Protein Synthase III (FabH) Is a Determining Factor in Branched-Chain Fatty Acid Biosynthesis," *J. Bacteriol.*, 182(2): 365-370 (Jan. 2000).
Heath et al., "The Claisen condensation in biology," *Nat. Prod. Rep.*, 19: 581-596 (2002).
Jin, "Role of Genetic Redundancy in Polyhydroxyalkanoate (PHA) Polymerases in PHA Biosynthesis in Rhodospirillum Rubrum," *Journal of Bacteriology*, 194(20): 5522-5529 (2012).
Khandekar et al., "Identification, Substrate Specificity, and Inhibition of the *Streptococcus pneumoniae* β-Ketoacyl-Acyl Carrier Protein Synthase III (FabH)*," *J. Biol. Chem.* 276(32): 30024-30030 (2001).
Matsubara et al., "Alicyclobacillus Acidiphilus sp. nov., a Novel Thermo-Acidophilic, co-Alicyclic Fatty Acid-Containing Bacterium Isolated From Acidic Beverages," *International Journal of Systematic and Evolutionary Microbiology*, 52: 1681-1685 (2002).
Noel, "NSF Engineering Research Center for Biorenewable Chemicals, Fourth Annual Report," vol. II, T1.1—3-Ketoacyl-ACP Synthase: Characterization of Novel Biocatalysts for Diversifying FAS/PKS Metabolic Pathways. Center for Biorenewable Chemicals Annual Reports, Book 3, Digital Repository at Iowa State University, Apr. 2, 2012.
Nomura et al., "Expression of 3-Ketoacyl-Acyl Carrier Protein Reductase (*fabG*) Genes Enhances Production of Polyhydroxyalkanoate Copolymer From Glucose in Recombinant *Escherichia coli* JM109," *Applied and Environmental Microbiology*, 71(8): 4297-4306 (2005).

(Continued)

*Primary Examiner* — Iqbal H Chowdhury

(74) *Attorney, Agent, or Firm* — Carol Larcher; Larcher & Chao Law Group

(57) ABSTRACT

A mutant *Bacillus subtilis*, which does not express a functional KASIIIA and/or KASIIIB, and method of making; a mutant *Rhodospirillum rubrum*, which does not express a functional PhaC1, PhaC2, and/or PhaC3, and method of making; method of characterizing substrate specificity of KASIII; method of making mutant KASIII with altered substrate specificity and/or altered level of activity and nucleic acid, vector, host cell/organism, and mutant KASIII; an in vitro, high-throughput spectrophotometric method of assaying KASIII activity; and materials and methods for using KASIII for production of bi-functional fatty acids and the materials so produced.

8 Claims, 29 Drawing Sheets

Specification includes a Sequence Listing.

(56) References Cited

OTHER PUBLICATIONS

Qiu et al., "Crystal structure and substrate specificity of the β-ketoacyl-acyl carrier protein synthase III (FabH) from *Staphylococcus aureus,*" *Protein Science*, 14:2087-2094 (2005).
Qiu et al., "Crystal Structure of β-Ketoacyl-Acyl Carrier Protein Synthase III," *J. Biol. Chem.*, 274(51): 36465-36471 (1999).
Tai et al., "Cloning of a cDNA Encoding 3-Ketoacyl-Acyl Carrier Protein Synthase III from *Arabidopsis*[1] ," *Plant Physiol.* 106: 801-802 (1994).
Tsay et al., "Isolation and Characterization of the β-Ketoacyl-acyl Carrier Protein Synthase III Gene (*fabH*) from *Escherichia coli* K-12*," *J. Biol. Chem.* 267(10): 6807-6814 (1992).
Yu et al., "In Vitro Reconstitution and Steady-State Analysis of the Fatty Acid Synthase From *Escherichia coli,*" *PNAS*, 108(46): 18643-18648 (2011).
Search Report issued in Int'l App. No. PCT/US2014/012616 (2014).

Davies *et al.*, 2000

Isobutyryl CoA

ACETYL CoA

In-vitro *L. pneumophila* KASIIIa Activity with Branched Chain Substrate (Isobutyryl CoA)

In-vitro *L. Pneumophila* KASIIIa Activity with Hydroxylated Substrate (β-Hydroxybutyryl CoA)

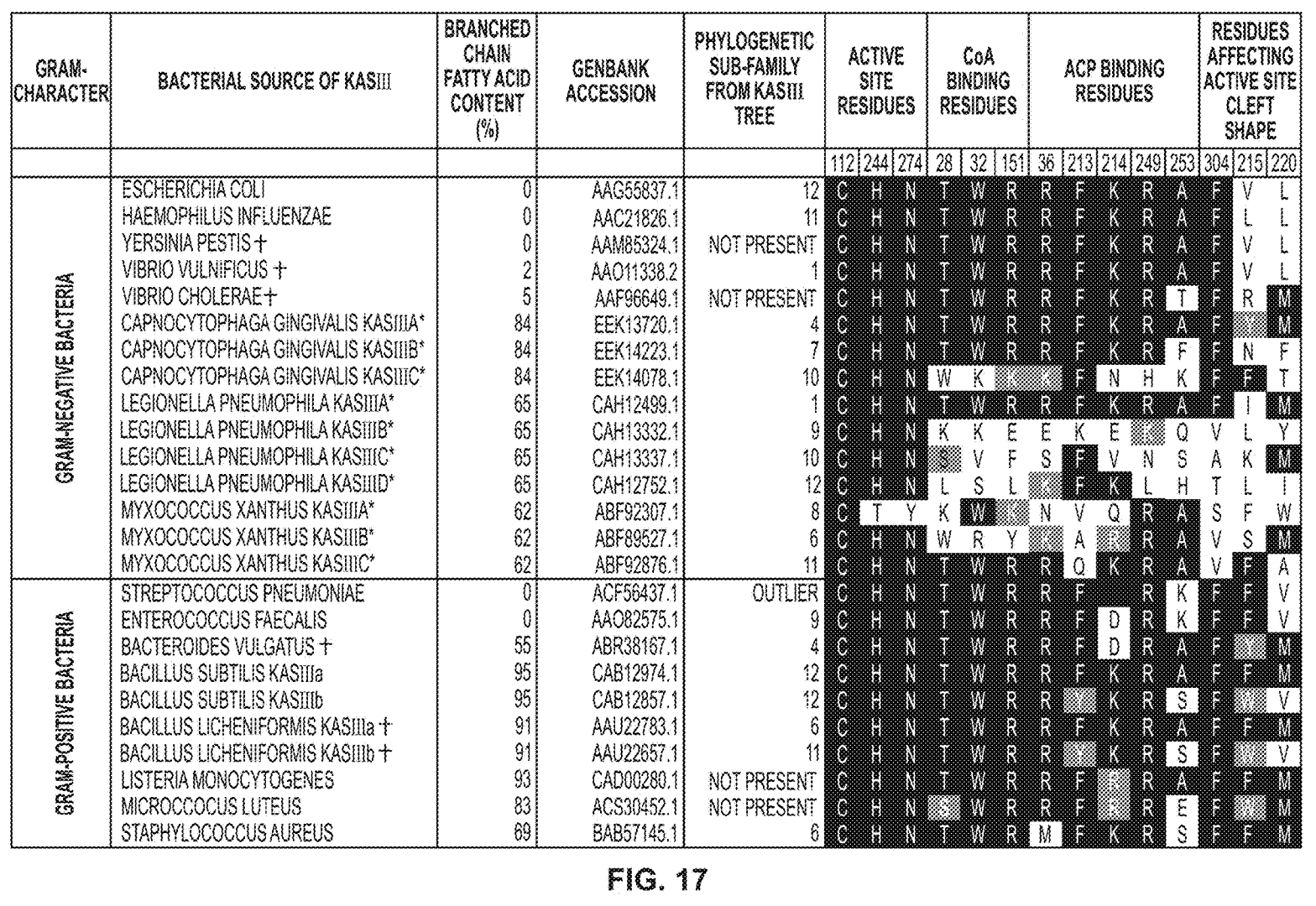

| GRAM-CHARACTER | BACTERIAL SOURCE OF KASIII | BRANCHED CHAIN FATTY ACID CONTENT (%) | GENBANK ACCESSION | PHYLOGENETIC SUB-FAMILY FROM KASIII TREE | ACTIVE SITE RESIDUES | | | CoA BINDING RESIDUES | | | ACP BINDING RESIDUES | | | | | RESIDUES AFFECTING ACTIVE SITE CLEFT SHAPE | | |
|---|---|---|---|---|---|---|---|---|---|---|---|---|---|---|---|---|---|---|
| | | | | | 112 | 244 | 274 | 28 | 32 | 151 | 36 | 213 | 214 | 249 | 253 | 304 | 215 | 220 |
| GRAM-NEGATIVE BACTERIA | ESCHERICHIA COLI | 0 | AAG55837.1 | 12 | C | H | N | T | W | R | R | F | K | R | A | F | V | L |
| | HAEMOPHILUS INFLUENZAE | 0 | AAC21826.1 | 11 | C | H | N | T | W | R | R | F | K | R | A | F | L | L |
| | YERSINIA PESTIS † | 0 | AAM85324.1 | NOT PRESENT | C | H | N | T | W | R | R | F | K | R | A | F | V | L |
| | VIBRIO VULNIFICUS † | 2 | AAO11338.2 | 1 | C | H | N | T | W | R | R | F | K | R | A | F | V | L |
| | VIBRIO CHOLERAE † | 5 | AAF96649.1 | NOT PRESENT | C | H | N | T | W | R | R | F | K | R | T | F | R | M |
| | CAPNOCYTOPHAGA GINGIVALIS KASIIIA* | 84 | EEK13720.1 | 4 | C | H | N | T | W | R | R | F | K | R | A | F | [illegible] | M |
| | CAPNOCYTOPHAGA GINGIVALIS KASIIIB* | 84 | EEK14223.1 | 7 | C | H | N | T | W | R | R | F | K | R | F | F | N | F |
| | CAPNOCYTOPHAGA GINGIVALIS KASIIIC* | 84 | EEK14078.1 | 10 | C | H | N | W | K | [illegible] | [illegible] | F | N | H | K | F | F | T |
| | LEGIONELLA PNEUMOPHILA KASIIIA* | 65 | CAH12499.1 | 1 | C | H | N | T | W | R | R | F | K | R | A | F | I | M |
| | LEGIONELLA PNEUMOPHILA KASIIIB* | 65 | CAH13332.1 | 9 | C | H | N | K | K | E | E | K | E | [illegible] | Q | V | L | Y |
| | LEGIONELLA PNEUMOPHILA KASIIIC* | 65 | CAH13337.1 | 10 | C | H | N | S | V | F | S | F | V | N | S | A | K | M |
| | LEGIONELLA PNEUMOPHILA KASIIID* | 65 | CAH12752.1 | 12 | C | H | N | L | S | L | [illegible] | F | K | L | H | T | L | I |
| | MYXOCOCCUS XANTHUS KASIIIA* | 62 | ABF92307.1 | 8 | C | T | Y | K | W | [illegible] | N | V | Q | R | A | S | F | W |
| | MYXOCOCCUS XANTHUS KASIIIB* | 62 | ABF89527.1 | 6 | C | H | N | W | R | Y | [illegible] | A | [illegible] | R | A | V | S | M |
| | MYXOCOCCUS XANTHUS KASIIIC* | 62 | ABF92876.1 | 11 | C | H | N | T | W | R | R | Q | K | R | A | V | F | A |
| GRAM-POSITIVE BACTERIA | STREPTOCOCCUS PNEUMONIAE | 0 | ACF56437.1 | OUTLIER | C | H | N | T | W | R | R | F | | R | K | F | F | V |
| | ENTEROCOCCUS FAECALIS | 0 | AAO82575.1 | 9 | C | H | N | T | W | R | R | F | D | R | K | F | F | V |
| | BACTEROIDES VULGATUS † | 55 | ABR38167.1 | 4 | C | H | N | T | W | R | R | F | D | R | A | F | [illegible] | M |
| | BACILLUS SUBTILIS KASIIIa | 95 | CAB12974.1 | 12 | C | H | N | T | W | R | R | F | K | R | A | F | F | M |
| | BACILLUS SUBTILIS KASIIIb | 95 | CAB12857.1 | 12 | C | H | N | T | W | R | R | [illegible] | K | R | S | F | [illegible] | V |
| | BACILLUS LICHENIFORMIS KASIIIa † | 91 | AAU22783.1 | 6 | C | H | N | T | W | R | R | F | K | R | A | F | F | M |
| | BACILLUS LICHENIFORMIS KASIIIb † | 91 | AAU22657.1 | 11 | C | H | N | T | W | R | R | [illegible] | K | R | S | F | [illegible] | V |
| | LISTERIA MONOCYTOGENES | 93 | CAD00280.1 | NOT PRESENT | C | H | N | T | W | R | R | F | [illegible] | R | A | F | F | M |
| | MICROCOCCUS LUTEUS | 83 | ACS30452.1 | NOT PRESENT | C | H | N | S | W | R | R | F | [illegible] | R | E | F | [illegible] | M |
| | STAPHYLOCOCCUS AUREUS | 69 | BAB57145.1 | 6 | C | H | N | T | W | R | M | F | K | R | S | F | F | M |

FIG. 17

| Phylogenetic structure-function group | Organismal data: Bacterial source of KASIII | Organismal data: Branched chain fatty acid content (%) | Structural data: Residues proposed to affect substrate specificity | Structural data: Rotamer conformation of the substrate-limiting Phe (from crystal structures) | Functional data (Specific activity): Straight chain acyl-CoA substrates utilized | Functional data (Specific activity): Branched chain acyl-CoA substrates utilized | KASIII functional class (experimentally determined) |
|---|---|---|---|---|---|---|---|
| Group 1a | *Escherichia coli* | 0 | F V L | Active site distal | C2:0, C3:0 | Very low activity | Narrow |
| | *Yersinia pestis* | 0 | F V L | N.D. | N.D. | N.D. | N.D. |
| | *Vibrio vulnificus* | 2 | F V L | N.D. | N.D. | N.D. | N.D. |
| | *Haemophilus influenzae* | 0 | F L L | Active site distal | N.D. | N.D. | N.D. |
| Group 1b | *Legionella pneumophila* KASIIIa* | 65 | F I M | N.D. | C2:0, C3:0, C4:0 | i-C4:0, i-C5:0 | Broad |
| | *Capnocytophaga gingivalis* KASIIIb* | 84 | F N F | N.D. | No activity shown | No activity shown | N.D. |
| | *Aquifex aeolicus* | | M V M | Not applicable | N.D. | N.D. | N.D. |
| | *Vibrio cholerae* | 5 | F R M | N.D. | N.D. | N.D. | N.D. |
| | *Streptococcus pneumoniae* | 0 | F F V | N.D. | C2:0, C3:0, C4:0 | i-C4:0, i-C5:0 | Broad |
| | *Enterococcus faecalis* | 0 | F F V | Active site proximal | N.D. | N.D. | N.D. |
| Group 2a | *Xanthomonas oryzae* | 12 | I E A | Not applicable | N.D. | N.D. | N.D. |
| | *Myxococcus xanthus* KASIIIc* | 62 | V F A | Not applicable | C2:0, C3:0, C4:0, C6:0 | i-C4:0, i-C5:0 | Broad |
| | *Capnocytophaga gingivalis* KASIIIc* | 84 | F F T | N.D. | C2:0, C3:0, C4:0 | i-C4:0, i-C5:0 | Broad |

FIG. 19

| | | | | | | | | | |
|---|---|---|---|---|---|---|---|---|---|
| **Group 2b** | *Streptomyces glaucescens* | 90 | F | W | M | N.D. | C2:0, C4:0, | i-C4:0 | Broad |
| | *Micrococcus luteus* | 83 | F | W | M | Active site proximal | C12:0 | N.D. | Broad |
| | *Mycobacterium tuberculosis* | Mycolic acids | Y | W | M | Active site proximal | C8:0, C10:0, C12:0, C14:0C16:0, C18:0i | N.D. | Broad |
| **Group 3** | *Thermus thermophilus* | 99 | F | F | M | Active site proximal | N.D. | N.D. | N.D. |
| | *Bacillus subtilis* KASIIIa | 95 | F | F | M | N.D. | C2:0, C3:0, C4:0, C5:0, C6:0 C7:0, C8:0 | i-C4:0, iC5:0, a-C5:0 | Broad |
| | *Bacillus licheniformis* KASIIIa | 91 | F | F | M | N.D. | N.D. | N.D. | N.D. |
| | *Listeria monogenes* | 93 | F | F | M | N.D. | C2:0 | i-C4:0, i-C5:0, a-C5:0 | Broad |
| | *Staphylococcus aureus* | 69 | F | F | M | Active site proximal | C2:0, C3:0, C4:0, C6:0, C12:0, C16:0 | i-C4:0, i-C5:0 | Broad |
| | *Bacillus subtilis* KASIIIb | 95 | F | W | V | N.D. | C2:0, C3:0, C4:0, C5:0, C6:0, C7:0 | i-C4:0, i-C5:0, a-C5:0 | Broad |
| | *Bacillus licheniformis* KASIIIb | 91 | F | W | V | N.D. | N.D. | N.D. | N.D. |
| | *Capnocytophaga gingivalis* KASIIIa* | 84 | F | Y | M | N.D. | C3:0 | i-C4:0, i-C5:0 | Broad |
| **Non-functional KASIII** | *Myxococcus xanthus* KASIIIa* | 62 | S | F | W | Not applicable | No activity shown | No activity shown | |
| | *Myxococcus xanthus* KASIIIb* | 62 | V | S | M | Not applicable | No activity shown | No activity shown | |
| | *Legionella pneumophila* KASIIIb* | 65 | V | L | Y | Not applicable | No activity shown | No activity shown | |
| | *Legionella pneumophila* KASIIIc* | 65 | A | K | M | Not applicable | No activity shown | No activity shown | |
| | *Legionella pneumophila* KASIIId* | 65 | T | L | I | Not applicable | No activity shown | No activity shown | |

FIG. 19 (Cont.)

SEQUENCE LISTING

```
<160> NUMBER OF SEQ ID NOS: 134

<210> SEQ ID NO 1
<211> LENGTH: 28
<212> TYPE: DNA
<213> ORGANISM: Artificial
<220> FEATURE:
<223> OTHER INFORMATION: Synthetic

<400> SEQUENCE: 1

catgccatgg taatgaaagc tggaatac                                    28


<210> SEQ ID NO 2
<211> LENGTH: 26
<212> TYPE: DNA
<213> ORGANISM: Artificial
<220> FEATURE:
<223> OTHER INFORMATION: Synthetic

<400> SEQUENCE: 2

gcgggatccg gagataatgc tccaag                                      26
```

<210> SEQ ID NO 3
<211> LENGTH: 26
<212> TYPE: DNA
<213> ORGANISM: Artificial
<220> FEATURE:
<223> OTHER INFORMATION: Synthetic

<400> SEQUENCE: 3
cgcggatcca ttcatatgtc aaaagc 26

<210> SEQ ID NO 4
<211> LENGTH: 25
<212> TYPE: DNA
<213> ORGANISM: Artificial
<220> FEATURE:
<223> OTHER INFORMATION: Synthetic

<400> SEQUENCE: 4
agggaagctt cagaagaaca gccgg 25

<210> SEQ ID NO 5
<211> LENGTH: 26
<212> TYPE: DNA
<213> ORGANISM: Artificial
<220> FEATURE:
<223> OTHER INFORMATION: Synthetic

<400> SEQUENCE: 5
aagcttaaca agctgaagtg gctgct 26

<210> SEQ ID NO 6
<211> LENGTH: 26
<212> TYPE: DNA
<213> ORGANISM: Artificial
<220> FEATURE:
<223> OTHER INFORMATION: Synthetic

<400> SEQUENCE: 6
ggatccatca ctgactggcc cgacta 26

<210> SEQ ID NO 7
<211> LENGTH: 26
<212> TYPE: DNA
<213> ORGANISM: Artificial
<220> FEATURE:
<223> OTHER INFORMATION: Synthetic

<400> SEQUENCE: 7
aagcttgccg gagagacgtt atcaaa 26

<210> SEQ ID NO 8
<211> LENGTH: 26
<212> TYPE: DNA
<213> ORGANISM: Artificial
<220> FEATURE:
<223> OTHER INFORMATION: Synthetic

<400> SEQUENCE: 8
ggatcccgtg tttccgtagt gctcaa 26

<210> SEQ ID NO 9
<211> LENGTH: 28
<212> TYPE: DNA
<213> ORGANISM: Artificial
<220> FEATURE:
<223> OTHER INFORMATION: Synthetic -continued

<400> SEQUENCE: 9
ttaattaata ttaaccatca cggtgcaa 28

<210> SEQ ID NO 10
<211> LENGTH: 26
<212> TYPE: DNA
<213> ORGANISM: Artificial
<220> FEATURE:
<223> OTHER INFORMATION: Synthetic

<400> SEQUENCE: 10
gtcgacgaat gtaacgtcca acacca 26

<210> SEQ ID NO 11
<211> LENGTH: 25
<212> TYPE: DNA
<213> ORGANISM: Artificial
<220> FEATURE:
<223> OTHER INFORMATION: Synthetic

<400> SEQUENCE: 11
gtcgactgga agccggtaaa atcaa 25

<210> SEQ ID NO 12
<211> LENGTH: 26
<212> TYPE: DNA
<213> ORGANISM: Artificial
<220> FEATURE:
<223> OTHER INFORMATION: Synthetic

<400> SEQUENCE: 12
ctgcaggccg acaatttctc cgtaaa 26

<210> SEQ ID NO 13
<211> LENGTH: 26
<212> TYPE: DNA
<213> ORGANISM: Artificial
<220> FEATURE:
<223> OTHER INFORMATION: Synthetic

<400> SEQUENCE: 13
ctgcagatat aaaaccgccg ggacat 26

<210> SEQ ID NO 14
<211> LENGTH: 27
<212> TYPE: DNA
<213> ORGANISM: Artificial
<220> FEATURE:
<223> OTHER INFORMATION: Sythetic

<400> SEQUENCE: 14
gtcgacgcat aggtgccgat agctgta 27

<210> SEQ ID NO 15
<211> LENGTH: 26
<212> TYPE: DNA
<213> ORGANISM: Artificial
<220> FEATURE:
<223> OTHER INFORMATION: Synthetic

<400> SEQUENCE: 15
gtcgactcaa atcgttttgc ttttcg 26

<210> SEQ ID NO 16
<211> LENGTH: 29

<212> TYPE: DNA
<213> ORGANISM: Artificial
<220> FEATURE:
<223> OTHER INFORMATION: Synthetic

<400> SEQUENCE: 16
ttaattaacc aaacaggaga tatcgatgc 29

<210> SEQ ID NO 17
<211> LENGTH: 26
<212> TYPE: DNA
<213> ORGANISM: Artificial
<220> FEATURE:
<223> OTHER INFORMATION: Synthetic

<400> SEQUENCE: 17
gaattcatat aaaaccgccg ggacat 26

<210> SEQ ID NO 18
<211> LENGTH: 28
<212> TYPE: DNA
<213> ORGANISM: Artificial
<220> FEATURE:
<223> OTHER INFORMATION: Synthetic

<400> SEQUENCE: 18
gtcgacgcat aggtgccgat agctgtaa 28

<210> SEQ ID NO 19
<211> LENGTH: 26
<212> TYPE: DNA
<213> ORGANISM: Artificial
<220> FEATURE:
<223> OTHER INFORMATION: Synthetic

<400> SEQUENCE: 19
gtcgactcaa atcgttttgc ttttcg 26

<210> SEQ ID NO 20
<211> LENGTH: 25
<212> TYPE: DNA
<213> ORGANISM: Artificial
<220> FEATURE:
<223> OTHER INFORMATION: Synthetic

<400> SEQUENCE: 20
aagcttccaa agatgatgcc attca 25

<210> SEQ ID NO 21
<211> LENGTH: 27
<212> TYPE: DNA
<213> ORGANISM: Artificial
<220> FEATURE:
<223> OTHER INFORMATION: Synthetic

<400> SEQUENCE: 21
gtcgaccaaa tttacaaaag cgactca 27

<210> SEQ ID NO 22
<211> LENGTH: 25
<212> TYPE: DNA
<213> ORGANISM: Artificial
<220> FEATURE:
<223> OTHER INFORMATION: Synthetic

<400> SEQUENCE: 22

-continued gtcgacgagg ccctttcgtc ttcaa 25

<210> SEQ ID NO 23
<211> LENGTH: 20
<212> TYPE: DNA
<213> ORGANISM: Artificial
<220> FEATURE:
<223> OTHER INFORMATION: Synthetic

<400> SEQUENCE: 23
gacagtatcg gcctcaggaa 20

<210> SEQ ID NO 24
<211> LENGTH: 20
<212> TYPE: DNA
<213> ORGANISM: Artificial
<220> FEATURE:
<223> OTHER INFORMATION: Synthetic

<400> SEQUENCE: 24
tgctgttcct cctccttctc 20

<210> SEQ ID NO 25
<211> LENGTH: 20
<212> TYPE: DNA
<213> ORGANISM: Artificial
<220> FEATURE:
<223> OTHER INFORMATION: Synthetic

<400> SEQUENCE: 25
gacagtatcg gcctcaggaa 20

<210> SEQ ID NO 26
<211> LENGTH: 24
<212> TYPE: DNA
<213> ORGANISM: Artificial
<220> FEATURE:
<223> OTHER INFORMATION: Synthetic

<400> SEQUENCE: 26
ggagtgattc atatgtcaaa agca 24

<210> SEQ ID NO 27
<211> LENGTH: 20
<212> TYPE: DNA
<213> ORGANISM: Artificial
<220> FEATURE:
<223> OTHER INFORMATION: Synthetic

<400> SEQUENCE: 27
gcatacgcct cctttccata 20

<210> SEQ ID NO 28
<211> LENGTH: 20
<212> TYPE: DNA
<213> ORGANISM: Artificial
<220> FEATURE:
<223> OTHER INFORMATION: Synthetic

<400> SEQUENCE: 28
tttgccggat attcttcagc 20

<210> SEQ ID NO 29
<211> LENGTH: 20
<212> TYPE: DNA
<213> ORGANISM: Artificial

<220> FEATURE:
<223> OTHER INFORMATION: Synthetic

<400> SEQUENCE: 29
caatgttaag ccggaaggaa 20

<210> SEQ ID NO 30
<211> LENGTH: 20
<212> TYPE: DNA
<213> ORGANISM: Artificial
<220> FEATURE:
<223> OTHER INFORMATION: Synthetic

<400> SEQUENCE: 30
agcagccgta aatgccatac 20

<210> SEQ ID NO 31
<211> LENGTH: 35
<212> TYPE: DNA
<213> ORGANISM: E. coli

<400> SEQUENCE: 31
gcaacgaagt cttcaagttt gcggtaacgg aactg 35

<210> SEQ ID NO 32
<211> LENGTH: 35
<212> TYPE: DNA
<213> ORGANISM: E. coli

<400> SEQUENCE: 32
cagttccgtt accgcaaact tgaagacttc gttgc 35

<210> SEQ ID NO 33
<211> LENGTH: 33
<212> TYPE: DNA
<213> ORGANISM: E. coli

<400> SEQUENCE: 33
ttcaaggttg cggtaacgga aatggcgcac atc 33

<210> SEQ ID NO 34
<211> LENGTH: 33
<212> TYPE: DNA
<213> ORGANISM: E. coli

<400> SEQUENCE: 34
gatgtgcgcc atttccgtta ccgcaacctt gaa 33

<210> SEQ ID NO 35
<211> LENGTH: 35
<212> TYPE: DNA
<213> ORGANISM: E. coli

<400> SEQUENCE: 35
gcaacgaagt cttcaagttt gcggtaacgg aactg 35

<210> SEQ ID NO 36
<211> LENGTH: 35
<212> TYPE: DNA
<213> ORGANISM: E. coli

<400> SEQUENCE: 36
cagttccgtt accgcaaact tgaagacttc gttgc 35

-continued

<210> SEQ ID NO 37
<211> LENGTH: 33
<212> TYPE: DNA
<213> ORGANISM: E. coli

<400> SEQUENCE: 37
ttcaaggttg cggtaacgga aatggcgcac atc 33

<210> SEQ ID NO 38
<211> LENGTH: 33
<212> TYPE: DNA
<213> ORGANISM: E. coli

<400> SEQUENCE: 38
gatgtgcgcc atttccgtta ccgcaacctt gaa 33

<210> SEQ ID NO 39
<211> LENGTH: 34
<212> TYPE: DNA
<213> ORGANISM: E. coli

<400> SEQUENCE: 39
ggttctgctt gaagccgctg gcggtggatt cacc 34

<210> SEQ ID NO 40
<211> LENGTH: 34
<212> TYPE: DNA
<213> ORGANISM: E. coli

<400> SEQUENCE: 40
ggtgaatcca ccgccagcgg cttcaagcag aacc 34

<210> SEQ ID NO 41
<211> LENGTH: 35
<212> TYPE: DNA
<213> ORGANISM: B. subtilis

<400> SEQUENCE: 41
gaatggacga gaagttttca aagttgcagt ccgcc 35

<210> SEQ ID NO 42
<211> LENGTH: 35
<212> TYPE: DNA
<213> ORGANISM: B. subtilis

<400> SEQUENCE: 42
ggcggactgc aactttgaaa acttctcgtc cattc 35

<210> SEQ ID NO 43
<211> LENGTH: 35
<212> TYPE: DNA
<213> ORGANISM: B. subtilis

<400> SEQUENCE: 43
caaatttgca gtccgccaat tgggagaatc atgcg 35

<210> SEQ ID NO 44
<211> LENGTH: 35
<212> TYPE: DNA
<213> ORGANISM: B. subtilis

<400> SEQUENCE: 44
cgcatgattc tcccaattgg cggactgcaa atttg 35

<210> SEQ ID NO 45
<211> LENGTH: 35
<212> TYPE: DNA
<213> ORGANISM: B. subtilis

<400> SEQUENCE: 45
gaatggacga gaagttttca aagttgcagt ccgcc 35

<210> SEQ ID NO 46
<211> LENGTH: 35
<212> TYPE: DNA
<213> ORGANISM: B. subtilis

<400> SEQUENCE: 46
cgcatgattc tcccaattgg cggactgcaa atttg 35

<210> SEQ ID NO 47
<211> LENGTH: 35
<212> TYPE: DNA
<213> ORGANISM: B. subtilis

<400> SEQUENCE: 47
caaagttgca gtccgccaat tgggagaatc atgcg 35

<210> SEQ ID NO 48
<211> LENGTH: 35
<212> TYPE: DNA
<213> ORGANISM: B. subtilis

<400> SEQUENCE: 48
cgcatgattc tcccaattgg cggactgcaa ctttg 35

<210> SEQ ID NO 49
<211> LENGTH: 34
<212> TYPE: DNA
<213> ORGANISM: B. subtilis

<400> SEQUENCE: 49
ggtcgttatg gtaggggccg gcggaggact aaca 34

<210> SEQ ID NO 50
<211> LENGTH: 34
<212> TYPE: DNA
<213> ORGANISM: B. subtilis

<400> SEQUENCE: 50
tgttagtcct ccgccggccc ctaccataac gacc 34

<210> SEQ ID NO 51
<211> LENGTH: 40
<212> TYPE: DNA
<213> ORGANISM: B. subtilis

<400> SEQUENCE: 51
gcaaaacgga cgcgaggtat ataaagtggc cgcaagaacc 40

<210> SEQ ID NO 52
<211> LENGTH: 40
<212> TYPE: DNA
<213> ORGANISM: B. subtilis

<400> SEQUENCE: 52

-continued ggttcttgcg gccactttat atacctcgcg tccgttttgc 40

<210> SEQ ID NO 53
<211> LENGTH: 27
<212> TYPE: DNA
<213> ORGANISM: B. subtiliis

<400> SEQUENCE: 53
ggccgcaaga accctccctg gcgaatt 27

<210> SEQ ID NO 54
<211> LENGTH: 27
<212> TYPE: DNA
<213> ORGANISM: B. subtilis

<400> SEQUENCE: 54
aattcgccag ggagggttct tgcggcc 27

<210> SEQ ID NO 55
<211> LENGTH: 40
<212> TYPE: DNA
<213> ORGANISM: B. subtilis

<400> SEQUENCE: 55
gcaaaacgga cgcgaggtat ataaagtggc cgcaagaacc 40

<210> SEQ ID NO 56
<211> LENGTH: 40
<212> TYPE: DNA
<213> ORGANISM: B. subtilis

<400> SEQUENCE: 56
ggttcttgcg gccactttat atacctcgcg tccgttttgc 40

<210> SEQ ID NO 57
<211> LENGTH: 27
<212> TYPE: DNA
<213> ORGANISM: B. subtilis

<400> SEQUENCE: 57
ggccgcaaga accctccctg gcgaatt 27

<210> SEQ ID NO 58
<211> LENGTH: 27
<212> TYPE: DNA
<213> ORGANISM: B. subtilis

<400> SEQUENCE: 58
aattcgccag ggagggttct tgcggcc 27

<210> SEQ ID NO 59
<211> LENGTH: 40
<212> TYPE: DNA
<213> ORGANISM: B. subtilis

<400> SEQUENCE: 59
aatcgttttg cttttcgggg ctggcggcgg attaacctat 40

<210> SEQ ID NO 60
<211> LENGTH: 40
<212> TYPE: DNA
<213> ORGANISM: B. subtilis

<400> SEQUENCE: 60
ataggttaat ccgccgccag ccccgaaaag caaaacgatt 40

<210> SEQ ID NO 61
<211> LENGTH: 954
<212> TYPE: DNA
<213> ORGANISM: E. coli

<400> SEQUENCE: 61
atgtatacga agattattgg tactggcagc tatctgcccg aacaagtgcg gacaaacgcc 60
gatttggaaa aaatggtgga cacctctgac gagtggattg tcactcgtac cggtatccgc 120
gaacgccaca ttgccgcgcc aaacgaaacc gtttcaacca tgggctttga agcggcgaca 180
cgcgcaattg agatggcggg cattgagaaa gaccagattg gcctgatcgt tgtggcaacg 240
acttctgcta cgcacgcttt cccgagcgca gcttgtcaga ttcaaagcat gttgggcatt 300
aaaggttgcc cggcatttga cgttgcagca gcctgcgcag gtttcaccta tgcattaagc 360
gtagccgatc aatacgtgaa atctggggcg gtgaagtatg ctctggtcgt cggttccgat 420
gtactggcgc gcacctgcga tccaaccgat cgtgggacta ttattatttt tggcgatggc 480
gcgggcgctg cggtgctggc tgcctctgaa gagccgggaa tcatttccac ccatctgcat 540
gccgacggta gttatggtga attgctgacg ctgccaaacg ccgaccgcgt gaatccagag 600
aattcaattc atctgacgat ggcgggcaac gaagtcttca aggttgcggt aacggaactg 660
gcgcacatcg ttgatgagac gctggcggcg aataatcttg accgttctca actggactgg 720
ctggttccgc atcaggctaa cctgcgtatt atcagtgcaa cggcgaaaaa actcggtatg 780
tctatggata atgtcgtggt gacgctggat cgccacggta atacctctgc ggcctctgtc 840
ccgtgcgcgc tggatgaagc tgtacgcgac gggcgcatta agccggggca gttggttctg 900
cttgaagcct ttggcggtgg attcacctgg ggctccgcgc tggttcgttt ctag 954

<210> SEQ ID NO 62
<211> LENGTH: 317
<212> TYPE: PRT
<213> ORGANISM: E. coli

<400> SEQUENCE: 62

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly

-continued 145 150 155 160

Ala Gly Ala Ala Val Leu Ala Ala Ser Glu Glu Pro Gly Ile Ile Ser
165 170 175

Thr His Leu His Ala Asp Gly Ser Tyr Gly Glu Leu Leu Thr Leu Pro
180 185 190

Asn Ala Asp Arg Val Asn Pro Glu Asn Ser Ile His Leu Thr Met Ala
195 200 205

Gly Asn Glu Val Phe Lys Val Ala Val Thr Glu Leu Ala His Ile Val
210 215 220

Asp Glu Thr Leu Ala Ala Asn Asn Leu Asp Arg Ser Gln Leu Asp Trp
225 230 235 240

Leu Val Pro His Gln Ala Asn Leu Arg Ile Ile Ser Ala Thr Ala Lys
245 250 255

Lys Leu Gly Met Ser Met Asp Asn Val Val Val Thr Leu Asp Arg His
260 265 270

Gly Asn Thr Ser Ala Ala Ser Val Pro Cys Ala Leu Asp Glu Ala Val
275 280 285

Arg Asp Gly Arg Ile Lys Pro Gly Gln Leu Val Leu Leu Glu Ala Phe
290 295 300

Gly Gly Gly Phe Thr Trp Gly Ser Ala Leu Val Arg Phe
305 310 315

<210> SEQ ID NO 63
<211> LENGTH: 939
<212> TYPE: DNA
<213> ORGANISM: B. subtilis

<400> SEQUENCE: 63
atgaaagctg gaatacttgg tgttggacgt tacattcctg agaaggtttt aacaaatcat 60
gatcttgaaa aaatggttga aacttctgac gagtggattc gtacaagaac aggaatagaa 120
gaaagaagaa tcgcagcaga tgatgtgttt tcatcacata tggctgttgc agcagcgaaa 180
aatgcgctgg aacaagctga agtggctgct gaggatctgg atatgatctt ggttgcaact 240
gttacacctg atcagtcatt ccctacggtc tcttgtatga ttcaagaaca actcggcgcg 300
aagaaagcgt gtgctatgga tatcagcgcg gcttgtgcgg gcttcatgta cggggttgta 360
accggtaaac aatttattga atccggaacc tacaagcatg ttctagttgt tggtgtagag 420
aagctctcaa gcattaccga ctgggaagac cgcaatacag ccgttctgtt tggagacgga 480
gcaggcgctg cggtagtcgg gccagtcagt gatgacagag gaatcctttc atttgaacta 540
ggagccgacg gcacaggcgg tcagcacttg tatctgaatg aaaaacgaca tacaatcatg 600
aatggacgag aagttttcaa atttgcagtc cgccaaatgg gagaatcatg cgtaaatgtc 660
attgaaaaag ccggactttc aaaagaggat gtcgactttt tgattccgca tcaggcgaac 720
atccgtatca tggaagctgc tcgcgagcgt ttagagcttc ctgtcgaaaa gatgtctaaa 780
actgttcata aatatggaaa tacttctgcc gcatccattc cgatctctct tgtagaagaa 840
ttggaagccg gtaaaatcaa agacggcgat gtggtcgtta tggtagggtt cggcggagga 900
ctaacatggg gcgccattgc aatccgctgg ggccgataa 939

<210> SEQ ID NO 64
<211> LENGTH: 312
<212> TYPE: PRT
<213> ORGANISM: B. subtilis

<400> SEQUENCE: 64

```
Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30

Ile Arg Thr Arg Thr Gly Ile Glu Glu Arg Arg Ile Ala Ala Asp Asp
        35                  40                  45

Val Phe Ser Ser His Met Ala Val Ala Ala Ala Lys Asn Ala Leu Glu
    50                  55                  60

Gln Ala Glu Val Ala Ala Glu Asp Leu Asp Met Ile Leu Val Ala Thr
65                  70                  75                  80

Val Thr Pro Asp Gln Ser Phe Pro Thr Val Ser Cys Met Ile Gln Glu
                85                  90                  95

Gln Leu Gly Ala Lys Lys Ala Cys Ala Met Asp Ile Ser Ala Ala Cys
            100                 105                 110

Ala Gly Phe Met Tyr Gly Val Val Thr Gly Lys Gln Phe Ile Glu Ser
        115                 120                 125

Gly Thr Tyr Lys His Val Leu Val Val Gly Val Glu Lys Leu Ser Ser
    130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190

Asn Glu Lys Arg His Thr Ile Met Asn Gly Arg Glu Val Phe Lys Phe
        195                 200                 205

Ala Val Arg Gln Met Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Val Val Met Val Gly Phe Gly Gly Gly Leu Thr Trp Gly
    290                 295                 300

Ala Ile Ala Ile Arg Trp Gly Arg
305                 310
```

<210> SEQ ID NO 65
<211> LENGTH: 978
<212> TYPE: DNA
<213> ORGANISM: B. subtilis

<400> SEQUENCE: 65

```
atgtcaaaag caaaaattac agctatcggc acctatgcgc cgagcagacg tttaaccaat     60

gcagatttag aaaagatcgt tgatacctct gatgaatgga tcgttcagcg cacaggaatg    120

agagaacgcc ggattgcgga tgaacatcaa tttacctctg atttatgcat agaagcggtg    180

aagaatctca agagccgtta taaaggaacg cttgatgatg tcgatatgat cctcgttgcc    240

acaaccacat ccgattacgc ctttccgagt acggcatgcc gcgtacagga atatttcggc    300
```

-continued

```
tgggaaagca ccggcgcgct ggatattaat gcgacatgcg ccgggctgac atacggcctc    360

catttggcaa atggattgat cacatctggc cttcatcaaa aaattctcgt catcgccgga    420

gagacgttat caaaggtaac cgattatacc gatcgaacga catgcgtact gttcggcgat    480

gccgcgggtg cgctgttagt agaacgagat gaagagacgc cgggatttct tgcgtctgta    540

caaggaacaa gcgggaacgg cggcgatatt ttgtatcgtg ccggactgcg aaatgaaata    600

aacggtgtgc agcttgtcgg ttccggaaaa atggtgcaaa acggacgcga ggtatataaa    660

tgggccgcaa gaaccgtccc tggcgaattt gaacggcttt tacataaagc aggactcagc    720

tccgatgatc tcgattggtt tgttcctcac agcgccaact tgcgcatgat cgagtcaatt    780

tgtgaaaaaa caccgttccc gattgaaaaa acgctcacta gtgttgagca ctacggaaac    840

acgtcttcgg tttcaattgt tttggcgctc gatctcgcag tgaaagccgg gaagctgaaa    900

aaagatcaaa tcgttttgct tttcgggttt ggcggcggat taacctatac aggattgctt    960

attaaatggg ggatgtaa                                                  978
```

```
<210> SEQ ID NO 66
<211> LENGTH: 325
<212> TYPE: PRT
<213> ORGANISM: B. subtilis

<400> SEQUENCE: 66

Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Trp Ala Ala Arg
    210                 215                 220

Thr Val Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255
```

```
Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Phe Gly Phe Gly Gly Gly Leu Thr Tyr Thr Gly Leu Leu
305                 310                 315                 320

Ile Lys Trp Gly Met
                325
```

<210> SEQ ID NO 67
<211> LENGTH: 1122
<212> TYPE: DNA
<213> ORGANISM: Aeromonas hydrophila

<400> SEQUENCE: 67

```
atgacgtcta tcgttatctc gggctcgggt ctgtatacgc cgccgtttgc cgtgtccaat     60

gaagaactgg tcgccgcctt taatcagtat gttgatctgt acaacgaaga aaatgccagc    120

gcaattgacg ccggccaact gccggcaaaa cagcatagct ctagtgaatt tattgaaaaa    180

gcctccggca tcaaatcacg ttatctggtg tctaaagaag gtgttctgga tccggacatc    240

atgcagccgc tgctgccgga acgtccggat gacaaaccgt ccattatggt tgaaatggca    300

gtcgcagcag cagaacaggc cctgatcgct gcaggtcgtg aaccgggtga aattgatctg    360

gtcatcgtgg ccgcatccaa catgccgcgc ccgtatccgg cgctgtcaat tgaactgcag    420

cactacctgg gcgcctcggg tatggcattt gatatgaatg ttgcttgctc ctcagcgacc    480

ttcggcatca aaacggctgc ggatatgctg gccgcaggtt ctgcccgtct ggcactggtg    540

gttaacccgg aaatttgtag cggccatctg aatttccgtg atcgcgactc tcactttatc    600

ttcggtgatg cttgcaccgc gatgctgctg gaacgcgaag ctgactgtaa agtcgcgaac    660

ccgtggcaac tggtcgcctc gaaactggtg acccagtaca gcaacaacat ccgtaacaac    720

ttcggtttcc tgaaccgcct gagtccgcgt acgcgctacg gcgatgacaa actgtttcgt    780

cagcaaggtc gcaaagtgtt caaagaagtt ctgccgctgg tctgcgatca gattgcgggc    840

caactggacg aacagggttg ggctgcgaac tctctgagtc gtctgtggct gcatcaagca    900

aacctgacca tgaatcagtt tattgcgcgc aaactgctgg gccacgatgc cagccagcaa    960

gaagcaccgg tgatcctgga ctcttacggc aacacgtcga gcgctggtag tattatcgca   1020

ttccatctgc acaatggtga tctgccggct ggcgcgcgtg gtgttctgtg ctcctttggt   1080

gctggctact ccattggctc gctgctgctg acccgcctgt ga                      1122
```

<210> SEQ ID NO 68
<211> LENGTH: 373
<212> TYPE: PRT
<213> ORGANISM: Aeromonas hydrophila

<400> SEQUENCE: 68

```
Met Thr Ser Ile Val Ile Ser Gly Ser Gly Leu Tyr Thr Pro Pro Phe
1               5                   10                  15

Ala Val Ser Asn Glu Glu Leu Val Ala Ala Phe Asn Gln Tyr Val Asp
            20                  25                  30

Leu Tyr Asn Glu Glu Asn Ala Ser Ala Ile Asp Ala Gly Gln Leu Pro
        35                  40                  45
```

-continued

```
Ala Lys Gln His Ser Ser Ser Glu Phe Ile Glu Lys Ala Ser Gly Ile
    50                  55                  60

Lys Ser Arg Tyr Leu Val Ser Lys Glu Gly Val Leu Asp Pro Asp Ile
65                  70                  75                  80

Met Gln Pro Leu Leu Pro Glu Arg Pro Asp Asp Lys Pro Ser Ile Met
                85                  90                  95

Val Glu Met Ala Val Ala Ala Ala Glu Gln Ala Leu Ile Ala Ala Gly
            100                 105                 110

Arg Glu Pro Gly Glu Ile Asp Leu Val Ile Val Ala Ala Ser Asn Met
        115                 120                 125

Pro Arg Pro Tyr Pro Ala Leu Ser Ile Glu Leu Gln His Tyr Leu Gly
    130                 135                 140

Ala Ser Gly Met Ala Phe Asp Met Asn Val Ala Cys Ser Ser Ala Thr
145                 150                 155                 160

Phe Gly Ile Lys Thr Ala Ala Asp Met Leu Ala Ala Gly Ser Ala Arg
                165                 170                 175

Leu Ala Leu Val Val Asn Pro Glu Ile Cys Ser Gly His Leu Asn Phe
            180                 185                 190

Arg Asp Arg Asp Ser His Phe Ile Phe Gly Asp Ala Cys Thr Ala Met
        195                 200                 205

Leu Leu Glu Arg Glu Ala Asp Cys Lys Val Ala Asn Pro Trp Gln Leu
    210                 215                 220

Val Ala Ser Lys Leu Val Thr Gln Tyr Ser Asn Asn Ile Arg Asn Asn
225                 230                 235                 240

Phe Gly Phe Leu Asn Arg Leu Ser Pro Arg Thr Arg Tyr Gly Asp Asp
                245                 250                 255

Lys Leu Phe Arg Gln Gln Gly Arg Lys Val Phe Lys Glu Val Leu Pro
            260                 265                 270

Leu Val Cys Asp Gln Ile Ala Gly Gln Leu Asp Glu Gln Gly Trp Ala
        275                 280                 285

Ala Asn Ser Leu Ser Arg Leu Trp Leu His Gln Ala Asn Leu Thr Met
    290                 295                 300

Asn Gln Phe Ile Ala Arg Lys Leu Leu Gly His Asp Ala Ser Gln Gln
305                 310                 315                 320

Glu Ala Pro Val Ile Leu Asp Ser Tyr Gly Asn Thr Ser Ser Ala Gly
                325                 330                 335

Ser Ile Ile Ala Phe His Leu His Asn Gly Asp Leu Pro Ala Gly Ala
            340                 345                 350

Arg Gly Val Leu Cys Ser Phe Gly Ala Gly Tyr Ser Ile Gly Ser Leu
        355                 360                 365

Leu Leu Thr Arg Leu
    370
```

<210> SEQ ID NO 69
<211> LENGTH: 954
<212> TYPE: DNA
<213> ORGANISM: Legionella pneumophila

<400> SEQUENCE: 69

```
atgaaaaacg ctgttatcaa cggtacgggt agttattcgc cggaacgcca aatgaccaac      60

gcagaactgg aaacgatgct ggacacgagc gatgaatgga ttgttacccg tacgggtatc     120

agctctcgct ctgtcgcgca ggaacatgaa accacgtcct atatggcctc acgtgcggcc     180

gaacaagcgc tggaagccag tggcctggat gcagaagaaa ttgacctgat cctggtggct     240
```

```
acctgcacgc cggattactt tttcccgtcc gtcgcgtgtc atgtgcagca cgccctgggt    300

attaaacgcc cgatcccggc gtttgatatt ggtgcagctt gcagtggctt cgtttatgca    360

atggacgtcg ctaaacaata catcgccacc ggtgcggcca aacatgttct ggtggttggc    420

agtgaatcca tgtcacgtgc agtcgattgg accgaccgca gcatttgtgt gctgtttggc    480

gatggtgcag gtgcagtcgt gctgtcggca agcgaccgtc agggtatcat gggctcggtg    540

ctgcacagcg cctatgattc tgacaaactg ctggttctgc gcaacagcac ctttgaacaa    600

gatcgtgcaa cgattggtat gcgcggcaat gaagtgttca aaattgctgt taacatcatg    660

ggcaatattg tggatgaagt tctggaagca tcacatctga aaaaatcgga tatcgactgg    720

ctgattccgc accaggcgaa cattcgtatt atccaagcaa tcgctaaaaa actgagtctg    780

ccgatgtccc acgttattgt caccatcggt aaccagggca atacgtctgc agctagtatt    840

ccgctggccc tggattactc tatcaaaaac aaccgtatca aacgcgacga aatcctgctg    900

attgaatctt ttggcggtgg tatgacctgg ggtgcgatgg ttatccgtta ctaa          954


<210> SEQ ID NO 70
<211> LENGTH: 317
<212> TYPE: PRT
<213> ORGANISM: Legionella pneumophila

<400> SEQUENCE: 70

Met Lys Asn Ala Val Ile Asn Gly Thr Gly Ser Tyr Ser Pro Glu Arg
1               5                   10                  15

Gln Met Thr Asn Ala Glu Leu Glu Thr Met Leu Asp Thr Ser Asp Glu
            20                  25                  30

Trp Ile Val Thr Arg Thr Gly Ile Ser Ser Arg Ser Val Ala Gln Glu
        35                  40                  45

His Glu Thr Thr Ser Tyr Met Ala Ser Arg Ala Ala Glu Gln Ala Leu
    50                  55                  60

Glu Ala Ser Gly Leu Asp Ala Glu Glu Ile Asp Leu Ile Leu Val Ala
65                  70                  75                  80

Thr Cys Thr Pro Asp Tyr Phe Phe Pro Ser Val Ala Cys His Val Gln
                85                  90                  95

His Ala Leu Gly Ile Lys Arg Pro Ile Pro Ala Phe Asp Ile Gly Ala
            100                 105                 110

Ala Cys Ser Gly Phe Val Tyr Ala Met Asp Val Ala Lys Gln Tyr Ile
        115                 120                 125

Ala Thr Gly Ala Ala Lys His Val Leu Val Val Gly Ser Glu Ser Met
    130                 135                 140

Ser Arg Ala Val Asp Trp Thr Asp Arg Ser Ile Cys Val Leu Phe Gly
145                 150                 155                 160

Asp Gly Ala Gly Ala Val Val Leu Ser Ala Ser Asp Arg Gln Gly Ile
                165                 170                 175

Met Gly Ser Val Leu His Ser Ala Tyr Asp Ser Asp Lys Leu Leu Val
            180                 185                 190

Leu Arg Asn Ser Thr Phe Glu Gln Asp Arg Ala Thr Ile Gly Met Arg
        195                 200                 205

Gly Asn Glu Val Phe Lys Ile Ala Val Asn Ile Met Gly Asn Ile Val
    210                 215                 220

Asp Glu Val Leu Glu Ala Ser His Leu Lys Lys Ser Asp Ile Asp Trp
225                 230                 235                 240

Leu Ile Pro His Gln Ala Asn Ile Arg Ile Ile Gln Ala Ile Ala Lys
                245                 250                 255
```

```
Lys Leu Ser Leu Pro Met Ser His Val Ile Val Thr Ile Gly Asn Gln
            260                 265                 270

Gly Asn Thr Ser Ala Ala Ser Ile Pro Leu Ala Leu Asp Tyr Ser Ile
        275                 280                 285

Lys Asn Asn Arg Ile Lys Arg Asp Glu Ile Leu Leu Ile Glu Ser Phe
    290                 295                 300

Gly Gly Gly Met Thr Trp Gly Ala Met Val Ile Arg Tyr
305                 310                 315


<210> SEQ ID NO 71
<211> LENGTH: 1062
<212> TYPE: DNA
<213> ORGANISM: Legionella pneumophila

<400> SEQUENCE: 71

atgaacatcc tgaaaccgaa catccaattt gaaatcacgg gtgcttctcg cattctgccg     60

gcgtctggtc cgatcacgaa cctggaaatt ctgaaaaact ttccgcgtac cgctgataaa    120

agccagggct ttctggaaaa attcgcggaa aaaatcggcg aagaatttgg tttccatacc    180

cgttattggt gccacaaacc gtgggaatcc ctggataact cacgcgaact gagctctgaa    240

agcctggcta tgcaggcggt tgacaaactg attacgcata gtaaatccaa agatgtcgac    300

gcctttctgc tgggttcgac cacgaataaa cgtttcaccg gtagccaagc agcagcagtg    360

ctgggtaacc tgaaactgaa tgccccggca tacgatctga aaaccggctg ttcaacgtcg    420

ctgagcaccc tgcactttgc ttatgcgatg atggccctgg gttaccagaa aatcctggtc    480

tgctgttcgg aaacgctgag caaagtgatt gatccggaaa acgaaaaaac ctggatcggc    540

ctggcagacg gtgctgcgtc tctgctgctg gaaaaatcta aagaaggcag tttcacgatt    600

gaaaaatctt tctttagcac cgatggccag tatgttaatg cttttaccac gcaaggtgtc    660

ttcccgccga cgcatgaaca gatcgattct gtgggctacc acctggttgg tgacgaaacc    720

ctgatgaaag aactggcata tagtcgttac atgcaaatgc tggataacct gctgccgacg    780

gaaaaagaga aaaacgaaat tacctgggtc atcccgcatc aggtgaaccg caaactgatt    840

gaccaagtgc tgcatgaatc ccacctgaac aataaaacga ttatctggga tgccgacacc    900

attggtaata tcggcggtgc aagtgtgctg tataccctgg cccgtgcagt tgaagaaaaa    960

ctgtttgatc gctccggcaa aatcctgctg atgtcagttg gtggcggtct gtcgtatgcg   1020

ggtcaagtcc tgaactacca aaaagcaagc tactccaact ga                      1062


<210> SEQ ID NO 72
<211> LENGTH: 353
<212> TYPE: PRT
<213> ORGANISM: Legionella pneumophila

<400> SEQUENCE: 72

Met Asn Ile Leu Lys Pro Asn Ile Gln Phe Glu Ile Thr Gly Ala Ser
1               5                   10                  15

Arg Ile Leu Pro Ala Ser Gly Pro Ile Thr Asn Leu Glu Ile Leu Lys
            20                  25                  30

Asn Phe Pro Arg Thr Ala Asp Lys Ser Gln Gly Phe Leu Glu Lys Phe
        35                  40                  45

Ala Glu Lys Ile Gly Glu Glu Phe Gly Phe His Thr Arg Tyr Trp Cys
    50                  55                  60

His Lys Pro Trp Glu Ser Leu Asp Asn Ser Arg Glu Leu Ser Ser Glu
65                  70                  75                  80
```

```
Ser Leu Ala Met Gln Ala Val Asp Lys Leu Ile Thr His Ser Lys Ser
                85                  90                  95

Lys Asp Val Asp Ala Phe Leu Leu Gly Ser Thr Thr Asn Lys Arg Phe
            100                 105                 110

Thr Gly Ser Gln Ala Ala Ala Val Leu Gly Asn Leu Lys Leu Asn Ala
        115                 120                 125

Pro Ala Tyr Asp Leu Lys Thr Gly Cys Ser Thr Ser Leu Ser Thr Leu
    130                 135                 140

His Phe Ala Tyr Ala Met Met Ala Leu Gly Tyr Gln Lys Ile Leu Val
145                 150                 155                 160

Cys Cys Ser Glu Thr Leu Ser Lys Val Ile Asp Pro Glu Asn Glu Lys
                165                 170                 175

Thr Trp Ile Gly Leu Ala Asp Gly Ala Ala Ser Leu Leu Leu Glu Lys
            180                 185                 190

Ser Lys Glu Gly Ser Phe Thr Ile Glu Lys Ser Phe Phe Ser Thr Asp
        195                 200                 205

Gly Gln Tyr Val Asn Ala Phe Thr Thr Gln Gly Val Phe Pro Pro Thr
    210                 215                 220

His Glu Gln Ile Asp Ser Val Gly Tyr His Leu Val Gly Asp Glu Thr
225                 230                 235                 240

Leu Met Lys Glu Leu Ala Tyr Ser Arg Tyr Met Gln Met Leu Asp Asn
                245                 250                 255

Leu Leu Pro Thr Glu Lys Glu Lys Asn Glu Ile Thr Trp Val Ile Pro
            260                 265                 270

His Gln Val Asn Arg Lys Leu Ile Asp Gln Val Leu His Glu Ser His
        275                 280                 285

Leu Asn Asn Lys Thr Ile Ile Trp Asp Ala Asp Thr Ile Gly Asn Ile
    290                 295                 300

Gly Gly Ala Ser Val Leu Tyr Thr Leu Ala Arg Ala Val Glu Glu Lys
305                 310                 315                 320

Leu Phe Asp Arg Ser Gly Lys Ile Leu Leu Met Ser Val Gly Gly Gly
                325                 330                 335

Leu Ser Tyr Ala Gly Gln Val Leu Asn Tyr Gln Lys Ala Ser Tyr Ser
            340                 345                 350

Asn
```

<210> SEQ ID NO 73
<211> LENGTH: 1011
<212> TYPE: DNA
<213> ORGANISM: Legionella pneumophila

<400> SEQUENCE: 73

```
atgaacttct tccgttgtga aaaaccgatt tatatcaaag gcccgtgtgt cgcactgccg      60

gaccgtatta tgtcaaacca ggatgtgctg aactggatgg atagtaccca gaatccggcc     120

gtgattggct tctccacggg tatcaaaaac cgtcattggg ttaatgaaga tcaggcgtgc     180

tctgacctgg cagtccaggc agcagaacaa ctgtttatgg aaaaaccgcg cgaaaaacac     240

aaagtcaacc aagtgattct ggcgaccatc agtggcgatt atccgtcccc gccgagctct     300

ccgctggttc agtaccgtct gggtctgcaa aatgctggcg cgttcgacat tggtgcagct     360

tgtgccggct ttgtggttgg tctgcatacc tcagcggccc tggcccagac gaacgatggt     420

tcggtcctgc tgattgcaag cgaaatccgc tctaaattcc tgaacaaaaa caacttcgca     480

accagcgtgc tgtttggcga tggtgcagct gcgtgctgtg tttctcaaga taaagaagaa     540
```

```
gctgactttc gtttcatcgc cagtgcactg tttgcggatg gcgaagtcta tgacgccgtg    600

tcaacgccgg caggcggttc gcgtctgccg gcagcagtgt gcaacgacaa tgaacagttc    660

tacattacca tcaaagaaag cacggctctg tttgttaaag cggtccatgg catgtcagat    720

tcggcgaaag acttcctgaa agaactgaac ctgaccattt ccgatatcca gtggctggtt    780

ccgcaccaag gcaacaaaaa tctggtgctg agtgttgcca aacagctggg ttttccggaa    840

gaaaaaacca ttaaaacggt cgaagaaacc ggcaatacga gcggtagttc cgtgggcatt    900

gcactggatc gtctgcgcag cgacggcaaa atcaaatctg gtgaaaaagt tctgctggtt    960

gctgcgggcg gtggtggcat tgcggcttgc tccctgctgg aagttatttg a            1011
```

<210> SEQ ID NO 74
<211> LENGTH: 336
<212> TYPE: PRT
<213> ORGANISM: Legionella pneumophila

<400> SEQUENCE: 74

```
Met Asn Phe Phe Arg Cys Glu Lys Pro Ile Tyr Ile Lys Gly Pro Cys
1               5                   10                  15

Val Ala Leu Pro Asp Arg Ile Met Ser Asn Gln Asp Val Leu Asn Trp
            20                  25                  30

Met Asp Ser Thr Gln Asn Pro Ala Val Ile Gly Phe Ser Thr Gly Ile
        35                  40                  45

Lys Asn Arg His Trp Val Asn Glu Asp Gln Ala Cys Ser Asp Leu Ala
    50                  55                  60

Val Gln Ala Ala Glu Gln Leu Phe Met Glu Lys Pro Arg Glu Lys His
65                  70                  75                  80

Lys Val Asn Gln Val Ile Leu Ala Thr Ile Ser Gly Asp Tyr Pro Ser
                85                  90                  95

Pro Pro Ser Ser Pro Leu Val Gln Tyr Arg Leu Gly Leu Gln Asn Ala
            100                 105                 110

Gly Ala Phe Asp Ile Gly Ala Ala Cys Ala Gly Phe Val Val Gly Leu
        115                 120                 125

His Thr Ser Ala Ala Leu Ala Gln Thr Asn Asp Gly Ser Val Leu Leu
    130                 135                 140

Ile Ala Ser Glu Ile Arg Ser Lys Phe Leu Asn Lys Asn Asn Phe Ala
145                 150                 155                 160

Thr Ser Val Leu Phe Gly Asp Gly Ala Ala Ala Cys Cys Val Ser Gln
                165                 170                 175

Asp Lys Glu Glu Ala Asp Phe Arg Phe Ile Ala Ser Ala Leu Phe Ala
            180                 185                 190

Asp Gly Glu Val Tyr Asp Ala Val Ser Thr Pro Ala Gly Gly Ser Arg
        195                 200                 205

Leu Pro Ala Ala Val Cys Asn Asp Asn Glu Gln Phe Tyr Ile Thr Ile
    210                 215                 220

Lys Glu Ser Thr Ala Leu Phe Val Lys Ala Val His Gly Met Ser Asp
225                 230                 235                 240

Ser Ala Lys Asp Phe Leu Lys Glu Leu Asn Leu Thr Ile Ser Asp Ile
                245                 250                 255

Gln Trp Leu Val Pro His Gln Gly Asn Lys Asn Leu Val Leu Ser Val
            260                 265                 270

Ala Lys Gln Leu Gly Phe Pro Glu Glu Lys Thr Ile Lys Thr Val Glu
        275                 280                 285
```

```
Glu Thr Gly Asn Thr Ser Gly Ser Ser Val Gly Ile Ala Leu Asp Arg
    290                 295                 300

Leu Arg Ser Asp Gly Lys Ile Lys Ser Gly Glu Lys Val Leu Leu Val
305                 310                 315                 320

Ala Ala Gly Gly Gly Gly Ile Ala Ala Cys Ser Leu Leu Glu Val Ile
                325                 330                 335


<210> SEQ ID NO 75
<211> LENGTH: 984
<212> TYPE: DNA
<213> ORGANISM: Legionella pneumophila

<400> SEQUENCE: 75

atgtcctccg ctaaaatcat tggtatgggt aaatatctgc cggctaacat cgtcttctct      60

tctgacctgg ataaaaaact gaatctgccg gaaggctccg tgcagaaaaa atctggtctg     120

gtttctcgtc atttcgctcg cgtcaacgaa accacgagtt atatggcatc ccaggcagca     180

ctgcacgctg ttgaacaagc gggcattacc ctggccgaaa tcgatgcaat tatcggtgcc     240

tgcggcgcag gtgaacaacc gattccgtgt accgcagttc tggtccagaa acaactgggc     300

ctggataaca gcggtattgc ctgctttgac atcaattcaa cctgtctgtc gttcctgacg     360

gcactggatg cagctagcta tatgctgtct ggcggtcgtt ttaaccgcat tctgatcgtc     420

agctctgaca ttccgagttt cggcctggat tggtccgacc tggaaacctg cacgatcttt     480

ggcgatggtg cggccgcatg tgtggttgaa cgttctaatg acagttcccg cattctgtca     540

gcgcatatga aaacctactc gctgggtgct gcgttttgcg aagtgcaggc cggcggtacg     600

ctgatgccgc cggcaagcga atacgataaa aaatacggcc tgttcaaaat ggacggtaaa     660

cgtgtgttca aactggccag ccagatgatt gaaccgatgc aagaagaact gttcgctaaa     720

gcgtctatca ccctgaacga tgttgactgg gtcgtgccgc accaggctag tctgctggcg     780

atgcatcaca ttcgtaaaaa actgggcatc ccgggtgaaa aatttgtgga tatttacacc     840

acgcatggca atcagatggc cgcatcactg ccgtcggcgc tgtgtcacct gatccataac     900

cacaatctgg aacgcggtca actggtctat ctgctgggta cgggtgctgg tctgtctgct     960

gcgggcatga tcctggaata ctga                                            984


<210> SEQ ID NO 76
<211> LENGTH: 327
<212> TYPE: PRT
<213> ORGANISM: Legionella pneumophila

<400> SEQUENCE: 76

Met Ser Ser Ala Lys Ile Ile Gly Met Gly Lys Tyr Leu Pro Ala Asn
1               5                   10                  15

Ile Val Phe Ser Ser Asp Leu Asp Lys Lys Leu Asn Leu Pro Glu Gly
            20                  25                  30

Ser Val Gln Lys Lys Ser Gly Leu Val Ser Arg His Phe Ala Arg Val
        35                  40                  45

Asn Glu Thr Thr Ser Tyr Met Ala Ser Gln Ala Ala Leu His Ala Val
    50                  55                  60

Glu Gln Ala Gly Ile Thr Leu Ala Glu Ile Asp Ala Ile Ile Gly Ala
65                  70                  75                  80

Cys Gly Ala Gly Glu Gln Pro Ile Pro Cys Thr Ala Val Leu Val Gln
                85                  90                  95

Lys Gln Leu Gly Leu Asp Asn Ser Gly Ile Ala Cys Phe Asp Ile Asn
            100                 105                 110
```

```
Ser Thr Cys Leu Ser Phe Leu Thr Ala Leu Asp Ala Ala Ser Tyr Met
        115                 120                 125

Leu Ser Gly Gly Arg Phe Asn Arg Ile Leu Ile Val Ser Ser Asp Ile
    130                 135                 140

Pro Ser Phe Gly Leu Asp Trp Ser Asp Leu Glu Thr Cys Thr Ile Phe
145                 150                 155                 160

Gly Asp Gly Ala Ala Ala Cys Val Val Glu Arg Ser Asn Asp Ser Ser
                165                 170                 175

Arg Ile Leu Ser Ala His Met Lys Thr Tyr Ser Leu Gly Ala Ala Phe
            180                 185                 190

Cys Glu Val Gln Ala Gly Gly Thr Leu Met Pro Pro Ala Ser Glu Tyr
        195                 200                 205

Asp Lys Lys Tyr Gly Leu Phe Lys Met Asp Gly Lys Arg Val Phe Lys
    210                 215                 220

Leu Ala Ser Gln Met Ile Glu Pro Met Gln Glu Glu Leu Phe Ala Lys
225                 230                 235                 240

Ala Ser Ile Thr Leu Asn Asp Val Asp Trp Val Val Pro His Gln Ala
                245                 250                 255

Ser Leu Leu Ala Met His His Ile Arg Lys Lys Leu Gly Ile Pro Gly
            260                 265                 270

Glu Lys Phe Val Asp Ile Tyr Thr Thr His Gly Asn Gln Met Ala Ala
        275                 280                 285

Ser Leu Pro Ser Ala Leu Cys His Leu Ile His Asn His Asn Leu Glu
    290                 295                 300

Arg Gly Gln Leu Val Tyr Leu Leu Gly Thr Gly Ala Gly Leu Ser Ala
305                 310                 315                 320

Ala Gly Met Ile Leu Glu Tyr
                325


<210> SEQ ID NO 77
<211> LENGTH: 1005
<212> TYPE: DNA
<213> ORGANISM: Bacteroides vulgatus

<400> SEQUENCE: 77

atggaaaaaa tcaatgcggt tatcacgggc gttggtggct atgtgccgga ctatgtgctg      60

acgaatgaag aaatctcacg tatggtcgat acgaatgacg aatggatcat gacccgtatt     120

ggcgtgaaag aacgtcgcat cctgaacgaa gaaggcctgg gcacgtcata tatggcccgc     180

aaagcggcca aacagctgat gcaaaaaacc gcatcgaatc cggatgacat cgatgctgtg     240

attgttgcga ccacgacccc ggactaccat tttccgagta ccgcgtccat tctgtgcgat     300

aaactgggcc tgaaaaacgc ctttgcattc gacctgcagg cagcttgctg tggtttcctg     360

tatctgatgg aaaccgcagc cagcctgatc gcttctggtc gtcacaagaa aattatcatt     420

gtcggtgcgg ataaaatgag ctctatggtg aattatcagg atcgcgccac gtgcccgatt     480

tttggcgacg gtgcagctgc gtgtatggtt gaagcaacga ccgaagatta cggtatcatg     540

gactcaattc tgcgtaccga tggcaaaggt ctgccgtttc tgcatatgaa agccggcggt     600

agtgtgtgcc cgccgtccta tttcacggtt gatcataaaa tgcactatct gtaccaggaa     660

ggccgcaccg tcttcaaata cgcagtgtca aatatgtcgg atatcacggc caccattgca     720

gagaaaaacg gtctgaataa agataacatc gactgggtta ttccgcacca agccaacctg     780

cgtatcattg atgctgtcgc gagccgcctg gaagttccgc tggaaaaagt catgatcaat     840
```

```
attcagcgtt atggcaacac gtctggtgct accctgccgc tgtgtctgtg ggattacgaa    900

aaacaactga aaaaaggcga caacctgatt tttaccgcgt tcggtgcggg ctttacctat    960

ggtgcggtgt atgtgaaatg gggctacgac ggcagcaaac gctaa                   1005


<210> SEQ ID NO 78
<211> LENGTH: 334
<212> TYPE: PRT
<213> ORGANISM: Bacteroides vulgatus

<400> SEQUENCE: 78

Met Glu Lys Ile Asn Ala Val Ile Thr Gly Val Gly Gly Tyr Val Pro
1               5                   10                  15

Asp Tyr Val Leu Thr Asn Glu Glu Ile Ser Arg Met Val Asp Thr Asn
            20                  25                  30

Asp Glu Trp Ile Met Thr Arg Ile Gly Val Lys Glu Arg Arg Ile Leu
        35                  40                  45

Asn Glu Glu Gly Leu Gly Thr Ser Tyr Met Ala Arg Lys Ala Ala Lys
    50                  55                  60

Gln Leu Met Gln Lys Thr Ala Ser Asn Pro Asp Asp Ile Asp Ala Val
65                  70                  75                  80

Ile Val Ala Thr Thr Thr Pro Asp Tyr His Phe Pro Ser Thr Ala Ser
                85                  90                  95

Ile Leu Cys Asp Lys Leu Gly Leu Lys Asn Ala Phe Ala Phe Asp Leu
            100                 105                 110

Gln Ala Ala Cys Cys Gly Phe Leu Tyr Leu Met Glu Thr Ala Ala Ser
        115                 120                 125

Leu Ile Ala Ser Gly Arg His Lys Lys Ile Ile Ile Val Gly Ala Asp
    130                 135                 140

Lys Met Ser Ser Met Val Asn Tyr Gln Asp Arg Ala Thr Cys Pro Ile
145                 150                 155                 160

Phe Gly Asp Gly Ala Ala Ala Cys Met Val Glu Ala Thr Thr Glu Asp
                165                 170                 175

Tyr Gly Ile Met Asp Ser Ile Leu Arg Thr Asp Gly Lys Gly Leu Pro
            180                 185                 190

Phe Leu His Met Lys Ala Gly Gly Ser Val Cys Pro Pro Ser Tyr Phe
        195                 200                 205

Thr Val Asp His Lys Met His Tyr Leu Tyr Gln Glu Gly Arg Thr Val
    210                 215                 220

Phe Lys Tyr Ala Val Ser Asn Met Ser Asp Ile Thr Ala Thr Ile Ala
225                 230                 235                 240

Glu Lys Asn Gly Leu Asn Lys Asp Asn Ile Asp Trp Val Ile Pro His
                245                 250                 255

Gln Ala Asn Leu Arg Ile Ile Asp Ala Val Ala Ser Arg Leu Glu Val
            260                 265                 270

Pro Leu Glu Lys Val Met Ile Asn Ile Gln Arg Tyr Gly Asn Thr Ser
        275                 280                 285

Gly Ala Thr Leu Pro Leu Cys Leu Trp Asp Tyr Glu Lys Gln Leu Lys
    290                 295                 300

Lys Gly Asp Asn Leu Ile Phe Thr Ala Phe Gly Ala Gly Phe Thr Tyr
305                 310                 315                 320

Gly Ala Val Tyr Val Lys Trp Gly Tyr Asp Gly Ser Lys Arg
                325                 330


<210> SEQ ID NO 79
```

<211> LENGTH: 1002
<212> TYPE: DNA
<213> ORGANISM: Capnocytophaga gingivalis

<400> SEQUENCE: 79

```
atgaccaaaa ttaccgctgc gattacgggt gtgggtggct acgtgccgga tttcgtcctg      60

agcaactccc tgctggaaca gatggtggat accacggacg aatggattac cacgcgtacc     120

ggtattaaag aacgtcgcat cctgaaagaa gaaggcaaag gtgcgagctt tctgggtaaa     180

aaagccgtcg aagacctgtt tcgcaaaacc ggcacgaacc cggcagatat tgacctggtt     240

atctttgcta gcgtcacccc ggatatgccg gttgcaattt ctggtgcata tctggctacg     300

gaaattggcg ctgtcaatgc gtttgccatc gatctgcagg cggcctgcag ctctttcctg     360

tacggcatgt cagttgcagc tcgttatatc gaatcgggtc gctacaaaaa agtcctgctg     420

gttggcgcgg ataaaatgag ttccattatc gattataccg accgtgccac gtgtattatc     480

tttggcgacg gtgcaggcgc tgtcctgttc gaaccgaact atgaaggtct gggcgtgcaa     540

gatgaatacc tgcgtagtga cggtaccggc cgcgaatacc tgaaaattga agcaggcggt     600

tccattctgc cgaccacgat cgaaaccctg caggaaggta aaaacaatct gtatcaagat     660

ggcaaaaccg tgttcaaata cgcggttagc cgtatggccg atgtgacgga cattatcctg     720

gaacgcaacc atctgaatgc ggaaaacctg aattggctgg ttccgcacca ggccaacaaa     780

cgtattatcg atgcgaccgc cgaccgcatg ggtctgacgc atgataaagt gatggttaac     840

atccagcact atggcaatac cacgtctgca accctgccgc tggctctgta tgattacgaa     900

aaacaactgc gcaaaggtga caatattatc tttgtggcct tcggtggcgg ctttacctgg     960

ggcgcactgt atctgaaatg ggcgtataac ccgatccaat ga                       1002
```

<210> SEQ ID NO 80
<211> LENGTH: 333
<212> TYPE: PRT
<213> ORGANISM: Capnocytophaga gingivalis

<400> SEQUENCE: 80

```
Met Thr Lys Ile Thr Ala Ala Ile Thr Gly Val Gly Gly Tyr Val Pro
1               5                   10                  15

Asp Phe Val Leu Ser Asn Ser Leu Leu Glu Gln Met Val Asp Thr Thr
            20                  25                  30

Asp Glu Trp Ile Thr Thr Arg Thr Gly Ile Lys Glu Arg Arg Ile Leu
        35                  40                  45

Lys Glu Glu Gly Lys Gly Ala Ser Phe Leu Gly Lys Lys Ala Val Glu
    50                  55                  60

Asp Leu Phe Arg Lys Thr Gly Thr Asn Pro Ala Asp Ile Asp Leu Val
65                  70                  75                  80

Ile Phe Ala Ser Val Thr Pro Asp Met Pro Val Ala Ile Ser Gly Ala
                85                  90                  95

Tyr Leu Ala Thr Glu Ile Gly Ala Val Asn Ala Phe Ala Ile Asp Leu
            100                 105                 110

Gln Ala Ala Cys Ser Ser Phe Leu Tyr Gly Met Ser Val Ala Ala Arg
        115                 120                 125

Tyr Ile Glu Ser Gly Arg Tyr Lys Lys Val Leu Leu Val Gly Ala Asp
    130                 135                 140

Lys Met Ser Ser Ile Ile Asp Tyr Thr Asp Arg Ala Thr Cys Ile Ile
145                 150                 155                 160

Phe Gly Asp Gly Ala Gly Ala Val Leu Phe Glu Pro Asn Tyr Glu Gly
```

```
                165                 170                 175

Leu Gly Val Gln Asp Glu Tyr Leu Arg Ser Asp Gly Thr Gly Arg Glu
            180                 185                 190

Tyr Leu Lys Ile Glu Ala Gly Gly Ser Ile Leu Pro Thr Thr Ile Glu
        195                 200                 205

Thr Leu Gln Glu Gly Lys Asn Asn Leu Tyr Gln Asp Gly Lys Thr Val
    210                 215                 220

Phe Lys Tyr Ala Val Ser Arg Met Ala Asp Val Thr Asp Ile Ile Leu
225                 230                 235                 240

Glu Arg Asn His Leu Asn Ala Glu Asn Leu Asn Trp Leu Val Pro His
                245                 250                 255

Gln Ala Asn Lys Arg Ile Ile Asp Ala Thr Ala Asp Arg Met Gly Leu
            260                 265                 270

Thr His Asp Lys Val Met Val Asn Ile Gln His Tyr Gly Asn Thr Thr
        275                 280                 285

Ser Ala Thr Leu Pro Leu Ala Leu Tyr Asp Tyr Glu Lys Gln Leu Arg
    290                 295                 300

Lys Gly Asp Asn Ile Ile Phe Val Ala Phe Gly Gly Gly Phe Thr Trp
305                 310                 315                 320

Gly Ala Leu Tyr Leu Lys Trp Ala Tyr Asn Pro Ile Gln
                325                 330
```

<210> SEQ ID NO 81
<211> LENGTH: 1008
<212> TYPE: DNA
<213> ORGANISM: Capnocytophaga gingivalis

<400> SEQUENCE: 81

```
atgtataact cgacgattat cggtacgggc tactatgtgc cggaaaatat tgtgaccaac      60

gacgacctga gcaaactgat ggacaccagc gatgaatgga ttcgtgaacg cacgggtatc     120

gaacagcgtc gctttgcaac ccgtggtaaa gacaccacga cctctatggg tgtccgtgca     180

gcagaacgtg ctatcgaaaa agcgaaaatc aacaaagaag atatcgactt tctgatcttc     240

gcgacgctgt caccggatta ttacttcccg ggctgcggtg ttctggccca gaaagaactg     300

ggcctgggta ccattggtgc actggatatc cgtaaccagt gttcaggctt tgtgtatgcc     360

ctgtcggttg cagaccaatt catcaaaacg ggcatgtaca aaaacattct ggtgatcgct     420

agtgaaatgc agtccccggc actggatctg aacacccgtg gtcgcaatat ggcagttctg     480

tttggtgacg gtgcaggtgc agtggttctg agtcgtacga cccaagaagg taaaggcatt     540

ctgagctctc atctgcactc cgaaggtgca catgctgaag aactggcgat tgttacgccg     600

ggtgtcggca aaaaatgggt gaccgatctg atcaaagaaa acgatccgga agacacctca     660

tattacccgt atatgaacgg ccagtttgtt ttcaaaaatg ctgtcgtgcg tttttcggaa     720

gtcattatgg aaggtctgaa agcaaacaat ctgaccgaag gcgatattga cctgttcatc     780

ccgcaccagg cgaatctgcg catcagccaa ttcatccagc aaaaattcaa actgtctgat     840

gcccaggttt tcaacaacat ccaaaaatac ggtaacacga ccgcagcttc cattggcatc     900

gcactggcag aagcagtcga acagggtcgc gtgaaagaaa atgatctgct ggtgctggcg     960

gcatttggtt cgggctttac ctggggttca gtggttatcc gttactaa                 1008
```

<210> SEQ ID NO 82
<211> LENGTH: 335
<212> TYPE: PRT
<213> ORGANISM: Capnocytophaga gingivalis

<400> SEQUENCE: 82

```
Met Tyr Asn Ser Thr Ile Ile Gly Thr Gly Tyr Tyr Val Pro Glu Asn
1               5                   10                  15

Ile Val Thr Asn Asp Asp Leu Ser Lys Leu Met Asp Thr Ser Asp Glu
            20                  25                  30

Trp Ile Arg Glu Arg Thr Gly Ile Glu Gln Arg Arg Phe Ala Thr Arg
        35                  40                  45

Gly Lys Asp Thr Thr Thr Ser Met Gly Val Arg Ala Ala Glu Arg Ala
    50                  55                  60

Ile Glu Lys Ala Lys Ile Asn Lys Glu Asp Ile Asp Phe Leu Ile Phe
65                  70                  75                  80

Ala Thr Leu Ser Pro Asp Tyr Tyr Phe Pro Gly Cys Gly Val Leu Ala
                85                  90                  95

Gln Lys Glu Leu Gly Leu Gly Thr Ile Gly Ala Leu Asp Ile Arg Asn
            100                 105                 110

Gln Cys Ser Gly Phe Val Tyr Ala Leu Ser Val Ala Asp Gln Phe Ile
        115                 120                 125

Lys Thr Gly Met Tyr Lys Asn Ile Leu Val Ile Ala Ser Glu Met Gln
    130                 135                 140

Ser Pro Ala Leu Asp Leu Asn Thr Arg Gly Arg Asn Met Ala Val Leu
145                 150                 155                 160

Phe Gly Asp Gly Ala Gly Ala Val Val Leu Ser Arg Thr Thr Gln Glu
                165                 170                 175

Gly Lys Gly Ile Leu Ser Ser His Leu His Ser Glu Gly Ala His Ala
            180                 185                 190

Glu Glu Leu Ala Ile Val Thr Pro Gly Val Gly Lys Lys Trp Val Thr
        195                 200                 205

Asp Leu Ile Lys Glu Asn Asp Pro Glu Asp Thr Ser Tyr Tyr Pro Tyr
    210                 215                 220

Met Asn Gly Gln Phe Val Phe Lys Asn Ala Val Val Arg Phe Ser Glu
225                 230                 235                 240

Val Ile Met Glu Gly Leu Lys Ala Asn Asn Leu Thr Glu Gly Asp Ile
                245                 250                 255

Asp Leu Phe Ile Pro His Gln Ala Asn Leu Arg Ile Ser Gln Phe Ile
            260                 265                 270

Gln Gln Lys Phe Lys Leu Ser Asp Ala Gln Val Phe Asn Asn Ile Gln
        275                 280                 285

Lys Tyr Gly Asn Thr Thr Ala Ala Ser Ile Gly Ile Ala Leu Ala Glu
    290                 295                 300

Ala Val Glu Gln Gly Arg Val Lys Glu Asn Asp Leu Leu Val Leu Ala
305                 310                 315                 320

Ala Phe Gly Ser Gly Phe Thr Trp Gly Ser Val Val Ile Arg Tyr
                325                 330                 335
```

<210> SEQ ID NO 83
<211> LENGTH: 981
<212> TYPE: DNA
<213> ORGANISM: Capnocytophaga gingivalis

<400> SEQUENCE: 83

```
atgaaatcct acatcaaagc aattagcacc tacttcccga aaaataccct gacgaatgac      60

acgatcagcg aacagttccc ggaatggaac tccgaaaaaa ttctgcagaa aattggtatc     120

gaacaacgtt atatcgcaga taaagacgaa tgcgctagcg atatggcggc ccaggcggtt     180
```

```
ctgaccctga ttgaagaaca tcacctggat aaaaacgcca tcgactttct gctgctgtgc    240

acccagacgc cggatcatat tctgccgacc acggcatgta tcgttcaaga caaagtcggt    300

ctgccgacca cgtgcgcagc tctggatatt aatcaaggct gttcgggtta tatctacggt    360

ctgagcgtcg ctagctctct gattacgtct ggcaacttta aaaatgtgat cctggtcacc    420

gtggacacct atacgaaata cgttcacccg aaagataaag gtaatctgtc tattttcggt    480

gacgcagcaa ccgcaacgct gattagtacg gaaggcgaat atctgatcgg taaaccgacc    540

ctgggtacgg atggtaccgg tgcagaaaac ctgattatcc gtaatggcgg tacccgtagc    600

gctcgcaacg aaaatccgga tgactgggat aacttcatcg acatgaaagg tgccaaaatc    660

ttcaacttca tcgtgaaacg caccccggaa gtggtttaca acaatctgga aattaacggc    720

ctgaacaaag aagatatcga cctgtttatc ttccatcagg cgaacacgca catcctgaat    780

aaagtccgtg aagatatgga aattccggaa gaaaaatttg tgatcgaaat gcgctattac    840

ggtaacacca ttagttcctc aattccgatc gcgttcctgg aacatctgcg caaataccg     900

gaaaaagcca aaaataaaat ccaactgatc ggctttggcg tgggctactc gtggggtgct    960

atctgtattg aaaaatcgta a                                              981
```

<210> SEQ ID NO 84
<211> LENGTH: 326
<212> TYPE: PRT
<213> ORGANISM: Capnocytophaga gingivalis

<400> SEQUENCE: 84

```
Met Lys Ser Tyr Ile Lys Ala Ile Ser Thr Tyr Phe Pro Lys Asn Thr
1               5                   10                  15

Leu Thr Asn Asp Thr Ile Ser Glu Gln Phe Pro Glu Trp Asn Ser Glu
            20                  25                  30

Lys Ile Leu Gln Lys Ile Gly Ile Glu Gln Arg Tyr Ile Ala Asp Lys
        35                  40                  45

Asp Glu Cys Ala Ser Asp Met Ala Ala Gln Ala Val Leu Thr Leu Ile
    50                  55                  60

Glu Glu His His Leu Asp Lys Asn Ala Ile Asp Phe Leu Leu Leu Cys
65                  70                  75                  80

Thr Gln Thr Pro Asp His Ile Leu Pro Thr Thr Ala Cys Ile Val Gln
                85                  90                  95

Asp Lys Val Gly Leu Pro Thr Thr Cys Ala Ala Leu Asp Ile Asn Gln
            100                 105                 110

Gly Cys Ser Gly Tyr Ile Tyr Gly Leu Ser Val Ala Ser Ser Leu Ile
        115                 120                 125

Thr Ser Gly Asn Phe Lys Asn Val Ile Leu Val Thr Val Asp Thr Tyr
    130                 135                 140

Thr Lys Tyr Val His Pro Lys Asp Lys Gly Asn Leu Ser Ile Phe Gly
145                 150                 155                 160

Asp Ala Ala Thr Ala Thr Leu Ile Ser Thr Glu Gly Glu Tyr Leu Ile
                165                 170                 175

Gly Lys Pro Thr Leu Gly Thr Asp Gly Thr Gly Ala Glu Asn Leu Ile
            180                 185                 190

Ile Arg Asn Gly Gly Thr Arg Ser Ala Arg Asn Glu Asn Pro Asp Asp
        195                 200                 205

Trp Asp Asn Phe Ile Asp Met Lys Gly Ala Lys Ile Phe Asn Phe Ile
    210                 215                 220
```

```
Val Lys Arg Thr Pro Glu Val Val Tyr Asn Asn Leu Glu Ile Asn Gly
225                 230                 235                 240

Leu Asn Lys Glu Asp Ile Asp Leu Phe Ile Phe His Gln Ala Asn Thr
                245                 250                 255

His Ile Leu Asn Lys Val Arg Glu Asp Met Glu Ile Pro Glu Glu Lys
            260                 265                 270

Phe Val Ile Glu Met Arg Tyr Tyr Gly Asn Thr Ile Ser Ser Ser Ile
        275                 280                 285

Pro Ile Ala Phe Leu Glu His Leu Arg Lys Tyr Pro Glu Lys Ala Lys
    290                 295                 300

Asn Lys Ile Gln Leu Ile Gly Phe Gly Val Gly Tyr Ser Trp Gly Ala
305                 310                 315                 320

Ile Cys Ile Glu Lys Ser
                325


<210> SEQ ID NO 85
<211> LENGTH: 1002
<212> TYPE: DNA
<213> ORGANISM: Brevibacterium linens

<400> SEQUENCE: 85

atgccgacgc tgaaaaccgc tgaaccgggc tcctttagca aaatcacggg tattggtgcc      60

tatcgcgctg aaaatctggt cacgaatgat gacatcgttg gtccgattaa cagctctgat     120

gaatggattc gccagcgtac cggtattatc acgcgtcgcc gtgccagtaa agatgtcggc     180

gtgctggaca tgtgcgaaga agcggccctg gaagccatcg caagttccgg cctgaaaccg     240

gaagatattg gcggtattat cattgcgacc gttacgtttg aatatttcac cccgtcatcg     300

gcagctgcac tgaccgatcg tctgggtacg ggtcatatcc cggcttggga cattagcgcc     360

gcatgcgcgg gttattgtta cggcatcggt caagctgatg cgctggtccg cagcggtgcc     420

atggacaaca tcctggtgat tggcgcagaa aaactgtctg aagttattga tccggaagac     480

cgttcgatca gctttattct gggcgatggt gccggcgcag tggttgtcag ctctagtgac     540

gaaccgggca tctccaaaac cgtctggggt tcaaaaggcg aaaattggtc gaccattcgt     600

atgacggaaa gcctgtacga tgtgcgcgat gaccgtgaaa ccccgtttcc gacgctgcgc     660

caggatggtc cgaccgtttt ccgttgggca gtctgggacg gcgccgaagt ggcaaaagaa     720

gctctggcgg aatctggtat cgaagcgagt gatctggctg cgttcattcc gcaccaggct     780

aatatgcgca tcattgatga actggccaaa caactgaaac tgccggaatc tgtggttatc     840

gctcgtgata ttgcggacaa cggcaatacc tcctcagcca gtattccgct ggcaacggaa     900

cgcctgctgc gtgaacaacc ggaactgtcc ggcggtctgg cgctgcaaat cggtttcggt     960

gccggtctgg tcttcggtgc ccaagttatc cgtctgccgt ga                       1002


<210> SEQ ID NO 86
<211> LENGTH: 333
<212> TYPE: PRT
<213> ORGANISM: Brevibacterium linens

<400> SEQUENCE: 86

Met Pro Thr Leu Lys Thr Ala Glu Pro Gly Ser Phe Ser Lys Ile Thr
1               5                   10                  15

Gly Ile Gly Ala Tyr Arg Ala Glu Asn Leu Val Thr Asn Asp Asp Ile
            20                  25                  30

Val Gly Pro Ile Asn Ser Ser Asp Glu Trp Ile Arg Gln Arg Thr Gly
        35                  40                  45
```

Ile Ile Thr Arg Arg Arg Ala Ser Lys Asp Val Gly Val Leu Asp Met
    50                  55                  60

Cys Glu Glu Ala Ala Leu Glu Ala Ile Ala Ser Ser Gly Leu Lys Pro
65                  70                  75                  80

Glu Asp Ile Gly Gly Ile Ile Ile Ala Thr Val Thr Phe Glu Tyr Phe
                85                  90                  95

Thr Pro Ser Ser Ala Ala Ala Leu Thr Asp Arg Leu Gly Thr Gly His
            100                 105                 110

Ile Pro Ala Trp Asp Ile Ser Ala Ala Cys Ala Gly Tyr Cys Tyr Gly
        115                 120                 125

Ile Gly Gln Ala Asp Ala Leu Val Arg Ser Gly Ala Met Asp Asn Ile
    130                 135                 140

Leu Val Ile Gly Ala Glu Lys Leu Ser Glu Val Ile Asp Pro Glu Asp
145                 150                 155                 160

Arg Ser Ile Ser Phe Ile Leu Gly Asp Gly Ala Gly Ala Val Val Val
                165                 170                 175

Ser Ser Ser Asp Glu Pro Gly Ile Ser Lys Thr Val Trp Gly Ser Lys
            180                 185                 190

Gly Glu Asn Trp Ser Thr Ile Arg Met Thr Glu Ser Leu Tyr Asp Val
        195                 200                 205

Arg Asp Asp Arg Glu Thr Pro Phe Pro Thr Leu Arg Gln Asp Gly Pro
    210                 215                 220

Thr Val Phe Arg Trp Ala Val Trp Asp Gly Ala Glu Val Ala Lys Glu
225                 230                 235                 240

Ala Leu Ala Glu Ser Gly Ile Glu Ala Ser Asp Leu Ala Ala Phe Ile
                245                 250                 255

Pro His Gln Ala Asn Met Arg Ile Ile Asp Glu Leu Ala Lys Gln Leu
            260                 265                 270

Lys Leu Pro Glu Ser Val Val Ile Ala Arg Asp Ile Ala Asp Asn Gly
        275                 280                 285

Asn Thr Ser Ser Ala Ser Ile Pro Leu Ala Thr Glu Arg Leu Leu Arg
    290                 295                 300

Glu Gln Pro Glu Leu Ser Gly Gly Leu Ala Leu Gln Ile Gly Phe Gly
305                 310                 315                 320

Ala Gly Leu Val Phe Gly Ala Gln Val Ile Arg Leu Pro
                325                 330

<210> SEQ ID NO 87
<211> LENGTH: 1029
<212> TYPE: DNA
<213> ORGANISM: Brevibacterium linens

<400> SEQUENCE: 87
atggcaaatg gcaacgcaac cttccgtcat agcaatgtgg cactgctggg cctgaccgaa 60
atcctggctc cgaacgaagt tacctcacag gaatttgatg aacgtctggc ggacaccctg 120
tccacgctga acctgccgac cggtctgctg cagcgtgtgg caggtgttga tgcacgtcgc 180
aattgggacg tcccgtctca attcgcagat ggtgctattg cggccggcaa aaaagcgctg 240
gccgaaagtg gtgtgtcccc ggaatcaatc ggcctgatgg tcaacacctc ggtgacgcgt 300
gaacatctgg aaccgagcgt tgcagtcggt gtgcacgcag gtattggtct gggcagccag 360
gccatgaact ttgatatcac caatgcatgc ctgggtttcg ttaacggcat gacgctggca 420
gctaatatga ttgatgcggg tcagatcgaa tatgcactgg tggttgctgg cgaagacgcg 480

-continued

```
agtcgcgtgc aagaagctac cctgcgtcgc ctggcacgtc cggatatttc tcgcgaagaa    540

tacctgaacg aatttgctag tctgacgctg ggttcgggtg caagcgcagc agttctgggt    600

ccggcagaca aacatccgga aggccaccgt attctgggcg gtatcacccg cgcagctacg    660

cagcatcacg aactgtgtgt gggtgatcat aatggcatgt tcaccgacac gaaaggtctg    720

ctggcaggcg gtatggaact ggtcgtggcg gcctgggaag aagcccacga agatggctgg    780

gactggcgtg aaatggatcg ctatgttatg catcaagtct ctgacgttca cgtcaacagt    840

attaccaaag cagctaatct ggatccggac cgtatcccgg tgacgtaccc ggaactgggt    900

aatgttggtc cggcgtccct gccgatcacc ctgtcacgtg aagccagctc tctgaaaccg    960

ggcgatcgca tcctgtgtat gggtgtgggc agcggtctga acgcagcaat gacggaaatc   1020

gaatggtaa                                                           1029
```

```
<210> SEQ ID NO 88
<211> LENGTH: 342
<212> TYPE: PRT
<213> ORGANISM: Brevibacterium linens

<400> SEQUENCE: 88

Met Ala Asn Gly Asn Ala Thr Phe Arg His Ser Asn Val Ala Leu Leu
1               5                   10                  15

Gly Leu Thr Glu Ile Leu Ala Pro Asn Glu Val Thr Ser Gln Glu Phe
            20                  25                  30

Asp Glu Arg Leu Ala Asp Thr Leu Ser Thr Leu Asn Leu Pro Thr Gly
        35                  40                  45

Leu Leu Gln Arg Val Ala Gly Val Asp Ala Arg Arg Asn Trp Asp Val
    50                  55                  60

Pro Ser Gln Phe Ala Asp Gly Ala Ile Ala Ala Gly Lys Lys Ala Leu
65                  70                  75                  80

Ala Glu Ser Gly Val Ser Pro Glu Ser Ile Gly Leu Met Val Asn Thr
                85                  90                  95

Ser Val Thr Arg Glu His Leu Glu Pro Ser Val Ala Val Gly Val His
            100                 105                 110

Ala Gly Ile Gly Leu Gly Ser Gln Ala Met Asn Phe Asp Ile Thr Asn
        115                 120                 125

Ala Cys Leu Gly Phe Val Asn Gly Met Thr Leu Ala Ala Asn Met Ile
    130                 135                 140

Asp Ala Gly Gln Ile Glu Tyr Ala Leu Val Val Ala Gly Glu Asp Ala
145                 150                 155                 160

Ser Arg Val Gln Glu Ala Thr Leu Arg Arg Leu Ala Arg Pro Asp Ile
                165                 170                 175

Ser Arg Glu Glu Tyr Leu Asn Glu Phe Ala Ser Leu Thr Leu Gly Ser
            180                 185                 190

Gly Ala Ser Ala Ala Val Leu Gly Pro Ala Asp Lys His Pro Glu Gly
        195                 200                 205

His Arg Ile Leu Gly Gly Ile Thr Arg Ala Ala Thr Gln His His Glu
    210                 215                 220

Leu Cys Val Gly Asp His Asn Gly Met Phe Thr Asp Thr Lys Gly Leu
225                 230                 235                 240

Leu Ala Gly Gly Met Glu Leu Val Val Ala Ala Trp Glu Glu Ala His
                245                 250                 255

Glu Asp Gly Trp Asp Trp Arg Glu Met Asp Arg Tyr Val Met His Gln
            260                 265                 270
```

```
Val Ser Asp Val His Val Asn Ser Ile Thr Lys Ala Ala Asn Leu Asp
        275                 280                 285

Pro Asp Arg Ile Pro Val Thr Tyr Pro Glu Leu Gly Asn Val Gly Pro
    290                 295                 300

Ala Ser Leu Pro Ile Thr Leu Ser Arg Glu Ala Ser Ser Leu Lys Pro
305                 310                 315                 320

Gly Asp Arg Ile Leu Cys Met Gly Val Gly Ser Gly Leu Asn Ala Ala
                325                 330                 335

Met Thr Glu Ile Glu Trp
            340
```

<210> SEQ ID NO 89
<211> LENGTH: 969
<212> TYPE: DNA
<213> ORGANISM: Thermus aquaticus

<400> SEQUENCE: 89

```
atgtcgggca ttctggctct gggtgcatat acgccgcagc gtgtgatgaa aaatgaagac      60

tttgaagcat acctggatac gtcggatgaa tggattgtta cccgtacggg cattcgcgaa     120

cgtcgcatcg cagcaccgga tgaatatacc tctgacctgg catttaaagc tgtcgaagat     180

ctgctgcgtc gccatccggg tgcactggag ggtgtggacg gtgtcattgt ggccaccaac     240

acgccggatg cactgttccc ggacacggca gctctggtgc aggcacgttt tggcctgaat     300

gcgttcgcat atgatctgct ggcaggttgc ccgggttgga tctacgcact ggctcaagca     360

cacgccctgg tcgaagcagg tctggcacgt aaagtgctgg caattggtgc agaagctctg     420

tcaaaaatcc tggattggaa cgaccgcgcg accgccgttc tgtttggtga tgcgggcggt     480

gcagcagtgg ttggtaaagt tcgtgaaggc tttggtttcc gcagttttgt cctgggctcc     540

gatggcaccg gtgccaaaga actgttccat gcatgtgttg ctccgcgtct gccggacggc     600

acgtcgatgg aaaaacgtct gcacatgaac ggtcgcgaag tctttaaatt cgcggttcgc     660

gtcatgaata ccgcgacgct ggaagccatt gaaaaagcag gtctgacccc ggaagctatc     720

aaagtgttcg ttccgcatca ggcaaatctg cgcattatcg atgcagctcg tgaacgtctg     780

ggtctgccgt gggaacgtgt cgtggttaac gtggatcgct acggtaatac cagcacggcg     840

tctattccgc tggctctgaa agaagcggtg gatgaaggcc gtatccgcga aggtgaccac     900

gttctgctgg tctcgttcgg tgcgggcctg acctgggctg ctgccgttct gacctggggt     960

ggtgcctaa                                                             969
```

<210> SEQ ID NO 90
<211> LENGTH: 322
<212> TYPE: PRT
<213> ORGANISM: Thermus aquaticus

<400> SEQUENCE: 90

```
Met Ser Gly Ile Leu Ala Leu Gly Ala Tyr Thr Pro Gln Arg Val Met
1               5                   10                  15

Lys Asn Glu Asp Phe Glu Ala Tyr Leu Asp Thr Ser Asp Glu Trp Ile
            20                  25                  30

Val Thr Arg Thr Gly Ile Arg Glu Arg Arg Ile Ala Ala Pro Asp Glu
        35                  40                  45

Tyr Thr Ser Asp Leu Ala Phe Lys Ala Val Glu Asp Leu Leu Arg Arg
    50                  55                  60

His Pro Gly Ala Leu Glu Gly Val Asp Gly Val Ile Val Ala Thr Asn
65                  70                  75                  80
```

Thr Pro Asp Ala Leu Phe Pro Asp Thr Ala Ala Leu Val Gln Ala Arg
85 90 95

Phe Gly Leu Asn Ala Phe Ala Tyr Asp Leu Leu Ala Gly Cys Pro Gly
100 105 110

Trp Ile Tyr Ala Leu Ala Gln Ala His Ala Leu Val Glu Ala Gly Leu
115 120 125

Ala Arg Lys Val Leu Ala Ile Gly Ala Glu Ala Leu Ser Lys Ile Leu
130 135 140

Asp Trp Asn Asp Arg Ala Thr Ala Val Leu Phe Gly Asp Ala Gly Gly
145 150 155 160

Ala Ala Val Val Gly Lys Val Arg Glu Gly Phe Gly Phe Arg Ser Phe
165 170 175

Val Leu Gly Ser Asp Gly Thr Gly Ala Lys Glu Leu Phe His Ala Cys
180 185 190

Val Ala Pro Arg Leu Pro Asp Gly Thr Ser Met Glu Lys Arg Leu His
195 200 205

Met Asn Gly Arg Glu Val Phe Lys Phe Ala Val Arg Val Met Asn Thr
210 215 220

Ala Thr Leu Glu Ala Ile Glu Lys Ala Gly Leu Thr Pro Glu Ala Ile
225 230 235 240

Lys Val Phe Val Pro His Gln Ala Asn Leu Arg Ile Ile Asp Ala Ala
245 250 255

Arg Glu Arg Leu Gly Leu Pro Trp Glu Arg Val Val Val Asn Val Asp
260 265 270

Arg Tyr Gly Asn Thr Ser Thr Ala Ser Ile Pro Leu Ala Leu Lys Glu
275 280 285

Ala Val Asp Glu Gly Arg Ile Arg Glu Gly Asp His Val Leu Leu Val
290 295 300

Ser Phe Gly Ala Gly Leu Thr Trp Ala Ala Ala Val Leu Thr Trp Gly
305 310 315 320

Gly Ala

<210> SEQ ID NO 91
<211> LENGTH: 939
<212> TYPE: DNA
<213> ORGANISM: Bacillus licheniformis

<400> SEQUENCE: 91
atgaaagcgg gtattattgg tattggccgt tacatcccgg aaaaagtcct gacgaacttc 60
gacctggaaa aaatggtgga aacctcggat gaatggattc gtacccgcac gggcattgaa 120
gaacgtcgca tcgcggccga agatgaaaaa accagcgaca tggcagtggc agctgcacgt 180
cgcgctatgg aagatgcgaa cattgaaccg gaagatctgg acatgatcct ggtcgcaacc 240
gtgacgccgg atcaggcatt tccgaccgtt agttgcatga ttcaagaaaa actgggcgcc 300
ttcaatgcct gcgcaatgga tatctccgcc gcatgtgcag gttttatgta tggcctggtg 360
accggtaaac agttcattga agcaggcacg tacaaacatg tcctggtgat tggcgttgaa 420
aaactgagcg gtatcaccga ttgggatgac cgtaacacgg ctgttctgtt tggtgacggt 480
gcaggtgctg cagtggttgg tccggtctca gatgacaaag gtatcctgtc gttcgaactg 540
ggtgcagatg gtcgcggcgg taaacatctg tatctggatg aaaaagacca caccattatg 600
aacggccgtg aagtgtttaa attcgctgtt cgccagatgg gcgaaagctc tgttaatgtc 660
atcgaaaaag cgggtctgtc taaagaagat gttgactttc tggtcccgca tcaagccaac 720

```
attcgtatca tggaagccgc acgtgaacgc ctggaactgc cggtcgaaaa aatgagcaaa    780

accgtgcaca aatacggtaa tacgagtgct gcgtccattc cgatctctct ggtggaagaa    840

ctggaagcgg gcaaaattaa agatggtgac gtgatcgtta tggtcggttt tggtggcggt    900

ctgacgtggg gtgctatcgc tatgcgttgg ggtcgctga                           939
```

```
<210> SEQ ID NO 92
<211> LENGTH: 312
<212> TYPE: PRT
<213> ORGANISM: Bacillus licheniformis

<400> SEQUENCE: 92

Met Lys Ala Gly Ile Ile Gly Ile Gly Arg Tyr Ile Pro Glu Lys Val
1               5                   10                  15

Leu Thr Asn Phe Asp Leu Glu Lys Met Val Glu Thr Ser Asp Glu Trp
            20                  25                  30

Ile Arg Thr Arg Thr Gly Ile Glu Glu Arg Arg Ile Ala Ala Glu Asp
        35                  40                  45

Glu Lys Thr Ser Asp Met Ala Val Ala Ala Ala Arg Arg Ala Met Glu
    50                  55                  60

Asp Ala Asn Ile Glu Pro Glu Asp Leu Asp Met Ile Leu Val Ala Thr
65                  70                  75                  80

Val Thr Pro Asp Gln Ala Phe Pro Thr Val Ser Cys Met Ile Gln Glu
                85                  90                  95

Lys Leu Gly Ala Phe Asn Ala Cys Ala Met Asp Ile Ser Ala Ala Cys
            100                 105                 110

Ala Gly Phe Met Tyr Gly Leu Val Thr Gly Lys Gln Phe Ile Glu Ala
        115                 120                 125

Gly Thr Tyr Lys His Val Leu Val Ile Gly Val Glu Lys Leu Ser Gly
    130                 135                 140

Ile Thr Asp Trp Asp Asp Arg Asn Thr Ala Val Leu Phe Gly Asp Gly
145                 150                 155                 160

Ala Gly Ala Ala Val Val Gly Pro Val Ser Asp Asp Lys Gly Ile Leu
                165                 170                 175

Ser Phe Glu Leu Gly Ala Asp Gly Arg Gly Gly Lys His Leu Tyr Leu
            180                 185                 190

Asp Glu Lys Asp His Thr Ile Met Asn Gly Arg Glu Val Phe Lys Phe
        195                 200                 205

Ala Val Arg Gln Met Gly Glu Ser Ser Val Asn Val Ile Glu Lys Ala
    210                 215                 220

Gly Leu Ser Lys Glu Asp Val Asp Phe Leu Val Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Ile Val Met Val Gly Phe Gly Gly Gly Leu Thr Trp Gly
    290                 295                 300

Ala Ile Ala Met Arg Trp Gly Arg
305                 310

<210> SEQ ID NO 93
```

<211> LENGTH: 996
<212> TYPE: DNA
<213> ORGANISM: Bacillus licheniformis

<400> SEQUENCE: 93

```
atgaaaaccc tgagtaaagc ccgcatctct gctatcggca cctatgtccc ggaaaaacgc      60

atgacgaata aagaatttga aaaaatcgtg gatacgtctg acgaatggat tatccagcgc     120

accggtatga aagaacgtcg cattgctggc agtcatgaat ttacgtccga tctgtgcatc     180

aaagcggtgg aagacctgaa aaaccgttat agcggtaccc tggatgacat cgatatgatt     240

atcgtttcaa ccacgaccgc ggactacgcc tttccgtcga cggcctgcca ggtccaagaa     300

cacttcggtt ggaacgaagt gggcgcagtg gatgttaatg caacctgtgc tggtctggcg     360

tatggcctgc atatggccaa tggtctgatt acgagtggcc tgcaccgcaa aattctggtc     420

atctcaggcg aaaccctgtc gaaaacgacc gattacacgg accgcaccag ttgtatcctg     480

tttggcgatg gtgcgggcgc cctgctggtt gaacgtgatg acaaagatcc gtcctttatt     540

acgttcgccc aagataccaa aggtgacggc gcacgtcatc tgtatcgcac cggtctgcgt     600

agcgatctga aaggcgaacc gctgtctggt gaaggcaaaa tggttcagaa cggtcgcgaa     660

gtctacaaat gggctgtccg tagcgtgccg gaaggcgtta aaaaactgct ggcacaagct     720

gaaatggaac tgaaagatat tgactggttc gtcccgcaca gtgcaaatct gcgtatgatt     780

gaatccatct gcgaaaaaac cgaaattccg gccgaaaaag cactgacgag cgttgaatgg     840

tttggtaaca ccagctctgc gtctatcgtg ctggctctgg atgaagcggt taaaaatggt     900

aaactgaaaa aaggcgacac cctgattctg ttcggctttg gcggcggcct gacctacacg     960

ggtctgattg tgaaatgggg cgcaccggcg tcgtaa                               996
```

<210> SEQ ID NO 94
<211> LENGTH: 331
<212> TYPE: PRT
<213> ORGANISM: Bacillus licheniformis

<400> SEQUENCE: 94

```
Met Lys Thr Leu Ser Lys Ala Arg Ile Ser Ala Ile Gly Thr Tyr Val
1               5                   10                  15

Pro Glu Lys Arg Met Thr Asn Lys Glu Phe Glu Lys Ile Val Asp Thr
            20                  25                  30

Ser Asp Glu Trp Ile Ile Gln Arg Thr Gly Met Lys Glu Arg Arg Ile
        35                  40                  45

Ala Gly Ser His Glu Phe Thr Ser Asp Leu Cys Ile Lys Ala Val Glu
    50                  55                  60

Asp Leu Lys Asn Arg Tyr Ser Gly Thr Leu Asp Asp Ile Asp Met Ile
65                  70                  75                  80

Ile Val Ser Thr Thr Thr Ala Asp Tyr Ala Phe Pro Ser Thr Ala Cys
                85                  90                  95

Gln Val Gln Glu His Phe Gly Trp Asn Glu Val Gly Ala Val Asp Val
            100                 105                 110

Asn Ala Thr Cys Ala Gly Leu Ala Tyr Gly Leu His Met Ala Asn Gly
        115                 120                 125

Leu Ile Thr Ser Gly Leu His Arg Lys Ile Leu Val Ile Ser Gly Glu
    130                 135                 140

Thr Leu Ser Lys Thr Thr Asp Tyr Thr Asp Arg Thr Ser Cys Ile Leu
145                 150                 155                 160

Phe Gly Asp Gly Ala Gly Ala Leu Leu Val Glu Arg Asp Asp Lys Asp
```

```
                165                 170                 175

Pro Ser Phe Ile Thr Phe Ala Gln Asp Thr Lys Gly Asp Gly Ala Arg
            180                 185                 190

His Leu Tyr Arg Thr Gly Leu Arg Ser Asp Leu Lys Gly Glu Pro Leu
        195                 200                 205

Ser Gly Glu Gly Lys Met Val Gln Asn Gly Arg Glu Val Tyr Lys Trp
    210                 215                 220

Ala Val Arg Ser Val Pro Glu Gly Val Lys Lys Leu Leu Ala Gln Ala
225                 230                 235                 240

Glu Met Glu Leu Lys Asp Ile Asp Trp Phe Val Pro His Ser Ala Asn
                245                 250                 255

Leu Arg Met Ile Glu Ser Ile Cys Glu Lys Thr Glu Ile Pro Ala Glu
            260                 265                 270

Lys Ala Leu Thr Ser Val Glu Trp Phe Gly Asn Thr Ser Ser Ala Ser
        275                 280                 285

Ile Val Leu Ala Leu Asp Glu Ala Val Lys Asn Gly Lys Leu Lys Lys
    290                 295                 300

Gly Asp Thr Leu Ile Leu Phe Gly Phe Gly Gly Gly Leu Thr Tyr Thr
305                 310                 315                 320

Gly Leu Ile Val Lys Trp Gly Ala Pro Ala Ser
                325                 330
```

<210> SEQ ID NO 95
<211> LENGTH: 996
<212> TYPE: DNA
<213> ORGANISM: Myxococcus xanthus

<400> SEQUENCE: 95

```
atgcgctacg ctcaaatcct gtctacgggt cgctatgtgc cggaaaaagt cctgacgaac     60

gctgatgtgg aaaaaatcct gggtgaaaaa gttgatgaat ggctgcagca aaacgtcggc    120

atccgtgaac gccatatgat ggcagatgac caggctacca gcgatctgtg cgtgggtgca    180

gcacgtcaag cgctggaacg tgccggtacc aaaccggaag aactggacct gattatcatt    240

gccaccgata cgccggacta tctgagcccg gcaaccgcct ctgtggttca ggcaaaactg    300

ggcgcggtta acgccggcac gtacgatctg aattgcgcat gtgctggctg ggtgaccgca    360

ctggacgttg gtagtaaaac gatcgcagct gatgactcct atcagcgtat tctggtcgtg    420

ggcgcctatg gcatgtcacg ctacattaac tggaaagata agaaaaccgc aacgctgttc    480

gctgacggtg caggtgcagt tgtcctgggt gcaggtgata ccccgggctt tatgggtgcg    540

aaactgctgg ccaacggcga atatcatgac gccctgggtg tgtacaccgg cggtacgaat    600

cgtccggcaa ccgctgaatc gctggaactg acgggcggta aaccggcagt ccagtttgtg    660

cgtaaattcc cggctacctt taatacggaa cgctggccga tgctgctgga tcagctgctg    720

aaacgtcaaa acctgaaact ggatgacgtt aaacagtttg tcttcaccca actgaatctg    780

cgcaccatcg aagcaacgat gaaaattctg ggtcagccga tggaaaaagc tcactatacc    840

atggataaat ggggctacac gggtagtgcg tgtatcccga tgaccctgga tgacgccgtg    900

gttcagggca aagtccaacg cggtgatctg gtggcgctgt gtgcttcggg tggtggtctg    960

gcaatggcat ccgccctgta tcgttggacg gcttga                              996
```

<210> SEQ ID NO 96
<211> LENGTH: 331
<212> TYPE: PRT
<213> ORGANISM: Myxococcus xanthus

<400> SEQUENCE: 96

```
Met Arg Tyr Ala Gln Ile Leu Ser Thr Gly Arg Tyr Val Pro Glu Lys
1               5                   10                  15

Val Leu Thr Asn Ala Asp Val Glu Lys Ile Leu Gly Glu Lys Val Asp
            20                  25                  30

Glu Trp Leu Gln Gln Asn Val Gly Ile Arg Glu Arg His Met Met Ala
        35                  40                  45

Asp Asp Gln Ala Thr Ser Asp Leu Cys Val Gly Ala Ala Arg Gln Ala
    50                  55                  60

Leu Glu Arg Ala Gly Thr Lys Pro Glu Glu Leu Asp Leu Ile Ile Ile
65                  70                  75                  80

Ala Thr Asp Thr Pro Asp Tyr Leu Ser Pro Ala Thr Ala Ser Val Val
                85                  90                  95

Gln Ala Lys Leu Gly Ala Val Asn Ala Gly Thr Tyr Asp Leu Asn Cys
            100                 105                 110

Ala Cys Ala Gly Trp Val Thr Ala Leu Asp Val Gly Ser Lys Thr Ile
        115                 120                 125

Ala Ala Asp Asp Ser Tyr Gln Arg Ile Leu Val Val Gly Ala Tyr Gly
    130                 135                 140

Met Ser Arg Tyr Ile Asn Trp Lys Asp Lys Lys Thr Ala Thr Leu Phe
145                 150                 155                 160

Ala Asp Gly Ala Gly Ala Val Val Leu Gly Ala Gly Asp Thr Pro Gly
                165                 170                 175

Phe Met Gly Ala Lys Leu Leu Ala Asn Gly Glu Tyr His Asp Ala Leu
            180                 185                 190

Gly Val Tyr Thr Gly Gly Thr Asn Arg Pro Ala Thr Ala Glu Ser Leu
        195                 200                 205

Glu Leu Thr Gly Gly Lys Pro Ala Val Gln Phe Val Arg Lys Phe Pro
    210                 215                 220

Ala Thr Phe Asn Thr Glu Arg Trp Pro Met Leu Leu Asp Gln Leu Leu
225                 230                 235                 240

Lys Arg Gln Asn Leu Lys Leu Asp Asp Val Lys Gln Phe Val Phe Thr
                245                 250                 255

Gln Leu Asn Leu Arg Thr Ile Glu Ala Thr Met Lys Ile Leu Gly Gln
            260                 265                 270

Pro Met Glu Lys Ala His Tyr Thr Met Asp Lys Trp Gly Tyr Thr Gly
        275                 280                 285

Ser Ala Cys Ile Pro Met Thr Leu Asp Asp Ala Val Val Gln Gly Lys
    290                 295                 300

Val Gln Arg Gly Asp Leu Val Ala Leu Cys Ala Ser Gly Gly Gly Leu
305                 310                 315                 320

Ala Met Ala Ser Ala Leu Tyr Arg Trp Thr Ala
                325                 330
```

<210> SEQ ID NO 97
<211> LENGTH: 1113
<212> TYPE: DNA
<213> ORGANISM: Myxococcus xanthus

<400> SEQUENCE: 97

```
atgacgccga atgtttgtgt tgttggtgca ggtgcctttg tgccgagtcg tgttgttagt     60

aatgaacgca tcgcccgtgc tattccgggt tggccggccg aacgtattga agaaaaagtg    120

ggcatccgcg aacgtcgctt tctgtgggat attgacgaag caaccggtcg tgcaatcccg    180
```

-continued

```
ccgccggaaa acgatggcca tatttatccg gccaacaata cggacatgtg cgaagtggca    240

ctgcagaaag cactggctca agcgggtgtt gatgctaaag aactggacgc gctgtttgtg    300

gttacctgta cgccggatgc tccgcatttc aatcacgacg cgatggaact gcaccgtcgc    360

ctggaactgc gcgaagatgc attcggtctg gtcgtggatg acggttgcgg tggtaccccg    420

tatgttctgg acatggtgaa gaaaatgatg gaaggcggtc gttttcgcac cgtggcggtt    480

gtcgccagtg cattcacgtc cccgctggtg aaccgtgaag tttacaccga tgaactgccg    540

ccgggtccgg gtcgtagcaa aacgctgcag ggctatctgt ctatgtacgt tttggtgat    600

ggcgctggtg cggtggttct gcaatcaaaa ccgggcgaat cgggtgccga aggcattctg    660

gcgagctttt ctggtaatgc gtatggcgat ctggtgatcc gtaaaggcgg tggcctgctg    720

aaactgccgt accagccggg tcgtatgcgt ccggctgata tggcgtttgt cgtggacggc    780

ttccgtgttg ctcgcagtta tccggaatac atgcagaaat gcctggatgc agtcctgggt    840

ccgcgtccgg aactgcgttc aaaagttgaa cgttactact tccatcaacc gaacaaacgc    900

gttatggatg ctttcgtcga acgtgcaggt ctgccgcgtg aagcagtcgc atgtaacgtg    960

gaccgctatg gtaataccag cgcagccggt atgctgatcc tgctggcaga agatctggaa   1020

gcaggtcgtg tgcgtctggg ttccggtgac ctggtcgtgg tggcggcggt gggtgctaac   1080

gtccattacg gtgctcaact ggtgcgtctg tga                                1113
```

```
<210> SEQ ID NO 98
<211> LENGTH: 370
<212> TYPE: PRT
<213> ORGANISM: Myxococcus xanthus

<400> SEQUENCE: 98

Met Thr Pro Asn Val Cys Val Val Gly Ala Gly Ala Phe Val Pro Ser
1               5                   10                  15

Arg Val Val Ser Asn Glu Arg Ile Ala Arg Ala Ile Pro Gly Trp Pro
            20                  25                  30

Ala Glu Arg Ile Glu Glu Lys Val Gly Ile Arg Glu Arg Arg Phe Leu
        35                  40                  45

Trp Asp Ile Asp Glu Ala Thr Gly Arg Ala Ile Pro Pro Pro Glu Asn
    50                  55                  60

Asp Gly His Ile Tyr Pro Ala Asn Asn Thr Asp Met Cys Glu Val Ala
65                  70                  75                  80

Leu Gln Lys Ala Leu Ala Gln Ala Gly Val Asp Ala Lys Glu Leu Asp
                85                  90                  95

Ala Leu Phe Val Val Thr Cys Thr Pro Asp Ala Pro His Phe Asn His
            100                 105                 110

Asp Ala Met Glu Leu His Arg Arg Leu Glu Leu Arg Glu Asp Ala Phe
        115                 120                 125

Gly Leu Val Val Asp Asp Gly Cys Gly Gly Thr Pro Tyr Val Leu Asp
    130                 135                 140

Met Val Lys Lys Met Met Glu Gly Gly Arg Phe Arg Thr Val Ala Val
145                 150                 155                 160

Val Ala Ser Ala Phe Thr Ser Pro Leu Val Asn Arg Glu Val Tyr Thr
                165                 170                 175

Asp Glu Leu Pro Pro Gly Pro Gly Arg Ser Lys Thr Leu Gln Gly Tyr
            180                 185                 190

Leu Ser Met Tyr Val Phe Gly Asp Gly Ala Gly Ala Val Val Leu Gln
        195                 200                 205
```

```
Ser Lys Pro Gly Glu Ser Gly Ala Glu Gly Ile Leu Ala Ser Phe Ser
    210                 215                 220

Gly Asn Ala Tyr Gly Asp Leu Val Ile Arg Lys Gly Gly Gly Leu Leu
225                 230                 235                 240

Lys Leu Pro Tyr Gln Pro Gly Arg Met Arg Pro Ala Asp Met Ala Phe
                245                 250                 255

Val Val Asp Gly Phe Arg Val Ala Arg Ser Tyr Pro Glu Tyr Met Gln
            260                 265                 270

Lys Cys Leu Asp Ala Val Leu Gly Pro Arg Pro Glu Leu Arg Ser Lys
        275                 280                 285

Val Glu Arg Tyr Tyr Phe His Gln Pro Asn Lys Arg Val Met Asp Ala
    290                 295                 300

Phe Val Glu Arg Ala Gly Leu Pro Arg Glu Ala Val Ala Cys Asn Val
305                 310                 315                 320

Asp Arg Tyr Gly Asn Thr Ser Ala Ala Gly Met Leu Ile Leu Leu Ala
                325                 330                 335

Glu Asp Leu Glu Ala Gly Arg Val Arg Leu Gly Ser Gly Asp Leu Val
            340                 345                 350

Val Val Ala Ala Val Gly Ala Asn Val His Tyr Gly Ala Gln Leu Val
        355                 360                 365

Arg Leu
    370


<210> SEQ ID NO 99
<211> LENGTH: 1005
<212> TYPE: DNA
<213> ORGANISM: Myxococcus xanthus

<400> SEQUENCE: 99

atgtatctgc acgcactggg ccattttcat ccgccgaacc tgctgacgaa cgcattcttt     60

gaagaactgg gtctggaaac ctccgacgcg tggattgttg atcgtgtcgg catccgtacc    120

cgccatacgg tgctgccgct ggattatctg cgtgaaaccc gtaaccgtga cgttcgtgca    180

gcacaggaag cagctctgtt ttcaaatgca gaaaccggtc gtcgcgcagc actgatggca    240

ctggaacgtg ctggcctgaa accgtcggat attggtctgg tggttgccgg cggttgcagc    300

ccggacgaat gtattccggc ggaatctaac cgcgttgccc agctgctgaa tatccatgca    360

ccggctgtcg atctgcagag cgcctgcagc tctttttgta tgcaactgca cttcctggcc    420

ggtatgcgtc cggaacgtct gccggattat gtgctggtcg tgaacatgga caattctacc    480

cgtgttgtcg attacacgga ccgtagttcc gcagtcctgt ggggtgatgg tgcatcagca    540

gctatcctgt cgccgcgtgt tccgggtcgt tggcagctga ccgaaacgct gctggcaggc    600

gatccgtcag gtgctgacaa agtccgtgtg ccgcgcatgg gccattttac ccagaacggc    660

ggtgaagtgc aaaaattcgc gattcgtcgc gccggtgaaa cctttcaagc gctgcgtacg    720

cgcttcatgg aacgtcatcc ggataaaggt gcaggtgcag tgtccttcat cggtcaccag    780

gcaaatctgc gcatgctgga agctgtgcaa cgtcgctgcg aagttccgga cgcgcgtcat    840

ttctttaacg ttcacacccg tggtaatacg ggtgcagcag gtgcaccggg tgtcctgagt    900

gaacactggg atgacccggc agtgggtgat gctgtggttc tgtccgttgt cggtagcggc    960

ctgacctggg ctggcgctct gctggaacgc accccggctc aataa                   1005


<210> SEQ ID NO 100
<211> LENGTH: 334
```

<212> TYPE: PRT
<213> ORGANISM: Myxococcus xanthus

<400> SEQUENCE: 100

Met Tyr Leu His Ala Leu Gly His Phe His Pro Pro Asn Leu Leu Thr
1 5 10 15

Asn Ala Phe Phe Glu Glu Leu Gly Leu Glu Thr Ser Asp Ala Trp Ile
20 25 30

Val Asp Arg Val Gly Ile Arg Thr Arg His Thr Val Leu Pro Leu Asp
35 40 45

Tyr Leu Arg Glu Thr Arg Asn Arg Asp Val Arg Ala Ala Gln Glu Ala
50 55 60

Ala Leu Phe Ser Asn Ala Glu Thr Gly Arg Arg Ala Ala Leu Met Ala
65 70 75 80

Leu Glu Arg Ala Gly Leu Lys Pro Ser Asp Ile Gly Leu Val Val Ala
85 90 95

Gly Gly Cys Ser Pro Asp Glu Cys Ile Pro Ala Glu Ser Asn Arg Val
100 105 110

Ala Gln Leu Leu Asn Ile His Ala Pro Ala Val Asp Leu Gln Ser Ala
115 120 125

Cys Ser Ser Phe Cys Met Gln Leu His Phe Leu Ala Gly Met Arg Pro
130 135 140

Glu Arg Leu Pro Asp Tyr Val Leu Val Val Asn Met Asp Asn Ser Thr
145 150 155 160

Arg Val Val Asp Tyr Thr Asp Arg Ser Ser Ala Val Leu Trp Gly Asp
165 170 175

Gly Ala Ser Ala Ala Ile Leu Ser Pro Arg Val Pro Gly Arg Trp Gln
180 185 190

Leu Thr Glu Thr Leu Leu Ala Gly Asp Pro Ser Gly Ala Asp Lys Val
195 200 205

Arg Val Pro Arg Met Gly His Phe Thr Gln Asn Gly Gly Glu Val Gln
210 215 220

Lys Phe Ala Ile Arg Arg Ala Gly Glu Thr Phe Gln Ala Leu Arg Thr
225 230 235 240

Arg Phe Met Glu Arg His Pro Asp Lys Gly Ala Gly Ala Val Ser Phe
245 250 255

Ile Gly His Gln Ala Asn Leu Arg Met Leu Glu Ala Val Gln Arg Arg
260 265 270

Cys Glu Val Pro Asp Ala Arg His Phe Phe Asn Val His Thr Arg Gly
275 280 285

Asn Thr Gly Ala Ala Gly Ala Pro Gly Val Leu Ser Glu His Trp Asp
290 295 300

Asp Pro Ala Val Gly Asp Ala Val Val Leu Ser Val Val Gly Ser Gly
305 310 315 320

Leu Thr Trp Ala Gly Ala Leu Leu Glu Arg Thr Pro Ala Gln
325 330

<210> SEQ ID NO 101
<211> LENGTH: 978
<212> TYPE: DNA
<213> ORGANISM: Bacillus subtilis subsp. spizizenii

<400> SEQUENCE: 101
atgagcaaag caaaaattac cgctattggc acctacgcac cgagccgccg cctgaccaac 60
gctgacctgg aaaaaatcgt ggatacctct gatgaatgga ttgtgcagcg tacgggcatg 120

-continued cgcgaacgtc gcatcgcgga tgaacagcaa tttacctcag acctgtgcat tgaagccgtt 180
aaagatctga aatcgcgcta tgaaggtacc ctggataacg tcgacatgat cctggtggca 240
accacgacct cagactatgc gtttccgtcg acggcctgcc gtgtgcagga atacttcggc 300
tgggaaagca ccggtgccct ggatattaac gcgacgtgtg ccggcctgac ctatggtctg 360
catctggcaa atggcctgat cacgagcggt ctgcaccaaa aaattctggt gatcgctggc 420
gaaaccctgt ctaaagttac ggattacacc gaccgcacga cctgtgtcct gtttggcgat 480
gcggccggtg cactgctggt tgaacgtgac gaagaaacgc cgggtttcct ggctagtgtc 540
cagggcacct ccggtaacgg cggtgatatt ctgtatcgcg caggcctgcg taacgaacgc 600
aatggtgttc agctggctgg cagtggtaaa atggttcaaa atggccgtga agtctacaaa 660
tgggcagctc gtacggtgcc gcgcgaattt gaacgtctgc tgcatcaagc gggcctgacc 720
agcggtgatc tggactggtt cgttccgcac agcgccaacc tgcgcatgat tgaatctatc 780
tgcgaaaaaa ccccgttccc gattgaaaaa acgctgacca gtgtggaata ttacggcaat 840
accagctctg tgtccatcgt tctggcgctg gatctggcag ttaaagctgg taaactgaaa 900
aaagaccaga ccgtcatgct gttcggcttt ggcggcggtc tgacgtacac gggtctgctg 960
gtgaaatggg gcatgtga 978

<210> SEQ ID NO 102
<211> LENGTH: 325
<212> TYPE: PRT
<213> ORGANISM: Bacillus subtilis subsp. spizizenii

<400> SEQUENCE: 102

```
Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

Gln Gln Phe Thr Ser Asp Leu Cys Ile Glu Ala Val Lys Asp Leu Lys
    50                  55                  60

Ser Arg Tyr Glu Gly Thr Leu Asp Asn Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Arg Asn Gly Val Gln Leu Ala Gly Ser
        195                 200                 205

Gly Lys Met Val Gln Asn Gly Arg Glu Val Tyr Lys Trp Ala Ala Arg
```

```
    210                 215                 220

Thr Val Pro Arg Glu Phe Glu Arg Leu Leu His Gln Ala Gly Leu Thr
225                 230                 235                 240

Ser Gly Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu Tyr Tyr Gly Asn Thr Ser Ser Val Ser Ile Val Leu
        275                 280                 285

Ala Leu Asp Leu Ala Val Lys Ala Gly Lys Leu Lys Lys Asp Gln Thr
    290                 295                 300

Val Met Leu Phe Gly Phe Gly Gly Gly Leu Thr Tyr Thr Gly Leu Leu
305                 310                 315                 320

Val Lys Trp Gly Met
                325


<210> SEQ ID NO 103
<211> LENGTH: 1125
<212> TYPE: DNA
<213> ORGANISM: Haliangium ochraceum

<400> SEQUENCE: 103

atgtcaacgg gcacggctat cacgggtacg ggcatccatg tctcggaaaa tgtggtctcc      60

aacgaagaac tgtgtgctat ctttaacgcg tatgtccagc gtgaaaatca acgcaacgca     120

gcagcaattg ctgcaggtga agcacagccg ctggcagaaa gctctccggc atttattgtt     180

aaagcaagcg gcatcgaacg tcgccatgtg gttgacgcgg aaggtattct ggatatcgac     240

cgtatgaccc cgaatatccc ggatcgcccg gatgacgaac tgtgcgtcca agccgaatac     300

gcagtgcgtg ccgcagaaaa agccctggct gcagcaggtc gtgcagctga agaaattgat     360

ctggtgatcc tggcaacctc cacgctgcag cgtccgtatc cgagtatttc cgttgaaatc     420

caacacgctc tgggcgcgcg cggttatgcc tacgatatga ccatgggctg cagttccgtg     480

acgtacggta ttcgtgcggc cagcgatgcg atccgttgtg gccatgccaa acgcgcactg     540

gtcgtgaacg ccgaactgtg caccccgttt gcagacttcc gtgatcgcga ctgtcacttt     600

attttcggcg atgctggtac ggcggttctg gtcgaaccgt gcgatgacgt tgcgcgtgcc     660

ggtgcatttg aaattctgtc atcgcgcgct ttcgcgtcat actcgaacaa catccgtaac     720

aacatcggcc atatcaatcg ctgtgatccg gacaaccagc acgcccgtga taaactgttt     780

taccagcaag gtcgtcgcgt gttcaaagat attgttccgc tggcgtcacg ctttatcctg     840

gaccatctgg aagctcacga actggcgccg caggatattg ctcgtttctg gctgcatcaa     900

gccaactcga atatgaacga tctgatcgcg aaacgcgttc tgggccacga accgagcacc     960

gaatctgctc cgctggtcct ggcggaatat ggcaatacgg caagctctgg tagtattatc    1020

gcgttcgatc agcatcacga agacctggca gctggctcct acggttttct gtgctccttc    1080

ggtgctggtt actccatcgg ttctgccctg ctgcgtcgta tgtga                    1125


<210> SEQ ID NO 104
<211> LENGTH: 374
<212> TYPE: PRT
<213> ORGANISM: Haliangium ochraceum

<400> SEQUENCE: 104

Met Ser Thr Gly Thr Ala Ile Thr Gly Thr Gly Ile His Val Ser Glu
1               5                   10                  15
```

```
Asn Val Val Ser Asn Glu Glu Leu Cys Ala Ile Phe Asn Ala Tyr Val
            20                  25                  30

Gln Arg Glu Asn Gln Arg Asn Ala Ala Ala Ile Ala Ala Gly Glu Ala
        35                  40                  45

Gln Pro Leu Ala Glu Ser Ser Pro Ala Phe Ile Val Lys Ala Ser Gly
    50                  55                  60

Ile Glu Arg Arg His Val Val Asp Ala Glu Gly Ile Leu Asp Ile Asp
65                  70                  75                  80

Arg Met Thr Pro Asn Ile Pro Asp Arg Pro Asp Asp Glu Leu Cys Val
                85                  90                  95

Gln Ala Glu Tyr Ala Val Arg Ala Ala Glu Lys Ala Leu Ala Ala Ala
            100                 105                 110

Gly Arg Ala Ala Glu Glu Ile Asp Leu Val Ile Leu Ala Thr Ser Thr
        115                 120                 125

Leu Gln Arg Pro Tyr Pro Ser Ile Ser Val Glu Ile Gln His Ala Leu
    130                 135                 140

Gly Ala Arg Gly Tyr Ala Tyr Asp Met Thr Met Gly Cys Ser Ser Val
145                 150                 155                 160

Thr Tyr Gly Ile Arg Ala Ala Ser Asp Ala Ile Arg Cys Gly His Ala
                165                 170                 175

Lys Arg Ala Leu Val Val Asn Ala Glu Leu Cys Thr Pro Phe Ala Asp
            180                 185                 190

Phe Arg Asp Arg Asp Cys His Phe Ile Phe Gly Asp Ala Gly Thr Ala
        195                 200                 205

Val Leu Val Glu Pro Cys Asp Asp Val Ala Arg Ala Gly Ala Phe Glu
    210                 215                 220

Ile Leu Ser Ser Arg Ala Phe Ala Ser Tyr Ser Asn Asn Ile Arg Asn
225                 230                 235                 240

Asn Ile Gly His Ile Asn Arg Cys Asp Pro Asp Asn Gln His Ala Arg
                245                 250                 255

Asp Lys Leu Phe Tyr Gln Gln Gly Arg Arg Val Phe Lys Asp Ile Val
            260                 265                 270

Pro Leu Ala Ser Arg Phe Ile Leu Asp His Leu Glu Ala His Glu Leu
        275                 280                 285

Ala Pro Gln Asp Ile Ala Arg Phe Trp Leu His Gln Ala Asn Ser Asn
    290                 295                 300

Met Asn Asp Leu Ile Ala Lys Arg Val Leu Gly His Glu Pro Ser Thr
305                 310                 315                 320

Glu Ser Ala Pro Leu Val Leu Ala Glu Tyr Gly Asn Thr Ala Ser Ser
                325                 330                 335

Gly Ser Ile Ile Ala Phe Asp Gln His His Glu Asp Leu Ala Ala Gly
            340                 345                 350

Ser Tyr Gly Phe Leu Cys Ser Phe Gly Ala Gly Tyr Ser Ile Gly Ser
        355                 360                 365

Ala Leu Leu Arg Arg Met
    370
```

<210> SEQ ID NO 105
<211> LENGTH: 975
<212> TYPE: DNA
<213> ORGANISM: Alicyclobacillus acidocaldarius

<400> SEQUENCE: 105

```
atgtataaag cggtgattcg tggcgtcggc tcatatctgc cggaaacccg tctgaccaac      60
```

```
gtggaaattg aacaaatggt ggctaccagc gatgaatgga ttcagacccg cacgggtatt    120

gcggaacgtc gcatcgcccg tccggatgaa gcaacctctg actttgctta tctggcggcc    180

caggcagctc tggcagatgc taaactgcat ccgaccgata ttgacctgct gatcgtggcc    240

accgaaacgc cggactacct gctgccgccg gtcgcatgcc aggtgcaagc acgtctgggt    300

tgtcgtaaca tcggcgcatt tgatctgcac gcaacctgcg ctggtttcct gagtgcgctg    360

caggttgccg aacaatttgt taaatccggt gtccatgaac acgtgctgat tgttggcgca    420

gataccctgt cacgcttcac cgattatacg gaccgtggca cgtgtatcct gtttgctgat    480

ggtgcgggcg ccttcgtggt ttcacgctcg gatgaccgtg cagcacgcgg tgtgattgca    540

accacgatcc attcagatgg cacctatttt cacaacctgt acattccggg cggtggctcg    600

cgcacgccgt acggtgatgg cgcaaaagct aaaattgtga tggacggtcg taaaatcttc    660

aaactggcgg ttaatgtcat gagctctacc gttgaagaac tgctgcagaa aacgggccgt    720

caacgcgatg aaattgactg gctgatcccg catcaggcca accaacgtat tatcgatgcg    780

gtcgccgaaa gcctggactt cccgcaggaa aaagtcgtgt ctaccattca aaatatcggc    840

aacaatagtt ccgcgaccat tccgatcgca gttgatacgg ctattcgtga cggtcgcatc    900

cagcgtggcg atctgctgat gctggttgct ttcggtggtg gtctggtttg ggcggtgctt    960

atggttgaat actaa                                                     975


<210> SEQ ID NO 106
<211> LENGTH: 324
<212> TYPE: PRT
<213> ORGANISM: Alicyclobacillus acidocaldarius

<400> SEQUENCE: 106

Met Tyr Lys Ala Val Ile Arg Gly Val Gly Ser Tyr Leu Pro Glu Thr
1               5                   10                  15

Arg Leu Thr Asn Val Glu Ile Glu Gln Met Val Ala Thr Ser Asp Glu
            20                  25                  30

Trp Ile Gln Thr Arg Thr Gly Ile Ala Glu Arg Arg Ile Ala Arg Pro
        35                  40                  45

Asp Glu Ala Thr Ser Asp Phe Ala Tyr Leu Ala Ala Gln Ala Ala Leu
    50                  55                  60

Ala Asp Ala Lys Leu His Pro Thr Asp Ile Asp Leu Leu Ile Val Ala
65                  70                  75                  80

Thr Glu Thr Pro Asp Tyr Leu Leu Pro Pro Val Ala Cys Gln Val Gln
                85                  90                  95

Ala Arg Leu Gly Cys Arg Asn Ile Gly Ala Phe Asp Leu His Ala Thr
            100                 105                 110

Cys Ala Gly Phe Leu Ser Ala Leu Gln Val Ala Glu Gln Phe Val Lys
        115                 120                 125

Ser Gly Val His Glu His Val Leu Ile Val Gly Ala Asp Thr Leu Ser
    130                 135                 140

Arg Phe Thr Asp Tyr Thr Asp Arg Gly Thr Cys Ile Leu Phe Ala Asp
145                 150                 155                 160

Gly Ala Gly Ala Phe Val Val Ser Arg Ser Asp Asp Arg Ala Ala Arg
                165                 170                 175

Gly Val Ile Ala Thr Thr Ile His Ser Asp Gly Thr Tyr Phe His Asn
            180                 185                 190

Leu Tyr Ile Pro Gly Gly Gly Ser Arg Thr Pro Tyr Gly Asp Gly Ala
        195                 200                 205
```

Lys Ala Lys Ile Val Met Asp Gly Arg Lys Ile Phe Lys Leu Ala Val
    210                 215                 220

Asn Val Met Ser Ser Thr Val Glu Glu Leu Leu Gln Lys Thr Gly Arg
225                 230                 235                 240

Gln Arg Asp Glu Ile Asp Trp Leu Ile Pro His Gln Ala Asn Gln Arg
                245                 250                 255

Ile Ile Asp Ala Val Ala Glu Ser Leu Asp Phe Pro Gln Glu Lys Val
            260                 265                 270

Val Ser Thr Ile Gln Asn Ile Gly Asn Asn Ser Ser Ala Thr Ile Pro
        275                 280                 285

Ile Ala Val Asp Thr Ala Ile Arg Asp Gly Arg Ile Gln Arg Gly Asp
    290                 295                 300

Leu Leu Met Leu Val Ala Phe Gly Gly Gly Leu Val Trp Gly Gly Ala
305                 310                 315                 320

Met Val Glu Tyr

<210> SEQ ID NO 107
<211> LENGTH: 993
<212> TYPE: DNA
<213> ORGANISM: Desulfovibrio vulgaris

<400> SEQUENCE: 107
atgaccgcga gccgtgatat tgcgtgccgt gtccgtggtt ttggtgccta taccccggtt     60
gatgtgctga cgaactttga cctggaaaaa tttgtggaaa ccacggatga atggattacc    120
acgcgtaccg gcatccgtca gcgtcatcgt ctggctgaag gtcaaaatgc gagcgatgca    180
gcaacggaag cagctcgtct ggcactggca gacgccggta tggaaccggg tgaaattacc    240
cacgttatca acgcgacctg cacgccggat tatctgtgcc cgaatacggc ctgtctggtc    300
gaagcaaaac tgggcattat gggtgctatg gcgtttgact tcaacgcggc ctgtagtggc    360
tatgtttacg gtctgtccat ggcccgcgca atcgttgcag ctcagccgga agcacgtgtc    420
ctgctgaccg ccacggaagc actgacccgt cgcctgaatt gggcggatcg caccacgtgc    480
gtgctgtttg gtgacggcgc tggtgcgtca gttattacgg ctgaaggcga aggtgcgctg    540
ctggaagatg tgctgtgtgc atcggacggt aacctgggcg gtctgctgac catcggcggt    600
ggcacccata cgccgtacgc aaaaggcgat ccggtgggtg aagacttttt cgttcagatg    660
aacggccgcg atgttttcaa acacgcggtc cgtaatatgg cggccattag tcaagacgtt    720
ctggcccgca acggtctgac cattgatgac gtcgccctgg tgatcccgca tcaagcaaat    780
ctgcgtatta tcgaagctgt cggtgatcgt ctgggtgtgc cggcagaacg tgtgtttgtt    840
aacctgcacg aatttggtaa taccagcgca gcttctgtcc cgctggccat cgcagatgct    900
cgtgcaaaag gtgtgctgcg tccgggtatg cgtgtgctgc tggcgacctt tggtggcggc    960
tttacctggg gtgctgctct gctgcatttt tga                                 993

<210> SEQ ID NO 108
<211> LENGTH: 330
<212> TYPE: PRT
<213> ORGANISM: Desulfovibrio vulgaris

<400> SEQUENCE: 108

Met Thr Ala Ser Arg Asp Ile Ala Cys Arg Val Arg Gly Phe Gly Ala
1               5                   10                  15

Tyr Thr Pro Val Asp Val Leu Thr Asn Phe Asp Leu Glu Lys Phe Val
            20                  25                  30

Glu Thr Thr Asp Glu Trp Ile Thr Thr Arg Thr Gly Ile Arg Gln Arg
35 40 45

His Arg Leu Ala Glu Gly Gln Asn Ala Ser Asp Ala Ala Thr Glu Ala
50 55 60

Ala Arg Leu Ala Leu Ala Asp Ala Gly Met Glu Pro Gly Glu Ile Thr
65 70 75 80

His Val Ile Asn Ala Thr Cys Thr Pro Asp Tyr Leu Cys Pro Asn Thr
85 90 95

Ala Cys Leu Val Glu Ala Lys Leu Gly Ile Met Gly Ala Met Ala Phe
100 105 110

Asp Phe Asn Ala Ala Cys Ser Gly Tyr Val Tyr Gly Leu Ser Met Ala
115 120 125

Arg Ala Ile Val Ala Ala Gln Pro Glu Ala Arg Val Leu Leu Thr Ala
130 135 140

Thr Glu Ala Leu Thr Arg Arg Leu Asn Trp Ala Asp Arg Thr Thr Cys
145 150 155 160

Val Leu Phe Gly Asp Gly Ala Gly Ala Ser Val Ile Thr Ala Glu Gly
165 170 175

Glu Gly Ala Leu Leu Glu Asp Val Leu Cys Ala Ser Asp Gly Asn Leu
180 185 190

Gly Gly Leu Leu Thr Ile Gly Gly Gly Thr His Thr Pro Tyr Ala Lys
195 200 205

Gly Asp Pro Val Gly Glu Asp Phe Phe Val Gln Met Asn Gly Arg Asp
210 215 220

Val Phe Lys His Ala Val Arg Asn Met Ala Ala Ile Ser Gln Asp Val
225 230 235 240

Leu Ala Arg Asn Gly Leu Thr Ile Asp Asp Val Ala Leu Val Ile Pro
245 250 255

His Gln Ala Asn Leu Arg Ile Ile Glu Ala Val Gly Asp Arg Leu Gly
260 265 270

Val Pro Ala Glu Arg Val Phe Val Asn Leu His Glu Phe Gly Asn Thr
275 280 285

Ser Ala Ala Ser Val Pro Leu Ala Ile Ala Asp Ala Arg Ala Lys Gly
290 295 300

Val Leu Arg Pro Gly Met Arg Val Leu Leu Ala Thr Phe Gly Gly Gly
305 310 315 320

Phe Thr Trp Gly Ala Ala Leu Leu His Phe
325 330

<210> SEQ ID NO 109
<211> LENGTH: 1224
<212> TYPE: DNA
<213> ORGANISM: Staphylococcus aureus

<400> SEQUENCE: 109
atttcatact gaaatttgac gataataaag cattaaaatt ttattaacta gtcaatattc 60
ctacctctga cttgagttta aaaagtaatc tatgttaaat taatacctgg tattaaaaat 120
tttattaaga aggtgttcaa ctatgaacgt gggtattaaa ggttttggtg catatgcacc 180
agaaaagatt attgacaatg cctattttga gcaatttttta gatacatctg atgaatggat 240
ttctaagatg actggaatta aagaaagaca ttgggcagat gacgatcaag atacttcaga 300
tttagcatat gaagcaagtg taaaagcaat cgctgacgct ggtattcagc ctgaagatat 360
agatatgata attgttgcca cagcaactgg agatatgcca tttccaactg tcgcaaatat 420

-continued

```
gttgcaagaa cgtttaggga cgggcaaagt tgcctctatg gatcaacttg cagcatgttc    480

tggatttatg tattcaatga ttacagctaa acaatatgtt caatctggag attatcataa    540

tattttagtt gtcggtgcag ataaattatc taaaataaca gatttaactg accgttctac    600

tgcagttcta tttggagatg gtgcaggtgc ggttatcatc ggtgaagttt cagaaggcag    660

aggtattata agttatgaaa tgggttctga tggcactggt ggtaaacatt tatatttaga    720

taaagatact ggtaaactga aaatgaatgg tcgagaagta tttaaatttg ctgttagaat    780

tatgggtgat gcatcaacac gtgtagttga aaaagcgaat ttaacatcag atgatataga    840

tttatttatt cctcatcaag ctaatattag aattatggaa tcagctagag aacgcttagg    900

tatttcaaaa gacaaaatga gtgtttctgt aaataaatat ggaaatactt cagctgcgtc    960

aataccttta agtatcgatc aagaattaaa aaatggtaaa ctcaaagatg atgatacaat   1020

tgttcttgtc ggattcggtg gcggcctaac ttggggcgca atgacaataa aatggggaaa   1080

ataggaggat aacgaatgag tcaaaataaa agagtagtta ttacaggtat gggagccctt   1140

tctccaatcg gtaatgatgt caaaacaaca tgggagaatg ctctaaaagg cgtaaatggt   1200

atcgataaaa ttacacgtat cgat                                          1224
```

<210> SEQ ID NO 110
<211> LENGTH: 313
<212> TYPE: PRT
<213> ORGANISM: Staphylococcus aureus

<400> SEQUENCE: 110

```
Met Asn Val Gly Ile Lys Gly Phe Gly Ala Tyr Ala Pro Glu Lys Ile
1               5                   10                  15

Ile Asp Asn Ala Tyr Phe Glu Gln Phe Leu Asp Thr Ser Asp Glu Trp
            20                  25                  30

Ile Ser Lys Met Thr Gly Ile Lys Glu Arg His Trp Ala Asp Asp Asp
        35                  40                  45

Gln Asp Thr Ser Asp Leu Ala Tyr Glu Ala Ser Val Lys Ala Ile Ala
    50                  55                  60

Asp Ala Gly Ile Gln Pro Glu Asp Ile Asp Met Ile Ile Val Ala Thr
65                  70                  75                  80

Ala Thr Gly Asp Met Pro Phe Pro Thr Val Ala Asn Met Leu Gln Glu
                85                  90                  95

Arg Leu Gly Thr Gly Lys Val Ala Ser Met Asp Gln Leu Ala Ala Cys
            100                 105                 110

Ser Gly Phe Met Tyr Ser Met Ile Thr Ala Lys Gln Tyr Val Gln Ser
        115                 120                 125

Gly Asp Tyr His Asn Ile Leu Val Val Gly Ala Asp Lys Leu Ser Lys
    130                 135                 140

Ile Thr Asp Leu Thr Asp Arg Ser Thr Ala Val Leu Phe Gly Asp Gly
145                 150                 155                 160

Ala Gly Ala Val Ile Ile Gly Glu Val Ser Glu Gly Arg Gly Ile Ile
                165                 170                 175

Ser Tyr Glu Met Gly Ser Asp Gly Thr Gly Gly Lys His Leu Tyr Leu
            180                 185                 190

Asp Lys Asp Thr Gly Lys Leu Lys Met Asn Gly Arg Glu Val Phe Lys
        195                 200                 205

Phe Ala Val Arg Ile Met Gly Asp Ala Ser Thr Arg Val Val Glu Lys
    210                 215                 220
```

-continued

```
Ala Asn Leu Thr Ser Asp Asp Ile Asp Leu Phe Ile Pro His Gln Ala
225                 230                 235                 240

Asn Ile Arg Ile Met Glu Ser Ala Arg Glu Arg Leu Gly Ile Ser Lys
                245                 250                 255

Asp Lys Met Ser Val Ser Val Asn Lys Tyr Gly Asn Thr Ser Ala Ala
            260                 265                 270

Ser Ile Pro Leu Ser Ile Asp Gln Glu Leu Lys Asn Gly Lys Leu Lys
        275                 280                 285

Asp Asp Asp Thr Ile Val Leu Val Gly Phe Gly Gly Gly Leu Thr Trp
    290                 295                 300

Gly Ala Met Thr Ile Lys Trp Gly Lys
305                 310
```

```
<210> SEQ ID NO 111
<211> LENGTH: 954
<212> TYPE: DNA
<213> ORGANISM: E.coli mutant
<220> FEATURE:
<221> NAME/KEY: misc_feature
<222> LOCATION: (215)..(215)
<223> OTHER INFORMATION: valine at amino acid position 215 replaced
      with phenylalanine

<400> SEQUENCE: 111

atgtatacga agattattgg tactggcagc tatctgcccg aacaagtgcg gacaaacgcc      60

gatttggaaa aaatggtgga cacctctgac gagtggattg tcactcgtac cggtatccgc     120

gaacgccaca ttgccgcgcc aaacgaaacc gtttcaacca tgggctttga agcggcgaca     180

cgcgcaattg agatggcggg cattgagaaa gaccagattg gcctgatcgt tgtggcaacg     240

acttctgcta cgcacgcttt cccgagcgca gcttgtcaga ttcaaagcat gttgggcatt     300

aaaggttgcc cggcatttga cgttgcagca gcctgcgcag gtttcaccta tgcattaagc     360

gtagccgatc aatacgtgaa atctggggcg gtgaagtatg ctctggtcgt cggttccgat     420

gtactggcgc gcacctgcga tccaaccgat cgtgggacta ttattatttt tggcgatggc     480

gcgggcgctg cggtgctggc tgcctctgaa gagccgggaa tcatttccac ccatctgcat     540

gccgacggta gttatggtga attgctgacg ctgccaaacg ccgaccgcgt gaatccagag     600

aattcaattc atctgacgat ggcgggcaac gaagtcttca agtttgcggt aacggaactg     660

gcgcacatcg ttgatgagac gctggcggcg aataatcttg accgttctca actggactgg     720

ctggttccgc atcaggctaa cctgcgtatt atcagtgcaa cggcgaaaaa actcggtatg     780

tctatggata atgtcgtggt gacgctggat cgccacggta atacctctgc ggcctctgtc     840

ccgtgcgcgc tggatgaagc tgtacgcgac gggcgcatta agccggggca gttggttctg     900

cttgaagcct ttggcggtgg attcacctgg ggctccgcgc tggttcgttt ctag           954
```

```
<210> SEQ ID NO 112
<211> LENGTH: 317
<212> TYPE: PRT
<213> ORGANISM: E. coli mutant
<220> FEATURE:
<221> NAME/KEY: MISC_FEATURE
<222> LOCATION: (215)..(215)
<223> OTHER INFORMATION: valine at amino acid position 215 replaced with
      phenylalanine

<400> SEQUENCE: 112

Met Tyr Thr Lys Ile Ile Gly Thr Gly Ser Tyr Leu Pro Glu Gln Val
1               5                   10                  15
```

```
Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Phe Ala Val Thr Glu Leu Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Phe
    290                 295                 300

Gly Gly Gly Phe Thr Trp Gly Ser Ala Leu Val Arg Phe
305                 310                 315


<210> SEQ ID NO 113
<211> LENGTH: 954
<212> TYPE: DNA
<213> ORGANISM: E. coli mutant
<220> FEATURE:
<221> NAME/KEY: misc_feature
<222> LOCATION: (220)..(220)
<223> OTHER INFORMATION: leucine at amino acid position 220 replaced
      with methionine

<400> SEQUENCE: 113

atgtatacga agattattgg tactggcagc tatctgcccg aacaagtgcg gacaaacgcc      60

gatttggaaa aaatggtgga cacctctgac gagtggattg tcactcgtac cggtatccgc     120

gaacgccaca ttgccgcgcc aaacgaaacc gtttcaacca tgggctttga agcggcgaca     180

cgcgcaattg agatggcggg cattgagaaa gaccagattg gcctgatcgt tgtggcaacg     240

acttctgcta cgcacgcttt cccgagcgca gcttgtcaga ttcaaagcat gttgggcatt     300
```

```
aaaggttgcc cggcatttga cgttgcagca gcctgcgcag gtttcaccta tgcattaagc    360

gtagccgatc aatacgtgaa atctggggcg gtgaagtatg ctctggtcgt cggttccgat    420

gtactggcgc gcacctgcga tccaaccgat cgtgggacta ttattatttt tggcgatggc    480

gcgggcgctg cggtgctggc tgcctctgaa gagccgggaa tcatttccac ccatctgcat    540

gccgacggta gttatggtga attgctgacg ctgccaaacg ccgaccgcgt gaatccagag    600

aattcaattc atctgacgat ggcgggcaac gaagtcttca aggttgcggt aacggaaatg    660

gcgcacatcg ttgatgagac gctggcggcg aataatcttg accgttctca actggactgg    720

ctggttccgc atcaggctaa cctgcgtatt atcagtgcaa cggcgaaaaa actcggtatg    780

tctatggata atgtcgtggt gacgctggat cgccacggta atacctctgc ggcctctgtc    840

ccgtgcgcgc tggatgaagc tgtacgcgac gggcgcatta agccggggca gttggttctg    900

cttgaagcct ttggcggtgg attcacctgg ggctccgcgc tggttcgttt ctag          954
```

```
<210> SEQ ID NO 114
<211> LENGTH: 317
<212> TYPE: PRT
<213> ORGANISM: E. coli mutant
<220> FEATURE:
<221> NAME/KEY: MISC_FEATURE
<222> LOCATION: (220)..(220)
<223> OTHER INFORMATION: leucine at amino acid position 220 replaced
      with methionine

<400> SEQUENCE: 114

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Val Ala Val Thr Glu Met Ala His Ile Val
    210                 215                 220

Asp Glu Thr Leu Ala Ala Asn Asn Leu Asp Arg Ser Gln Leu Asp Trp
```

225 230 235 240

Leu Val Pro His Gln Ala Asn Leu Arg Ile Ile Ser Ala Thr Ala Lys
245 250 255

Lys Leu Gly Met Ser Met Asp Asn Val Val Val Thr Leu Asp Arg His
260 265 270

Gly Asn Thr Ser Ala Ala Ser Val Pro Cys Ala Leu Asp Glu Ala Val
275 280 285

Arg Asp Gly Arg Ile Lys Pro Gly Gln Leu Val Leu Leu Glu Ala Phe
290 295 300

Gly Gly Gly Phe Thr Trp Gly Ser Ala Leu Val Arg Phe
305 310 315

<210> SEQ ID NO 115
<211> LENGTH: 954
<212> TYPE: DNA
<213> ORGANISM: E. coli mutant
<220> FEATURE:
<221> NAME/KEY: misc_feature
<222> LOCATION: (215)..(215)
<223> OTHER INFORMATION: valine at amino acid position 215 replaced with phenylalanine
<220> FEATURE:
<221> NAME/KEY: misc_feature
<222> LOCATION: (220)..(220)
<223> OTHER INFORMATION: leucine at amino acid position 220 replaced with methionine

<400> SEQUENCE: 115
atgtatacga agattattgg tactggcagc tatctgcccg aacaagtgcg gacaaacgcc 60
gatttggaaa aaatggtgga cacctctgac gagtggattg tcactcgtac cggtatccgc 120
gaacgccaca ttgccgcgcc aaacgaaacc gtttcaacca tgggctttga agcggcgaca 180
cgcgcaattg agatggcggg cattgagaaa gaccagattg gcctgatcgt tgtggcaacg 240
acttctgcta cgcacgcttt cccgagcgca gcttgtcaga ttcaaagcat gttgggcatt 300
aaaggttgcc cggcatttga cgttgcagca gcctgcgcag gtttcaccta tgcattaagc 360
gtagccgatc aatacgtgaa atctggggcg gtgaagtatg ctctggtcgt cggttccgat 420
gtactggcgc gcacctgcga tccaaccgat cgtgggacta ttattatttt tggcgatggc 480
gcgggcgctg cggtgctggc tgcctctgaa gagccgggaa tcatttccac ccatctgcat 540
gccgacggta gttatggtga attgctgacg ctgccaaacg ccgaccgcgt gaatccagag 600
aattcaattc atctgacgat ggcgggcaac gaagtcttca agtttgcggt aacggaaatg 660
gcgcacatcg ttgatgagac gctggcggcg aataatcttg accgttctca actggactgg 720
ctggttccgc atcaggctaa cctgcgtatt atcagtgcaa cggcgaaaaa actcggtatg 780
tctatggata atgtcgtggt gacgctggat cgccacggta atacctctgc ggcctctgtc 840
ccgtgcgcgc tggatgaagc tgtacgcgac gggcgcatta agccggggca gttggttctg 900
cttgaagcct ttggcggtgg attcacctgg ggctccgcgc tggttcgttt ctag 954

<210> SEQ ID NO 116
<211> LENGTH: 317
<212> TYPE: PRT
<213> ORGANISM: E. coli mutant
<220> FEATURE:
<221> NAME/KEY: MISC_FEATURE
<222> LOCATION: (215)..(215)
<223> OTHER INFORMATION: valine at amino acid position 215 replaced with phenylalanine
<220> FEATURE:
<221> NAME/KEY: MISC_FEATURE

```
<222> LOCATION: (220)..(220)
<223> OTHER INFORMATION: leucine at amino acid position 220 replaced
      with methionine

<400> SEQUENCE: 116

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Phe Ala Val Thr Glu Met Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Phe
    290                 295                 300

Gly Gly Gly Phe Thr Trp Gly Ser Ala Leu Val Arg Phe
305                 310                 315


<210> SEQ ID NO 117
<211> LENGTH: 954
<212> TYPE: DNA
<213> ORGANISM: E. coli mutant
<220> FEATURE:
<221> NAME/KEY: misc_feature
<222> LOCATION: (304)..(304)
<223> OTHER INFORMATION: phenylalanine at amino acid position 304
      replaced with alanine

<400> SEQUENCE: 117
```

-continued

```
atgtatacga agattattgg tactggcagc tatctgcccg aacaagtgcg gacaaacgcc      60

gatttggaaa aaatggtgga cacctctgac gagtggattg tcactcgtac cggtatccgc     120

gaacgccaca ttgccgcgcc aaacgaaacc gtttcaacca tgggctttga agcggcgaca     180

cgcgcaattg agatggcggg cattgagaaa gaccagattg gcctgatcgt tgtggcaacg     240

acttctgcta cgcacgcttt cccgagcgca gcttgtcaga ttcaaagcat gttgggcatt     300

aaaggttgcc cggcatttga cgttgcagca gcctgcgcag gtttcaccta tgcattaagc     360

gtagccgatc aatacgtgaa atctggggcg gtgaagtatg ctctggtcgt cggttccgat     420

gtactggcgc gcacctgcga tccaaccgat cgtgggacta ttattatttt tggcgatggc     480

gcgggcgctg cggtgctggc tgcctctgaa gagccgggaa tcatttccac ccatctgcat     540

gccgacggta gttatggtga attgctgacg ctgccaaacg ccgaccgcgt gaatccagag     600

aattcaattc atctgacgat ggcgggcaac gaagtcttca aggttgcggt aacggaactg     660

gcgcacatcg ttgatgagac gctggcggcg aataatcttg accgttctca actggactgg     720

ctggttccgc atcaggctaa cctgcgtatt atcagtgcaa cggcgaaaaa actcggtatg     780

tctatggata atgtcgtggt gacgctggat cgccacggta atacctctgc ggcctctgtc     840

ccgtgcgcgc tggatgaagc tgtacgcgac gggcgcatta agccggggca gttggttctg     900

cttgaagccg ctggcggtgg attcacctgg ggctccgcgc tggttcgttt ctag           954
```

<210> SEQ ID NO 118
<211> LENGTH: 317
<212> TYPE: PRT
<213> ORGANISM: E. coli mutant
<220> FEATURE:
<221> NAME/KEY: MISC_FEATURE
<222> LOCATION: (304)..(304)
<223> OTHER INFORMATION: phenylalanine at amino acid position 304
      replaced with alanine

<400> SEQUENCE: 118

```
Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
```

```
            180                 185                 190

Asn Ala Asp Arg Val Asn Pro Glu Asn Ser Ile His Leu Thr Met Ala
        195                 200                 205

Gly Asn Glu Val Phe Lys Phe Ala Val Thr Glu Met Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
            260                 265                 270

Gly Asn Thr Ser Ala Ala Ser Val Pro Cys Ala Leu Asp Glu Ala Val
        275                 280                 285

Arg Asp Gly Arg Ile Lys Pro Gly Gln Leu Val Leu Leu Glu Ala Ala
    290                 295                 300

Gly Gly Gly Phe Thr Trp Gly Ser Ala Leu Val Arg Phe
305                 310                 315


<210> SEQ ID NO 119
<211> LENGTH: 939
<212> TYPE: DNA
<213> ORGANISM: B. subtilis KASIIIA mutant
<220> FEATURE:
<221> NAME/KEY: misc_feature
<222> LOCATION: (208)..(208)
<223> OTHER INFORMATION: phenylalanine at amino acid position 208
      replaced with valine

<400> SEQUENCE: 119

atgaaagctg gaatacttgg tgttggacgt tacattcctg agaaggtttt aacaaatcat      60

gatcttgaaa aaatggttga aacttctgac gagtggattc gtacaagaac aggaatagaa     120

gaaagaagaa tcgcagcaga tgatgtgttt tcatcacata tggctgttgc agcagcgaaa     180

aatgcgctgg aacaagctga agtggctgct gaggatctgg atatgatctt ggttgcaact     240

gttacacctg atcagtcatt ccctacggtc tcttgtatga ttcaagaaca actcggcgcg     300

aagaaagcgt gtgctatgga tatcagcgcg gcttgtgcgg gcttcatgta cggggttgta     360

accggtaaac aatttattga atccggaacc tacaagcatg ttctagttgt tggtgtagag     420

aagctctcaa gcattaccga ctgggaagac cgcaatacag ccgttctgtt tggagacgga     480

gcaggcgctg cggtagtcgg gccagtcagt gatgacagag gaatcctttc atttgaacta     540

ggagccgacg gcacaggcgg tcagcacttg tatctgaatg aaaaacgaca tacaatcatg     600

aatggacgag aagttttcaa agttgcagtc cgccaaatgg gagaatcatg cgtaaatgtc     660

attgaaaaag ccggactttc aaaagaggat gtcgactttt tgattccgca tcaggcgaac     720

atccgtatca tggaagctgc tcgcgagcgt ttagagcttc ctgtcgaaaa gatgtctaaa     780

actgttcata aatatggaaa tacttctgcc gcatccattc cgatctctct tgtagaagaa     840

ttggaagccg gtaaaatcaa agacggcgat gtggtcgtta tggtagggtt cggcggagga     900

ctaacatggg gcgccattgc aatccgctgg ggccgataa                            939


<210> SEQ ID NO 120
<211> LENGTH: 312
<212> TYPE: PRT
<213> ORGANISM: B. subtilis KASIIIA mutant
<220> FEATURE:
<221> NAME/KEY: MISC_FEATURE
<222> LOCATION: (208)..(208)
```

<223> OTHER INFORMATION: phenylalanine at amino acid position 208
replaced with valine

<400> SEQUENCE: 120

Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30

Ile Arg Thr Arg Thr Gly Ile Glu Glu Arg Arg Ile Ala Ala Asp Asp
        35                  40                  45

Val Phe Ser Ser His Met Ala Val Ala Ala Ala Lys Asn Ala Leu Glu
    50                  55                  60

Gln Ala Glu Val Ala Ala Glu Asp Leu Asp Met Ile Leu Val Ala Thr
65                  70                  75                  80

Val Thr Pro Asp Gln Ser Phe Pro Thr Val Ser Cys Met Ile Gln Glu
                85                  90                  95

Gln Leu Gly Ala Lys Lys Ala Cys Ala Met Asp Ile Ser Ala Ala Cys
            100                 105                 110

Ala Gly Phe Met Tyr Gly Val Val Thr Gly Lys Gln Phe Ile Glu Ser
        115                 120                 125

Gly Thr Tyr Lys His Val Leu Val Val Gly Val Glu Lys Leu Ser Ser
    130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190

Asn Glu Lys Arg His Thr Ile Met Asn Gly Arg Glu Val Phe Lys Val
        195                 200                 205

Ala Val Arg Gln Met Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Val Val Met Val Gly Phe Gly Gly Gly Leu Thr Trp Gly
    290                 295                 300

Ala Ile Ala Ile Arg Trp Gly Arg
305                 310

<210> SEQ ID NO 121
<211> LENGTH: 939
<212> TYPE: DNA
<213> ORGANISM: B. subtilis KASIIIA mutant
<220> FEATURE:
<221> NAME/KEY: misc_feature
<222> LOCATION: (213)..(213)
<223> OTHER INFORMATION: methionine at amino acid position 213 replaced
with leucine

<400> SEQUENCE: 121
atgaaagctg gaatacttgg tgttggacgt tacattcctg agaaggtttt aacaaatcat     60

```
gatcttgaaa aaatggttga aacttctgac gagtggattc gtacaagaac aggaatagaa    120

gaaagaagaa tcgcagcaga tgatgtgttt tcatcacata tggctgttgc agcagcgaaa    180

aatgcgctgg aacaagctga agtggctgct gaggatctgg atatgatctt ggttgcaact    240

gttacacctg atcagtcatt ccctacggtc tcttgtatga ttcaagaaca actcggcgcg    300

aagaaagcgt gtgctatgga tatcagcgcg gcttgtgcgg gcttcatgta cggggttgta    360

accggtaaac aatttattga atccggaacc tacaagcatg ttctagttgt tggtgtagag    420

aagctctcaa gcattaccga ctgggaagac cgcaatacag ccgttctgtt tggagacgga    480

gcaggcgctg cggtagtcgg gccagtcagt gatgacagag gaatcctttc atttgaacta    540

ggagccgacg gcacaggcgg tcagcacttg tatctgaatg aaaaacgaca tacaatcatg    600

aatggacgag aagttttcaa atttgcagtc cgccaattgg gagaatcatg cgtaaatgtc    660

attgaaaaag ccggactttc aaaagaggat gtcgactttt tgattccgca tcaggcgaac    720

atccgtatca tggaagctgc tcgcgagcgt ttagagcttc ctgtcgaaaa gatgtctaaa    780

actgttcata aatatggaaa tacttctgcc gcatccattc cgatctctct tgtagaagaa    840

ttggaagccg gtaaaatcaa agacggcgat gtggtcgtta tggtagggtt cggcggagga    900

ctaacatggg gcgccattgc aatccgctgg ggccgataa                           939
```

<210> SEQ ID NO 122
<211> LENGTH: 312
<212> TYPE: PRT
<213> ORGANISM: B. subtilis KASIIIA mutant
<220> FEATURE:
<221> NAME/KEY: MISC_FEATURE
<222> LOCATION: (213)..(213)
<223> OTHER INFORMATION: methionine at amino acid position 213 replaced with leucine

<400> SEQUENCE: 122

```
Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30

Ile Arg Thr Arg Thr Gly Ile Glu Glu Arg Arg Ile Ala Ala Asp Asp
        35                  40                  45

Val Phe Ser Ser His Met Ala Val Ala Ala Ala Lys Asn Ala Leu Glu
    50                  55                  60

Gln Ala Glu Val Ala Ala Glu Asp Leu Asp Met Ile Leu Val Ala Thr
65                  70                  75                  80

Val Thr Pro Asp Gln Ser Phe Pro Thr Val Ser Cys Met Ile Gln Glu
                85                  90                  95

Gln Leu Gly Ala Lys Lys Ala Cys Ala Met Asp Ile Ser Ala Ala Cys
            100                 105                 110

Ala Gly Phe Met Tyr Gly Val Val Thr Gly Lys Gln Phe Ile Glu Ser
        115                 120                 125

Gly Thr Tyr Lys His Val Leu Val Val Gly Val Glu Lys Leu Ser Ser
    130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190
```

```
Asn Glu Lys Arg His Thr Ile Met Asn Gly Arg Glu Val Phe Lys Phe
        195                 200                 205

Ala Val Arg Gln Leu Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Val Val Met Val Gly Phe Gly Gly Gly Leu Thr Trp Gly
    290                 295                 300

Ala Ile Ala Ile Arg Trp Gly Arg
305                 310


<210> SEQ ID NO 123
<211> LENGTH: 939
<212> TYPE: DNA
<213> ORGANISM: B. subtilis KASIIIA double mutant
<220> FEATURE:
<221> NAME/KEY: misc_feature
<222> LOCATION: (208)..(208)
<223> OTHER INFORMATION: phenylalanine at amino acid position 208
      replaced with valine
<220> FEATURE:
<221> NAME/KEY: misc_feature
<222> LOCATION: (213)..(213)
<223> OTHER INFORMATION: methionine at amino acid position 213 replaced
      with leucine

<400> SEQUENCE: 123

atgaaagctg gaatacttgg tgttggacgt tacattcctg agaaggtttt aacaaatcat     60

gatcttgaaa aaatggttga aacttctgac gagtggattc gtacaagaac aggaatagaa    120

gaaagaagaa tcgcagcaga tgatgtgttt tcatcacata tggctgttgc agcagcgaaa    180

aatgcgctgg aacaagctga agtggctgct gaggatctgg atatgatctt ggttgcaact    240

gttacacctg atcagtcatt ccctacggtc tcttgtatga ttcaagaaca actcggcgcg    300

aagaaagcgt gtgctatgga tatcagcgcg gcttgtgcgg gcttcatgta cggggttgta    360

accggtaaac aatttattga atccggaacc tacaagcatg ttctagttgt tggtgtagag    420

aagctctcaa gcattaccga ctgggaagac cgcaatacag ccgttctgtt tggagacgga    480

gcaggcgctg cggtagtcgg gccagtcagt gatgacagag gaatcctttc atttgaacta    540

ggagccgacg gcacaggcgg tcagcacttg tatctgaatg aaaaacgaca tacaatcatg    600

aatggacgag aagttttcaa agttgcagtc cgccaattgg gagaatcatg cgtaaatgtc    660

attgaaaaag ccggactttc aaaagaggat gtcgactttt tgattccgca tcaggcgaac    720

atccgtatca tggaagctgc tcgcgagcgt ttagagcttc ctgtcgaaaa gatgtctaaa    780

actgttcata aatatggaaa tacttctgcc gcatccattc cgatctctct tgtagaagaa    840

ttggaagccg gtaaaatcaa agacggcgat gtggtcgtta tggtagggtt cggcggagga    900

ctaacatggg gcgccattgc aatccgctgg ggccgataa                           939


<210> SEQ ID NO 124
<211> LENGTH: 312
<212> TYPE: PRT
```

<213> ORGANISM: B. subtilis KASIIIA double mutant
<220> FEATURE:
<221> NAME/KEY: MISC_FEATURE
<222> LOCATION: (208)..(208)
<223> OTHER INFORMATION: phenylalanine at amino acid position 208 replaced with valine
<220> FEATURE:
<221> NAME/KEY: MISC_FEATURE
<222> LOCATION: (213)..(213)
<223> OTHER INFORMATION: methionine at amino acid position 213 replaced with leucine

<400> SEQUENCE: 124

```
Met Lys Ala Gly Ile Leu Gly Val Gly Arg Tyr Ile Pro Glu Lys Val
1               5                   10                  15

Leu Thr Asn His Asp Leu Glu Lys Met Val Glu Thr Ser Asp Glu Trp
            20                  25                  30

Ile Arg Thr Arg Thr Gly Ile Glu Glu Arg Arg Ile Ala Ala Asp Asp
        35                  40                  45

Val Phe Ser Ser His Met Ala Val Ala Ala Ala Lys Asn Ala Leu Glu
    50                  55                  60

Gln Ala Glu Val Ala Ala Glu Asp Leu Asp Met Ile Leu Val Ala Thr
65                  70                  75                  80

Val Thr Pro Asp Gln Ser Phe Pro Thr Val Ser Cys Met Ile Gln Glu
                85                  90                  95

Gln Leu Gly Ala Lys Lys Ala Cys Ala Met Asp Ile Ser Ala Ala Cys
            100                 105                 110

Ala Gly Phe Met Tyr Gly Val Val Thr Gly Lys Gln Phe Ile Glu Ser
        115                 120                 125

Gly Thr Tyr Lys His Val Leu Val Val Gly Val Glu Lys Leu Ser Ser
    130                 135                 140

Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190

Asn Glu Lys Arg His Thr Ile Met Asn Gly Arg Glu Val Phe Lys Val
        195                 200                 205

Ala Val Arg Gln Leu Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Val Val Met Val Gly Phe Gly Gly Gly Leu Thr Trp Gly
    290                 295                 300

Ala Ile Ala Ile Arg Trp Gly Arg
305                 310
```

<210> SEQ ID NO 125
<211> LENGTH: 939
<212> TYPE: DNA
<213> ORGANISM: B. subtilis KASIIIA mutant
<220> FEATURE:
<221> NAME/KEY: misc_feature
<222> LOCATION: (297)..(297)
<223> OTHER INFORMATION: phenylalanine at amino acid position 297 replaced with alanine

<400> SEQUENCE: 125
atgaaagctg gaatacttgg tgttggacgt tacattcctg agaaggtttt aacaaatcat 60
gatcttgaaa aaatggttga aacttctgac gagtggattc gtacaagaac aggaatagaa 120
gaaagaagaa tcgcagcaga tgatgtgttt tcatcacata tggctgttgc agcagcgaaa 180
aatgcgctgg aacaagctga agtggctgct gaggatctgg atatgatctt ggttgcaact 240
gttacacctg atcagtcatt ccctacggtc tcttgtatga ttcaagaaca actcggcgcg 300
aagaaagcgt gtgctatgga tatcagcgcg gcttgtgcgg gcttcatgta cggggttgta 360
accggtaaac aatttattga atccggaacc tacaagcatg ttctagttgt tggtgtagag 420
aagctctcaa gcattaccga ctgggaagac cgcaatacag ccgttctgtt tggagacgga 480
gcaggcgctg cggtagtcgg gccagtcagt gatgacagag gaatcctttc atttgaacta 540
ggagccgacg gcacaggcgg tcagcacttg tatctgaatg aaaaacgaca tacaatcatg 600
aatggacgag aagttttcaa atttgcagtc cgccaaatgg gagaatcatg cgtaaatgtc 660
attgaaaaag ccggactttc aaaagaggat gtcgactttt tgattccgca tcaggcgaac 720
atccgtatca tggaagctgc tcgcgagcgt ttagagcttc ctgtcgaaaa gatgtctaaa 780
actgttcata aatatggaaa tacttctgcc gcatccattc cgatctctct tgtagaagaa 840
ttggaagccg gtaaaatcaa agacggcgat gtggtcgtta tggtaggggc cggcggagga 900
ctaacatggg gcgccattgc aatccgctgg ggccgataa 939

<210> SEQ ID NO 126
<211> LENGTH: 312
<212> TYPE: PRT
<213> ORGANISM: B. subtilis KASIIIA mutant
<220> FEATURE:
<221> NAME/KEY: MISC_FEATURE
<222> LOCATION: (297)..(297)
<223> OTHER INFORMATION: phenylalanine at amino acid position 297 replaced with alanine

<400> SEQUENCE: 126

Met Lys Ala Gly Ile Leu Gly Val Gly Arg Tyr Ile Pro Glu Lys Val
1 5 10 15

Leu Thr Asn His Asp Leu Glu Lys Met Val Glu Thr Ser Asp Glu Trp
20 25 30

Ile Arg Thr Arg Thr Gly Ile Glu Glu Arg Arg Ile Ala Ala Asp Asp
35 40 45

Val Phe Ser Ser His Met Ala Val Ala Ala Ala Lys Asn Ala Leu Glu
50 55 60

Gln Ala Glu Val Ala Ala Glu Asp Leu Asp Met Ile Leu Val Ala Thr
65 70 75 80

Val Thr Pro Asp Gln Ser Phe Pro Thr Val Ser Cys Met Ile Gln Glu
85 90 95

Gln Leu Gly Ala Lys Lys Ala Cys Ala Met Asp Ile Ser Ala Ala Cys
100 105 110

Ala Gly Phe Met Tyr Gly Val Val Thr Gly Lys Gln Phe Ile Glu Ser
115 120 125

Gly Thr Tyr Lys His Val Leu Val Val Gly Val Glu Lys Leu Ser Ser
130 135 140

-continued

```
Ile Thr Asp Trp Glu Asp Arg Asn Thr Ala Val Leu Phe Gly Asp Gly
145                 150                 155                 160

Ala Gly Ala Ala Val Val Gly Pro Val Ser Asp Asp Arg Gly Ile Leu
                165                 170                 175

Ser Phe Glu Leu Gly Ala Asp Gly Thr Gly Gly Gln His Leu Tyr Leu
            180                 185                 190

Asn Glu Lys Arg His Thr Ile Met Asn Gly Arg Glu Val Phe Lys Val
        195                 200                 205

Ala Val Arg Gln Leu Gly Glu Ser Cys Val Asn Val Ile Glu Lys Ala
    210                 215                 220

Gly Leu Ser Lys Glu Asp Val Asp Phe Leu Ile Pro His Gln Ala Asn
225                 230                 235                 240

Ile Arg Ile Met Glu Ala Ala Arg Glu Arg Leu Glu Leu Pro Val Glu
                245                 250                 255

Lys Met Ser Lys Thr Val His Lys Tyr Gly Asn Thr Ser Ala Ala Ser
            260                 265                 270

Ile Pro Ile Ser Leu Val Glu Glu Leu Glu Ala Gly Lys Ile Lys Asp
        275                 280                 285

Gly Asp Val Val Val Met Val Gly Ala Gly Gly Gly Leu Thr Trp Gly
    290                 295                 300

Ala Ile Ala Ile Arg Trp Gly Arg
305                 310
```

<210> SEQ ID NO 127
<211> LENGTH: 978
<212> TYPE: DNA
<213> ORGANISM: B. subtilis KASIIIB mutant
<220> FEATURE:
<221> NAME/KEY: misc_feature
<222> LOCATION: (221)..(221)
<223> OTHER INFORMATION: tryptophan at amino acid position 221 replaced with valine

<400> SEQUENCE: 127

```
atgtcaaaag caaaaattac agctatcggc acctatgcgc cgagcagacg tttaaccaat      60

gcagatttag aaaagatcgt tgatacctct gatgaatgga tcgttcagcg cacaggaatg     120

agagaacgcc ggattgcgga tgaacatcaa tttacctctg atttatgcat agaagcggtg     180

aagaatctca agagccgtta taaaggaacg cttgatgatg tcgatatgat cctcgttgcc     240

acaaccacat ccgattacgc ctttccgagt acggcatgcc gcgtacagga atatttcggc     300

tgggaaagca ccggcgcgct ggatattaat gcgacatgcg ccgggctgac atacggcctc     360

catttggcaa atggattgat cacatctggc cttcatcaaa aaattctcgt catcgccgga     420

gagacgttat caaaggtaac cgattatacc gatcgaacga catgcgtact gttcggcgat     480

gccgcgggtg cgctgttagt agaacgagat gaagagacgc cgggatttct tgcgtctgta     540

caaggaacaa gcgggaacgg cggcgatatt ttgtatcgtg ccggactgcg aaatgaaata     600

aacggtgtgc agcttgtcgg ttccggaaaa atggtgcaaa acggacgcga ggtatataaa     660

gtggccgcaa gaaccgtccc tggcgaattt gaacggcttt tacataaagc aggactcagc     720

tccgatgatc tcgattggtt tgttcctcac agcgccaact tgcgcatgat cgagtcaatt     780

tgtgaaaaaa caccgttccc gattgaaaaa acgctcacta gtgttgagca ctacggaaac     840

acgtcttcgg tttcaattgt tttggcgctc gatctcgcag tgaaagccgg gaagctgaaa     900

aaagatcaaa tcgttttgct tttcgggttt ggcggcggat taacctatac aggattgctt     960

attaaatggg ggatgtaa                                                   978
```

```
<210> SEQ ID NO 128
<211> LENGTH: 325
<212> TYPE: PRT
<213> ORGANISM: B. subtilis KASIIIB mutant
<220> FEATURE:
<221> NAME/KEY: MISC_FEATURE
<222> LOCATION: (221)..(221)
<223> OTHER INFORMATION: tryptophan at amino acid position 221 replaced
      with valine

<400> SEQUENCE: 128

Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Val Ala Ala Arg
    210                 215                 220

Thr Val Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Phe Gly Phe Gly Gly Gly Leu Thr Tyr Thr Gly Leu Leu
305                 310                 315                 320

Ile Lys Trp Gly Met
                325
```

<210> SEQ ID NO 129
<211> LENGTH: 990
<212> TYPE: DNA
<213> ORGANISM: B. subtilis KASIIIB mutant
<220> FEATURE:
<221> NAME/KEY: misc_feature
<222> LOCATION: (226)..(226)
<223> OTHER INFORMATION: valine at amino acid position 226 replaced with leucine

<400> SEQUENCE: 129

```
atgtcaaaag caaaaattac agctatcggc acctatgcgc cgagcagacg tttaaccaat     60

gcagatttag aaaagatcgt tgatacctct gatgaatgga tcgttcagcg cacaggaatg    120

agagaacgcc ggattgcgga tgaacatcaa tttacctctg atttatgcat agaagcggtg    180

aagaatctca agagccgtta taaaggaacg cttgatgatg tcgatatgat cctcgttgcc    240

acaaccacat ccgattacgc ctttccgagt acggcatgcc gcgtacagga atatttcggc    300

tgggaaagca ccggcgcgct ggatattaat gcgacatgcg ccgggctgac atacggcctc    360

catttggcaa atggattgat cacatctggc cttcatcaaa aaattctcgt catcgccgga    420

gagacgttat caaaggtaac cgattatacc gatcgaacga catgcgtact gttcggcgat    480

gccgcgggtg cgctgttagt agaacgagat gaagagacgc cgggatttct tgcgtctgta    540

caaggaacaa gcgggaacgg cggcgatatt ttgtatcgtg ccggactgcg aaatgaaata    600

aacggtgtgc agcttgtcgg ttccggaaaa atggtgcaaa acggacgcga ggtatataaa    660

tgggccgcaa gaaccgccgc aagaaccctc cctggcgaat ttgaacggct tttacataaa    720

gcaggactca gctccgatga tctcgattgg tttgttcctc acagcgccaa cttgcgcatg    780

atcgagtcaa tttgtgaaaa aacaccgttc ccgattgaaa aaacgctcac tagtgttgag    840

cactacggaa acacgtcttc ggtttcaatt gttttggcgc tcgatctcgc agtgaaagcc    900

gggaagctga aaaaagatca aatcgttttg cttttcgggt ttggcggcgg attaacctat    960

acaggattgc ttattaaatg ggggatgtaa                                     990
```

<210> SEQ ID NO 130
<211> LENGTH: 325
<212> TYPE: PRT
<213> ORGANISM: B. subtilis KASIIIB mutant
<220> FEATURE:
<221> NAME/KEY: MISC_FEATURE
<222> LOCATION: (226)..(226)
<223> OTHER INFORMATION: valine at amino acid position 226 replaced with leucine

<400> SEQUENCE: 130

```
Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110
```

-continued

```
Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Trp Ala Ala Arg
    210                 215                 220

Thr Leu Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Phe Gly Phe Gly Gly Gly Leu Thr Tyr Thr Gly Leu Leu
305                 310                 315                 320

Ile Lys Trp Gly Met
                325
```

<210> SEQ ID NO 131
<211> LENGTH: 978
<212> TYPE: DNA
<213> ORGANISM: B. subtilis KASIIIB double mutant
<220> FEATURE:
<221> NAME/KEY: misc_feature
<222> LOCATION: (221)..(221)
<223> OTHER INFORMATION: tryptophan at amino acid position 221 replaced with valine
<220> FEATURE:
<221> NAME/KEY: misc_feature
<222> LOCATION: (226)..(226)
<223> OTHER INFORMATION: valine at amino acid position 226 replaced with leucine

<400> SEQUENCE: 131

```
atgtcaaaag caaaaattac agctatcggc acctatgcgc cgagcagacg tttaaccaat      60

gcagatttag aaaagatcgt tgatacctct gatgaatgga tcgttcagcg cacaggaatg     120

agagaacgcc ggattgcgga tgaacatcaa tttacctctg atttatgcat agaagcggtg     180

aagaatctca agagccgtta taaaggaacg cttgatgatg tcgatatgat cctcgttgcc     240

acaaccacat ccgattacgc ctttccgagt acggcatgcc gcgtacagga atatttcggc     300

tgggaaagca ccggcgcgct ggatattaat gcgacatgcg ccgggctgac atacggcctc     360

catttggcaa atggattgat cacatctggc cttcatcaaa aaattctcgt catcgccgga     420

gagacgttat caaaggtaac cgattatacc gatcgaacga catgcgtact gttcggcgat     480

gccgcgggtg cgctgttagt agaacgagat gaagagacgc cgggatttct tgcgtctgta     540

caaggaacaa gcgggaacgg cggcgatatt ttgtatcgtg ccggactgcg aaatgaaata     600
```

aacggtgtgc agcttgtcgg ttccggaaaa atggtgcaaa acggacgcga ggtatataaa 660
gtggccgcaa gaaccctccc tggcgaattt gaacggcttt tacataaagc aggactcagc 720
tccgatgatc tcgattggtt tgttcctcac agcgccaact tgcgcatgat cgagtcaatt 780
tgtgaaaaaa caccgttccc gattgaaaaa acgctcacta gtgttgagca ctacggaaac 840
acgtcttcgg tttcaattgt tttggcgctc gatctcgcag tgaaagccgg gaagctgaaa 900
aaagatcaaa tcgttttgct tttcgggttt ggcggcggat taacctatac aggattgctt 960
attaaatggg ggatgtaa 978

<210> SEQ ID NO 132
<211> LENGTH: 325
<212> TYPE: PRT
<213> ORGANISM: B. subtilis KASIIIB double mutant
<220> FEATURE:
<221> NAME/KEY: MISC_FEATURE
<222> LOCATION: (221)..(221)
<223> OTHER INFORMATION: tryptophan at amino acid position 221 replaced with valine
<220> FEATURE:
<221> NAME/KEY: MISC_FEATURE
<222> LOCATION: (226)..(226)
<223> OTHER INFORMATION: valine at amino acid position 226 replaced with leucine

<400> SEQUENCE: 132

Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Val Ala Ala Arg
    210                 215                 220

Thr Leu Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

-continued

```
Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Phe Gly Phe Gly Gly Gly Leu Thr Tyr Thr Gly Leu Leu
305                 310                 315                 320

Ile Lys Trp Gly Met
                325


<210> SEQ ID NO 133
<211> LENGTH: 978
<212> TYPE: DNA
<213> ORGANISM: B. subtilis KASIIIB mutant
<220> FEATURE:
<221> NAME/KEY: misc_feature
<222> LOCATION: (310)..(310)
<223> OTHER INFORMATION: phenyalanine at amino acid position 310
      replaced with alanine

<400> SEQUENCE: 133

atgtcaaaag caaaaattac agctatcggc acctatgcgc cgagcagacg tttaaccaat     60

gcagatttag aaaagatcgt tgatacctct gatgaatgga tcgttcagcg cacaggaatg    120

agagaacgcc ggattgcgga tgaacatcaa tttacctctg atttatgcat agaagcggtg    180

aagaatctca agagccgtta taaaggaacg cttgatgatg tcgatatgat cctcgttgcc    240

acaaccacat ccgattacgc ctttccgagt acggcatgcc gcgtacagga atatttcggc    300

tgggaaagca ccggcgcgct ggatattaat gcgacatgcg ccgggctgac atacggcctc    360

catttggcaa atggattgat cacatctggc cttcatcaaa aaattctcgt catcgccgga    420

gagacgttat caaaggtaac cgattatacc gatcgaacga catgcgtact gttcggcgat    480

gccgcgggtg cgctgttagt agaacgagat gaagagacgc cgggatttct tgcgtctgta    540

caaggaacaa gcgggaacgg cggcgatatt ttgtatcgtg ccggactgcg aaatgaaata    600

aacggtgtgc agcttgtcgg ttccggaaaa atggtgcaaa acggacgcga ggtatataaa    660

tgggccgcaa gaaccgtccc tggcgaattt gaacggcttt tacataaagc aggactcagc    720

tccgatgatc tcgattggtt tgttcctcac agcgccaact tgcgcatgat cgagtcaatt    780

tgtgaaaaaa caccgttccc gattgaaaaa acgctcacta gtgttgagca ctacggaaac    840

acgtcttcgg tttcaattgt tttggcgctc gatctcgcag tgaaagccgg gaagctgaaa    900

aaagatcaaa tcgttttgct tttcggggct ggcggcggat taacctatac aggattgctt    960

attaaatggg ggatgtaa                                                  978


<210> SEQ ID NO 134
<211> LENGTH: 325
<212> TYPE: PRT
<213> ORGANISM: B. subtilis KASIIIB mutant
<220> FEATURE:
<221> NAME/KEY: MISC_FEATURE
<222> LOCATION: (310)..(310)
<223> OTHER INFORMATION: phenyalanine at amino acid position 310
      replaced with alanine
```

-continued

<400> SEQUENCE: 134

```
Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Trp Ala Ala Arg
    210                 215                 220

Thr Val Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Glu Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Ala Gly Phe Gly Gly Gly Leu Thr Tyr Thr Gly Leu Leu
305                 310                 315                 320

Ile Lys Trp Gly Met
                325
```

MATERIALS AND METHODS FOR CHARACTERIZING AND USING A 3-KETOACYL-ACYL CARRIER PROTEIN (ACP) SYNTHASE III (KASIII) FOR PRODUCTION OF BI-FUNCTIONAL FATTY ACIDS

CROSS-REFERENCE TO RELATED APPLICATIONS

This application is a Divisional of U.S. patent application Ser. No. 14/762,791, filed Jul. 29, 2015, as a National Stage Entry of international patent application no. PCT/US14/12616, filed Jan. 22, 2014, and which claims priority to U.S. provisional patent application No. 61/755,946, filed Jan. 23, 2013, which applications are incorporated herein by reference in their entireties.

STATEMENT REGARDING FEDERALLY SPONSORED RESEARCH OR DEVELOPMENT

The work described herein was supported, at least in part, by The National Science Foundation under contract nos. EEC0813570 and IIP1237247. Therefore, the Government of the United States of America has certain rights in the invention.

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

TECHNICAL FIELD

The present disclosure relates to enzymes, mutants thereof, fatty acid synthesis, nucleic acids, host cells and organisms, assays, bi-functional fatty acid compositions, and uses thereof.

BACKGROUND

The biochemical mechanism of fatty acid biosynthesis is universally similar among all organisms. Generally, fatty acids are synthesized by the repeated iteration of four-reactions, which start with an acyl-primer, which is elongated, two carbons per cycle, using carbon atoms derived from a malonyl moiety. The four sequential reactions that make up this cycle generate 3-ketoacyl-thioester, 3-hydroxyacyl-thioester, and 2-enoyl-thioester derivative intermediates, and finally an acyl-thioester derivative that is two carbons longer than the initial acyl primer. In bacteria, typified by the *E. coli* system, and higher plant plastids, these reactions are catalyzed by a dissociable, type II fatty acid synthase that is composed of the four enzymes 3-ketoacyl-ACP synthase (KAS), 3-ketoacyl-ACP reductase (encoded by fabG), 3-hydroxyacyl-ACP dehydratase (encoded by fabA), and enoyl-ACP reductase (encoded by fabI) (Rock et al., Biochim Biophys. Acta 1302: 1-16 (1996)). In contrast, a type I fatty acid synthase, which is composed of four enzyme components that occur as domains on a multifunctional protein(s), occurs in other eukaryotes (Jenni et al., Science 311: 1263-1267 (2006); and Maier et al., Science 311: 1258-1262 (2006)). However, in both type I and type II fatty acid synthase systems acyl derivatives are bound to phosphopantetheine cofactors.

In the type II fatty acid synthase system, there are three genetically and biochemically distinct KAS isomers, namely KASI (encoded by fabB), KASII (encoded by fabF), and KASIII (encoded by fabH) (Rock et al. (1996), supra; Garwin et al., J. Biol. Chem. 255: 11949-11956 (1980)); and Jackowski et al., J. Biol. Chem. 262: 7927-7931 (1987)). Their functions have been studied extensively in *E. coli*. They differ in their specificities for acyl-thioester substrates, having optimum activities for substrates of different acyl-chain lengths and different thioesters. While KASI and KASII catalyze the condensation between acyl-ACP (of longer acyl-chain length) with malonyl-ACP substrates, KASIII specifically utilizes acetyl-CoA as a substrate for the condensing reaction with malonyl-ACP (Tsay et al., J. Biol. Chem. 267: 6807-6814 (1992); and Heath et al., J. Biol. Chem. 271: 1833-1836 (1996)), and thus initiates fatty acid biosynthesis.

The general mechanism of fatty acid biosynthesis in Gram-positive bacteria, such as *B. subtilis*, is similar to that of *E. coli* (Magnuson et al., Microbiol. Rev. 57: 522-542 (1993)). One major difference is that *B. subtilis* produces large quantities of branched-chain fatty acids (BCFAs) and unsaturated fatty acids as a result of the expression of a unique Δ5 desaturase (Aguilar et al., J. Bacteriol. 180: 2194-2200 (1998)). The BCFAs and the unsaturated fatty acids together maintain membrane fluidity in response to lower growth temperatures. The BCFAs are branched with methyl groups at the iso- and anteiso positions (i.e., 13-methyltetradecanoic, 12-methyltetradecanoic acid, and 14-methylpentadecanoic acid), and they are biosynthesized by a type II FAS that has the ability to initiate this process by using branched acyl-CoAs that are derived from the branched chain amino acids, leucine, isoleucine, and valine (Willecke et al., J. Biol. Chem. 246: 5264-5272 (1971)). Thus, the *B. subtilis* FAS enzyme must have the capacity to utilize such branched acyl-CoA substrates. Genomics-based analysis of the *B. subtilis* genome has led to the identification of KASII (Shujman et al., J. Bacteriol. 183: 3032-3040 (2001)) and KASIII homologous genes; however, it appears that this bacterium does not contain a sequence-recognizable KASI homolog. In *B. subtilis* KASII is an essential enzyme, which is encoded by yjaY. Two *B. subtilis* KASIII-encoding genes, bfabHA (yjaX) and bfabHB (yhfB), have been characterized, and these have the capacity to catalyze the condensation of branched acyl-CoAs with malonyl-ACP (Choi et al., J. Bacteriol. 182: 365-370 (2000); and Smirnova et al., J. Bacteriol. 183: 2335-2342 (2001)). These two genes code for 312- and 325-residue proteins that share 43% sequence identity.

KASIII has been characterized in several bacterial (Tsay et al., J. Biol. Chem. 267: 6807-6814 (1992); Han et al., J. Bacteriol. 180: 4481-4486 (1998); Qiu et al., J. Biol. Chem. 274: 36465-36471 (1999); Choi et al., J. Bacteriol. 182: 365-370 (2000a); Choi et al., J. Bacteriol. 182: 365-370 (2000b); Choi et al., J. Biol. Chem. 275: 28201-28207 (2000c); Davies et al., Structure 8: 185-195 (2000); Khandekar et al., Biochem. Biophys. Res. Comm 270: 100-107 (2000); Khandekar et al., J. Biol. Chem. 276: 30024-30030 (2001); Qiu et al., J. Mol. Biol. 307: 341-356 (2001); Revill et al., J. Bacteriol. 183: 3526-3530 (2001); Huynh et al., Acta Crystallogr. Sect. F. Struct. Biol. Cryst. Comm 65: 460-462 (2009); Wen et al., Protein Expr. Purif. 65: 83-91 (2009); Singh et al., FEMS Microbiol. Lett. 301: 188-192 (2009); Gajiwala et al., FEBS Lett. 583: 2939-2946 (2009); and Pereira et al., Acta Crystallogr. D. Biol. Crystallogr. 68: 1320-1328 (2012)), protozoan (Waters et al., Mol. Biochem. Parsitol. 123: 85-94 (2002); and Prigge et al., Biochem. 42: 1160-1169 (2003)), and plant species (Clough et al., J. Biol. Chem. 267: 20992-20998 (1992); Jaworski et al., Plant Physiol. 90: 41-44 (1989); Tai et al., Plant Physiol. 106: 801-802 (1994); Abbadi et al., Biochem. J. 345 (Pt. 1): 153-160 (2000); Dehesh et al., Plant Physiol. 125: 1103-1114 (2001); Li et al., Tree Physiol. 28: 921-927 (2008); and Gonzalez-Mellado et al., Planta 231: 1277-1289 (2010)). Functionally characterized KASIII enzymes exhibit diverse substrate specificities, utilizing acyl-CoA substrates ranging from short, straight-chain acyl-CoAs (e.g. acetyl-CoA, propionyl-CoA (Choi et al. (2000a), supra; Clough et al. (1992), supra; and Abbadi et al. (2000), supra), branched-chain acyl-CoAs (e.g., isobutyryl-CoA and ante-isovaleryl-CoA (Han et al. (1998), supra; Choi et al. (2000a), supra; Khandekar et al. (2001), supra; Singh et al. (2009), supra; and Qiu et al., Protein Sci. 14: 2087-2094 (2005)) to long-chain acyl-CoAs (e.g., lauroyl-CoA, palmitoyl-CoA (Choi et al. (2000b), supra; and Scarsdale et al., J. Biol. Chem. 276: 20516-20522 (2001)).

By virtue of diverse substrate specificities shown by KASIII enzymes from different organisms, this enzyme is thought to determine the fatty acid profile of the organism, particularly the structure of the omega-end of the fatty acid products (Choi et al. (2000a), supra; Gajiwala et al. (2009), supra; and Pereira et al. (2012), supra). For example, in many Gram-positive bacteria (i.e., *Bacillus subtilis, Streptomyces glaucescens*, and *Staphylococcus aureus*), KASIII can utilize both branched-chain and straight-chain substrates, resulting in the production of both branched- and straight-chain fatty acids (Han et al. (1998), supra; Choi et al. (2000a), supra; Pereira et al. (2012), supra; and Qiu et al. (2005), supra). In contrast, KASIII from Gram-negative bacteria (e.g., *E. coli*) appears to prefer straight-chain acyl-CoA substrates, which results in the production of straight-chain fatty acids (Choi et al. (2000a), supra).

The active site residues and substrate binding pocket are well conserved among KASIII from different species. Three residues, Cys112, His244 and Asn274, form the catalytic triad in *E. coli* KASIII and carry out two half reactions as a part of the Claisen condensation (FIG. 1) of acyl-CoA and malonyl-ACP (Heath et al., Nat. Prod. Rep. 19: 581-596 (2002)). Qiu et al. (J. Biol. Chem. 274: 36465-36471 (1999)) and Davies et al. (Structure 8: 185-195 (2000)) have proposed different mechanisms for the reaction at the active site. The mechanism proposed by Davies et al., which is supported by crystallographic data, is shown in FIG. 2. The first step is the transfer of the acyl group from the acyl-CoA primer to the enzyme and covalent linkage of the acyl group to the Cys112 residue. As per Davies et al., the thiol group of Cys112 is deprotonated by the dipole effect of the α-helix in which it is located. The resulting nucleophilic thiolate ion on Cys112 attacks acyl-CoA and forms a thioester with the acyl group, with the release of CoA-SH. The second step is the entry of ionized malonyl-ACP into the active site, where it is decarboxylated through the aid of Phe205.

After decarboxylation, the resulting negative charge on its thioester carbonyl is stabilized by His244 and Asn274. A carbanion is formed on its α-carbon that attacks the acetate bound to Cys112. The tetrahedral transition state is stabilized by an oxyanion hole formed by Cys112 and Gly306, which eventually breaks down to give acetoacetyl-ACP as the product.

The US imports almost 10 million barrels of petroleum a day (U.S.E.I. Administration Monthly Energy Review (2011), on the worldwide web at eia(dot)gov(forwardslash) energy_in_brief/foreign_oil_dependence.cfm) to create a multi-billion dollar plastics and specialty chemical industry that obtains its monomers from petroleum feedstocks. Currently, only a limited number of bio-based products are available in the market including polylactic acid (PLA), polyhydroxybutyrate (PHB), and polyethylene terephthalate (PET), which is based on 1,3-propanediol, and emerging products based on succinic acid and adipic acid (Frost and Sullivan, Global Bio-Based Plastics Market (2009), on the worldwide web at frost(dot)com(forward slash)prod/servlet/report-toc.pag?repid=M4A1-01-00-00-00). However, the global marketplace for the bio-plastics "green" market is projected to expand to over a billion dollars (Ceresana Research, Market Study: Bioplastics (2011), on the worldwide web at ceresana(dot)com(forward slash) en/market-studies/plastics/bioplastics), and with increasing awareness about reduced environmental impacts of bio-based plastics, the market for these products will continue to grow.

The present disclosure seeks to provide materials and methods for characterizing and using 3-ketoacyl-acyl carrier protein (ACP) synthases III (KASIII) in the production of bi-functional fatty acids. This and other objects and advantages, as well as inventive features, will become apparent from the detailed description provided herein.

SUMMARY

A mutant *Bacillus subtilis* is provided. The mutant *B. subtilis* does not express a functional 3-ketoacyl-acyl carrier protein (ACP) synthase III (KASIII) selected from the group consisting of KASIIIA and KASIIIB. In an embodiment, the mutant *B. subtilis* does not express a functional KASIIIA and a functional KASIIIB.

A method of making the mutant *B. subtilis* is also provided. The method comprises introducing into wild-type *B. subtilis* a mutation selected from the group consisting of a mutation that prevents expression of a functional KASIIIA and a mutation that prevents expression of a functional KASIIIB. In an embodiment, the method comprises introducing into wild-type *B. subtilis* a mutation that prevents expression of a functional KASIIIA and a mutation that prevents expression of a functional KASIIIB.

Also provided is a mutant *Rhodospirillum rubrum*. The mutant *R. rubrum* does not express a functional polyhydroxyalkanoate (PHA) polymerase selected from the group consisting of PhaC1, PhaC2, and PhaC3. In an embodiment, the mutant *R. rubrum* does not express a functional PhaC1, a functional PhaC2, and a functional PhaC3.

Thus, also provided is a method of making the mutant *R. rubrum*. The method comprises introducing into wild-type *R. rubrum* a mutation selected from the group consisting of a mutation that prevents expression of a functional PhaC1, a mutation that prevents expression of a functional PhaC2, and a mutation that prevents expression of a functional PhaC3. In an embodiment, the method comprises introducing into wild-type *R. rubrum* a mutation that prevents expression of a functional PhaC1, a mutation that prevents expression of a functional PhaC2, and a mutation that prevents expression of a functional PhaC3.

Further provided is a method of characterizing substrate specificity of a KASIII. The method comprises expressing the KASIII, which is not expressed in wild-type *B. subtilis*, in an above-described mutant *B. subtilis* and assessing the production of ω-functionalized fatty acids. In an embodiment, the KASIII is derived from an organism, the wild-type of which produces ω-functionalized fatty acids. In another embodiment, the KASIII is derived from an organism, the wild-type of which does not normally produce ω-functionalized fatty acids.

Still further provided is another method of characterizing substrate specificity of a KASIII enzyme. The method comprises expressing the KASIII, which is not expressed in wild-type *R. rubrum*, in an above-described mutant *R. rubrum* and assessing the production of ω-functionalized fatty acids. In an embodiment, the KASIII is derived from an organism, the wild-type of which produces ω-functionalized fatty acids. In another embodiment, the KASIII is derived from an organism, the wild-type of which does not normally produce ω-functionalized fatty acids.

Yet still further provided is a method of altering the specificity of a KASIII for at least one of its substrates. The method comprises introducing into the KASIII one or more mutations comprising at least one mutation, which causes the rotamer conformation of a phenylalanine in the KASIII corresponding to Phe304 in KASIII from *E. coli* to change. In one embodiment, the KASIII is from *E. coli*, and the one or more mutations comprises a mutation of Leu220, alone or in further combination with Val215. The mutation of Leu220 can be Leu220Met, and the mutation of Val215 can be Val215Phe. The rotamer conformation of Phe304 can be changed from an active site-distal rotamer conformation, in which the Phe304 is oriented away from the active site, to an active site-proximal rotamer conformation, in which the side chain of Phe304 faces towards the active site. In another embodiment, the KASIII is KASIIIA from *B. subtilis*, and the one or more mutations comprises a mutation of Met213, alone or in further combination with Phe208. The mutation of Met213 can be Met213Leu, and the mutation of Phe208 can be Phe208Val. The rotamer conformation of Phe297 can be changed from an active site-distal rotamer conformation, in which the Phe297 is oriented away from the active site, to an active site-proximal rotamer conformation, in which the side chain of Phe297 faces towards the active site. In yet another embodiment, the KASIII is KASIIIB from *B. subtilis*, and the one or more mutations comprise a mutation of Trp221 and a mutation of Val226. The mutation of Trp221 can be Trp221Val, and the mutation of Val226 can be Val226Leu. The rotamer conformation of Phe310 can be changed from an active site-distal rotamer conformation, in which the Phe310 is oriented away from the active site, to an active site-proximal rotamer conformation, in which the side chain of Phe310 faces towards the active site. In still yet another embodiment, the KASIII is from the KASIII is from *Aeromonas hydrophila, Bacteroides vulgatus, Brevibacierium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius, Staphylococcus aureus, Legionella pneumophila*, or *Myxococcus xanthus*.

An isolated or purified nucleic acid molecule comprising a nucleotide sequence encoding a mutant KASIII is also provided. The isolated or purified nucleic acid molecule can be a vector. The mutant KASIII comprises one or more mutations comprising at least one mutation, which causes the rotamer conformation of a phenylalanine in the KASIII corresponding to Phe304 in KASIII from *E. coli* to change. In one embodiment, the KASIII is from *E. coli*, and the one or more mutations comprises a mutation of Leu220, alone or in further combination with Val215. The mutation of Leu220 can be Leu220Met, and the mutation of Val215 can be Val215Phe. The rotamer conformation of Phe304 can be changed from an active site-distal rotamer conformation, in which the Phe304 is oriented away from the active site, to an active site-proximal rotamer conformation, in which the side chain of Phe304 faces towards the active site. In another embodiment, the KASIII is KASIIIA from *B. subtilis*, and the one or more mutations comprises a mutation of Met213, alone or in further combination with Phe208. The mutation of Met213 can be Met213Leu, and the mutation of Phe208 can be Phe208Val. The rotamer conformation of Phe297 can be changed from an active site-proximal rotamer conformation to an active site-distal rotamer conformation. In yet another embodiment, the KASII is KASIIIB from *B. subtilis*, and the one or more mutations comprise a mutation of Trp221 and a mutation of Val226. The mutation of Trp221 can be Trp221Val, and the mutation of Val226 can be Val226Leu. The rotamer conformation of Phe310 can be changed from an active site-proximal rotamer conformation, in which the side chain of Phe310 faces towards the active site, to an active site-distal rotamer conformation, in which the Phe310 is oriented away from the active site. In still yet another embodiment, the KASIII is from the KASIII is from *Aeromonas hydrophila, Bacteroides vulgatus, Brevibacterium linens, Capnocytophaga gingivalis. Thermus aquaticus. Bacillus licheniformis, Desulfovibrio vulgaris, Bacillus subtilis* subsp. *S, Haliangium ochraceum, Alicyclobacillus acidocaldarius, Staphylococcus aureus, Legionella pneumophila*, or *Myxococcus xanthus*.

A host cell or organism is also provided. The host cell or organism comprises an above-described isolated or purified nucleic acid molecule.

Further provided is an isolated or purified mutant KASIII. The mutant KASIII comprises one or more mutations comprising at least one mutation, which causes the rotamer conformation of a phenylalanine in the KASIII corresponding to Phe304 in KASIII from *E. coli* to change. In one embodiment, the KASIII is from *E. coli*, and the one or more mutations comprises a mutation of Leu220, alone or in further combination with Val215. The mutation of Leu220 can be Leu220Met, and the mutation of Val215 can be Val215Phe. The rotamer conformation of Phe304 can be changed from an active site-distal rotamer conformation, in which the Phe304 is oriented away from the active site, to an active site-proximal rotamer conformation, in which the side chain of Phe304 faces towards the active site. In another embodiment, the KASIII is KASIIIA from *B. subtilis*, and the one or more mutations comprises a mutation of Met213, alone or in further combination with Phe208. The mutation of Met213 can be Met213Leu, and the mutation of Phe208 can be Phe208Val. The rotamer conformation of Phe297 can be changed from an active site-proximal rotamer conformation, in which the side chain of Phe297 faces towards the active site, to an active site-distal rotamer conformation, in which Phe297 is oriented away from the active site. In yet another embodiment, the KASIII is KASIIIB from *B. subtilis*, and the one or more mutations comprise a mutation of Trp221 and a mutation of Val226. The mutation of Trp221 can be Trp221Val, and the mutation of Val226 can be Val226Leu. The rotamer conformation of Phe310 can be changed from an active site-proximal rotamer conformation, in which the side chain of Phe310 faces towards the active site, to an active site-distal rotamer conformation, in which Phe310 is oriented away from the active site. In still yet another embodiment, the KASIII is from the KASIII is from *Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius, Staphylococcus aureus. Legionella pneumophila*, or *Myxococcus xanthus*.

Still further provided is an in vitro, high-throughput spectrophotometric method of assaying KASIII activity. The method comprises (i) incubating holo-ACP, malonyl-CoA, dithiothreitol (DTIT), acyl-CoA, NADPH, and malonyl-CoA:ACP transacylase (FabD), (ii) adding KASIII and 3-ketoacyl-ACP reductase (FabG), and (iii) measuring the change in absorbance at 340 nm when NADPH is converted to NADP+ during reduction of 3-ketoacyl-ACP to 3-hydroxyl-acyl-ACP by FabG. In an embodiment, the acyl-CoA is a straight-chain-CoA, a branched-chain-CoA or a hydroxylated-CoA. Preferably, incubating in (i) is for about two minutes, e.g., two minutes, in the presence of a buffer, such as sodium phosphate buffer, at neutral pH, e.g., pH 7.2.

Even still further provided is a method of producing bi-functional fatty acids in a host cell or organism. The method comprises introducing into a host cell or organism, which comprises one or more ω-functionalized acyl-CoAs, and expressing therein a nucleic acid molecule comprising a nucleotide sequence encoding a KASIII, which can use one or more of the ω-functionalized acyl-CoAs as a substrate. The one or more ω-functionalized acyl-CoAs can be functionalized at the ω-position with a moiety comprising a hydroxyl group, a benzoyl group, a cyclic group, a branched-chain group, an amino group, or a halo group. The host cell or organism can be a mutant *R. rubrum*, such as a mutant *R. rubrum* described above.

BRIEF DESCRIPTION OF THE FIGURES

FIG. 100C is a graph of protons of ligand isobutyryl-CoA vs. STD amplification factor ($STD_{af}$) for *E. coli* KASIII.

FIG. 17 shows an alignment of conserved residues of KASIIIs from Gram-negative and Gram-positive bacteria, including those KASIIIs analyzed in the Examples (*), nine experimentally confirmed KASIII enzymes, and six uncharacterized KASIII proteins (†). Seventeen conserved residues are shown, which are grouped into five structural categories. Branched-chain fatty acid content (%) is provided for each bacterium (Ratledge, C., and Wilkinson, S. G. (1988) *Microbial Lipids*, Academic Press, UK). Phylogenetic sub-family from KASIII tree is also provided for each bacterium (Chen et al., Protein Sci. 20: 1659-1667 (2011)). Residues conserved in KASIIIs from Gram-negative and Gram-positive bacteria are highlighted in black, whereas homologous substitutions are shown in gray, and non-conserved residues are shown in white. Residue numbering corresponds to the residue position in *E. coli* KASIII (GenBank Accession AAG55837.1).

FIG. 19 shows a comparison of structural and functional features of KASIIIs, including those analyzed in the Examples (*). The enzymes are grouped into five structure-function groups based on phylogenetic analysis (see Examples) and structural and functional features. Residues highlighted in black are similar or identical to the residues occurring in KASIII with broad substrate specificity, such as *S. aureus* KASIII. Non-functional KASIII proteins are highlighted in gray. N.D.=not determined.

DETAILED DESCRIPTION

Figure 1:
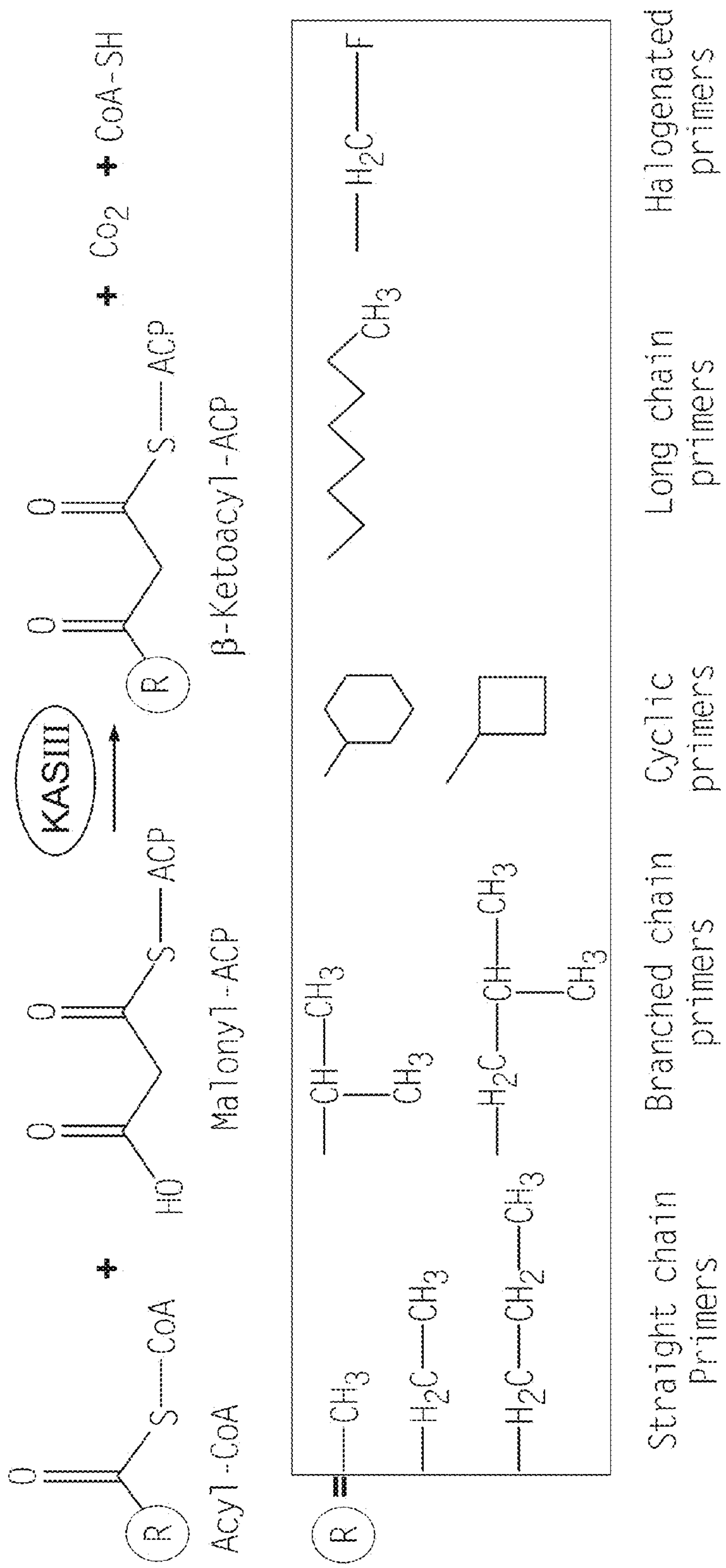
FIG. 1 is a schematic diagram of the Claisen condensation reaction catalyzed by KASIII.
Figure 2:
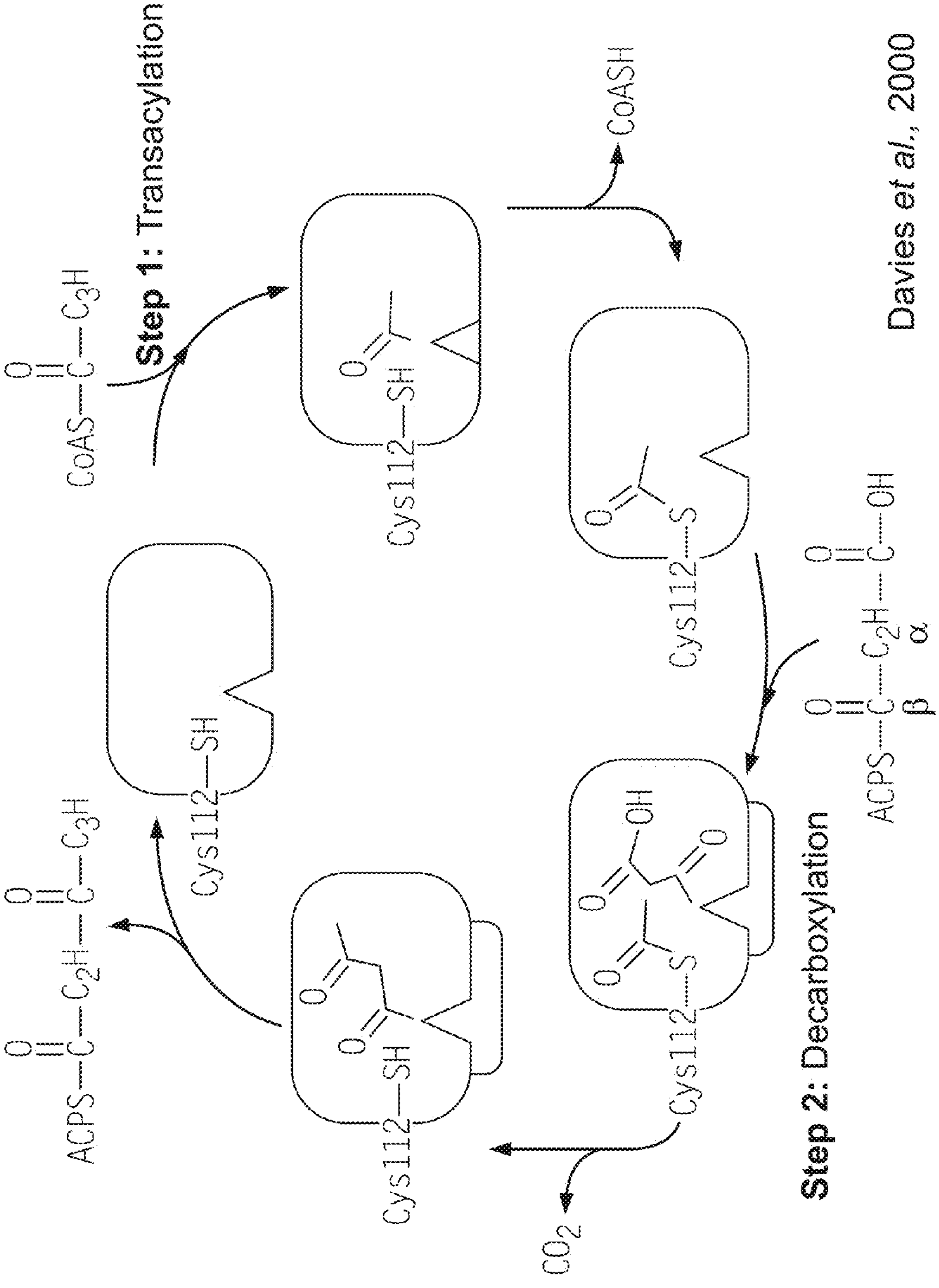
FIG. 2 is a schematic diagram of the reaction mechanism of *E. coli* FabH proposed by Davies et al.

The present disclosure is predicated, at least in part, on the discovery that bi-functional fatty acids, including bi-functional fatty acids that do not occur naturally, can be made by introducing into a host organism, which expresses one or more acyl-CoA starter substrates of interest, an exogenous 3-ketoacyl-acyl carrier protein (ACP) synthase III (KASIII), such as a wild-type KASIII from another organism, a natural variant thereof, or a mutant thereof. KASIII catalyzes a reaction that creates a new carbon-carbon bond that links two precursor molecules together. Precursor molecules (also referred to herein as "substrates" and "starter substrates"; e.g., acetyl-CoA, isobutyryl-CoA, hydroxyl acyl-CoA, or benzoyl-CoA) are extended by two carbon atoms by condensation with malonyl-ACP. The host organism can be modified to express more or less of a given acyl-CoA starter substrate or a different acyl-CoA starter substrate. Additionally or alternatively, the host organism can be modified to reduce, preferably eliminate, fatty acid degradation and/or termination of fatty acid elongation and/or to secrete fatty acids so produced. The materials and methods have application for bio-based chemicals, such as surfactants, lubricants, food oils, polymers, and the like.

"Bi-functional fatty acid" is used herein to refer to a fatty acid, which comprises a functional group, such as a carboxyl-containing group (—COOH), at the a end and another functional group, which can be the same or different, such as a hydroxyl-containing group (—OH), a benzoyl group, a nitrogen-containing group (—N), such as an amino-containing group (e.g., an amino-carboxylic acid), or a halogen-containing group (—X) at the ω end. The functional group can be a straight chain, a branched chain (e.g., iso or ante-iso), or a cyclic group. While the production of bi-functional fatty acids has been demonstrated in bacteria herein, such production can be adapted to other hosts, such as algae, yeast, plants, and animals.

Amino acids may be identified herein in accordance with convention. Either a three-letter code or a single-letter code may be used, wherein the 20 naturally occurring amino acids are identified as follows:

| Amino acid | Three-Letter Code | Single-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In view of the above, a mutant *Bacillus subtilis* is provided. The mutant *B. subtilis* does not express a functional KASIII selected from the group consisting of KASIIIA (BsKASIIIA (bfabHA (yjaX) locus); GenBank Accession No. CAB 12974.1; nucleotide sequence [SEQ ID NO:63]; amino acid sequence [SEQ ID NO:64]) and KASIIIB (BsKASIIIB (bfabHB (yhfB) locus); GenBank Accession No. CAB 12857.1; nucleotide sequence [SEQ ID NO:65]; amino acid sequence [SEQ ID NO:66]). In one embodiment, the mutant *B. subtilis* does not express a functional KASIIIA and a functional KASIIIB. While wild-type *B. subtilis* normally produces linear, iso-branched, and ante-iso-branched fatty acids, the double deletion mutant lacks KASIII activity and fails to grow unless provided with exogenous fatty acids.

Accordingly, also provided is a method of making a mutant *B. subtilis*. The method comprises introducing into wild-type *B. subtilis* a mutation selected from the group consisting of a mutation that prevents expression of a functional KASIIIA and a mutation that prevents expression of a functional KASIIIB. The method can comprise introducing into wild-type *B. subtilis* a mutation that prevents expression of a functional KASIIIA and a mutation that prevents expression of a functional KASIIIB. Preferably, the mutation is a gene knock-out. A gene-deletion knock-out mutation can be preferred because it eliminates the possibility of revertants occurring.

The double deletion mutant can be "rescued" by the expression therein of a functional KASIII gene (such as an exogenous KASIII gene, e.g., a KASIII gene from *Alicyclobacillus acidocaldarius*). Thus, the double deletion mutant can be used to characterize an exogenous KASIII, such as in accordance with the methods exemplified herein. Chemically modified carboxylic acids can be fed to the rescued double deletion mutant to determine whether or not the exogenous KASIII can incorporate these modified carboxylic acids into the ω-end of fatty acids. For example, the KASIII from *A. acidocaldarius* can use 3-hydroxybutyryl-CoA (generated from the 3-hydroxybutyric acid that was provided in the media) to produce hydroxypalmitate (16-carbon chain) and hydroxystearate (18-carbon chain).

In this regard, the mutant *B. subtilis* can be used to characterize an exogenous KASIII, which is a wild-type KASIII, a naturally occurring variant thereof, or a mutant thereof, e.g., a mutant with altered starter substrate specificity. "Altered starter substrate specificity," as used herein, can mean a change in the relative preference of a KASIII for one substrate over another substrate, the loss of the ability to use a given substrate, or the gain of the ability to use a given substrate. Thus, also provided is a method of characterizing substrate specificity of a KASIII. The method comprises expressing the KASIII, which is not expressed in wild-type *B. subtilis*, in a mutant *B. subtilis*, such as a mutant *B. subtilis*, which lacks a functional KASIIIA and a functional KASIIIB, in the presence of ω-functionalized carboxylic acid starter substrate and assessing the production of ω-functionalized fatty acids. The KASIII can be derived from an organism, the wild-type of which produces ω-functionalized fatty acids. Alternatively, the KASIII can be derived from an organism, the wild-type of which does not normally produce ω-functionalized fatty acids.

Also in view of the above, a mutant *Rhodospirillum rubrum* is provided. Wild-type *R. rubrum* generates large quantities of hydroxybutyryl-CoA, which is usually polymerized by polyhydroxyalkanoate (PHA) polymerase (encoded by the phaC gene), as a means of storing carbon and energy (Jin et al., J. Bacteriol. 194: 5522-5529 (2012)). *R. rubrum* specifically assembles polyhydroxybutyrate from hydroxybutyryl-CoA, which is produced from acetyl-CoA in a two-step reaction. The first step is the condensation of two acetyl-CoA molecules to form acetoacetyl-CoA (catalyzed by acetoacetyl-CoA thiolase, which is encoded by the phaA gene), and the second step is the reduction of acetoacetyl-CoA to form hydroxybutyryl-CoA (catalyzed by acetoacetyl-CoA reductase, which is encoded by the phaB gene). The *R. rubrum* genome contains three genes (Rru_A0275, Rru_A2413 and Rru_A1816) encoding PHA polymerases, which are designated phaC1, phaC2, and phaC3 (Jin et al., J. Bacteriol. 194: 5522-5529 (2012)). One of them (phaC1) is located in the pha operon, adjoining the phaA and the phaB genes. PhaC2 and PhaC3 share highest sequence conservation (50.2% identity), and PhaC1 is equally distinct from PhaC2 and PhaC3 (14.3% and 18.4% sequence identity, respectively). The mutant *R. rubrum* provided herein does not express a functional PHA polymerase selected from the group consisting of PhaC1, PhaC2, and PhaC3. In one embodiment, the mutant *R. rubrum* does not express a functional PhaC1, a functional PhaC2, and a functional PhaC3. The triple mutant fails to accumulate any PHA polymer, with only a slight impact on growth characteristics. The triple mutant still has the capacity to generate hydroxybutyryl-CoA.

A method of making a mutant *R. rubrum* is also provided. The method comprises introducing into wild-type *R. rubrum* a mutation selected from the group consisting of a mutation that prevents expression of a functional PhaC1, a mutation that prevents expression of a functional PhaC2, and a mutation that prevents expression of a functional PhaC3. The method can comprise introducing into wild-type *R. rubrum* a mutation that prevents expression of a functional PhaC1, a mutation that prevents expression of a functional PhaC2, and a mutation that prevents expression of a functional PhaC3. Preferably, the mutation is a gene knock-out. A gene knock-out mutation can be preferred because it eliminates the possibility of revertants occurring.

The mutant *R. rubrum* can be used to characterize an exogenous KASIII, such as in accordance with the methods described herein. The hydroxyacyl-CoA, such as hydroxybutyryl-CoA, present in the mutant *R. rubrum* is available as a starter substrate for the exogenous KASIII. Whether or not the exogenous KASIII incorporates the hydroxylacyl-CoA into fatty acids can be determined. Expression of *A. acidocaldarius* KASIII in the mutant *R. rubrum*, for example, results in the production of 15-hydroxy-palmitate, which does not occur normally in any known system.

In this regard, the mutant *R. rubrum* can be used to characterize an exogenous KASIII, which is a wild-type KASIII, a naturally occurring variant thereof, or a mutant thereof, e.g., a mutant with altered starter substrate specificity. Thus, also provided is a method of characterizing substrate specificity of a KASIII enzyme. The method comprises expressing the KASIII enzyme, which is not expressed in wild-type *R. rubrum*, in a mutant *R. rubrum*, such as a mutant *R. rubrum*, which lacks functional PhaC1, PhaC2, and PhaC3, in the presence of ω-functionalized acyl-CoA starter substrate and assessing the production of ω-functionalized fatty acids. The KASIII enzyme can be derived from an organism, the wild-type of which produces ω-functionalized fatty acids. Alternatively, the KASIII can be derived from an organism, the wild-type of which does not normally produce ω-functionalized fatty acids.

The above mutant *B. subtilis* and mutant *R. rubrum* can be generated in accordance with any suitable method known in the art, including, but not limited to, methods described and exemplified herein. Mutations, such as substitutions, insertions, deletions, and/or side chain modifications, can be introduced into the nucleotide and amino acid sequences of the gene of interest using any suitable technique known in the art, including site-directed mutagenesis (Wu, ed., Meth. Enzymol. 217, Academic Press (1993)). The lambda red recombinase method can be used to "knock out" genes (Datsenko et al., PNAS USA 97: 6640-6645 (2000)). A kanamycin disruption cassette flanked by FLP recognition target sites can be used to excise a cassette precisely and create an in-frame deletion (Baba et al., Mol. System. Biol. 2: 2006-2008 (2006)). Permanent, marker-free, multiple gene disruptions can be created. Non-naturally occurring nucleotides and amino acids also can be used.

An isolated or purified mutant (or chimeric) KASIII derived from a wild-type KASIII, such as a KASIII from family KS1 (ketoacyl synthase 1) on the worldwide web at enzyme(dot) cbirc(dot)iastate(dot)edu, which website is incorporated by reference herein for its teachings regarding KASIII, is also provided. Examples include a KASIII from a bacterium, such as *E. coli* and *B. subtilis*, as described and exemplified herein. Other examples include *Aeromonas hydrophila* (ATCC Deposit No. 7966; GenBank Accession No. YP_857537.1; nucleotide sequence [SEQ ID NO:67]; amino acid sequence [SEQ ID NO:68]), *Bacteroides vulgatus* (ATCC Deposit No. 8482; GenBank Accession No. ABR38167.1; YP_001297789.1; nucleotide sequence [SEQ ID NO:77]; amino acid sequence [SEQ ID NO:78]), *Brevibacterium linens* (KAS_BvL1: GenBank Accession No. AAGP010000; ZP_05913013.1; nucleotide sequence [SEQ ID NO:85]; amino acid sequence [SEQ ID NO:86]; KAS_BvL2: GenBank Accession No. AAGP010000;

ZP_05912949.1; nucleotide sequence [SEQ ID NO:87]; amino acid sequence [SEQ ID NO:88]), *Capnocytophaga gingivalis* (KAS_CG1: ATCC Deposit No. 33624; GenBank Accession No. EEK13720.1; ZP_04058441.1; nucleotide sequence [SEQ ID NO:79]: amino acid sequence [SEQ ID NO:80]; KAS_CG2: ATCC Deposit No. 33624; GenBank Accession No. EEK14223.1; ZP_04057621; nucleotide sequence [SEQ ID NO:81]; amino acid sequence [SEQ ID NO:82]; KAS_CG3: ATCC Deposit No. 33624; GenBank Accession No. EEK14078.1; ZP_04058132.1; nucleotide sequence [SEQ ID NO:83]; amino acid sequence [SEQ ID NO:84]). *Thermus aquaticus* (GenBank Accession No. EED09603.1; ZP_03497263.1; nucleotide sequence [SEQ ID NO:89]; amino acid sequence [SEQ ID NO:90]), *Bacillus licheniformis* (KAS_BaL1: ATCC Deposit No. 14580; GenBank Accession No. AAU22783.1; YP_078421.1; nucleotide sequence [SEQ ID NO:91]; amino acid sequence [SEQ ID NO:92]; KAS_BaL2: ATCC Deposit No. 14580; GenBank Accession No. AAU22657.1; nucleotide sequence [SEQ ID NO:93]; amino acid sequence [SEQ ID NO:94]), *Desulfovibrio vulgaris* (GenBank Accession No. ACL10038.1; YP_002437506.1; nucleotide sequence [SEQ ID NO:107]; amino acid sequence [SEQ ID NO:108], *Bacillus subtilis* subsp. S (ATCC Deposit No. 6633; GenBank Accession No. EFG91245.1; ZP_06874900.1; nucleotide sequence [SEQ ID NO:101]; amino acid sequence [SEQ ID NO:102]), *Haliangium ochraceum* (GenBank Accession No. ACY12771.1; YP_003264664.1; nucleotide sequence [SEQ ID NO: 103]; amino acid sequence [SEQ ID NO: 104]), *Alicyclobacillus acidocaldarius* (GenBank Accession No. ACV57087.1; nucleotide sequence [SEQ ID NO: 105]; amino acid sequence [SEQ ID NO: 106]), *Staphylococcus aureus* (GenBank Accession No. BAB57145.1; NP_371507.1; nucleotide sequence [SEQ ID NO:109]; amino acid sequence [SEQ ID NO: 110]), *Legionella pneumophila* (KAS_LP1: GenBank Accession No. CAH12499.1; YP_123672.1; nucleotide sequence [SEQ ID NO:69]; amino acid sequence [SEQ ID NO:70]; KAS_LP2: GenBank Accession No. CAH13332.1; YP_124492; nucleotide sequence [SEQ ID NO:71]; amino acid sequence [SEQ ID NO:72]; KAS_LP3: GenBank Accession No. CAH13337.1; YP_124497: nucleotide sequence [SEQ ID NO:73]; amino acid sequence [SEQ ID NO:74]; KAS_LP4: GenBank Accession No. CAH12752.1; YP_123920; nucleotide sequence [SEQ ID NO:75]; amino acid sequence [SEQ ID NO:76]), *Myxococcus xanthus* (KAS_MX1: GenBank Accession No. ABF92307.1; YP_628497.1; nucleotide sequence [SEQ ID NO:95]; amino acid sequence [SEQ ID NO:96]; KAS_MX2: GenBank Accession No. ABF89527.1; YP_635461.1; nucleotide sequence [SEQ ID NO:97]; amino acid sequence [SEQ ID NO:98]; KAS_MX3: GenBank Accession No. ABF92876.1; YP_629114.1; nucleotide sequence [SEQ ID NO:99]; amino acid sequence [SEQ ID NO:100]), and the like. Yet other examples include *Yersinia pestis* (ZP_02318831.1), *Stappia aggregata* (ZP_01545409.1), *Erythrobacter* sp. SD-21 (ZP_01865126.1 and ZP_01040217.1), *Physcomitrella patens* (XP_001754014.1), *Synechococcus* sp. CC9605 (ABB36118.1), *Renibacterium salmoninarum* (ATCC Deposit No. 33209; YP_001626411.1), *Chloroflexus aurantiacus*, and those set forth below in the "KASIII Enzymes" table. Also, see the "Examples" herein. Depending on the particular KASIII (e.g., a KASIII from family KS1 on the worldwide web at enzyme(dot)cbirc(dot)iastate(dot)edu that has been mutated, such mutants can have altered substrate specificity and/or altered level of activity. Mutants can be derived from wild-type KASIIIs in accordance with methods known in the art (e.g., site-directed mutagenesis) and described and exemplified herein. Also, the same amino acid sequence can be encoded by nucleotide sequences that vary due to the degeneracy of the genetic code.

KASIII Enzymes

| Genus Species | RefSeq |
|---|---|
| *Yersinia pestis* | ZP_02318831.1, YP_001678077.1 |
| *Yersinia enterocoliticas* | YP_001005922.1 |
| *Vibrio Cholerae*, O1 biovar E1 | ZP_04418348.1, NP_231657.1, ZP_04411352.1, ZP_04961806.1 |
| *Vibrio splendidus* | YP_002416637.1 |
| *Vibrio parahaemolyticus* RIMD | NP_798435.1, ZP_05904665.1 |
| *Vibrio alginolyticus* | ZP_06181412.1 |
| *Vibrio harveyi*, ATCC BAA | ZP_06176396.1, ZP_06176396.1 |
| *Aeromonas salmonicida* | YP_001141871.1 |
| *Aeromonas hydrophila* | YP_856773.1 |
| *Pasteurella multocida* | NP_246853.1 |
| *Haemophilus influenzae* | ZP_00154722.2, YP_001290328.1, ZP_01789313.1, ZP_01784255.1, ZP_01797068.1, NP_438327.1, ZP_01792978.1, YP_003519776.1, YP_003557294.1 |
| *Haemophilus ducreyi* | NP_873290.1 |
| *Serratia odorifera* | ZP_06640853.1, ZP_06189616.1 |
| *Serratia proteamaculans* | YP_001478135.1 |
| *Vibrio harveyi* | ZP_06176396.1 |
| *Vibrio harveyi*_ATCC_BAA-1 | YP_001446090.1 |
| *Vibrio splendidus* | YP_002416637.1 |
| *Vibrio vulnificus* | NP_761811.1 |
| *Xanthomonas campestris*_pv._c, a | YP_244293.1, NP_636392.1, ZP_06490218.1, YP_244293.1, NP_636392.1, ZP_06490218.1, YP_362874.1 |
| *Xanthomonas oryzae*_pv._oryz | ZP_02242169.1, YP_449832.1, |
| *Legionella longbeachae* | ZP_06185395.1, YP_003454953.1 |
| *Legionella pneumophila*_str | YP_123672.1, YP_126694.1 |
| *Neisseria cinerea* | ZP_05982749.1 |
| *Neisseria elongata* | ZP_06735426.1 |
| *Neisseria flavescens* | ZP_04757560.1, ZP_03720464.1 |

-continued

| KASIII Enzymes | |
|---|---|
| Genus Species | RefSeq |
| *Neisseria gonorrhoeae* | ZP_04735631.1, YP_209174.1, ZP_05795165.1 |
| *Neisseria lactamica* | ZP_05986719.1 |
| *Neisseria meningitidis* | YP_974421.1, YP_002342022.1, NP_274910.1, YP_003082489.1, CBA07454.1, CAX50870.1 |
| *Neisseria sicca* | ZP_05317661.1 |
| *Neisseria subflava* | ZP_05985366.2 |
| *Francisella tularensis*_subsp | ABK78999.1, YP_513827.1, YP_001428636.1, ABK78992.1, YP_763623.1 |
| *Thiobacillus denitrificans* | YP_315309.1 |
| *Escherichia coli* | YP_002292430.1, 1MZS, YP_001457935.1, YP_001002812.1, |
| *Escherichia coli*_K-12 | NP_669073.1 |
| *Shigella dysenteriae* | YP_403645.1 |
| *Shigella flexneri*_2a_str | NP_707007.1 |
| *Klebsiella pneumoniae* | YP_002239290.1, YP_001334752.1 |
| *Enterobacter_cloacae*_sub s | YP_003613037.1 |
| *Proteus mirabilis* | YP_002150616.1, ZP_03842098.1 |
| *Providencia stuartii* | ZP_02960986.1 |
| *Bordetella parapertussis* | NP_885474.1 |
| *Bordetella pertussis* | NP_881071.1 |
| *Xanthobacter autotrophicus* | P3H77, YP_001419263.1 |
| *Rhodomicrobium vannielii* | ZP_06349548.1 |
| *Rhodopseudomonas palustris* | YP_569816.1, YP_486263.1, ZP_06361298.1, NP_948084.1, YP_781743.1, YP_532544.1 |
| *Anabaena variabilis* | YP_323237.1 |
| *Synechocystis* sp. | BAA18018.1 |
| *Synechococcus* spp. | YP_001733788.1, ZP_01084650.1, ZP_01084650.1, ZP_01471198.1, YP_376322.1, ZP_01468767.1, NP_898337.1, ZP_05789459.1, ABB36118.1, YP_382673.2, ZP_01081021.1 |
| *Bacteroides ovatus* | ZP 06616069, ZP 02063379, ZP 02067060 |
| *Bacteroides thetaiotaomicron* | NP_81275, NP_809035 |
| *Bacteroides fragilis* | ZP_05283826, YP_101365, YP_100487, ZP_05282747 |
| *Bacteroides vulgatus* | YP_001297789 |
| *Bacteroides* sp. | ZP_06077075 |
| *Capnocytophaga ochracea* | YP_003140158.1 |
| *Capnocytophaga gingivalis* | ZP_04058441.1 |
| *Algoriphagus* sp. | ZP_01718224.1 |
| *Salinibacter ruber* DSM 13855 | YP_444197.1 |
| *Cytophaga hutchinsonii* | YP_678233.1 |
| *Micrococcus luteus* | YP_002957006.1, ZP_06503185.1 |
| *Peptostreptococcus anaerobius* | ZP_06425389.1 |
| *Mycobacterium tuberculosis* | P2AJ9, 2AHB, PNP_215047.1, 1M1M, ZP_02548981.1, |
| *Vibrio Cholerae* | ZP_01977036.1, ZP_04417767.1, ZP_06048029.1, ZP_01679181.1, ZP_01868999.1, |
| *Vibrio splendidus* | ZP_00993243.1, YP_002395289.1 |
| Vibrio parahaemolyticus RIMD | ZP_05118776.1, ZP_05905223.1, NP_800481.1, ZP_05909890.1 |
| *Vibrioharveyi*, ATCC BAA | YP_001447821.1, ZP_06178483.1, ZP_01985466.1 |
| *Vibrio vulnificus* | NP_936962.1, NP_762318.1 |
| *Aeromonas salmonicida* | YP_001142999.1 |
| *Aeromonas hydrophila* | YP_855582.1 |
| *Arthrobacter aurescens* TC1 | YP_948164.1 |
| *Brevibacterium linens* | ZP_05913013.1_ |
| *Cellulomonas flavigena* | YP_003637243.1 |
| *Rothia dentocariosa* | ZP_06906913.1 |
| *Streptomyces coelicolor* | NP_627458.1, NP_630009.1, NP_625558.1 |
| *Streptomyces griseus* | YP_001828147.1, AAQ08929.1 |
| *Streptomyces griseus* subsp | YP_001826619.1 |
| *Vibrioharveyi*_ATCC_BAA-1 | YP_001447821.1 |
| *Vibrio harveyi* | ZP_06178483.1, ZP_01985466.1 |
| *Vibrio splendidus* | ZP_00993243.1, YP_002395289.1 |
| *Vibriovulnificus* | NP_936962.1, NP_762318.1 |
| *Clostridium perfringens* E, str, C, CP | ZP 02633999.1, NP 561984.1, ZP 02863431, YP 695770.1, ZP 02640909.1, YP 698458.1 |
| *Clostridium botulinum* D st, B s, E3, B, Ba4, A s, F s, A3 | ZP_04862054, YP_001885344.1, YP_001920474.1, YP_001783240.1, YP_002864614.1, ZP_02618347.1, ZP_02615736.1, YP_001256083.1, YP_001392959.1, YP_001788947.1 |
| *Clostridium thermocellum* | YP 001037363.1, YP_001036566.1 |
| *Clostridium sporogenes* | ZP_02993884.1 |
| *Geobacillus* Y412MC10 | YP_002948901.1, ZP_05371368.1, ADI27688.1, ZP_03146734 |

-continued

| KASIII Enzymes | |
|---|---|
| Genus Species | RefSeq |
| *Staphylococcus aureus* | ZP_05601460.1, PNP_645682.1, CBI48861.1 |
| *Staphylococcus epidermidis* | NP_764232.1, ZP_04818718.1 |
| *Staphylococcus warneri* | ZP_04677499.1 |
| *Staphylococcus capitis* | ZP_03612995.1 |
| *Staphylococcus haemolyticus* | YP_253888.1 |
| *Staphylococcus hominis* | ZP_04059117.1 |
| *Staphylococcus saprophyticus* | YP_301888.1 |
| *Ruminococcus flavefaciens* | ZP_06142884.1 |
| *Ruminococcus albus* | ZP_06720344.1 |
| *Bacillus clausii* | YP_176043.1 |
| *Bacillus halodurans* | NP_243749.1 |
| *Bacillus pseudofirmus* | YP_003425377.1 |
| *Bacillus cellulosilyticus* | ZP_06363736.1 |
| *Bacillus selenitireducens* | ADH99048.1 |
| *Bacillus cytotoxicus* | YP_001374220.1 |
| *Bacillus cereus* | ZP_04216549.1, YP_002450207.1, ZP_03111602.1, YP_002365961.1, ZP_04232574.1, ZP_04299488.1, ZP_04226741.1, ZP_04202127.1 |
| *Bacillus mycoides* | ZP_04155996.1, ZP_04161820.1 |
| *Bacillus thuringiensis* | ZP_04144529.1, ZP_04119301.1, ZP_04064103.1 |
| *Bacillus coagulans* | ZP_04430458.1, ZP_01862223.1 |
| *Bacillus* sp. | ZP_01726102.1 |
| *Bacillus coahuilensis* | ZP_03225732.1 |
| *Bacillus amyloliquefacien* | YP_001420728.1 |
| *Bacillus pumilus* | YP_001486301.1 |
| *Bacillus licheniformis* | YP_078421.1 |
| *Desulfotomaculum acetoxid* | YP_003190685.1 |
| *Thermus aquaticus* | ZP_03497263.1 |
| *Thermus thermophilus* | YP_004024.1, P1UB7, ZP_05405201.1, YP_001113417.1, ZP_03734375.1 |
| *Campylobacter fetus*_subsp._f | YP_891441.1 |
| *Campylobacter jejuni*_subsp | ZP_06372697.1, ZP_06373244.1, YP_001398621.1, ZP_01067178.1, YP_178392.1, ZP_03222790.1, ZP_01810106.1, PZP_01100387.1, ZP_01069410.1, YP_001481881.1 |
| *Fusobacterium gonidiaformans* | ZP_05630604.1 |
| *Fusobacterium mortiferum* | ZP_04568082.1 |
| *Fusobacterium varium* | ZP_04859066.1 |
| *Myxococcus xanthus* | YP_635461.1 |
| *Stigmatella aurantiaca* | ZP_01460905.1 |
| *Capnocytophaga ochracea* | YP_003140583.1 |
| *Capnocytophaga gingivalis* | ZP_04057621 |
| *Algoriphagus* sp. | ZP_01720592.1 |
| *Flavobacterium johnsoniae* | YP_001192610.1 |
| *Cytophaga hutchinsonii* | YP_678504.1 |
| *Clostridium botulinum* F s, B1, Ba4, A s, A 2, A3, B s, E1 s, E3 | YP_001390078.1, YP_001780359.1, YP_002861584.1, ZP_02612773.1, YP_002803086.1, YP_001253259.1, YP_001786083.1, ZP_02618062.1, YP_001884875.1, ZP_04823833.1, YP_001920032.1 |
| *Clostridium sporogenes* | ZP_02994303.1 |
| *Bacillus thuringiensis* ser | ZP_04143036.1 |
| *Myxococcus xanthus* | YP_628497.1 |
| *Stigmatella aurantiaca* | ZP_01461080.1, ZP_01464359.1 |
| *Lactobacillus casei* | YP_807311.1 |
| *Lactobacillus plantarum* 1, su | NP_785253.1, ZP_04012979.1, YP_003062988.1 |
| *Lactobacillus helveticus* | YP_001578074.1 |
| *Lactobacillus fermentum* | YP_001843126.1 |
| *Lactobacillus delbrueckii* su | YP_812862.1, YP_618929.1 |
| *Desulfovibrio vulgaris* | YP_002437506.1, YP_010426.1 |
| *Desulfovibrio desulfuricans* | YP_388920.1 |
| *Streptococcus equi* subsp | YP_002122793.1 |
| *Streptococcus equi* subsp | YP_002745087.1 |
| *Legionella pneumophila*_str | YP_127488.1, YP_124492.1, YP_096240.1 |
| *Bacteroides fragilis* | YP_098105.1, ZP_05279764, YP_098107.1, ZP_05279766.1, ZP_05283454.1, ZP_05283453.1 |
| *Bacteroides* sp. | ZP_05284648, ZP_05286338.1, ZP_06076430.1, ZP_05288125.1, ZP_04850303.1, ZP_05284665.1, ZP_06093726.1, ZP_05285443.1 |
| Parabacteroides distasoni | ZP_05544531, YP_001304951.1 |

-continued

| KASIII Enzymes | |
|---|---|
| Genus Species | RefSeq |
| *Parabacteroides* sp. | ZP_05544549, ZP_05544544, ZP_05547823.1, ZP_05547825.1, ZP_05544531.1 |
| *Capnocytophaga gingivalis* | ZP_04058132.1 |
| *Clostridium thermocellum* | YP_001036564.1 |
| *Geobacillus* sp. | YP_003241015.1 |
| *Bacillus cereus* | ZP_04197006.1, ZP_04294582.1, ZP_04222169.1, ZP_03114282.1, YP_002450917.1, YP_083343.1, ZP_04283649.1, ZP_00239031.1, ZP_04322923.1, ZP_04185735.1 |
| *Bacillus mycoides* | ZP_04168455.1 |
| *Bacillus thuringiensis* | YP_894541.1, ZP_04078161.1 |
| *Vibrio Cholerae* | ZP_01982749.1 |
| *Vibrioharveyi* ATCC BAA | YP_001443904.1 |
| *Pseudomonas fluorescens* | YP_002873982.1, YP_258752.1, YP_347256.1, YP_002871305.1, YP_258783.1, YP_002871302.1, YP_002872773.1 |
| *Pseudomonas aeruginosa* PAO | ZP_03854283.1 |
| *Pseudomonas aeruginosa*_PA | YP_001670166.1, YP_002505552.1, YP_001349750.1 |
| *Pseudomonas aeruginosa* | ZP_06091406.1, YP_001349639.1, AAP35715.1, YP_560887.1, ZP_01364358.1, YP_002441910.1, PNP_249690.1, NP_252023.1 |
| *Pseudomonas aeruginosa*_PAO1 | NP_106422.1 |
| *Pseudomonas putida* | YP_001266829.1, YP_001750557.1 |
| *Pseudomonas syringae*_pv._t, tom, aver, pha, o, s, syr | ZP_03395719.1, NP_791771.1, ABQ23410.1, YP_275551.1, ZP_05638972.1, ZP_04587683.1, ZP_06499892.1, YP_236537.1, ZP_03395750.1, YP_275581.1, ZP_06460699.1 |
| *Vibrio harveyi*_ATCC_BAA-1 | YP_001443904.1 |
| *Xanthomonas campestris*_pv._v | YP_363742.1, ZP_06491606.1 |
| *Xanthomonas oryzae*_pv._oryz, | ZP_02243250.1, YP_451479.1, YP_201231.1, |
| *Legionella longbeachae* | ZP_06187897.1 |
| *Legionella pneumophila*_str | YP_127493.1, YP_096244.1, YP_001250982.1, YP_124497.1, NP_866833.1, ZP_04769890.1, |
| *Campylobacter coli* | ZP_00367350.1 |
| *Campylobacter jejuni*_subsp | ZP_06372437.1, YP_001397612.1, ZP_01068304.1, ZP_01069191.1, YP_179478.1, YP_001000977.1, ZP_03223081.1, ZP_06374174.1, ZP_01809975.1, ZP_01071227.1 |
| *Bacteroides* sp. | ZP 05287210.1 |
| *Parabacteroides johnsoni* | ZP 03477145 |
| *Lactobacillusplantarum* | YP 003062116.1, BAA93641.1 |
| *Staphylococcusepidermidis* | NP_863215.1, ZP_04818028.1 |
| *Staphylococcus capitis* | ZP_03613727.1 |
| *Bacillus cereus* | ZP_04218294.1, YP_002366551.1, NP_831535.1, ZP_04202709.1, ZP_04316975.1, YP_002445213.1, ZP_04227324.1, ZP_04294488.1, ZP_04196905.1, NP_978230.1, ZP_00236595.1, ZP_04288820.1, ZP_03108471.1, YP_083243.1, ZP_04283554.1, YP_002529555.1, YP_002337903.1 |
| *Bacillus cereus* | YP_002450821.1, ZP_04222067.1, ZP_04174069.1, ZP_04322830.1, ZP_04185649.1, ZP_04300078.1, YP_002749110.1, YP_245896.1 |
| *Bacillus mycoides* | ZP_04163379.1, ZP_04157778.1, ZP_04168363.1 |
| *Bacillus thuringiensis* | ZP_04071417.1, ZP_04101582.1, YP_003664162.1, ZP_04114339.1, ZP_04083919.1, ZP_04125963.1, ZP_00742862.1, YP_036004.1, ZP_04107829.1, ZP_04089938.1, YP_894441.1 |
| *Bacillus thuringiensis* ser | ZP_04096011.1, ZP_04078067.1 |
| *Bacillus subtilis* subsp. | ZP_06874900.1 |
| *Bacillus licheniformis* | YP_078295.1 |
| *Bacillus anthracis* str | NP_844246.1 |
| *Bacillus megaterium* | YP_003597285.1, YP_003562589.1, YP_003565870.1 |
| *Aeromonas salmonicida* | YP_001142803.1 |
| *Aeromonas hydrophila* | YP_857537.1 |
| *Haemophilus influenzae* | P3IL3 |
| *Pseudomonas putida* | YP_001670278.1, NP_746654.1, YP_001266689.1 |
| *Pseudomonas syringae*_pv._t, tom, a, o, pha | ZP_03399527.1, NP_793855.1, ZP_04587307.1, ZP_06482619.1, ZP_06460756.1, ZP_05640738.1, YP_273685.1 |
| *Myxococcus xanthus* | YP_629114.1 |
| *Rhodomicrobium vannielii* | ZP_06349538.1 |
| *Bacteroides* sp. | YP 001250373.1 |
| *Clostridium botulinum* A3, A s, B1, F s, A2 | ZP 02617328.1, YP 001787903.1, 001255081.1, 001782200.1, 001391882.1, 002805031.1, 02615189.1 |
| *Clostridium sporogenes* | ZP_02995301.1 |
| *Micrococcus luteus* | ZP_06503261.1, YP_002957382.1 |
| *Bacillus cereus* | ZP_03105077.1, ZP_04223379.1, ZP_04279606.1, YP_084527.1, ZP_04301428.1, ZP_04295615.1, ZP_04220174.1, |

-continued

| KASIII Enzymes | |
|---|---|
| Genus Species | RefSeq |
| *Bacillus mycoides* | ZP_04155556.1 |
| *Bacillus thuringiensis* ser | ZP_04085281.1, YP_895664.1, ZP_04109142.1 |
| *Bacillus subtilis* | yjaXTNP_389015.1 |
| *Bacillus subtilis* | yhfBTNP_388898.1 |
| *Bacillus subtilis* subsp. | BAI85702.1, NP_390087.1 |
| *Bacillus anthracis* str | NP_845551.1 |
| *Renibacterium salmoninaru* | YP_001626411.1 |
| *Yersinia pseudotuberculosis* | YP_070488.1, YP_001401081.1 |
| *Vibrio alginolyticus* | ZP_01258726.1, ZP_06180329.1 |
| *Vibrio vulnificus* | NP_760725.1 |
| *Brevibacterium linens* | ZP_05912949.1 |
| *Streptomycesgriseus* subsp g | AAF81237.1 |
| *Pseudomonas fluorescens* | YP_263190.1 |
| *Pseudomonas aeruginosa* | YP_001349751.1 |
| *Pseudomonas putida* | YP_095658.1 |
| *Pseudomonas syringae*_pv._a, s | ZP_06494049.1, ZP_06478421.1 |
| *Serratia odorifera* | ZP_06190585.1 |
| *Serratia proteamaculans* | YP_001479098.1 |
| *Vibrio vulnificus* | NP_760725.1 |
| *Xanthomonascampestris*_pv._c, a, pv, ca, v | ZP_06486563.1, AAM41717.1, YP_001903132.1, ZP_06483318.1, YP_364501.1 |
| Xanthomonas *oryzae*_pv._oryz, | ZP_02241404.1, ZP_06486563.1, |
| *Legionella longbeachae* | ZP_06186504.1 |
| *Legionella pneumophila*_str | YP_123920.1 |
| *Neisseria sicca* | ZP_05319573.1 |
| *Fusobacterium nucleatum*_su | ZP_06870819.1 |
| *Myxococcus xanthus* | YP_635355.1 |
| *Stigmatella aurantiaca* | ZP_01461725.1 |
| *Eschirichia coli*_K-12 | P3IL9 |
| *Escherichia coli*_O157:H7, *coli*_O127:H6 | fabHNP_287225.1, YP_002328892.1 |
| *Escherichia coli* | P1EBL, P1HNH, BAI54746.1, NP_753594.1 |

information obtained on the worldwide web at enzyme.cbirc.iastate.edu ( ©Iowa State University of Science and Technology; used with permission)

A KASIII can be mutated, for example, to alter the three-dimensional conformation of the active site, which, in turn can alter substrate specificity and/or level of activity. For example, by increasing the space available for substrate binding, a KASIII may utilize a branched-chain substrate whereas the corresponding wild-type KASIII is only able to utilize a straight-chain substrate. Conversely, by decreasing the space available for substrate binding, a KASIII may utilize a strain-chain substrate whereas the corresponding wild-type KASIII is additionally or only able to utilize a branched-chain substrate.

Figure 8A:
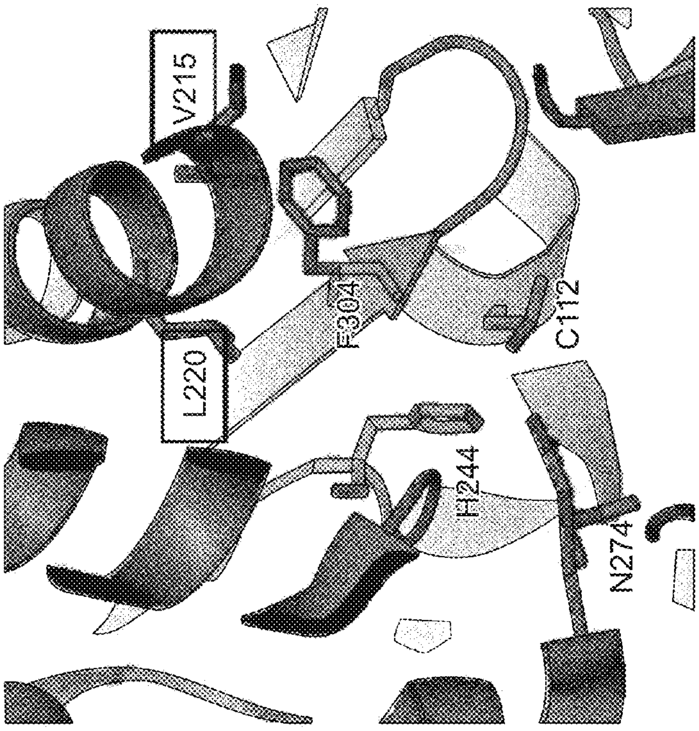
FIG. 8A is a schematic drawing of the crystal structure of *E. coli*'s KASIII (PDB code 3IL9) using Swiss Model in (A) showing the active site, which consists of C112, N274, and H244.
Figure 8B:
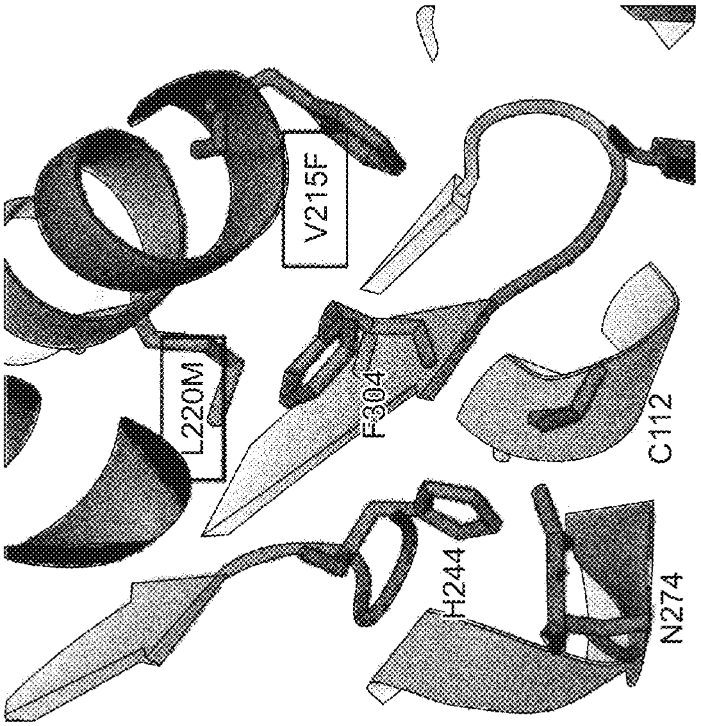
FIG. 8B is a schematic drawing of the crystal structure of *E. coli*'s KASIII showing the proposed effect of mutations L220M and V215F (modeled using PyMol (B)) on the orientation of Phe 304 and substrate specificity based on the orientation of F304 relative to V215 and L220 in the layer behind it.

By way of example, a KASIII from *E. coli* can be mutated in such a manner as to alter the orientation of F304 in relation to the active site, which consists of C112, N274, and H244 (see FIG. 8A, which is a schematic drawing of the crystal structure of *E. coli's* KASIII (PDB code 31L9) using Swiss Model). As shown in FIG. 8B, which is another schematic drawing of the crystal structure of *E. coli's* KASIII, mutations L220M and V215F (modeled using PyMol (B)) affect the orientation of F304 relative to the active site and substrate specificity based on the orientation of F304 relative to V215 and L220 in the layer behind it. By altering the orientation of F304 in relation to the active site, substrate specificity can be altered, such as by altering the relative specificity of the KASIII for one substrate over another or by changing the substrate specificity of the KASIII such that it is no longer specific for a given substrate and/or it is now specific for a new substrate. As demonstrated in Example 3 herein, altering the orientation of F304 in KASIII of *E. coli* to resemble the orientation of the corresponding amino acid in KASIII of *B. subtilis* resulted in altered, e.g., broadened, substrate specificity.

Figure 9A:
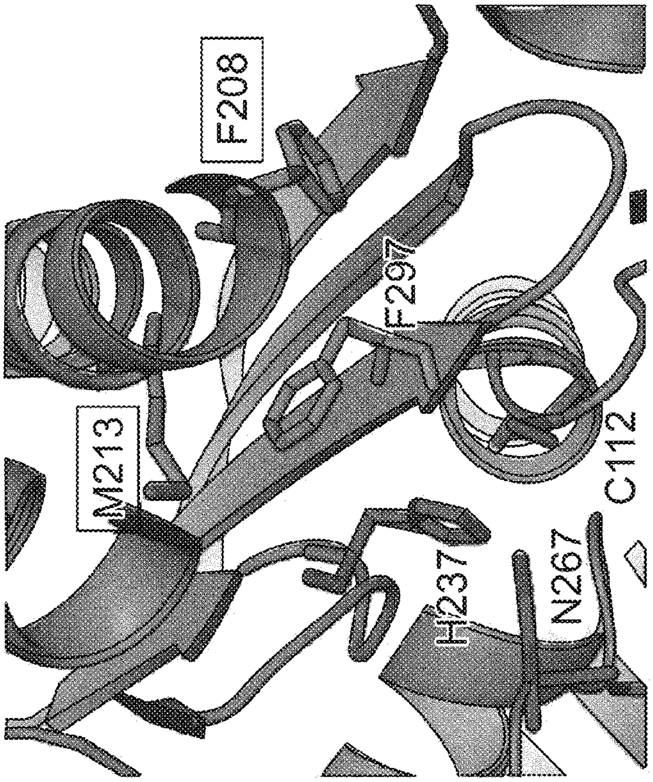
FIG. 9A is a schematic drawing of the predicted crystal structure of *B. subtilis*'s KASIIIA using Swiss Model in (A) showing the active site, which consists of C122, N267, and H237.
Figure 9B:
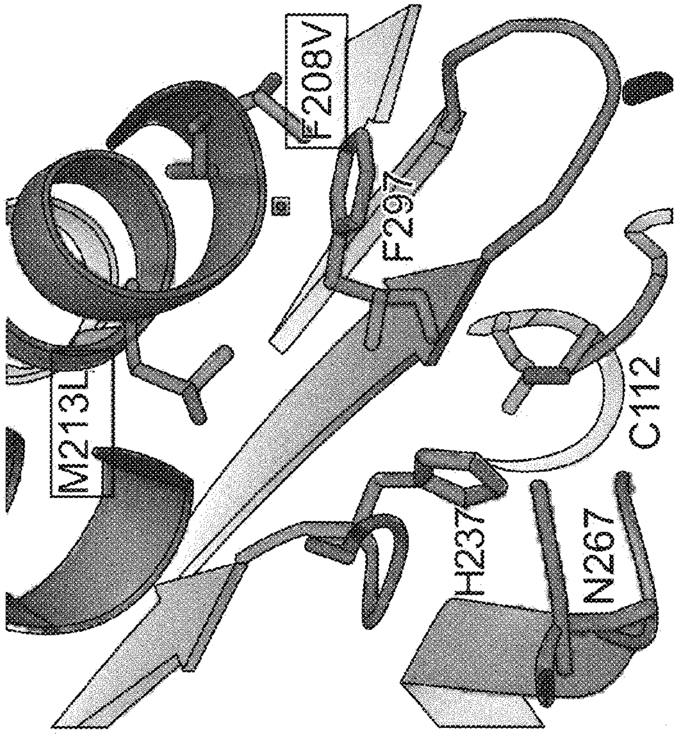
FIG. 9B is a schematic drawing of the predicted crystal structure of *B. subtilis*'s KASIIIA showing the proposed effect of mutations M213L and F208V (modeled using PyMol (B)) on the orientation of F297 and substrate specificity based on the orientation of F297 relative to M213 and F208 in the layer behind it.

By way of another example, a KASIII from *B. subtilis* can be mutated in such a manner as to alter the orientation of F297 in relation to the active site, which consists of C122, N267, and H237 (see FIG. 9A, which is a schematic drawing of the crystal structure of *E. coli's* KASIII (PDB code 31L9) using Swiss Model). As shown in FIG. 9B, which is another schematic drawing of the crystal structure of *B. subtilis*'s KASIII, mutations M213L and F208V (modeled using PyMol (B)) affect the orientation of F297 relative to the active site and substrate specificity based on the orientation of F297 relative to M213 and F208 in the layer behind it. By altering the orientation of F297 in relation to the active site, substrate specificity can be altered, such as by altering the relative specificity of the KASIII for one substrate over another or by changing the substrate specificity of the KASIII such that it is no longer specific for a given substrate and/or it is now specific for a new substrate. As demonstrated in Example 3 herein, altering the orientation of F297 in KASIII of *B. subtilis* to resemble the orientation of the corresponding amino acid in KASIII of *E. coli* resulted in altered, e.g., narrowed, substrate specificity.

Other KASIIIs, such as a KASIII from family KS1 (ketoacyl synthase 1) on the worldwide web at enzyme(dot) cbirc(dot)iastate(dot)edu, which website is incorporated by reference herein for its teachings regarding KASIII), in particular a KASIII from another bacterium, can be similarly mutated. For example, a KASIII from *Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius, Staphylococcus aureus, Legionella pneumophila*, or *Myxococcus xanthus* can be mutated.

Thus, in view of the above, a method of altering the specificity of a KASIII for at least one of its substrates is provided. The method comprises introducing into the KASII one or more mutations comprising at least one mutation, which causes the rotamer conformation of a phenylalanine in the KASIII corresponding to Phe304 in KASIII from *E. coli* to change. In one embodiment, the KASIII is from *E. coli* (GenBank Accession No. AAG55837.1; nucleotide sequence [SEQ ID NO:61]; amino acid sequence [SEQ ID NO:62]), and the one or more mutations comprises a mutation of Leu220, alone or in further combination with Val215. The mutation of Leu220 can be Leu220Met, and the mutation of Val215 can be Val215Phe. The rotamer conformation of Phe304 can be changed from the active site-distal rotamer conformation, in which the Phe304 is oriented away from the active site, to the active site-proximal rotamer conformation, in which the side chain of Phe304 faces towards the active site. In another embodiment, the KASIII is KASIIIA from *B. subtilis*, and the one or more mutations comprises a mutation of Met213, alone or in further combination with Phe208. The mutation of Met213 can be Met213Leu, and the mutation of Phe208 can be Phe208Val. The rotamer conformation of Phe297 can be changed from the active site-proximal rotamer conformation, in which the side chain of Phe297 faces towards the active site, to the active site-distal rotamer conformation, in which Phe297 is oriented away from the active site. In yet another embodiment, the KASIII is KASIIIB from *B. subtilis*, and the one or more mutations comprise a mutation of Trp221 and a mutation of Val226. The mutation of Trp221 can be Trp221Val, and the mutation of Val226 can be Val226Leu. The rotamer conformation of Phe310 can be changed from the active site-proximal rotamer conformation, in which the side chain of Phe310 faces towards the active site, to the active site-distal rotamer conformation, in which Phe310 is oriented away from the active site. In still yet another embodiment, the KASIII is from the KASIII is from *Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius, Staphylococcus aureus, Legionella pneumophila*, or *Myxococcus xanthus.*

The structure of KASIII can be found in the PDB database on the worldwide web at rcsb(dot)org(forward slash)pdb/home/home.do, which is hereby incorporated by reference for its teachings regarding same. The KASIII from *E. coli* has the PDB ID number 1EBL. The KASII from *S. aureus* has the PDB ID number 1ZOW. The phenylalanine in *S. aureus*, which corresponds to F304 in *E. coli*, has the active site-proximal rotamer orientation. "Altering the specificity of a KASIII for at least one of its substrates" can mean a change in the relative specificity of a given mutant KASIII for two or more substrates compared to the corresponding wild-type KASIII, gain of specificity for a substrate not utilized by the corresponding wild-type KASIII, or loss of specificity for a substrate utilized by the corresponding wild-type KASIII. Additionally or alternatively, the level of activity of a KASIII can be altered; for example, the level of activity of the mutant KASIII can be increased or decreased compared to the activity level of the corresponding wild-type KASIII. Preferably, activity levels are increased.

In view of the above, also provided is an isolated or purified nucleic acid molecule comprising a nucleotide sequence encoding a mutant KASIII. The isolated or purified nucleic acid molecule can be a vector. The mutant KASIII comprises one or more mutations comprising at least one mutation, which causes the rotamer conformation of a phenylalanine in the KASIII corresponding to Phe304 in KASIII from *E. coli* to change. In one embodiment, the KASIII is from *E. coli*, and the one or more mutations comprises a mutation of Leu220, alone or in further combination with Val215. The mutation of Leu220 can be Leu220Met, and the mutation of Val215 can be Val215Phe. The rotamer conformation of Phe304 can be changed from the active site-distal rotamer conformation, in which the Phe304 is oriented away from the active site, to the active site-proximal rotamer conformation, in which the side chain of Phe304 faces towards the active site. In another embodiment, the KASIII is KASIIIA from *B. subtilis*, and the one or more mutations comprises a mutation of Met213, alone or in further combination with Phe208. The mutation of Met213 can be Met213Leu. and the mutation of Phe208 can be Phe208Val. The rotamer conformation of Phe297 can be changed from the active site-proximal rotamer conformation, in which the side chain of Phe297 faces towards the active site, to the active site-distal rotamer conformation, in which Phe297 is oriented away from the active site. In yet another embodiment, the KASIII is KASIIIB from *B. subtilis*, and the one or more mutations comprise a mutation of Trp221 and a mutation of Val226. The mutation of Trp221 can be Trp221Val, and the mutation of Val226 can be Val226Leu. The rotamer conformation of Phe310 can be changed from the active site-proximal rotamer conformation, in which the side chain of Phe310 faces towards the active site, to the active site-distal rotamer conformation, in which Phe310 is oriented away from the active site. In still yet another embodiment, the KASIII is from *Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius, Staphylococcus aureus, Legionella pneumophila*, or *Myxococcus xanthus.*

When a KASIII gene is being mutated, such as to alter starter substrate specificity, mutations to the nucleotide sequence should not place the sequence out of reading frame and should not create complementary regions that could produce secondary mRNA structures. The mutant (or chimeric, such as when domains are swapped between genes) KASIII may have altered substrate specificity, e.g., reacts with an acyl-CoA substrate that differs in chain length, degree of saturation, or presence/absence of a side group (e.g., methyl group), from that which is acted upon by the wild-type (also referred to as "native") KASIII. Alternatively, the mutant or chimeric KASIII may have altered relative substrate specificity between two or more substrates, both of which are acted upon by the wild-type KASIII. Both types of alterations in substrate specificity are encompassed by references to alterations of substrate specificity and substrate specificity-altering mutations herein. Alternatively or additionally to altered substrate specificity, the mutant or chimeric KASIII may have an altered activity level, e.g., level of synthase activity, such as the total amount of fatty acids produced, including increased or decreased activity. Altered substrate specificity and altered activity can be detected by expression of the mutant KASIII in *E. coli*, for example, and assay of enzyme activity.

A nucleotide sequence encoding all or a part of a KASIII can be chemically synthesized, such as by the phosphoramidite method (Beaucage et al., Tetrahedron Letters 22: 1859-1869 (1981); and Matthes et al., EMBO J. 3: 801-805 (1984)). Alternatively, a nucleotide sequence encoding all or a part of a KASIII can be amplified from the genome or mRNA of an appropriate host using polymerase chain reaction (PCR) methods or amplified from an environmental DNA sample using PCR (see, e.g., metagenomics methods). Polynucleotides can be synthesized, purified, annealed to their complementary strand, ligated, and then, optionally, cloned into suitable vectors.

The isolated or purified nucleic acid molecule comprising a nucleotide sequence encoding a KASIII, such as a mutant/chimeric KASIII, can be a vector. The vector can contain, and preferably does contain, transcription and translation control regions. A promoter can be constitutive or regulatable, such as inducible. Additional sequences that can be present in the vector include pre-processing sequences, such as transit peptide sequences and plastid transit peptide sequences.

The KASIIIs and mutant/chimeric KASIIIs identified herein can be used in whole or in part as probes in hybridization assays to identify other KASIIIs that can be used in the methods described herein. The KASIIIs or fragments thereof also can be used as primers to amplify target DNA, such as by polymerase chain reaction (PCR) and other nucleic acid amplification methods. See, e.g., Sambrook et al., Molecular Cloning: A Laboratory Manual, $3^{rd}$ ed., Cold Spring Harbor Laboratory Press, Cold Spring Harbor, N.Y. (2001); Ausubel et al., eds., Short Protocols in Molecular Biology, $5^{th}$ ed., John Wiley & Sons (2002).

The nucleic acid molecule comprising a nucleotide sequence encoding a KASIII or a mutant/chimeric KASIII can be introduced into a host cell or a host organism using any suitable technique as is known in the art. See, e.g., Sambrook et al., Molecular Cloning: A Laboratory Manual, $3^{rd}$ ed., Cold Spring Harbor Laboratory Press, Cold Spring Harbor, N.Y. (2001); Ausubel et al., eds., Short Protocols in Molecular Biology, $5^{th}$ ed., John Wiley & Sons (2002). Such methods include microinjection, DNA particle bombardment, electroporation, liposome fusion, *Agrobacterium*-mediated transformation, and methods exemplified herein. Depending on the host cell or the host organism, one method can be preferred over another as readily appreciated by one of ordinary skill in the art. The nucleotide sequence can be codon-optimized for the recipient host cell or organism.

Also provided is an isolated or purified mutant KASIII. The mutant KASIII comprises one or more mutations comprising at least one mutation, which causes the rotamer conformation of a phenylalanine in the KASIII corresponding to Phe304 in KASIII from *E. coli* to change. In one embodiment, the KASIII is from *E. coli*, and the one or more mutations comprises a mutation of Leu220, alone or in further combination with Val215. The mutation of Leu220 can be Leu220Met, and the mutation of Val215 can be Val215Phe. The rotamer conformation of Phe304 can be changed from the active site-distal rotamer conformation, in which Phe304 is oriented away from the active site, to the active-site proximal rotamer conformation, in which the side chain of Phe304 faces towards the active site. In another embodiment, the KASIII is KASIIIA from *B. subtilis*, and the one or more mutations comprises a mutation of Met213, alone or in further combination with Phe208. The mutation of Met213 can be Met213Leu, and the mutation of Phe208 can be Phe208Val. The rotamer conformation of Phe297 can be changed from the active site-proximal rotamer conformation, in which the side chain of Phe297 faces towards the active site, to the active site-distal rotamer conformation, in which Phe297 is oriented away from the active site. In yet another embodiment, the KASIII is KASIIIB from *B. subtilis*, and the one or more mutations comprise a mutation of Trp221 and a mutation of Val226. The mutation of Trp221 can be Trp221 Val, and the mutation of Val226 can be Val226Leu. The rotamer conformation of Phe310 can be changed from the active site-proximal rotamer conformation, in which the side chain of Phe310 faces towards the active site, to the active site-distal rotamer conformation, in which the Phe310 is oriented away from the active site. In still yet another embodiment, the KASIII is from *Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius, Staphylococcus aureus, Legionella pneumophila*, or *Myxococcus xanthus.*

Once sequenced, polypeptides can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963), and Stewart and Young in *Solid Phase Peptide Syntheses* (2nd Ed., Pierce Chemical Company, 1984). Automated peptide synthesizers are commercially available, as are services that make peptides to order.

In view of the above, a host cell comprising an above-described isolated or purified nucleic acid molecule is also provided. The host cell or organism can be any suitable host cell or organism. The host cell or organism can be prokaryotic or eukaryotic, unicellular or multicellular, and undifferentiated or differentiated. If large-scale production of short-chain fatty acids is desired, e.g., as a source of a bio-based chemical (such as surfactants, lubricants, food oils, polymers, and the like) bacteria (see, e.g., U.S. Pat. App. Pub. No. 2012/0164700, which discloses examples of cyanobacteria, and U.S. Pat. App. Pub. No. 2009/0298143, which discloses methods of expression in bacteria, and both of which are hereby incorporated by reference for their teachings regarding same), yeast (see, e.g., U.S. Pat. App. Pub. No. 2011/0294174, which discloses examples of yeast in Table 26 and other fungi in Table 27 and which is hereby incorporated by reference for its teachings regarding same), and algae (see, e.g., U.S. Pat. App. Pub. No. 2011/0294174, which discloses examples of algae in Table 1 and which is hereby incorporated by reference for its teachings regarding same; also, see U.S. Pat. No. 7,935,515 and U.S. Pat. App. Pub. No. 2012/0164700, which disclose methods of expressing enzymes, specifically thioesterases, in microalgae and examples of microalgae and which are hereby incorporated by reference for their teachings regarding same; see, also, U.S. Pat. App. Pub. No. 2009/0317878, which is hereby incorporated by reference for its teachings regarding expression of genes in algae) can be preferred. A preferred bacterium is *Escherichia coli*, in particular the strain K27. A preferred yeast is *Saccharomyces cerevisiae.* Alternatively, a crop plant (e.g., maize, canola, and others), such as an oilseed crop plant or a seed cell thereof, can be preferred (see, e.g., U.S. Pat. No. 7,504,563, which discloses expression of a nucleic acid encoding an enzyme, specifically a thioesterase, in soybean seed and which is incorporated herein for its teachings regarding same). See, also, U.S. Pat. App. Pub. No. 2010/0154293, which discloses other examples of host cells in paragraph [0080] and which is incorporated herein by reference for its teachings regarding same.

Fatty acids can be harvested, or otherwise collected (e.g., isolation from media containing bacteria that secrete the fatty acids), from host cells or organisms by any convenient method. Cells can be lysed/disrupted (e.g., heat, enzymes, ultrasound, mechanical lysis, osmotic shock, acid/base addition, or infection with a lytic virus), and fatty acids can be separated from cell mass by centrifugation and extraction (e.g., extraction with hydrophobic solvent, liquefaction, supercritical $CO_2$ extraction, or hexane extraction after freeze-drying and pulverization) and further processed/refined as necessary. See, e.g., U.S. Pat. No. 7,935,515 and U.S. Pat. App. Pub. No. 2012/0135479, which are incorporated specifically by reference for their teachings regarding same.

In view of the above, a method of producing bi-functional fatty acids in a host cell or organism is also provided. The method comprises introducing into a host cell or organism, which comprises one or more ω-functionalized acyl-CoAs, and expressing therein a nucleic acid molecule comprising a nucleotide sequence encoding a KASIII (or a mutant or chimera thereof, such as a mutant or chimera with an altered substrate specificity or an altered level of activity), such as a KASIII from family KS1 (ketoacyl synthase 1) on the worldwide web at enzyme(dot)cbirc(dot)iastate(dot)edu (incorporated herein by reference for its teachings regarding KASIII), e.g., a KASIII from *A. acidocaldarius*, which can use one or more of the ω-functionalized acyl-CoAs as a substrate. The one or more ω-functionalized acyl-CoAs can be functionalized at the ω position with a moiety comprising a hydroxyl group, a benzoyl group, a cyclic group, a branched-chain group, an amino group, or a halogen group. The host cell or organism can be a mutant *R. rubrum*, such as a mutant *R. rubrum* described above. A preferred host cell or organism can be a bacterium, such as *E. coli*, an alga, or a plant. Preferably, the host cell or organism, e.g., *E. coli*, has been mutated so that it does not express endogenous KASIII (fabH gene). More preferably, the host cell or organism, e.g., *E. coli*, has been modified so that it overproduces acyl-CoA starter substrate, does not degrade fatty acid, does not terminate fatty acid elongation, and/or secretes fatty acids, such as into the surrounding medium. For example, the fadD gene, which codes for acyl-CoA synthetase, which initiates degradation of fatty acids (Kelin et al., European Journal of Biochem/FEBS 19:442-450 (1971)), can be deleted. Acyl-ACP thioesterase, which results in secretion of fatty acids, can be expressed (Li et al., Metabolic engineering 14: 380-387 (2012); Zhang et al., Metabolic engineering 13: 713-722 (2011); Jing et al., BMC Biochem 12: 44 (2011)). The PHA biosynthetic operon, specifically phaA and phaB without phaC, can be expressed/over-expressed, in an effort to produce enantiopure (R) and (S)-3-hydroxybutyrate (Tseng et al., Applied and Environmental Microbiology 75: 3137-3145 (2009)).

The bi-functional fatty acids produced in accordance with the above methods can be used in a variety of different applications, such as surfactants, which can vary somewhat in the length of the carbon chain of the fatty acid, lubricants, which also can vary somewhat in the length of the carbon chain of the fatty acid, and polymers (e.g., polyester), which preferably do not vary in the length of the carbon chain of the fatty acid. The provision of novel bi-functional, bio-based feedstocks (e.g., hydroxy fatty acids and amino fatty acids, such as for polyamides) to the emerging biorenewable chemical industry can lead to the production of novel "green" plastics and specialty chemicals. Such chemical products can act as substitutes for petroleum-based chemical products, and be precursors for novel bio-based products. Such chemical feedstocks can be used to manufacture polymers, specifically polyesters, as well as being utilized in detergents, surfactants, solvents, paints, varnishes, lubricants, cosmetics, and specialty chemical synthesis. Thus, further provided is a composition comprising a bi-functional fatty acid produced in accordance with a method described herein. The composition can be a feedstock, for example. Still further provided is a method of using the feedstock to manufacture a composition, such as a polymer, such as a polyester, a detergent, a surfactant, a solvent, a paint, a varnish, a lubricant, a cosmetic, and the like. Even still further provided is a composition, such as a polymer, e.g., a polyester, a detergent, a surfactant, a solvent, a paint, a varnish, a lubricant, a cosmetic, and the like, produced by the method. See, e.g., Nikolau et al., Plant J. 54: 536-545 (2008), which is hereby incorporated by reference for its teachings regarding same.

Further provided is an in vitro, high-throughput spectrophotometric method of assaying KASIII activity. The method comprises (i) incubating holo-ACP, malonyl-CoA, acyl-CoA, NADPH, and malonyl-CoA:ACP transacylase (FabD), (ii) adding KASIII and 3-ketoacyl-ACP reductase (FabG), and (iii) measuring the change in absorbance at 340 nm when NADPH is converted to NADP+ during reduction of 3-ketoacyl-ACP to 3-hydroxyl-acyl ACP by FabG. The acyl-CoA can be acetyl-CoA, propionyl-CoA, isobutyryl-CoA and/or hydroxybutyryl-CoA. Such acyl-CoAs are commercially available, such as from Sigma-Aldrich, and can be synthesized by a mixed anhydride reaction in accordance with methods known in the art. Preferably, incubating in (i) is for about two minutes, e.g., two minutes, in the presence of a buffer, such as sodium phosphate buffer, at slightly alkaline pH, e.g., pH 7.2. Preferably, a disulfide-reducing agent, such as dithiothreitol (DTIT), is used in step (i). The acyl-CoA can be a straight-chain-CoA, a branched-chain-CoA, or a hydroxylated-CoA. The method can be used to assess enzymes and evaluate/compare the catalytic efficiency of enzymes with different acyl-CoA substrates. The rate of change in absorbance can be used to calculate directly the rate of the KASIII-catalyzed reaction.

EXAMPLES

The following examples serve to illustrate the present disclosure. The examples are not intended to limit the scope of the claimed invention in any way.

Example 1

This example describes the selection of KASIII enzymes based on substrate diversity.

As many as 2,308 KASIII sequences collected in the ThYme database (on the worldwide web at enzyme(dot) cbirc(dot)iastate(dot)edu; Cantu et al., Nucleic Acids Res. 39: D342-D346 (2011)) were analyzed phylogenetically in collaboration with Dr. Peter Reilly (Iowa State University). Protein sequences were aligned, and a minimum evolution method with 250 bootstrap iterations was employed. Sequences were grouped into 12 sub-families. KASIII gene sequences were selected based on fatty acid profiles of the host organisms, occurrence of the same strain in multiple sub-families, and statistical analysis of clades, for which no fatty acid data are available. KASIII gene sequences from the following organisms were chemically synthesized with codon optimization for *E. coli: Aeromonas hydrophila, Erythrobacter* sp SD-21, *Haliangium ochraceum, Myxococcus xanthus* (three sequences), *Capnocytophaga gingivalis* (three sequences), *Brevibacterium* linens (two sequences), *Renibacterium salmoninarum, Legionella pneumophila* (four sequences), *Nocardiopsis dassonvillei, Desulfovibrio vulgaris* st., *Stappia aggregata, Methylosinus trichosporium, Escherichia coli* (the KASIII of which acts on straight-chain primers), *Aeromonas hydrophila* (two sequences), *Physcomitrella patens* subsp *patens, Synechococcus* sp CC9605, *Bacteroides* vulgatus, *Alicyclobacillus acidocaldarius* (the KASIII of which acts on cyclic primers), *Thermus aquaticus, Bacillus licheniformis* bFabHA, *Bacillus licheniformis* bFabHB, *Bacillus subtilis* subsp *spizizenii, Bacillus subtilis* (the KASIII of which acts on branched-chain primers) bFabHA, and *Bacillus subtilis* bFabHB. While not included, *Mycobacterium tuberculosis* KASIII prefers long-chain primers, whereas *Dichapetalum toxicarium* KASIII prefers halogenated primers.

Example 2

This example describes the generation and characterization of *B. subtilis* KASIII single and double deletion mutants.

—Bacterial Strains and Growth Conditions.

*B. subtilis* strain 168 was obtained from the *Bacillus* Genetic Stock Center (on the worldwide web at bgsc(dot) org). *Escherichia coli* strains DH5a and BL21(DE3) were obtained from Invitrogen Corporation (Carlsbad, CA).

*E. coli* and *B. subtilis* were routinely grown in LB medium at 37° C. *B. subtilis* minimal medium was composed of Spizizen salts (Spizizen, PNAS USA 44: 1072-1078 (1958)), supplemented with 0.5% glucose and amino acids (Sueoka et al., Cold Spring Harbor Symp. Quant. Biol. 33: 695-705 (1968)). As needed, media were supplemented with erythromycin (1 μg/ml) and ampicillin (100 μg/ml). IPTG and X-gal were used at concentrations of 0.4-1 mM and 40 μg/ml, respectively. As needed, media were supplemented with 10-100 μM individual fatty acids suspended in 0.01% (v/v) Brij 58P detergent. Fatty acids were obtained from Sigma-Aldrich Corporation (St. Louis, Mo.). The purity of the commercial sources of anteiso-C16:0, iso-C16:0 and palmitoleic acid were determined by GC-MS analysis (see Table 1). Cell density was determined by monitoring $A_{600}$ using a Spectronic 20D+ spectrophotometer (Thermo Fisher Scientific Inc., Waltham, Mass.) or in a 96-well plate using an ELx808 Absorbance Microplate Reader (BioTek Instruments, Inc., Winooski, Vt.). Doubling time ($T_d$) was determined from the log-phase time points of cultures.

TABLE 1

The purity of the commercial sources of anteiso-C16:0, iso-C16:0 and palmitoleic acid

| Composition | a-C16 | i-C16 | n-C16:1(n-7) |
|---|---|---|---|
| n-C12:0 | 0.04% | | |
| n-C14:0 | 0.24% | | |
| i-C15:0 | 0.74% | | |
| a-C15:0 | 0.02% | | |
| n-C15:0 | 0.08% | | |
| i-C16:0 | | 99.90% | |
| a-C16:0 | 96.73% | | |
| n-C16:1(9) | | | 99.94% |
| n-C16:0 | 1.53% | 0.10% | 0.06% |
| a-C17:0 | 0.01% | | |
| n-C18:0 | 0.61% | | |

—DNA Manipulation.

DNA manipulation techniques, such as PCR amplification, plasmid preparation, restriction endonuclease digestion, agarose gel electrophoresis, and genetic transformation, were carried out by standard methods (Sambrook et al., *Molecular Cloning: A laboratory manual,* 3rd ed., Cold Spring Harbor Laboratory Press, Cold Spring Harbor, N.Y. (2001)). Transformation of *B. subtilis* was conducted on modified competent medium (Kunst et al., "Signal transduction network controlling degradative enzyme synthesis and competence in *bacillus subtilis*," In: *Regulation of Bacterial Differentiation*, pp. 1-20, Piggot, editor, American Society for Microbiology, Washington, D.C. (1994)). All oligonucleotide sequences used are listed in Table 2.

TABLE 2

Primers used

| Fragment amplified for purpose | Primer name | Primer sequence |
|---|---|---|
| The bfabHA gene for construction of pET30a-bfabHA | Af1-Nco I | CATG***CCATGG***TAATGAAAGCTGGAATAC [SEQ ID NO: 1] |
| | Ar1-Eco RI | GCG***GGATCC***GGAGATAATGCTCCAG [SEQ ID NO: 2] |
| The bfabHB gene for construction of pET30a-bfabHB | Bf1-Bam HI | CGC***GGATCC***ATTCATATGTCAAAAGC [SEQ ID NO: 3] |
| | Br1-Hin dIII | AGGG***AAGCTT***CAGAAGAACAGCCGG [SEQ ID NO: 4] |
| 323-bp fragment of the bfabHA gene (nucleotide position from 191 to 513) for construction of vector pM4A | Af2-Hin dIII | ***AAGCTT***AACAAGCTGAAGTGGCTGCT [SEQ ID NO: 5] |
| | Ar2-Bam HI | ***GGATCC***ATCACTGACTGGCCCGACTA [SEQ ID NO: 6] |

TABLE 2-continued

| Primers used | | |
|---|---|---|
| Fragment amplified for purpose | Primer name | Primer sequence |
| 429-bp fragment of the bfabHB gene (nucleotide position from 415 to 843) for construction of vector pM4B | Bf2-Hin dIII | ***AAGCTT***GCCGGAGAGACGTTATCAAA [SEQ ID NO: 7] |
| | Br2-Bam HI | ***GGATCC***CGTGTTTCCGTAGTGCTCAA [SEQ ID NO: 8] |
| 897-bp upstream fragment of the bfabHA ORF for construction of vector pMU4A | AUf-Pac I | ***TTAATTAA***TATTAACCATCACGGTGCAA [SEQ ID NO: 9] |
| | AUr-Sal I | ***GTCGAC***GAATGTAACGTCCAACACCA [SEQ ID NO: 10] |
| 799-bp downstream fragment of the bfabHA ORF for construction of vector pMU4A | ADf-Sal I | ***GTCGAC***TGGAAGCCCGGTAAAATCAA [SEQ ID NO: 11] |
| | ADr-Pst I | ***CTGCAG***GCCGACAATTTCTCCGTAAA [SEQ ID NO: 12] |
| 836-bp upstream fragment of the bfabHB ORF for construction of vector pMU4B | BUf-Pst I | ***CTGCAG***ATATAAAACCGCCGGGACAT [SEQ ID NO: 13] |
| | BUr-Sal I | ***GTCGAC***GCATAGGTGCCGATAGCTGTA [SEQ ID NO: 14] |
| 802-bp downstream fragment of the bfabHB ORF for construction of vector pMU4B | BDF-Sal I | ***GTCGAC***TCAAATCGTTTTGCTTTTCG [SEQ ID NO: 15] |
| | BDr-Pac I | ***TTAATTAA***CCAAACAGGAGATATCGATGC [SEQ ID NO: 16] |
| 836-bp upstream fragment of the bfabHB ORF for construction of vector pUCB-erm | BUf2-Eco RI | ***GAATTC***ATATAAAACCGCCGGGACAT [SEQ ID NO: 18] |
| | BUr2-Sal I | ***GTCGAC***GCATAGGTGCCGATAGCTGTAA [SEQ ID NO: 18] |
| 738-bp downstream fragment of the bfabHB ORF for construction of vector pUCB-erm | BDf2-Sal I | ***GTCGAC***TCAAATCGTTTTGCTTTTCG [SEQ ID NO: 19] |
| | BDr2-Hin dIII | ***AAGCTT***CCAAAGATGATGCCATTCA [SEQ ID NO: 20] |
| erm gene fragment for construction of vector pUCB-erm | ermf | ***GTCGAC***CAAATTTACAAAAGCGACTA [SEQ ID NO: 21] |
| | ermr | ***GTCGAC***GAGGCCCTTTCGTCTTCAA [SEQ ID NO: 22] |
| Verification of the bfabHA::pM4A allele | RB | GACAGTATCGGCCTCAGGAA [SEQ ID NO: 23] |
| | AL | TGCTGTTCCTCCTCCTTCTC [SEQ ID NO: 24] |
| Verification of the bfabHA::pM4B allele | RB | GACAGTATCGGCCTCAGGAA [SEQ ID NO: 25] |
| | BL | GGAGTGATTCATATGTCAAAAGCA [SEQ ID NO: 26] |
| Verification of bfabHA deletion | lotAF | GCATACGCCTCCTTTCCATA [SEQ ID NO: 27] |
| | lotAr | TTTGCCGGATATTCTTCAGC [SEQ ID NO: 28] |
| Verification of bfabHB deletion | lotBf | CAATGTTAAGCCGGAAGGAA [SEQ ID NO: 29] |
| | lotBr | AGCAGCCGTAAATGCCATAC [SEQ ID NO: 30] |

[a]Restriction sites designed into the nucleotide sequences are indicated in bold and italics.

KASIII-coding genes were expressed in *E. coli* strain BL21 (DE3) using pET-based vectors (Novagen, Madison, Wis.). The bfabHA gene was PCR-amplified with the primers Af1-Nco I and Ar1-Eco RI. The resulting fragment was cloned into the Nco I and Eco RI restriction sites of the pET30a vector, resulting in expression vector pET30a-bfabHA. By the analogous procedure, the bfabHB gene was also cloned into the pET30a vector, resulting in the expression vector pET30a-bfabHB.

*B. subtilis* KASIII-coding genes were disrupted by the insertion of the pMUTIN4 vector (Vagner et al., Microbiology 144(Pt 11): 3097-3104 (1998)) via homologous recombination. A fragment of the bfabHA gene (nucleotides 191-513) was PCR-amplified with the primers Af2-Hin dIII and Ar2-Bam HI. This bfabHA PCR-fragment was cloned into the Hin dIII and Bam HI restriction sites of pMUTIN4 vector (Vagner et al. (1998), supra). By the analogous procedure, a bfabHB fragment (from nucleotide from 415 to 843) was also cloned into the pMUTIN4 vector. The recombinant pMUTIN4 plasmids carrying the bfabHA and bfabHB gene fragments were named pM4A and pM4B, respectively.

The two *B. subtilis* KASIII-coding genes were deleted by using the vectors pMU4A and pMU4B, respectively, which are derivatives of pMUTIN4 (Vagner et al. (1998), supra). The pMU4A vector contained two bfabHA-derived fragments, one 5' of the open reading frame (ORF), and the other 3' of the ORF. The 5'-, 897-bp DNA fragment spanned from 860 bp upstream of the bfabHA ORF to 37 bp within the bFabHA ORF, and the 3'-, 897-bp DNA fragment spanned from 799 bp downstream to 98 bp within the 3'-end of the bfabHA ORF. These two fragments were initially PCR-amplified with the primer pair AUf-Pac I and AUr-Sal I, and the primer pair ADf-Sal I and ADr-Pst I, and both fragments were cloned into pMUTIN4, at the Pac I and Pst I sites. The resulting pMU4A vector contained an in-frame 135-bp bfabHA fragment missing 804 bp from the middle of the ORF; the fact that this deletion allele carried an in-frame ORF avoided any polar effect on the downstream genes of the bfabHA-containing transcription unit. The vectors pMU4B and pUCB-erm, which were used to generate the deletion allele for bfabHB, were constructed by an analogous procedure, except that the vector pUCB-erm was constructed from plasmid pUC19 and the erythromycin-resistant gene erm was inserted between the downstream and upstream DNA fragments of bfabHB ORF.

—Construction of *B. subtilis* Mutants.

*B. subtilis* gene-insertion mutant alleles were generated by transforming *B. subtilis* strain 168 with the plasmids pM4A and pM4B, and the desired mutants were selected by virtue of their ability to grow in lethal doses of erythromycin. PCR reactions with primers that would support amplification only from appropriately recombined alleles were conducted to verify that the single cross-over recombination-mediated integration of the vectors occurred as expected. A genomic specific primer AL and a vector specific primer RB were used to confirm the bfabHA::pM4A allele. A genomic specific primer BL and a vector specific primer RB were used to confirm the bfabHB::pM4B allele (see Table 2).

Two single-deletion strains of *B. subtilis*, each lacking one or the other KASIII-coding gene, were generated by homologous recombination via a two-step procedure using the vector pMU4A and pMU4B, respectively. Briefly, plasmid pMU4A or pMU4B was transformed into wild-type strain 168, followed by selection for erythromycin resistance. The recovered integrant colonies were grown in LB liquid medium without erythromycin, the overnight cultures were diluted 1:$10^7$, and about 100 μl of the diluted culture were plated on LB medium with IPTG and X-gal and screened for white colonies, indicating the loss of the lacZ-containing pMUTIN4 sequence, which would result in the deletion of the appropriate KASIII-coding gene. The nature of the deletion mutants was confirmed by PCR amplification of a specific sequence of each deletion allele.

The double-deletion mutant strain, ΔbfabHA ΔbfabHB::erm, was generated by homologous recombination via a one-step procedure, by transforming the mutant ΔbfabHA strain with the Eco RI-linearized plasmid pUCB-erm followed by selection for erythromycin resistance on media containing anteiso-C16:0 fatty acid. Primers lofAf and lofAr were used to confirm the ΔbfabHA allele. Primers lofBf and lofBr were used to confirm the ΔbfabHB and ΔbfabHB::erm alleles (see Table 2).

—Assays of β-Galactosidase.

β-galactosidase activity, expressed as Miller units (Miller, *A Short Course in Bacterial Genetics: A Laboratory Manual and Handbook for Escherichia coli and Related Bacteria*, Cold Spring Harbor Laboratory Press, Cold Spring Harbor, N.Y. (1992)), was assayed as described (Cutting et al., "Genetic Analysis," In: *Molecular Biological Methods for Bacillus*, pp. 27-74, Harwood and Cutting, eds., John Wiley, Chichester (1990)) using o-nitrophenyl-β-D-galactoside as substrate.

—Protein Purification and Preparation of Antibodies.

The two *B. subtilis* KASIII proteins were expressed in *E. coli* BL21 (DE3) using the plasmid pET30a-bfabHA or pET30a-bfabHB (Novagen, San Diego, Calif.), and cultures were grown in LB medium containing the appropriate antibiotic. When the culture reached an $OD_{600}$ of 0.9, 1 mM IPTG was used to induce expression. Cells were harvested, and the proteins were purified by affinity chromatography on a Ni-NTA agarose column (Qiagen, Valencia, Calif.) according to the manufacturer's instructions. Antibodies directed against the KASIIIA and KASIIIB proteins were generated by injecting each recombinant protein into a rabbit using Freund's Complete and Incomplete Adjuvants (Pierce, Rockford, Ill.).

—Protein Analysis.

Protein extracts were prepared from bacterial cells collected by centrifugation of a 3-ml aliquot of early stationary-phase growth culture. The pellet was suspended in 0.3 ml extraction buffer, consisting of 30 mM Tris-HCl, pH 8, 10 mM EDTA, and 0.5 mg/ml lysozyme, and incubated at 37° C. for 30 minutes. The lysate was further disrupted by sonication. Following centrifugation for 10 minutes at 16,100 g, the supernatant was retained for analysis. Protein concentration was determined by Bradford's method (Bradford, Anal. Biochem. 72: 248-254 (1976)) using bovine serum albumin to generate a standard curve. Immunoblot analysis was performed as described previously (Li et al., Plant Physiol. 155: 293-314 (2011)).

—Fatty Acid Analysis.

A 0.5 ml aliquot of an overnight *B. subtilis* culture normalized for equal cell density was collected by centrifugation at 13,200×g for 30 seconds. The cell pellet was suspended in 50 ml minimal medium or LB rich medium. Cell cultures were shaken at 250 rpm. Cells were collected at late log phase by centrifugation at 5,000×g for 10 minutes. The collected cell pellets were lyophilized and stored at −20° C. until analysis. Lipids were extracted from lyophilized bacterial cell pellets using chloroform/methanol (Ways et al., J. Lipid Res. 5: 318-328 (1964)), and fatty acids were then converted to picolinyl ester (lipidlibrary.aocs.org/ms/ms02/index.htm) (Harvey, Biomed. Mass Spectrom. 9: 33-38 (1982)) or methyl esters using methanolic-HCl at 80° C. for 60 minutes (Broekman et al., J. Bacteriol. 116: 285-289 (1973); and Broekman et al., J. Bacteriol. 117: 971-977 (1974)). The recovered picolinyl ester or fatty acid methyl esters were concentrated as needed under a stream of nitrogen gas and analyzed with GC-MS interfaced with a Mass Detector 5973 (Agilent Technologies, Santa Clara, Calif.). The double bond positions in unsaturated fatty acids were determined by GC-MS analysis of dimethyl disulfide adducts (Buser et al., Anal. Chem. 55: 818-822 (1983)).

—Growth Characteristics of Single Gene Mutant Strains.

Figure 3A:
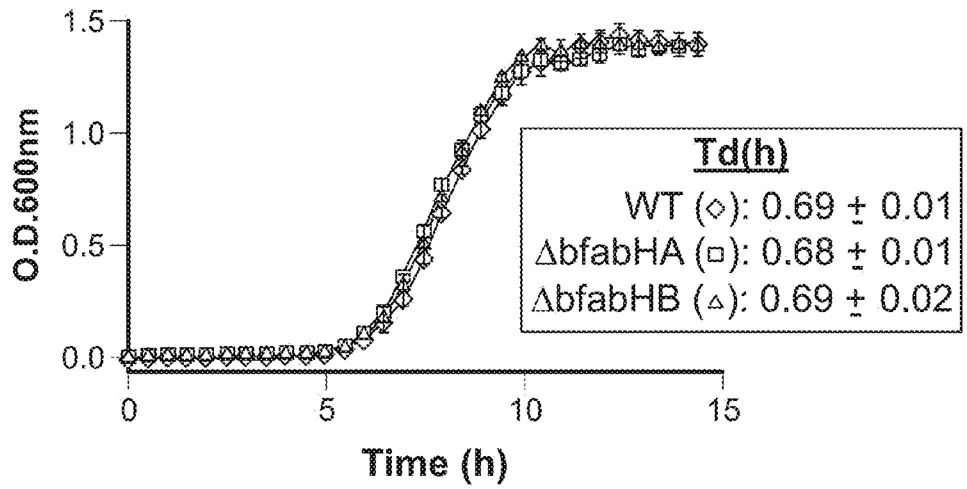
FIG. 3A is a graph of time (hours (h)) vs. OD at 600 nm, wherein WT is wild-type, ΔbfabHA is the deletion mutant for bfabHA, and ΔbfabHB is the deletion mutant for bfabHB (i.e., bfabHB::erm, in which the bfabHB gene has been replaced with a gene conferring resistance to erythromycin (erm)) cultured on minimal medium at 37° C. Data represent the average of three determinations±standard error.
Figure 3B:
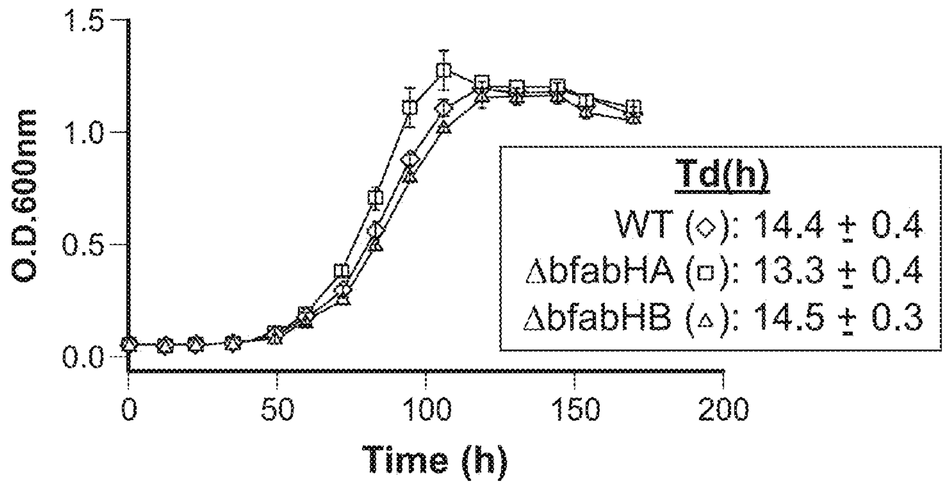
FIG. 3B is a graph of time (h) vs. OD at 600 nm for WT, ΔbfabHA, and ΔbfabHB (bfabHB::erm) cultured on minimal medium at 16° C. Data represent the average of three determinations±standard error.

The wild-type *B. subtilis* strain 168 and the isogenic mutant strains ΔbfabHA and ΔbfabHB, which lacked KASIIIA and KASIIIB, respectively, were grown at 37° C. and 16° C. (FIG. 3). At 37° C. there was no difference in the growth rate between the wild-type and either of the mutants (FIG. 3A). When these strains were cultured at the lower temperature (16° C.), however, the log-phase growth rate of the ΔbfabHA mutant was faster than that of the wild-type and the ΔbfabHB mutant (FIG. 3B) (doubling time was 13.3±0.4 hours as compared to 14.4±0.4 hours for the wild-type strain and 14.5±0.3 hours for ΔbfabHB mutant, p-value=0.04). In contrast, the log-phase growth rate of ΔbfabHB mutant was indistinguishable from that of the wild-type.

—Expression of bfabHA and bfabHB Genes.

Protein extracts from the wild-type, ΔbfabHA and ΔbfabHB mutant strains grown at 37° C. and 16° C. were analyzed by Western blot to confirm the nature of the mutant growth phenotype of the ΔbfabHA mutant strain. The KASIIIA protein, but not the KASIIIB protein, accumulated to detectable levels in the wild-type strain, and, as expected, the KASIIIA protein was not detected in the ΔbfabHA mutant. In contrast, the KASIIIB protein, which is undetectable in the wild-type strain, was induced in the ΔbfabHA mutant.

Figure 4:
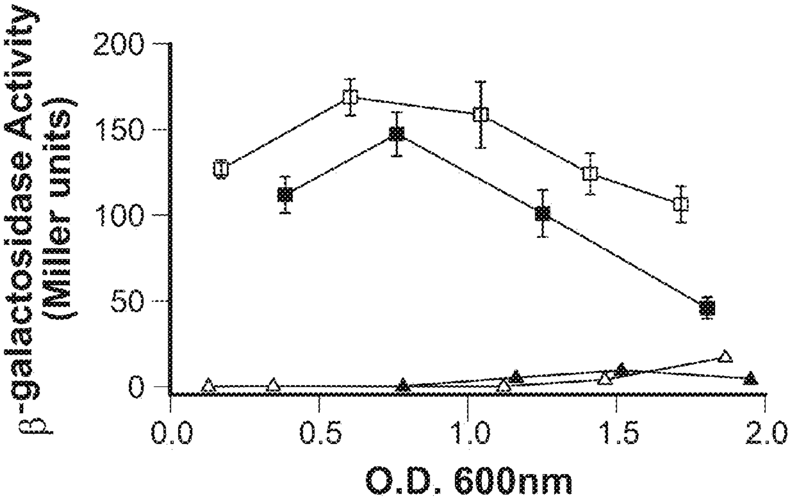
FIG. 4 is a graph of OD at 600 nm vs. β-galactosidase activity (Miller units), which shows the expression of the bfabHA and bfabHB genes. The strains bfabHA::pM4 (—▒—, —□—) and bfabHB::pM4B (—▲—, —Δ—), which carry lacZ reporter fusions for each KASIII-coding paralog were grown on LB medium at either 37° C. (····▒····, ····▲····) or 16° C. (····□····, ····Δ····). At the indicated optical density, aliquots of the cultures were removed and β-galactosidase activity was determined. Data represent average of three determinations±standard error.

Because the finding that the expression of the bfabHB gene is conditional on the absence of the bfabHA-encoded KASIII was unexpected, corroborative evidence for this finding was gained with an independent approach, i.e., promoter-lacZ fusion reporters. In this experiment these reporter alleles were generated by a single-crossover recombination event between a KASIII-encoding genomic locus (either bfabHA or bfabHB) and the plasmid pMUTIN4 (Vagner et al., Microbiology 144(Pt. 11): 3097-3104 (1998)), which carries one or the other KASIII-encoding fragment, fused to the lacZ gene. The resulting recombination event generated a transgenic new locus that expressed β-galactosidase under the transcriptional regulation of either of the bfabHA promoter or the bfabHB promoter. FIG. 4 shows that the bfabHA promoter was considerably more active than the bfabHB promoter, by a factor of at least 10-fold. Activity of the bfabHA promoter was similar, irrespective of the growth temperature, and maximal expression occurred at early to mid-log phase of growth, coincident with maximal need for membrane lipid deposition. Hence, the β-galactosidase reporter assays were consistent with the Western blot data and showed that the bfabHB gene was minimally expressed, while the bfabHA gene accounted for the major form of KASIII that was expressed under normal growth conditions.

These data therefore, indicate that, while the bfabHA gene is expressed in the wild-type, the bfabHB gene is normally silent, and its expression is induced in the absence of a functional bfabHA gene. Moreover, the growth characteristics of the two mutants ΔbfabHA and ΔbfabHB described in FIG. 3B indicate that the bfabHB-encoded KASIII confers a growth advantage at 16° C.

—Effect of bfabHA and bfabHB Gene Deletions on Fatty Acid Composition.

Fatty acid compositions of the ΔbfabHA and ΔbfabHB mutants were compared to the wild-type strain, and these comparisons were conducted on strains that were grown at either 37° C. or 16° C. Fatty acids were chemically identified by a combination of comparing retention indices to commercial standards, MS-fragmentation of picolinyl esters (Harvey, Biomed. Mass Spectrom. 9: 33-38 (1982)), and determination of double bond positions in unsaturated fatty acids by MS-fragmentation of DMDS adducts (Buser et al., Anal. Chem. 55: 818-822 (1983)).

Figure 5A:
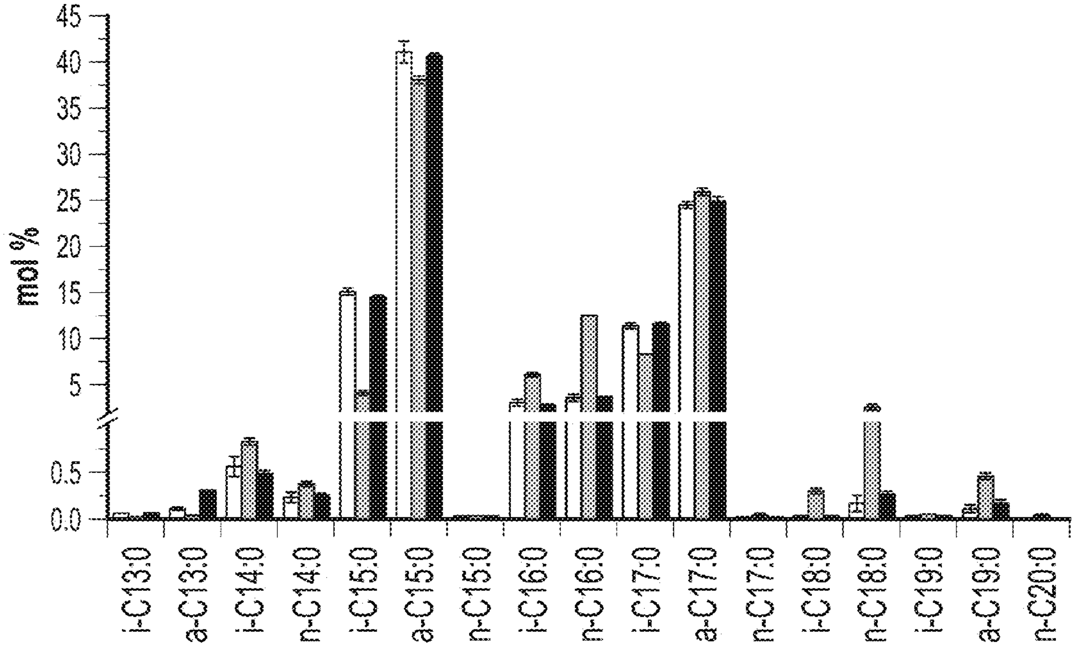
FIG. 5A is a graph of fatty acid vs. mol % for cultures of WT strain 169 (□) and mutant strains ΔbfabHA (▒) and ΔbfabHB (bfabHB::erm; ▓) grown on minimal medium at 37° C. showing the effect of deleting the bfabHA and bfabHB genes on fatty acid composition of *B. subtilis*. Data represent average of three determinations±standard error.
Figure 5B:
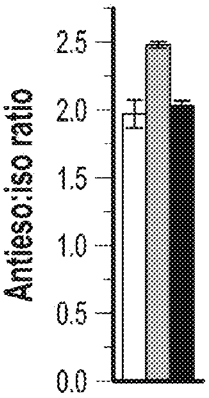
FIG. 5B is a graph of anteiso:iso ratio for cultures of WT strain 168 (□) and mutant strains ΔbfabHA (▒) and ΔbfabHB (bfabHB::erm; ▓) grown on minimal medium at 37° C. Data represent average of three determinations±standard error.
Figure 5C:
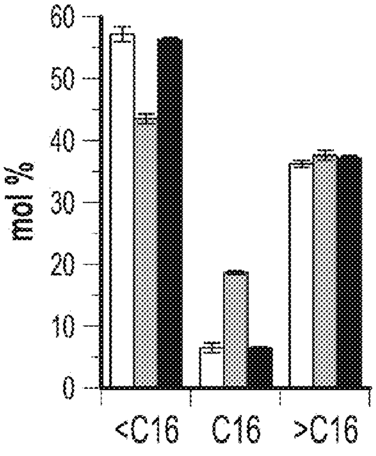
FIG. 5C is a graph of fatty acid chain length (<16, 16 or >16 carbon atoms) vs. mol % for cultures of WT strain 168 (o) and mutant strains ΔbfabHA (▒) and ΔbfabHB (bfabHB::erm; ▓) grown on minimal medium at 37° C. Data represent average of three determinations±standard error.
Figure 5D:
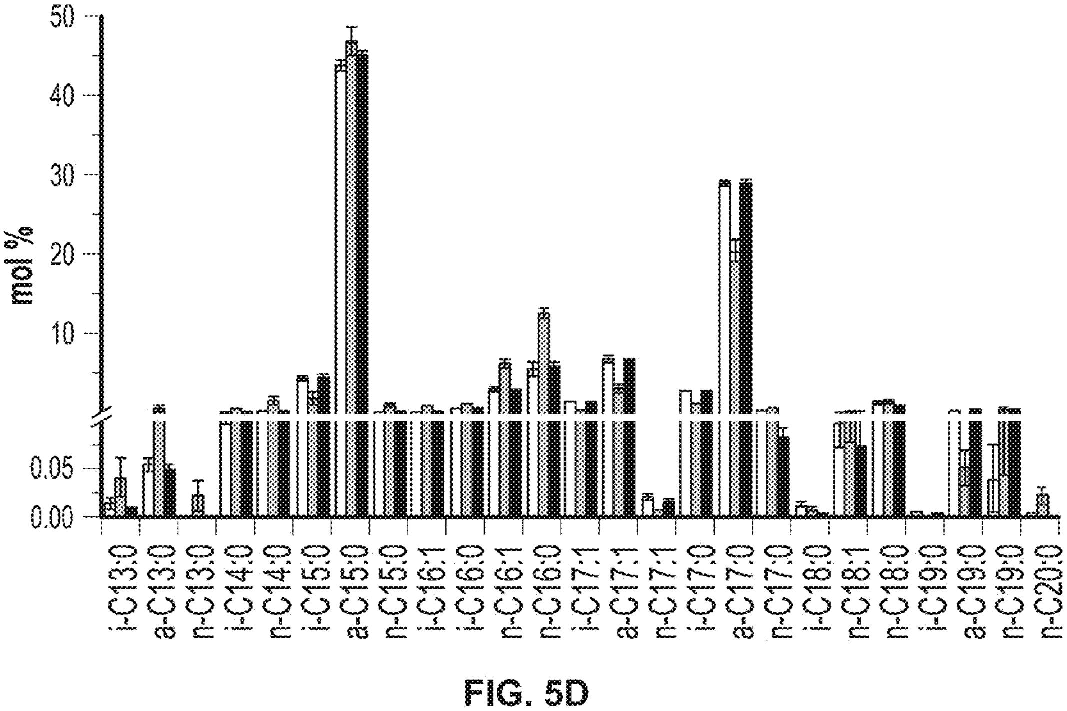
FIG. 5D is a graph of fatty acid vs. mol % showing the effect of deleting the bfabHA and bfabHB genes on fatty acid composition of *B. subtilis*. Cultures of WT strain 168 (□) and mutant strains ΔbfabHA (▒) and ΔbfabHB (bfabHB::erm; ▓) were grown on minimal medium at 16° C. Data represent average of three determinations±standard error.
Figure 5E:
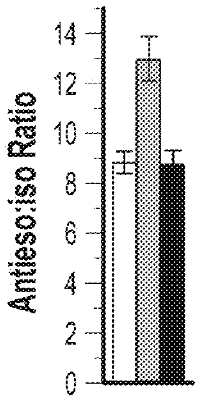
FIG. 5E is a graph of anteiso:iso ratio for cultures of WT strain 168 (□) and mutant strains ΔbfabHA (▒) and ΔbfabHB (bfabHB::erm; ▓) grown on minimal medium at 16° C. Data represent average of three determinations±standard error.
Figure 5F:
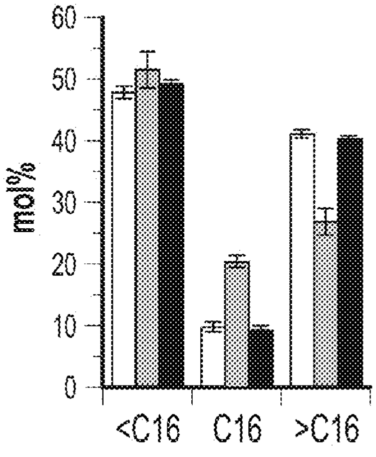
FIG. 5F is a graph of fatty acid chain length (<16, 16 or >16 carbon atoms) vs. mol % for cultures of WT strain 168 (□) and mutant strains ΔbfabHA (▒) and ΔbfabHB (bfabHB::erm; ▓) grown on minimal medium at 16° C. Data represent average of three determinations±standard error.
Figure 5G:
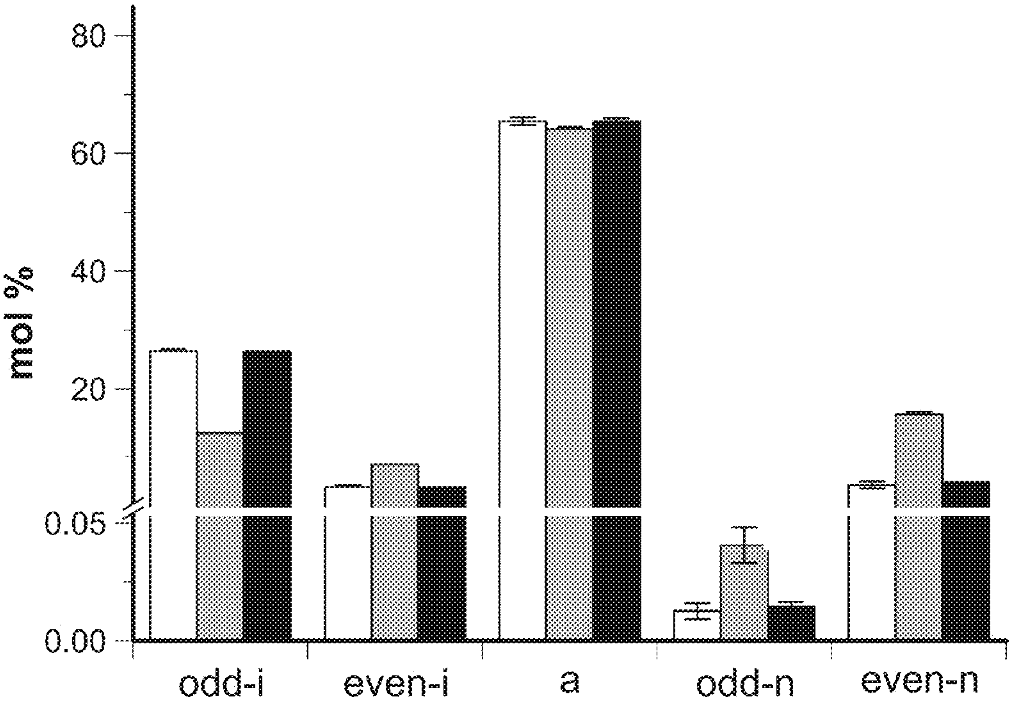
FIG. 5G is a graph of the proportion of different classes of fatty acids (based on the acyl-CoA primers used in their biosynthesis) vs. mol % at 37° C., wherein "odd-i" is odd-numbered iso-fatty acids, "even-i" is even-numbered iso-fatty acids, "a" is anteiso-fatty acids, "odd-n" is odd-numbered normal fatty acids, and "even-n" is even-numbered normal fatty acids. Data represent the average of three determinations±standard error.
Figure 5H:
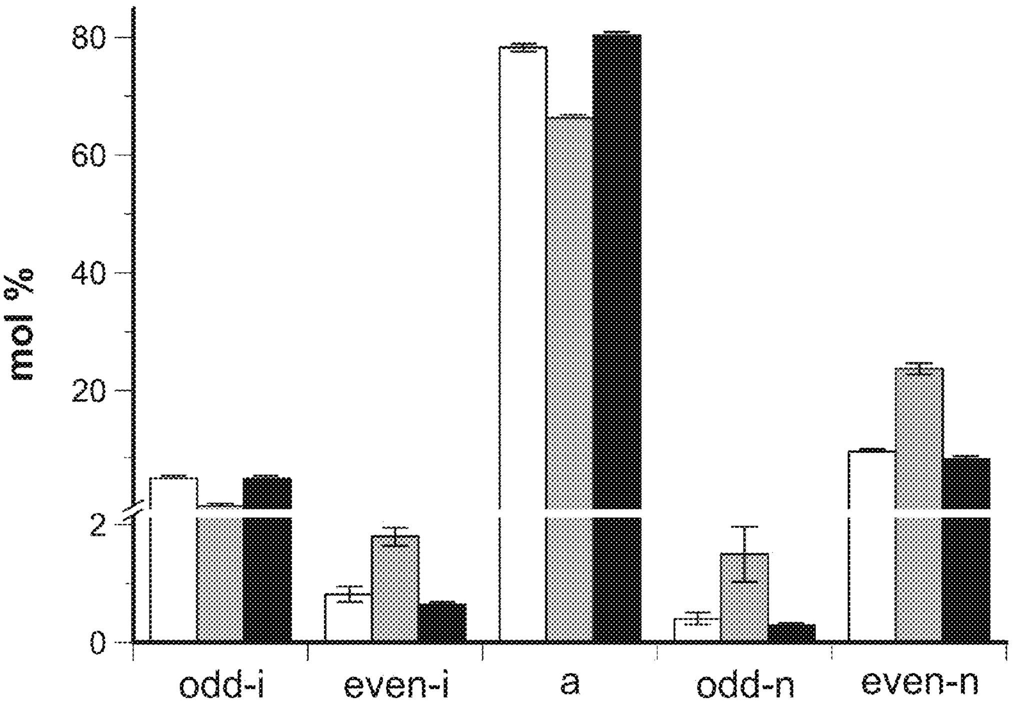
FIG. 5H is a graph of the proportion of different classes of fatty acids (based on the acyl-CoA primers used in their biosynthesis) vs. mol % at 16° C., wherein "odd-i" is odd-numbered iso-fatty acids, "even-i" is even-numbered iso-fatty acids, "a" is anteiso-fatty acid, "odd-n" is odd-numbered normal fatty acids, and "even-n" is even-numbered normal fatty acids. Data represent the average of three determinations±standard error.

These analyses indicated that, at both growth temperatures, the fatty acid composition of the ΔbfabHB mutant was nearly identical to that of wild-type (FIGS. 5A and 5D). This is consistent with the fact that the bfabHB gene was not expressed in the wild-type; thus, the deletion of this gene was functionally inconsequential. However, there were significant alterations in the fatty acid composition caused by the ΔbfabHA deletion (FIGS. 5A and 5D). Some of these genetic effects on the fatty acid composition were independent of the growth temperature, whereas the growth temperature further modulated the ΔbfabHA deletion effect on fatty acid composition. Specifically, at both growth temperatures, most of the fatty acids were similarly affected by the ΔbfabHA deletion (FIGS. 5A and 5D); for example, there was a significant increase in the proportion of even-numbered iso- and odd-numbered normal fatty acids at the expense of odd-numbered iso-fatty acids at both growth temperatures (FIGS. 5G and 5H). In addition, there was a significant increase in the ratio of anteiso:iso BCFAs in the ΔbfabHA mutant (FIGS. 5B and 5E). Finally, ΔbfabHA mutant accumulated significantly more C16 fatty acids (both normal and iso-branched saturated and unsaturated form) (FIGS. 5C and 5F). In contrast, the genetic effect of deleting the fabHA gene on the anteiso-fatty acids was unique in that it expressed at the lower temperature, whereas the accumulation of these fatty acids was not altered by the ΔbfabHA deletion at 37° C. (FIGS. 5G and 5H). Furthermore, at 37° C. the ΔbfabHA mutant accumulated significantly lesser amounts of shorter-chain fatty acids (<C16) than the wild-type strain (FIG. 5C), and this difference was not apparent at 16° C. (FIG. 5F). Rather, at the lower growth temperature, the ΔbfabHA strain expressed a lower level of the longer-chain fatty acids (>C16) (FIG. 5F). Finally, the genetic manipulations of the KASIII-coding genes did not affect the degree of fatty acid unsaturation; rather, in all three genotype strains, unsaturated fatty acids increased at the lower growth temperature (FIGS. 5A and 5D), consistent with the role of a Δ5 desaturase in the temperature adaptation of *B. subtilis* (Aguilar et al., J. Bacteriol. 180: 2194-2200 (1998)).

—Rescue of KASIII Deficiency in *B. subtilis* by Anteiso-, Iso- and Unsaturated Fatty Acids.

A KASIII-deficient strain was developed in the ΔbfabHA strain by inserting the erm gene into the bfabHB locus via a homologous double-crossover recombination event. The resulting ΔbfabHA ΔbfabHB::erm double-deletion mutant proved to be lethal, but could be rescued by the inclusion of BCFAs in the media, specifically anteiso-16:0. The absence of either KASIII proteins in the rescued double-mutant strain was confirmed by Western blot analysis. These findings established that KASIII is essential for *B. subtilis* cellular metabolism.

Although anteiso-16:0 could rescue the KASIII deficiency, the rescued strain grew considerably slower than the wild-type strain. Therefore, whether or not other fatty acids could improve the growth capabilities of the KASIII-deficient strain was examined. Rescue of the KASIII-deficient strain was attempted by the inclusion of anteiso- and iso-BCFAs, and normal saturated and unsaturated fatty acids of different chain lengths. These complementation experiments were conducted by providing these fatty acids in the media at three different concentrations (10, 30 and 100 μM each). At the lowest concentration tested, only anteiso-fatty acids supported the growth of the KASIII-deficient strain, and of all the chain-lengths attempted (anteiso-C5:0, C6:0, C7:0, C8:0, C9:0, C10:0, C12:0, C13:0 and C16:0), only C13:0 and C16:0 anteiso-fatty acids were successful in complementing the KASIII deficiency. At the higher concentration level (30 μM), iso-C16:0 was able to rescue growth, but none of the other shorter chain length iso-fatty acids that were attempted (i.e., iso-C4:0, C5:0, C6:0, C7:0, C9:0, and C10:0) could rescue the KASIII deficiency, even at 100 μM levels. None of the tested normal saturated chain fatty acids (n-C8:0, C10:0, C12:0, C14:0, C16:0 and C18:0) could rescue growth (at any of the tested concentrations). Rescue of this strain was also attempted with monounsaturated fatty acids, and of the three that were attempted, palmitoleic acid, n-C17:1(10) could rescue the KASIII deficiency when supplied at 30 μM, but oleic acid could not rescue the strain even at 100 μM. These results indicate that BCFAs, either iso- or anteiso, and mono-unsaturated fatty acids are important constituents that provide an essential function to *B. subtilis* membranes, most probably associated with maintaining membrane fluidity.

Figure 6A:
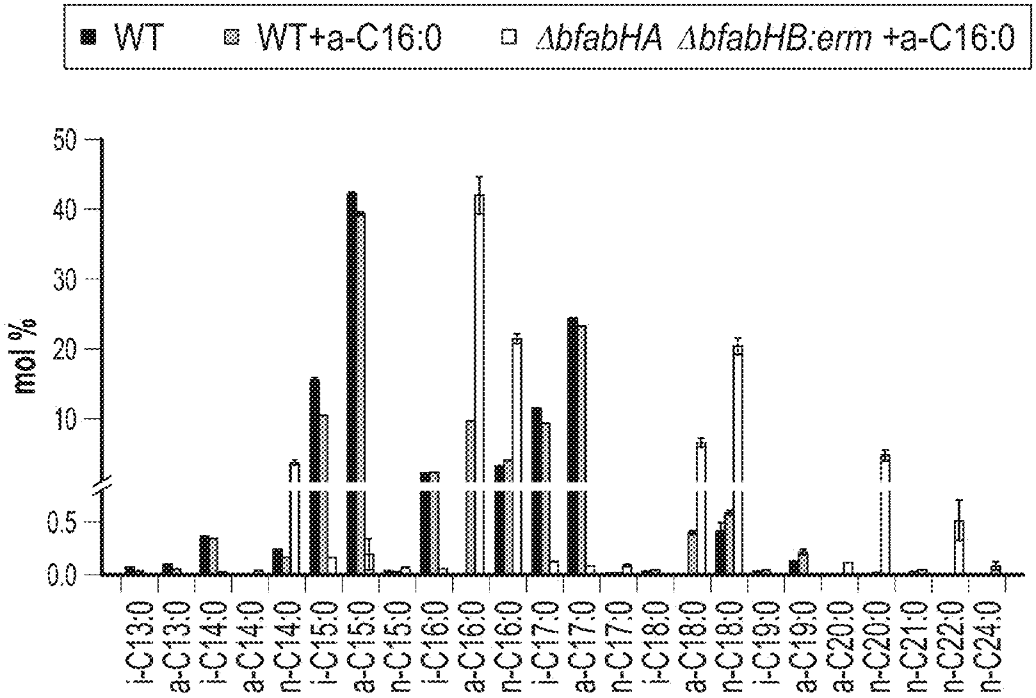
FIG. 6A is a graph of fatty acid vs. mol % of WT *B. subtilis* grown without (▓) or with (▒) 10 μM anteiso-C16 fatty acid, compared to the ΔbfabHA ΔbfabHB::erm double mutant rescued by the inclusion of 10 μM anteiso-C16 fatty acid in the media (□).

Because anteiso-16:0 is not a fatty acid that *B. subtilis* normally synthesizes, fatty acid analysis of the rescued strain provided novel insights into the fatty acid metabolism of this organism. For example, the anteiso-C16:0 rescued KASIII-deficient strain not only incorporated the exogenously provided fatty acid into the membrane lipids, but it metabolized this fatty acid by two rounds of elongation, indicated by the presence of anteiso-C18:0 and anteiso-C20:0, and one round of β-oxidation, indicated by the presence of anteiso-C14:0 (FIG. 6A). In total about 50% of the fatty acids recovered in the rescued strain was accounted by these metabolic derivatives of the exogenously provided anteiso-BCFAs (FIG. 6B).

Figure 6B:
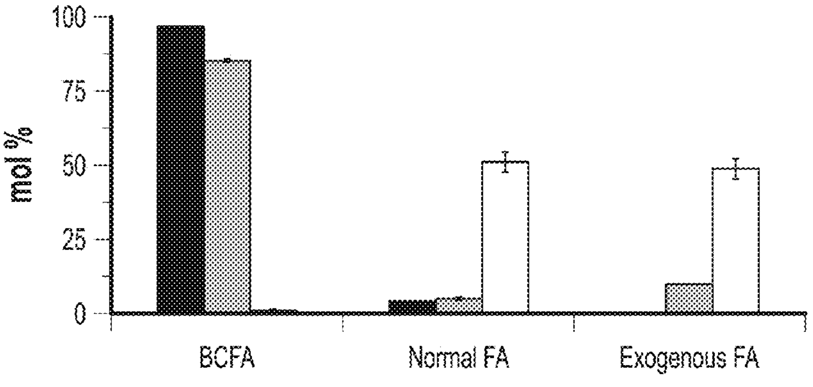
FIG. 6B is a graph of fatty acids vs. mol % of WT *B. subtilis* grown without (▓) or with (▒) anteiso-C16 fatty acid, compared to the ΔbfabHA ΔbfabHB::erm double mutant rescued by the inclusion of 10 μM anteiso-C16 fatty acid in the media (□), wherein BCFA is branched chain fatty acids, normal FA is normal fatty acids, and exogenous FA is exogenous fatty acids.
Figure 7A:
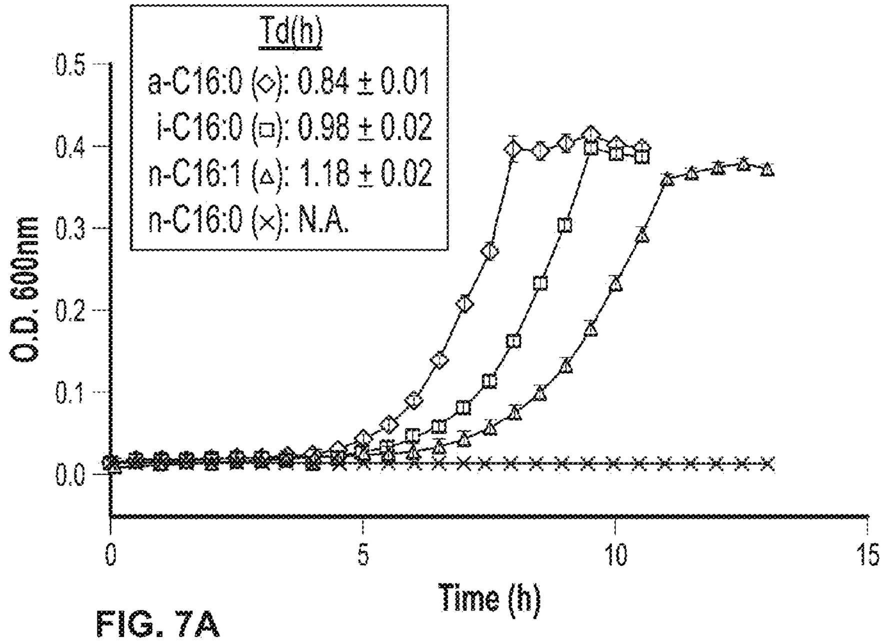
FIG. 7A is a graph of time (hours (h)) vs. OD at 600 nm with doubling times indicated for *B. subtilis* ΔbfabHA ΔbfabHB::erm double mutant strain grown in LB medium supplied with 30 μM anteiso-C16:0, iso-C16:0, palmitoleic acid or n-C16:0 at 37° C. Data represent average of three determinations±standard error. NA=not applicable.
Figure 7C:
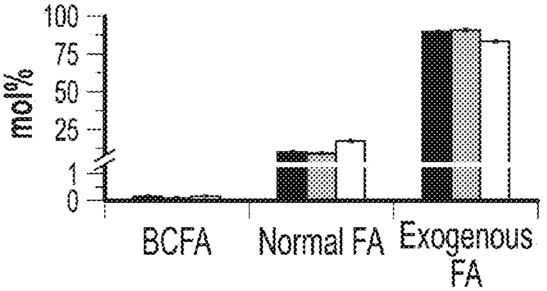
FIG. 7C is a graph of type of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 37° C., wherein BCFA is branched chain fatty acids, normal FA is normal fatty acids, and exogenous FA is exogenous fatty acids.
Figure 7B:
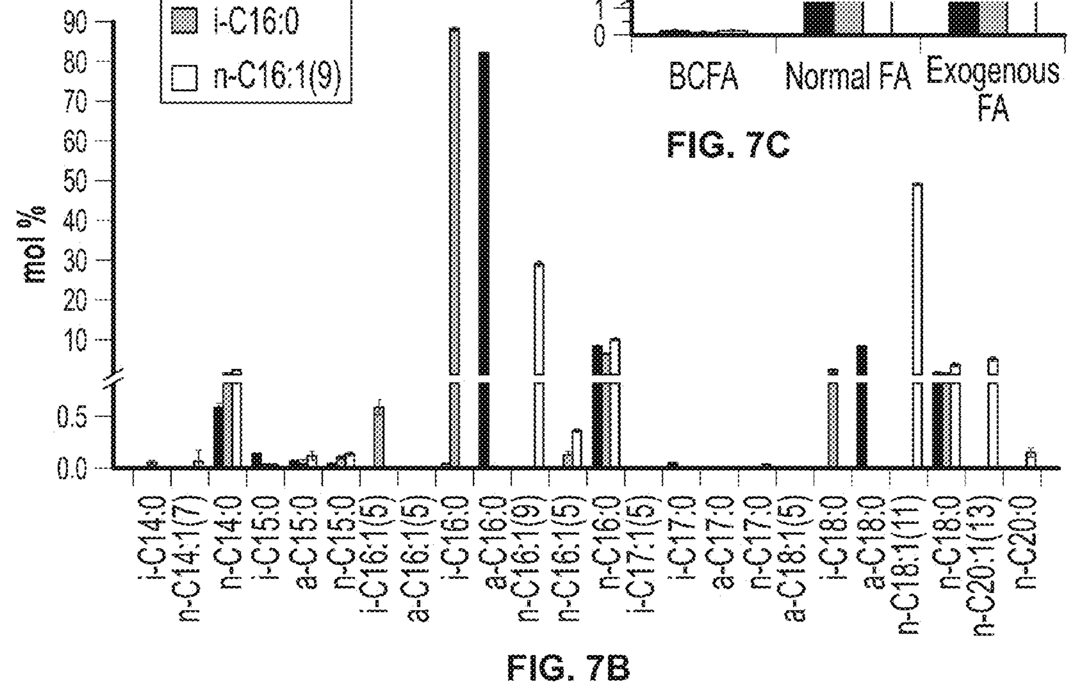
FIG. 7B is a graph of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 37° C.
Figure 7D:
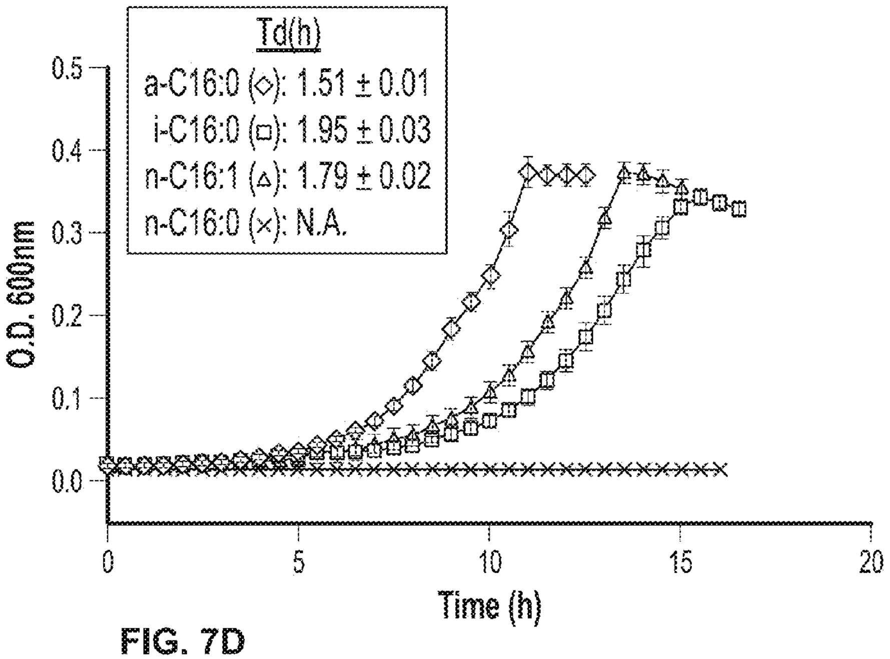
FIG. 7D is a graph of time (hours (h)) vs. OD at 600 nm with doubling times indicated for *B. subtilis* ΔbfabHA ΔbfabHB::erm double mutant strain grown in LB medium supplied with 30 μM anteiso-C16:0, iso-C16:0, palmitoleic acid or n-C16:0 at 30° C. Data represent average of three determinations±standard error. NA=not applicable.
Figure 7F:
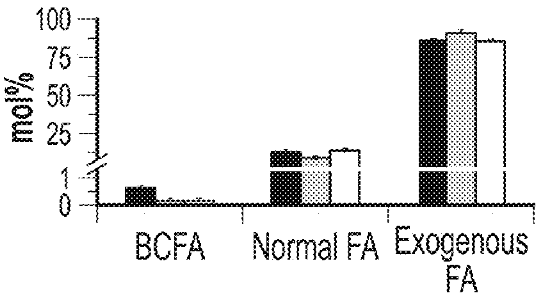
FIG. 7F is a graph of type of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 30° C., wherein BCFA is branched chain fatty acids, normal FA is normal fatty acids, and exogenous FA is exogenous fatty acids.
Figure 7E:
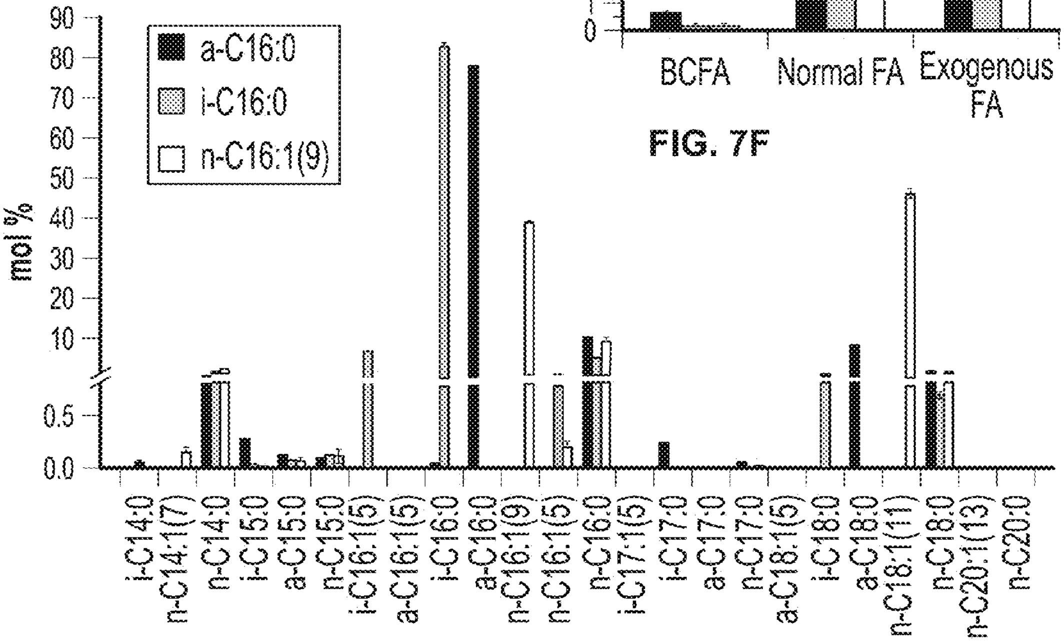
FIG. 7E is a graph of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 30° C.
Figure 7G:
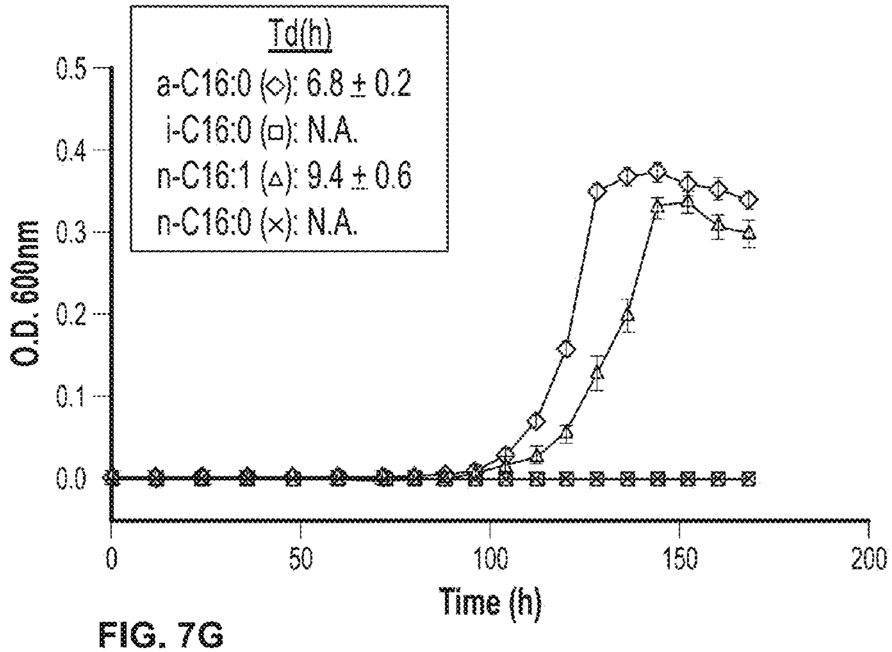
FIG. 7G is a graph of time (hours (h)) vs. OD at 600 nm with doubling times indicated for *B. subtilis* ΔbfabHA ΔbfabHB::erm double mutant strain grown in LB medium supplied with 30 μM anteiso-C16:0, iso-C16:0, palmitoleic acid or n-C16:0 at 20° C. Data represent average of three determinations±standard error. NA=not applicable.
Figure 7I:
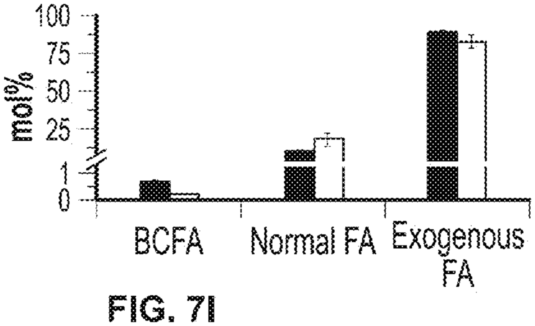
FIG. 7I is a graph of type of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 20° C., wherein BCFA is branched chain fatty acids, normal FA is normal fatty acids, and exogenous FA is exogenous fatty acids.
Figure 7H:
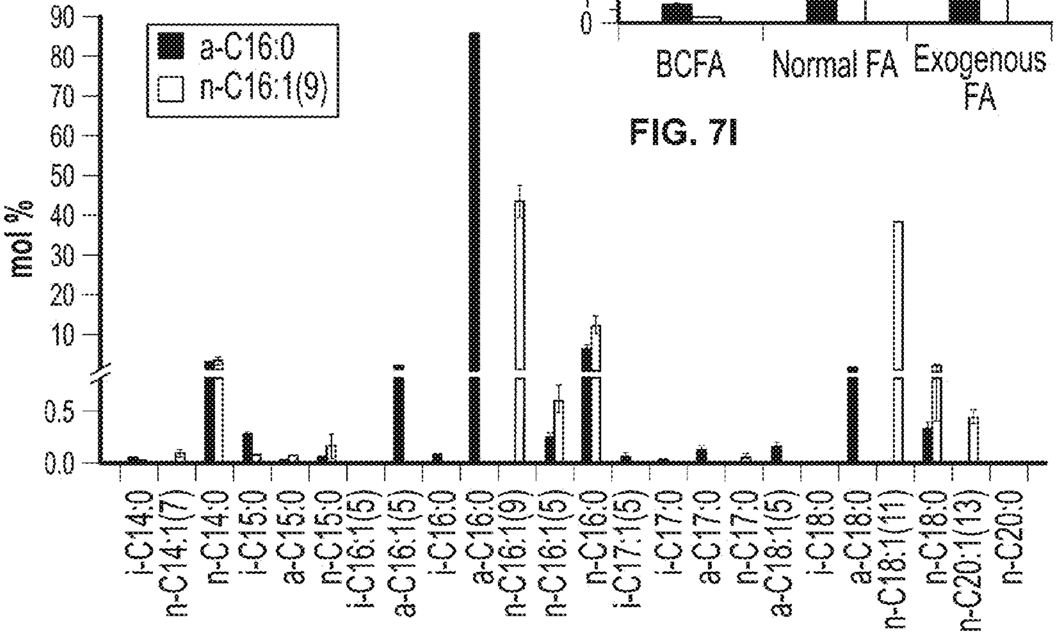
FIG. 7H is a graph of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 20° C.
Figure 7J:
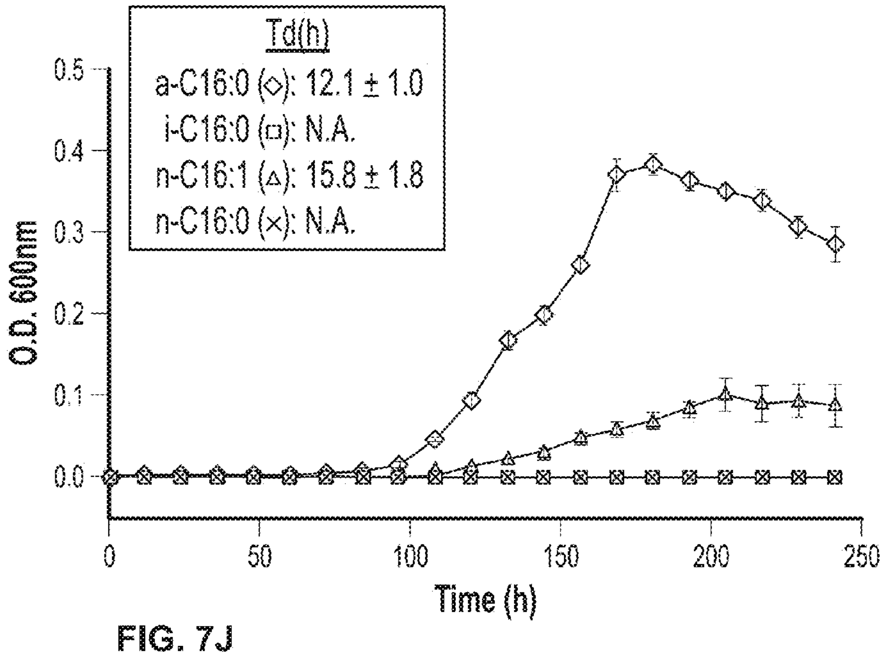
FIG. 7J is a graph of time (hours (h)) vs. OD at 600 nm with doubling times indicated for *B. subtilis* ΔbfabHA ΔbfabHB::erm double mutant strain grown in LB medium supplied with 30 μM anteiso-C16:0, iso-C16:0, palmitoleic acid or n-C16:0 at 16° C. Data represent average of three determinations±standard error. NA=not applicable.
Figure 7L:
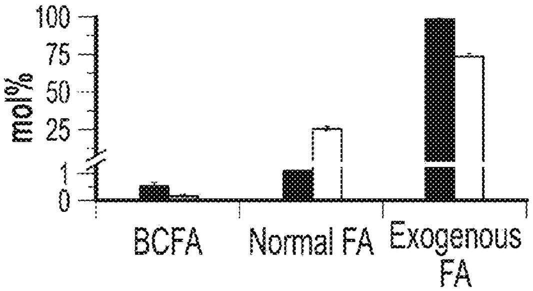
FIG. 7L is a graph of type of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 16° C., wherein BCFA is branched chain fatty acids, normal FA is normal fatty acids, and exogenous FA is exogenous fatty acids.
Figure 7K:
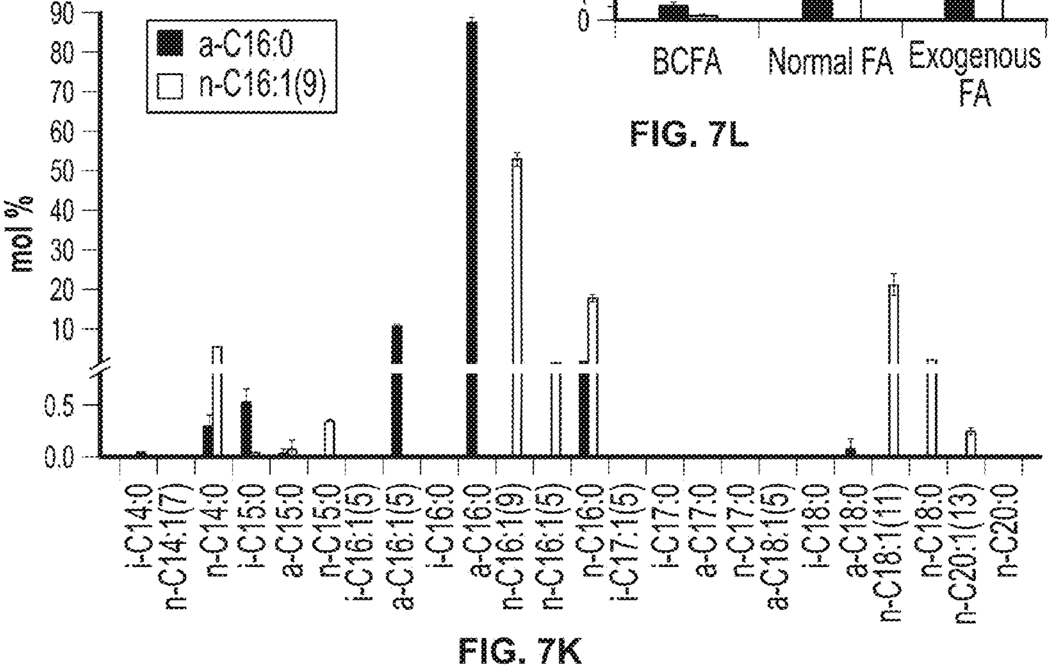
FIG. 7K is a graph of fatty acids vs. mol % for *B. subtilis* ΔbfabHA ΔbfabHB::erm double mutant strain grown in LB medium supplied with 30 μM anteiso-C16:0, iso-C16:0, palmitoleic acid or n-C16:0 at 16° C.

Interestingly, this anteiso-C16:0-rescued KASIII-deficient strain still had the ability to synthesize significant amounts of straight-chain fatty acids (FIG. 6A), and these accounted for about 50% of the recovered fatty acids (FIG. 6B). This observation therefore, indicates the occurrence of an alternative, KASIII-independent mechanism for initiating normal fatty acid biosynthesis. This mechanism is likely to involve the decarboxylation of malonyl-ACP to generate acetyl-ACP (Alberts et al., J. Biol. Chem. 247: 3190-3198 (1972); McGuire et al., Biochem. 40: 9836-9845 (2001); and Kaneda, Microbiol. Rev. 55: 288-302 (1991)), and subsequently the condensation of acetyl-ACP with malonyl-ACP to form 3-ketobutryl-ACP by KASII (encoded by yjaY), overcoming the need for KASIII function (Butterworth et al., Eur. J. Biochem. 12: 496-501 (1970)).

—Comparative Efficacy of Rescue of KASIII Deficiency by Anteiso-, Iso- and Unsaturated Fatty Acids at Different Growth Temperatures.

Presupposing that the chemo-physical properties of fatty acids determine their capacity to affect membrane function, the KASIII-deficient strain, which grew only in the presence of exogenously provided fatty acids that affect membrane fluidity, provided an excellent bio-system to test the relative ability of anteiso-, iso- and unsaturated fatty acids to rescue the KASIII deficiency by modulating membrane fluidity and, hence, supporting growth. Moreover, by conducting these tests at different growth temperatures, the degree to which these different types of fatty acids maintained membrane fluidity in response to thermal tolerance was assessed (Suutari et al., Crit. Rev. Microbiol. 20: 285-328 (1994)).

Four different types of 16-carbon fatty acids (anteiso-C16:0, iso-C16:0, palmitoleic acid, and palmitic acid) were supplied in the medium to evaluate the capacity of these different fatty acids to rescue the KASIII-deficient strain at four different temperatures between 16° C. and 37° C. The rescued strains grew at different rates depending upon the type of fatty acid that was provided, which was interpreted as an indication of each fatty acid's ability to contribute to membrane functionality, by maintaining membrane fluidity as the strain was challenged with lower temperatures. At all temperatures tested, anteiso-C16:0 was most efficient in supporting growth. The second most efficient fatty acid to support growth depended on the growth temperature. At 37° C. iso-C16:0 was better able to support growth than n-C16:1(9), but at lower temperatures n-C16:1(9) was more efficient than iso-C16:0. Indeed, at or below 20° C. iso-C16:0 was incapable of supporting growth, whereas anteiso-C16:0 and n-C16:1(9) rescued the KASIII deficiency, with the former being considerably more efficient (FIG. 7).

With the exception of the experiment conducted at 16° C., fatty acid analysis of the rescued strains indicated that the exogenously provided fatty acids and their metabolic derivatives accounted for about 90% of the cellular fatty acids (FIG. 7). The exception at 16° C., the exogenously provided anteiso-16:0 and its derivatives accounted for over 98% of the cellular fatty acids but, in contrast, the exogenously provided n-C16:1(9) and its derivatives accounted for only 75% of the cellular lipids at this temperature. At all temperatures tested and with all three types of fatty acids that rescued growth, the metabolic derivatives were the result of three types of conversions of the exogenously provided fatty acids: 1) elongation by one or two cycles of fatty acid synthase, resulting in the accumulation of 18- or 20-carbon fatty acids; 2) chain shortening, probably by one cycle of β-oxidation to generate 14-carbon fatty acids; and 3) desaturation, via the Δ5-desaturase (Aguilar et al. (1998), supra), generating mono-unsaturated fatty acids.

Example 3

This example describes the structural analysis of wild-type and mutant KASIII enzymes from *B. subtilis* and *E. coli*.

—Tertiary Structure Prediction of *B. subtilis* KASIII Enzymes.

Tertiary structures of KASIII homologs found in *B. subtilis* (i.e., KASIIIA and KASIIIB) were predicted using homology modeling. An NCBI BlastP search against the PDB database was used to identify sequences that shared>40% sequence identity with KASIIIA and KASIIIB protein sequences. For KASIIIA, *S. aureus* KASIII (PDB ID-1ZOW; chain A) showed maximum sequence identity (58%), followed by *Aquifex aeolicus* KASIII (PDB ID-2EBD; chain A) with 52% sequence identity. These two sequences were used as template sequences for KASIIIA, and each of these was aligned with the KASIIIA sequence using ClustalW alignment software (on the worldwide web at ebi(dot)ac(dot)uk). The target-template sequence alignments were used to model tertiary structures of KASIIIA using the alignment mode of Swiss Model (on the worldwide web at swissmodel(dot)expasy(dot)org). The two different models obtained were assessed for their quality using Verify3D, Gromos and Anolea, and the best model was chosen for further analysis. A similar approach was used for predicting the tertiary structure of *B. subtilis* KASIIIB using *Thermus thermophilus* KASIII (PDB ID-1UB7; chain A), which showed maximum sequence identity (44%), and *S. aureus* KASIII, which had 42% identity, as template sequences. The PDB files of selected models were analyzed using PyMol software (on the worldwide web at pymol(dot)org).

—Gene Cloning.

The *E. coli* fabH gene that encodes KASIII was PCR-amplified from *E. coli* strain MG1655 (*E. coli* Genetic Stock Center, New Haven, Conn.) and cloned into pDEST17 vector using Gateway cloning (Invitrogen, Carlsbad, Calif.), resulting in the pDEST_KASIII construct. The yhfB and yjaX genes encoding *B. subtilis* KASIIIA and KASIIIB, respectively, were PCR-amplified from *B. subtilis* strain 168 (*Bacillus* Genetic Stock Center, Columbus, Ohio). These genes were cloned into pET30a expression vector (Novagen, Merck, Germany) to construct pET30_KASIIIA and pET30_KASIIIB, and also were cloned into the pDEST17 expression vector using Gateway cloning to generate pDEST_KASIIIA and pDEST_KASIIIB. Each pDEST17 and pET30a construct encoded an N-terminal His-tag. The resulting plasmids were confirmed by sequencing.

—Expression and Purification of Recombinant Wild-Type and Mutant KASIII Proteins.

*E. coli* OverExpress™ C41 (Lucigen, Middletown, Wis.) strain was used for expression of KASIII proteins from constructs pDEST_KASIII, pET30_KASIIIA, pET30_KASIIIB, pDEST_KASIIIA and pDEST_KASIIIB. The transformants were grown at 37° C. in 50 ml Luria-Bertani medium, supplemented with 100 μg/ml ampicillin (Research Products International Corps., Mount Prospect, Ill.) for pDEST_KASIII, pDEST_KASIIIA, and pDEST_KASIIIB or 50 μg/ml kanamycin (RPI Corps.) for pET30_KASIIIA and pET30_KASIIIB. The cultures were induced by the addition of IPTG (Gold Biotechnology, Olivette, Mo.) to a final concentration of 0.4 mM when the $OD_{600}$ was 0.6-0.8. After incubation for another 16-18 hours at 25° C., cells were harvested by centrifugation (10,000×g, 4° C., 10 minutes). Soluble proteins were extracted by first suspending the cell pellet in lysis buffer (0.5 M NaCl, 5 mM imidazole, 20 mM Tris-HCl, pH 8.0, 0.1 mg/ml phenylmethylsulfonyl fluoride, and 0.1% Triton-X 100), followed by sonication (10-second pulses separated by three-second intervals for a total of three minutes) and centrifugation (10,000×g, 4° C., 30 minutes). The resulting supernatant (soluble protein fraction) was analyzed by running on SDS-PAGE gel. Based on the small-scale expression experiments that optimized the conditions for obtaining the highest yield of soluble recombinant KASIII proteins, the constructs pDEST_KASIII, pET30_KASIIIA, and pDEST_KASIIIB were used for large-scale expression and purification of wild-type and mutant proteins. Cultures were grown, induced, and harvested, and soluble protein was extracted as described in small-scale expression methods. The soluble protein fraction was filtered through a 0.45 μ filter (Corning, the Netherlands) and applied to 8 ml Ni-NTA His-bind resin. After washing the unbound protein with wash buffers I and II (0.5M NaCl, 20 mM Tris-HCl, pH 8.0) supplemented with 20 mM and 40 mM imidazole, respectively, the proteins of interest were eluted with the same buffer containing 250 mM imidazole. The purified His-tagged KASIII proteins were dialyzed against sodium phosphate buffer, pH 7.4, and concentrated using 10,000 molecular weight cut-off ultrafiltration centrifugation filters (Millipore, Billerica, Mass.) at 4° C. The concentrated proteins were either supplemented with 16% glycerol and stored at −80° C. or immediately used for Saturation Transfer Difference NMR experiments. Protein purity was assessed by Coomassie-staining SDS-PAGE gels, which showed the presence of near-homogenous, pure proteins (greater than 95% purity). Protein concentrations were determined by Bradford's assay (Bio-Rad, Hercules, Calif.).

—Site-Directed Mutagenesis of *E. coli* and *B. subtilis* KASIII Enzymes.

The QuikChange® Site-Directed Mutagenesis Kit (Stratagene, La Jolla, Calif.) was used for introducing point mutations in the pDEST_KASIII, pET30_KASIIIA, and pDEST_KASIIIB constructs. Four mutants were generated from each of these constructs as indicated in Table 3 using the listed primers and their complements.

TABLE 3

Primers for site-directed mutagenesis of *E. coli* and *B. subtilis* KASIII enzymes

| Gene | Construct | Mutation | QuikChange Forward Primer | QuikChange Reverse Primer |
|---|---|---|---|---|
| *E. coli* fabH (KASIII) | pDEST_KASIII | V215F | 5'-GCAACGAAGTCTTCAAGTTTG CGGTAACGGAACTG-3' [SEQ ID NO: 31] | 5'-CAGTTCCGTTACCGCAAACTTG AAGACTTCGTTGC-3' [SEQ ID NO: 32] |
| | | L220M | 5'-TTCAAGGTTGCGGTAACGGAA ATGGCGCACATC-3' [SEQ ID NO: 33] | 5'-GATGTGCGCCATTTCCGTTACC GCAACCTTGAA-3' [SEQ ID NO: 34] |
| | | V215F_L220M | 5'-GCAACGAAGTCTTCAAGTTTG CGGTAACGGAACTG-3' [SEQ ID NO: 35] 5'-TTCAAGGTTGCGGTAACGGAA ATGGCGCACATC-3' [SEQ ID NO: 37] | 5'-CAGTTCCGTTACCGCAAACTTG AAGACTTCGTTGC-3' [SEQ ID NO: 36] 5'-GATGTGCGCCATTTCCGTTACC GCAACCTTGAA-3' [SEQ ID NO: 38] |
| | | F304A | 5'-GGTTCTGCTTGAAGCCGCTGG CGGTGGATTCACC-3' [SEQ ID NO: 39] | 5'-GGTGAATCCACCGCCAGCGGCT TCAAGCAGAACC-3' [SEQ ID NO: 40] |
| *B. subtilis* yjaX (KASIIIA) | pET30_KASIIIA | F208V | 5'-GAATGGACGAGAAGTTTTCAA AGTTGCAGTCCGCC-3' [SEQ ID NO: 41] | 5'-GGCGGACTGCAACTTTGAAAAC TTCTCGTCCATTC-3' [SEQ ID NO: 42] |
| | | M213L | 5'-CAAATTTGCAGTCCGCCAATT GGGAGAATCATGCG-3' [SEQ ID NO: 43] | 5'-CGCATGATTCTCCCAATTGGCG GACTGCAAATTTG-3' [SEQ ID NO: 44] |
| | | F208V_M213L | 5'-GAATGGACGAGAAGTTTTCAA AGTTGCAGTCCGCC-3' [SEQ ID NO: 45] 5'-CAAAGTTGCAGTCCGCCAATT GGGAGAATCATGCG-3' [SEQ ID NO: 47] | 5'-CGCATGATTCTCCCAATTGGCG GACTGCAAATTTG-3' [SEQ ID NO: 46] 5'-CGCATGATTCTCCCAATTGGCG GACTGCAACTTTG-3' [SEQ ID NO: 48] |

TABLE 3-continued

Primers for site-directed mutagenesis of *E. coli* and *B. subtilis* KASIII enzymes

| Gene | Construct | Mutation | QuikChange Forward Primer | QuikChange Reverse Primer |
|---|---|---|---|---|
| | | F297A | 5'-GGTCGTTATGGTAGGGGCCGG CGGAGGACTAACA-3' [SEQ ID NO: 49] | 5'-TGTTAGTCCTCCGCCGGCCCCT ACCATAACGACC-3' [SEQ ID NO: 50] |
| *B. subtilis* yhfB (KASIIIB) | pDEST_KASIIIB | W221V | 5'-GCAAAACGGACGCGAGGTATA TAAAGTGGCCGCAAGAACC-3' [SEQ ID NO: 51] | 5'-GGTTCTTGCGGCCACTTTATAT ACCTCGCGTCCGTTTTGC-3' [SEQ ID NO: 52] |
| | | V226L | 5'-GGCCGCAAGAACCCTCCCTGG CGAATT-3' [SEQ ID NO: 53] | 5'-AATTCGCCAGGGAGGGTTCTTG CGGCC-3' [SEQ ID NO: 54] |
| | | W221VV226L | 5'-GCAAAACGGACGCGAGGTATA TAAAGTGGCCGCAAGAACC-3' [SEQ ID NO: 55] 5'-GGCCGCAAGAACCCTCCCTGG CGAATT-3' [SEQ ID NO: 57] | 5'-GGTTCTTGCGGCCACTTTATAT ACCTCGCGTCCGTTTTGC-3' [SEQ ID NO: 56] 5'-AATTCGCCAGGGAGGGTTCTT GCGGCC-3' [SEQ ID NO: 58] |
| | | F310A | 5'-AATCGTTTTGCTTTTCGGGGC TGGCGGCGGATTAACCTAT-3' [SEQ ID NO: 59] | 5'-ATAGGTTAATCCGCCGCCAGCC CCGAAAAGCAAAACGATT-3' [SEQ ID NO: 60] |

—Circular Dichroism (CD) Spectroscopy of KASIII Mutants.

All CD spectra of purified KASIII proteins (0.1-0.25 mg/ml in 10 mM sodium phosphate buffer, pH 7.4) were collected with Jasco J-710 Spectropolarimeter, in a 0.1 cm cell at 25° C. Far-UV spectra were recorded with a bandwidth of 1.0 nm and a time response of eight seconds with a total of two data accumulations.

—Saturation Transfer Difference NMR Experiments.

NMR experiments were performed at 25° C. on a Bruker AV700 MHz spectrometer equipped with a 5 mm HCN cryoprobe. Samples for STD NMR experiments were prepared in 0.1 M sodium phosphate buffer (pH 7.4) with 5% $D_2O$. The protein/ligand ratio was set as 1:100 with KASIII concentration in the 20-25 μM range. Saturation was applied as CW pulse with a power of 58-60 Hz, with on-resonance pulses at 0.62 ppm and 6.86 ppm for upfield and downfield, respectively. The off-resonance pulse was applied at 45 ppm. 3-9-19 WATERGATE suppression was used with a T1-ρ filter. Saturation time of five seconds with an additional delay of 5.1 seconds was used. A set of three replicates was acquired, with 32 scans in each replicate, for each STD NMR experiment of KASIII wild-type or mutated enzyme with a ligand, which was either acetyl-CoA or isobutyryl-CoA (Sigma-Aldrich, St. Louis, Mo.). The reference and the saturated spectra were obtained in an interleaved manner. Resonance assignments of 1H NMR spectra of free ligands were completed using 1D IH and COSY.

Control experiments were carried out by applying on- and off-resonance saturation pulses either to the ligand in the absence of protein, or to the ligand in the presence of denatured protein. Time dependence of the saturation transfer was calculated by varying the saturation times from 0.1 milliseconds to 100 seconds, which showed that five seconds were sufficient to transfer the saturation from protein to the ligand. Topspin (Bruker Biospin Corp., Billerica, Mass.) was used for processing the reference and saturated spectra and integrating areas of the peaks that showed STD effect.

Relative STD effects ($A_{STD}$) were calculated according to the equation $A_{STD}=(I_o-I_{sat})/I_o$ where $I_{sat}$ is the signal intensity of the saturated spectrum and $I_o$ is the signal intensity of the reference spectrum (Mayer et al., J. Am. Chem. Soc. 123: 6108-6117 (2001)). STD amplification factor was calculated according to the equation: $STD_{af}=A_{STD}$ X molar ligand excess.

Competition binding experiments were performed under the conditions described above, using a first ligand at constant concentration of 10 mM, and a competing ligand present at molar ratios of 1, 2, 4, 8 and 10-fold higher with respect to the first ligand.

—Differences in Active Site Residues of *E. coli* and *B. subtilis* KASIII Based on Homology Modeling.

The tertiary structures of *B. subtilis* KASIII homologs (KASIIIA encoded by yjaX, and KASIIIB encoded by yhfB) were predicted via homology modeling using the methods described above. Superposition of the *E. coli* KASIII crystal structure (PDB code 31L9) with predicted *B. subtilis* KASIIIA and KASIIIB structures allowed the identification of active site cleft residues that have different conformations in KASIII enzymes from the two organisms. A previous hypothesis suggests that the rotamer conformation of a conserved Phe (Phe-304 in *E. coli*) may impact substrate specificity (Gaijwala et al. (2009), supra). In accordance with this hypothesis, we observed that, whereas in Gram-negative *E. coli* KASIII, the side chain of this conserved Phe-304 residue is oriented away from the active site (i.e., its rotamer is in an active-site distal conformation) (FIG. 8A), in the predicted structure of Gram-positive *B. subtilis* KASIIIA, the side chain of Phe-297 faces towards the active site (i.e., it exhibits an active-site proximal conformation). Similarly, in the predicted structure of *B. subtilis* KASIIIB, Phe-310 rotamer shows the active-site proximal conformation. The conformation of this Phe residue correlates with the substrate specificity of the three KASIII enzymes, with the *E. coli* enzyme, which shows a narrow substrate specificity, having the active-site distal rotamer conformation, and the two *B. subtilis* KASIIIs, which show a broader substrate specificity, having the active-site proximal rotamer conformation for this Phe residue. Consistent with this correlation is the observation that KASIIIs of Gram-positive organisms that produce branched-chain fatty acids, and presumably have a KASIII with a broader substrate specificity, have bulky residues neighboring this Phe residue, and these bulky residues are assumed to force Phe's conformation to the active-site proximal rotamer conformation and orient the Phe side chain towards the active site cleft (Gajiwala et al. (2009), supra; Pereira et al. (2012), supra). These bulky residues were found to be Phe-208 and Met-213 in *B. subtilis* KASIIIA (FIG. 9A), and Trp-221 and Val-226 in *B. subtilis* KASIIIB, corresponding to smaller residues in *E. coli* KASIII, i.e., Val-215 and Leu-220. These bulky residues in the *B. subtilis* KASIIIs were postulated to cause the conserved Phe active-site proximal rotamers to orient differently from the *E. coli* KASIII Phe-304's active-site distal rotamer, thereby affecting the size and hydrophobicity of active site pockets, and subsequently imparting broad substrate specificity to the *B. subtilis* KASIIIs.

To verify these hypotheses, Val-215 and Leu-220 of *E. coli* KASIII were mutated to the corresponding residues in *B. subtilis* KASIIIA, i.e., Phe and Met, respectively (FIG. 8B). Two single mutants (V215F (nucleotide sequence [SEQ ID NO: 111]; amino acid sequence [SEQ ID NO: 112]) and L220M (nucleotide sequence [SEQ ID NO: 113]; amino acid sequence [SEQ ID NO: 114])) and one double mutant (V215F_L220M (nucleotide sequence [SEQ ID NO: 115]; amino acid sequence [SEQ ID NO:116]) were obtained. Similarly, residues in *B. subtilis* KASIIIA were mutated to equivalent residues in *E. coli* KASIII to generate two single mutants (F208V (nucleotide sequence [SEQ ID NO: 119]; amino acid sequence [SEQ ID NO: 120]) and M213L (nucleotide sequence [SEQ ID NO:121]; amino acid sequence [SEQ ID NO:122])) and a double mutant (F208V_M213L, FIG. 9B; nucleotide sequence [SEQ ID NO:123]; amino acid sequence [SEQ ID NO:124]). In *B. subtilis* KASIIIB, similar set of mutations generated two single mutants (W221V (nucleotide sequence [SEQ ID NO: 127]; amino acid sequence [SEQ ID NO: 128]) and V226L (nucleotide sequence [SEQ ID NO: 129]; amino acid sequence [SEQ ID NO:130])) and a double mutant (W221V_V226L; nucleotide sequence [SEQ ID NO:131]; amino acid sequence [SEQ ID NO: 132]). If substrate specificity is governed by the orientation of the conserved Phe and its orientation is determined by the residues listed above, we hypothesized that *E. coli* KASIII, when mutated to resemble *B. subtilis* KASIII at these sites, would have broadened substrate specificity for both straight- and branched-chain ligands (FIG. 8B). In contrast, *B. subtilis* KASIIIA and KASIIIB, when mutated to resemble *E. coli* KASIII at these sites, would have narrowed substrate specificity and be able to bind to only straight-chain substrates (FIG. 9B).

Each of the wild-type and mutated enzymes were purified to near homogeneity, with the exception of *B. subtilis* KASIIIB double mutant, which formed inclusion bodies and could not be purified. CD spectra of all purified proteins were obtained to ensure that the mutants folded the same as the wild-type KASIII proteins.

STD NMR experiments elucidated interactions of these purified enzymes (both wild-type and mutated) with straight-chain substrate (acetyl-CoA) and branched-chain substrate (isobutyryl-CoA) and enabled mapping of binding epitopes on the two substrates. Relative saturation transfer to each of the binding epitopes was measured and converted to the STD amplification factor ($STD_{af}$), which is an indicator of ligand binding (Mayer et al., J. Am. Chem. Soc. 123: 6108-6117 (2001)). Ligand epitopes with high $STD_{af}$ values are assumed to receive higher saturation transfer from the enzyme, and thus are in close contact with the enzyme. Comparison of $STD_{af}$ values revealed differences in interaction of wild-type and mutated enzymes with straight- and branched-chain ligands.

—Ligand Binding Epitopes for *E. coli* and *B. subtilis* KASIII Enzymes.

Figure 10A:
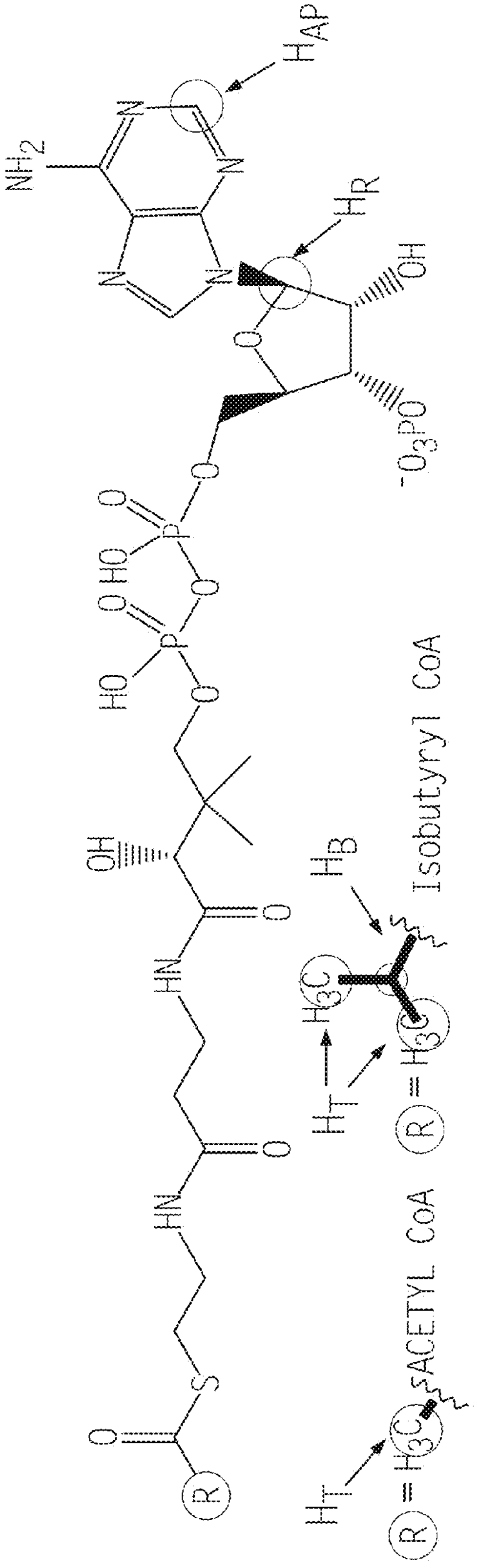
FIG. 10A is a schematic diagram showing the saturation transfer from KASIII enzymes to different ligand binding epitopes of acetyl-CoA and isobutyryl-CoA.
Figure 10B:
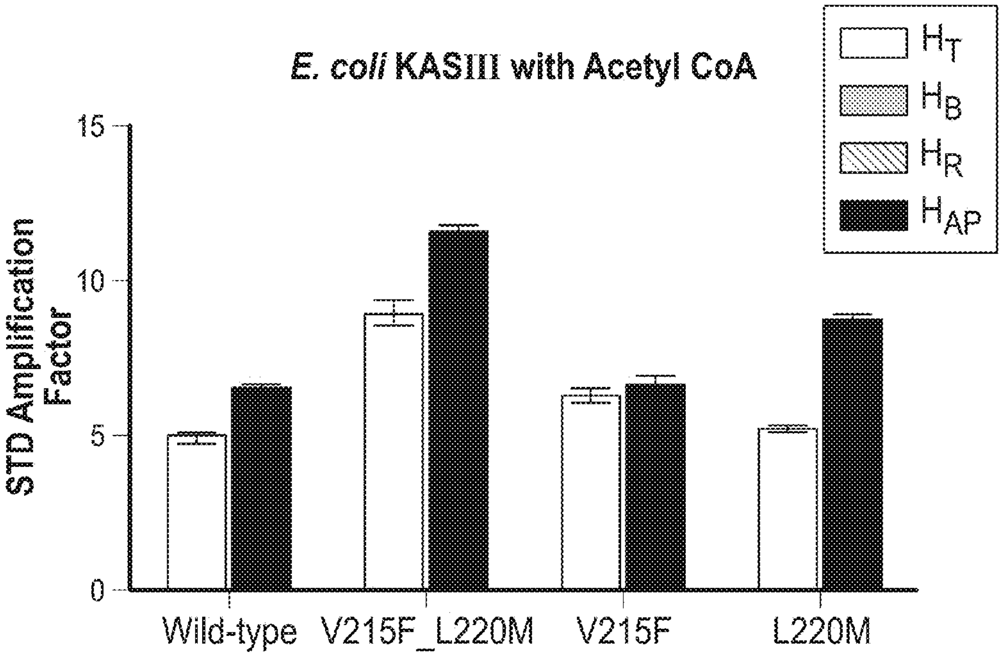
FIG. 10B is a graph of protons of ligand acetyl-CoA vs. STD amplification factor ($STD_{af}$) for *E. coli* KASIII.

From STD NMR experiments with *E. coli* KASIII, binding epitopes were found to be quite similar in the acetyl-CoA and isobutyryl-CoA ligands, irrespective of the wild-type or mutant state of KASIII tested. In both ligands the $H_{AP}$ proton, positioned at C-2 of the adenine ring of CoA, received the maximum saturation transfer (FIG. 10A). This indicates that $H_{AP}$ is in close contact with the KASIII enzyme. This result is in agreement with previous crystallographic data (Choi et al. (2000), supra; and Revill et al. (2001), supra) which showed the adenine ring of CoA sandwiched between Trp-32 and Arg-151 of *E. coli* KASIII. The second highest saturation was received by the terminal proton, $H_T$ (FIG. 10A), in acetyl-CoA, whereas proton $H_B$, which is located on C-2 of the isobutyryl portion of the ligand and is close to the $H_T$ protons, received the second highest saturation transfer in isobutyryl-CoA (FIG. 10B). Saturation transfer to all other protons in both acetyl-CoA and isobutyryl-CoA was very low, less than 38% relative to $H_{AP}$ whose $STD_{af}$ was normalized to 100%. Also, $H_{AP}$ is on the conserved pantethiene arm in each of the acyl-CoA ligands, whereas $H_T$ is on the variable acyl end that has been shown to interact with the active site Cys of KASIII (specifically, with Cys-112 of *E. coli* KASIII (Revill et al. (2001), supra)).

Figure 10C:
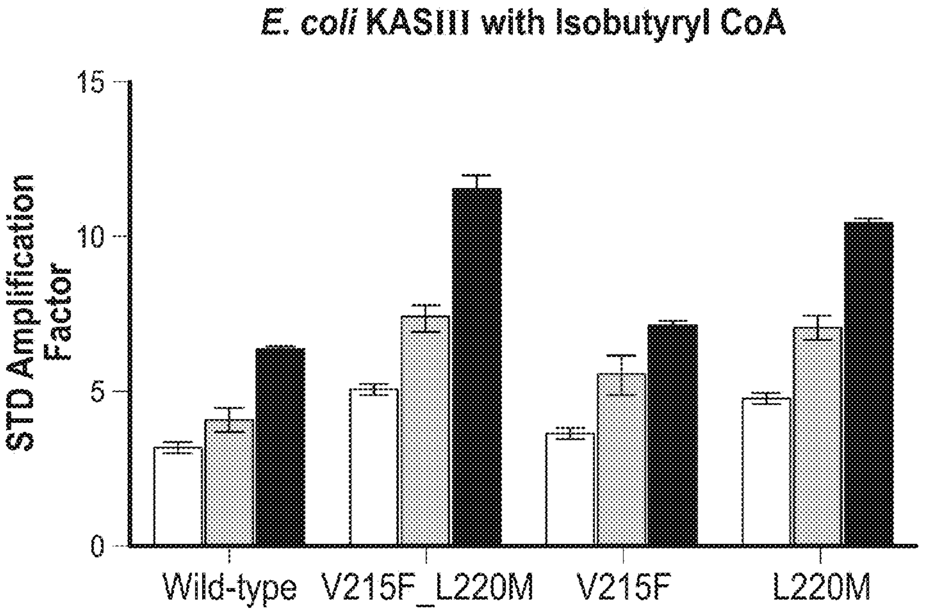
FIG. 10D is a graph of protons of ligand acetyl-CoA vs. STD amplification factor ($STD_{af}$) for *B. subtilis* KASIIIA.
FIG. 10E is a graph of protons of ligand isobutyryl-CoA vs. STD amplification factor ($STD_{af}$) for *B. subtilis* KASIIIA.
FIG. 10F is a graph of protons of ligand acetyl-CoA vs. STD amplification factor ($STD_{af}$) for *B. subtilis* KASIIIB.
FIG. 10G is a graph of protons of ligand isobutyryl-CoA vs. STD amplification factor ($STD_{af}$) for *B. subtilis* KASIIIB.

Similar to *E. coli* KASIII, for *B. subtilis* KASIIIA, the binding epitopes of acetyl-CoA were the methyl group carrying $H_T$ and the adenine moiety bearing $H_A$P, which received the largest saturation transfer (FIG. 10D), whereas other protons received very little saturation transfer (less than 35% relative to $H_{AP}$, which received the maximum saturation, i.e., 100%). Isobutyryl-CoA, surprisingly, had $H_B$ with maximum saturation, $H_{AP}$, and $H_T$ with the second and the third highest saturation transfer, respectively (FIG. 10E). Interestingly, for *B. subtilis* KASIIIB, binding epitopes were slightly different from its homolog KASIIIA and its ortholog *E. coli* KASIII. In addition to $H_T$. $H_{AP}$ in acetyl-CoA, and $H_T$, $H_B$ and $H_{AP}$ in isobutyryl-CoA, a new binding epitope, $H_R$, was identified that received strong saturation transfer in both acetyl and isobutyryl-CoA (FIGS. 10F and 10G). $H_R$ is located on C-5 of the ribose moiety of coenzyme A (FIG. 10A).

For *E. coli* KASIII and *B. subtilis* KASIIIA, because $H_T$. $H_{AP}$ protons in acetyl-CoA and $H_T$, $H_B$ and $H_{AP}$ in isobutyryl-CoA received strong saturation transfer, and consequently had the highest $STD_{af}$, focus was placed on differences in saturation transfer to these protons. As $H_T$ is on the acyl end of the ligand, the amount of saturation transferred to it indicated the extent of KASIII active site's interaction with the ligand. In *B. subtilis* KASIIIB, in addition to $H_T$. $H_{AP}$ in acetyl-CoA and $H_T$, $H_B$ and $H_{AP}$ in isobutyryl-CoA, focus also was placed on $H_R$ for comparing the effect of mutations on substrate binding because it received strong saturation transfer in both acetyl-CoA and isobutyryl-CoA.

—Val215Phe and Leu220Met Mutations Improve Branched-Chain Substrate Binding in *E. coli* KASIII but Decrease Catalytic Activity.

Wild-type *E. coli* KASIII showed binding with acetyl-CoA (FIG. 10B) with $STD_{af}$ values of ~5.0 and ~6.0 for the $H_T$ and $H_{AP}$ protons, respectively. In contrast, STD NMR of *E. coli* KASIII with isobutyryl-CoA as the ligand resulted in relatively lower saturation transfer, $STD_{af}$ of 2.5 to the $H_T$ proton and ~4.0 to the $H_B$ proton, indicating lower binding with branched-chain ligand (FIG. 10C). The *E. coli* double mutant V215F_L220M, on the other hand, exhibited increased $STD_{af}$ for $H_T$, $H_B$ and $H_{AP}$ as compared to wild-type *E. coli* KASIII for both acetyl and isobutyryl-CoA. This suggests that the double mutant, which was mutated to resemble the broad substrate specificity enzyme *B. subtilis* KASIIIA, is showing enhanced interactions with both straight- and branched-chain ligands.

Figure 10D:
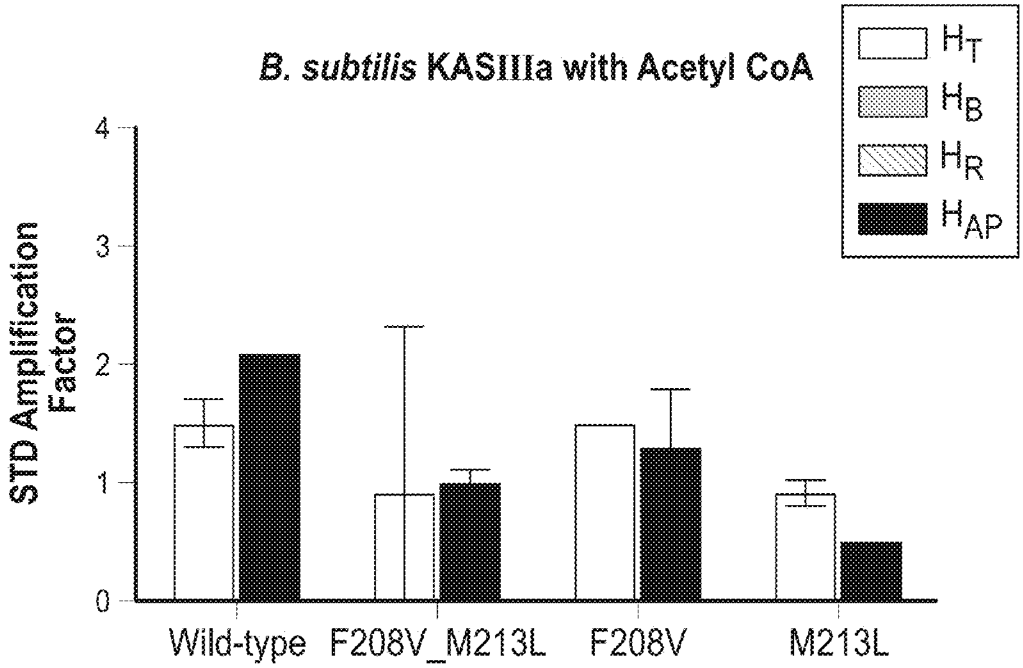
Figure 10E:
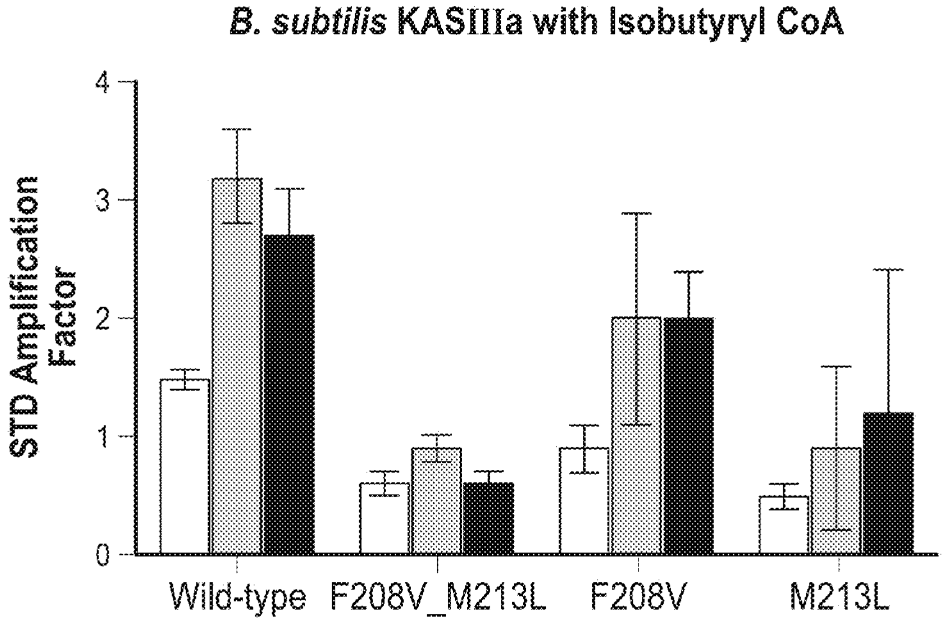
Figure 10F:
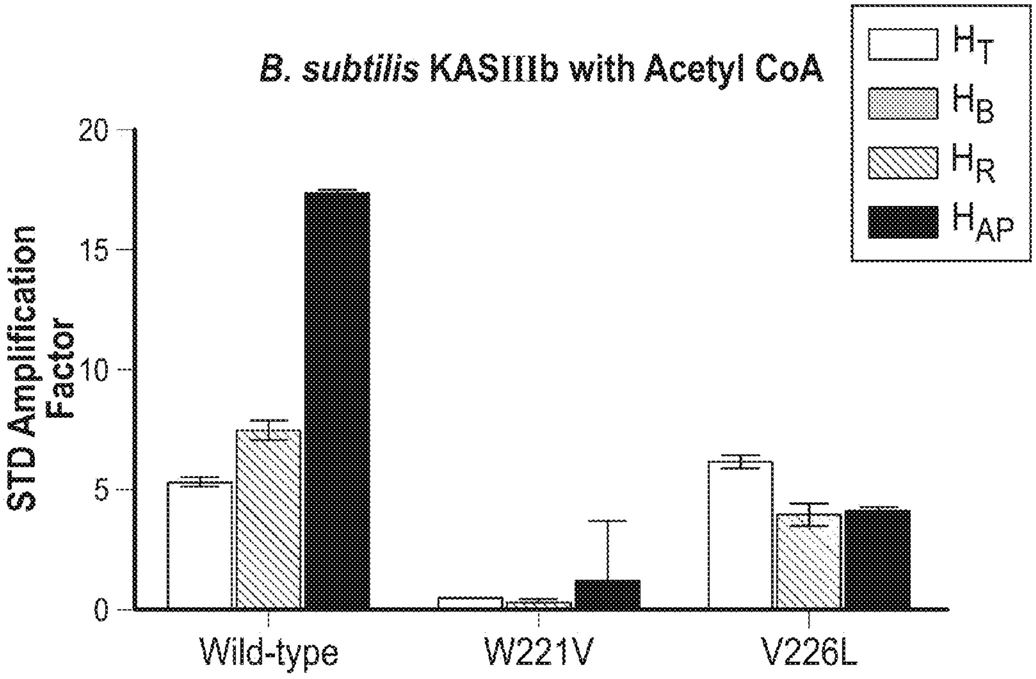
Figure 10G:
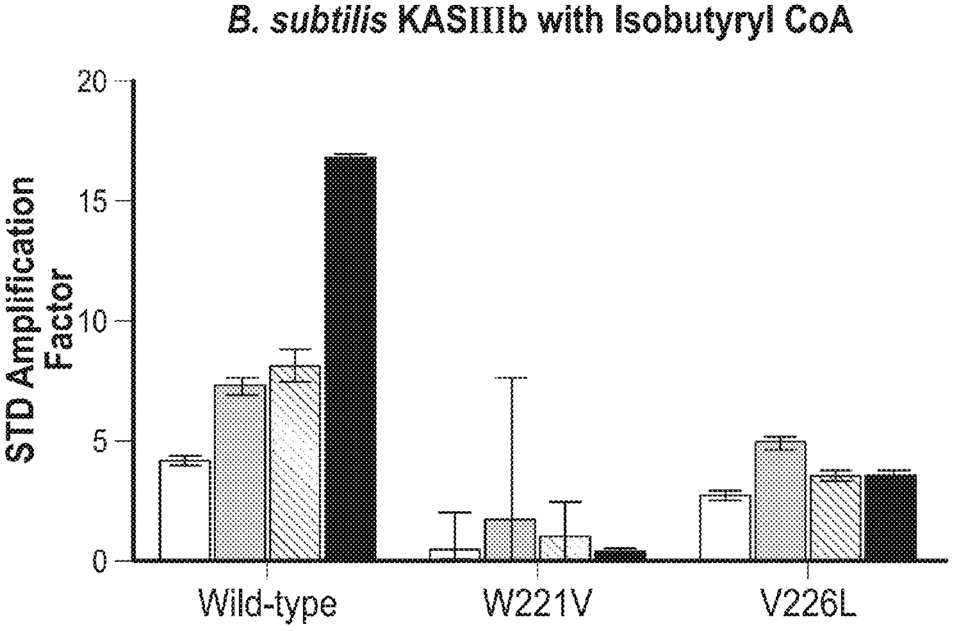

To identify which of the two mutations in the *E. coli* double mutant had a stronger effect on substrate binding, we examined STD amplification for each of the single mutants (i.e., *E. coli* V215F and *E. coli* L220M). The V215F mutation resulted in a slight increase in $STD_{af}$ for $H_T$ protons of both acetyl-CoA and isobutyryl-CoA as compared to the wild-type. However, the L220M mutation did not alter $STD_{af}$ for acetyl-CoA proton $H_T$ but significantly increased $STD_{af}$ for $H_T$ of isobutyryl-CoA (by ~66%) as compared to the wild-type (FIGS. 10B and 10C), suggesting that the substrate binding of *E. coli* KASIII is affected by Leu-220 tremendously and by Val-215 to a lesser extent. Enzymological assays of *E. coli* wild-type and mutant KASIII enzymes showed that both individual mutations at Leu-220 and Val-215 reduced catalytic activity of the enzyme (see Table 4). The double mutant had a decreased specific activity with both acetyl-CoA and isobutyryl-CoA as compared to the *E. coli* wild-type KASIII, whereas the single mutants showed negligible specific activity. In summary, these two mutations, which are proposed to influence the rotamer conformation of the conserved substrate-determining Phe residue (active site-distal rotamer in *E. coli* KASIII and active site-proximal rotamer in *B. subtilis* KASIIIs as depicted in FIG. 8), increased *E. coli* KASIII interaction with branched-chain substrate in addition to straight-chain acyl-CoA substrate but decreased the catalytic activity of the enzyme.

acetyl-CoA and isobutyryl-CoA, as evident by significantly decreased $STD_{af}$ for each ligand (FIGS. 10D and 10E). Although the single mutant *B. subtilis* KASIIIA F208V did not impact binding with acetyl-CoA much, it decreased saturation transfer to the isobutyryl-CoA $H_T$ and $H_B$ protons by ~40% in comparison to the wild-type. For the second single mutant, *B. subtilis* KASIIIA M213L, saturation transfer decreased to both acetyl-CoA and isobutyryl-CoA, with 40% decrease in $STD_{af}$ for acetyl-CoA $H_T$ proton, and 60-70% decrease in $STD_{af}$ for isobutyryl-CoA $H_T$ and $H_B$ protons. These data clearly indicate that the M213L mutation has a more pronounced negative effect on *B. subtilis* KASIIIA's interaction with substrates, especially with the branched-chain substrate (isobutyryl-CoA).

The decreased binding of acetyl-CoA and isobutyryl-CoA ligands by the *B. subtilis* KASIIIA mutants is accompanied by decreases in catalytic activity. Individual mutations of both residues (F208V and M213L) resulted in loss of catalytic activity with acetyl-CoA as the substrate and decreased catalytic activity towards isobutyryl-CoA (see Table 4). These data clearly indicate that both M213L and F208V mutations decrease binding and catalytic activity of *B. subtilis* KASIIIA enzyme with both straight- and branched-chain substrates. However, the M213L mutation has a more pronounced negative effect on the binding of substrates by *B. subtilis* KASIIIA, especially with the branched chain substrate (isobutyryl-CoA). Phe-208 also appears to influence branched-chain substrate binding, but to a lesser extent.

It can, therefore, be inferred that Met-213 is a critical residue for both straight- and branched-chain substrate recognition in *B. subtilis* KASIIIA. Phe-208 also appears to influence branched-chain substrate binding, but to a lesser extent.

TABLE 4

Specific Activity (nmol/min/mg) of wild-type and mutant KASIII with straight-chain and branched-chain acyl-CoA substrates

| Enzyme | Mutation | Acetyl-CoA | Isobutyryl-CoA |
|---|---|---|---|
| *E. coli* KASIII | Wild-type | 447 ± 68 | 36 ± 14 |
| | V215F | n.d. | n.d. |
| | L220M | n.d. | n.d. |
| | V215F_L220M | 221 ± 104 | 18 ± 5 |
| | F304A | n.d. | n.d. |
| *B. subtilis* KASIIIa | Wild-type | 64 ± 32 | 205 ± 139 |
| | F208V | n.d. | n.d. |
| | M213L | n.d. | 156 ± 47 |
| | F208V_M213L | n.d. | 17 ± 7 |
| | F297A | n.d. | 56 ± 28 |
| *B. subtilis* KASIIIb | Wild-type | n.d. | 279 ± 8 |
| | W221V | n.d. | n.d. |
| | V226L | n.d. | 134 ± 6 |

| Enzyme (wild-type) | Propionyl-CoA | Isovaleryl-CoA | Acetyl-CoA | Isobutyryl-CoA |
|---|---|---|---|---|
| *C. gingivalis* KASIIIa | 25 ± 2.7 | 53.5 ± 6.1 | n.d. | 166.08 ± 82.3 |
| *C. gingivalis* KASIIIc | 213 ± 70 | 22 ± 8.3 | 102.8 ± 5.7 | 26 ± 9.1 |
| *L. pneumophila* KASIIIa | 83.2 ± 17 | 90.5 ± 17.7 | 27.5 ± 9.7 | 304.9 ± 25.3 |
| *M. xanthus* KASIIIc | 37.4 ± 12.9 | 7.6 ± 1.8 | 45.2 ± 10.0 | 19.8 ± 3.0 |

n.d. = not detectable

—Phe208Val and Met213Leu Mutations Negatively Affect Substrate Binding in *B. subtilis* KASIIIA.

For wild-type *B. subtilis* KASIIIA, the $H_T$ protons of both acetyl and isobutyryl-CoA had similar $STD_{af}$ (1.5), whereas $H_{AP}$ proton of isobutyryl-CoA received ~28% higher saturation as compared to the acetyl-CoA $H_{AP}$ proton (FIGS. 10D and 10E). The double mutant F208V_M213L, which is mutated to resemble *E. coli* KASIII at two residues neighboring Phe-297 (FIG. 9), showed decreased binding with —Trp-221 and Val-226 are Critical for *B. subtilis* KASIIIB's Folding, Substrate Recognition, and Catalytic Activity.

The wild-type *B. subtilis* KASIIIB enzyme exhibited very high $STD_{af}$ values for both acetyl-CoA and isobutyryl-CoA, ranging from 5.0 to 10.0, as compared to $STD_{af}$ values of the same ligands with *B. subtilis* KASIIIA which ranged from 0.5 to 2.5 (FIGS. 10F and 10G). This could be either due to stronger enzyme-ligand interactions for *B. subtilis* KASIIIB or high $k_{off}$ rate for the ligands from the active site pocket of this enzyme. The double mutant of *B. subtilis* KASIIIB (W221V_V226L), which contains mutations to resemble *E. coli* KASIII at positions 221 and 226, could not be purified due to its poor solubility. The single mutants (*B. subtilis* KASIIIB W221V and *B. subtilis* KASIIIB V226L) could be purified but they did not exhibit efficient saturation transfer to either of the ligands. The W221V mutation appeared to result in complete loss of KASIIIB's interaction with acetyl-CoA and isobutyryl-CoA, as suggested by negligible $STD_{af}$ values (FIGS. 10F and 10G). The second mutation, V226L, resulted in less severe reduction of the STD amplification factors. Enzymatic assays of the wild-type and mutant *B. subtilis* KASIIIB enzymes with either acetyl-CoA or isobutyryl-CoA indicated a very high specific activity with isobutyryl-CoA and no activity with acetyl-CoA (see Table 4). The W221V mutation completely eliminated activity with isobutyryl-CoA, whereas the V226L mutation led to an approximately 50% loss of activity with isobutyryl-CoA. These observations, along with poor solubility of the *B. subtilis* KASIIIB double mutant, imply that both Trp-221 and Val-226 are important for substrate recognition by *B. subtilis* KASIIIB. Trp-221 in particular seems to be critical for proper folding, substrate binding, and catalytic functionality of *B. subtilis* KASIIIB.

—Role of the Conserved Phe in Substrate Binding of *E. coli* KASIII and *B. Subtilis* KASIIIA, KASIIIB.

Figures 11A, 11B, 11C, 11D:
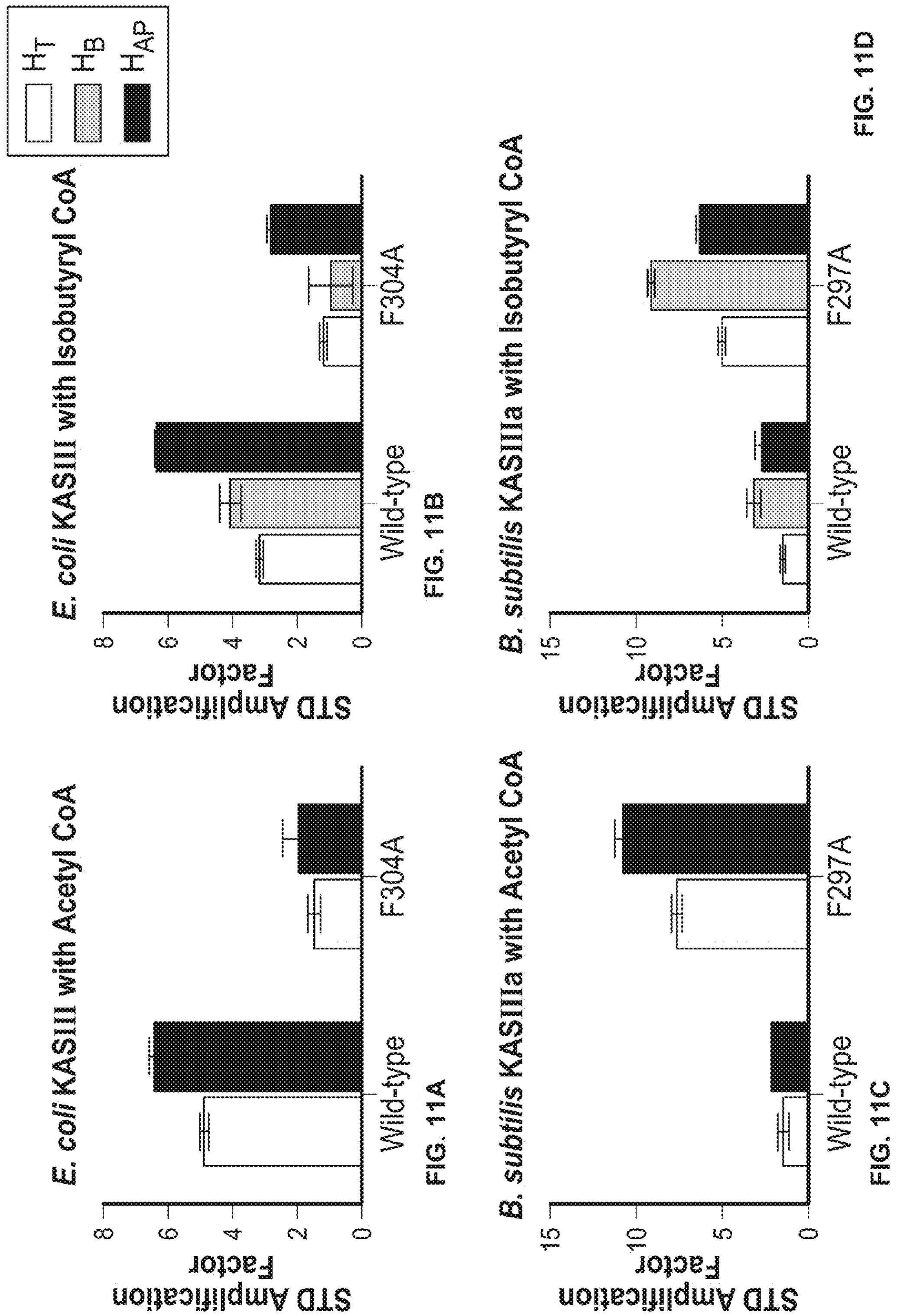
FIG. 11A is a graph of protons of ligand acetyl-CoA vs. STD amplification factor ($STD_{af}$) for *E. coli* containing an F304A mutation.
FIG. 11B is a graph of protons of ligand isobutyryl-CoA vs. STD amplification factor ($STD_{af}$) for *E. coli* KASIII containing an F304A mutation.
FIG. 11C is a graph of protons of ligand acetyl-CoA vs. STD amplification factor ($STD_{af}$) for *B. subtilis* KASIII containing an F297A mutation (nucleotide sequence [SEQ ID NO:125]; amino acid sequence [SEQ ID NO:126]).
FIG. 11D is a graph of protons of ligand isobutyryl-CoA vs. STD amplification factor ($STD_{af}$) for *B. subtilis* KASIII containing an F297A mutation.

For each of the three enzymes, mutating the two residues that were predicted to affect the orientation of the conserved Phe clearly impacted substrate binding. However, the putative roles of these mutations in determining the Phe rotamer conformation (active site-distal or active site-proximal) were not directly assessed by the STD NMR experiments. In order to investigate the role of the Phe itself in substrate binding, the conserved Phe was mutated to Ala in each of the three KASIII enzymes. The *E. coli* KASIII F304A mutant (nucleotide sequence [SEQ ID NO:117]; amino acid sequence [SEQ ID NO:118]) resulted in approximately 60% lower saturation transfer to the $H_T$ protons of acetyl-CoA and isobutyryl-CoA compared to the wild-type (FIGS. 11A and 11B). Thus, these mutations eliminate all enzymatic activity of the *E. coli* KASIII (see Table 4) but, in the case of the *B. subtilis* KASIIIa, about 25% of the catalytic activity with the isobutyryl-CoA substrate is retained and all catalytic activity with the acetyl-CoA substrate is eliminated (see Table 4). The *B. subtilis* KASIIIB F310A mutant (nucleotide sequence [SEQ ID NO: 133]; amino acid sequence [SEQ ID NO: 134]) could not be purified, owing to poor expression and solubility, suggesting that Phe-310 is required for proper folding of *B. subtilis* KASIIIB.

—Competition Binding Experiments Reveal Relative Affinities of Ligands to KASIII Enzymes.

Figure 12A:
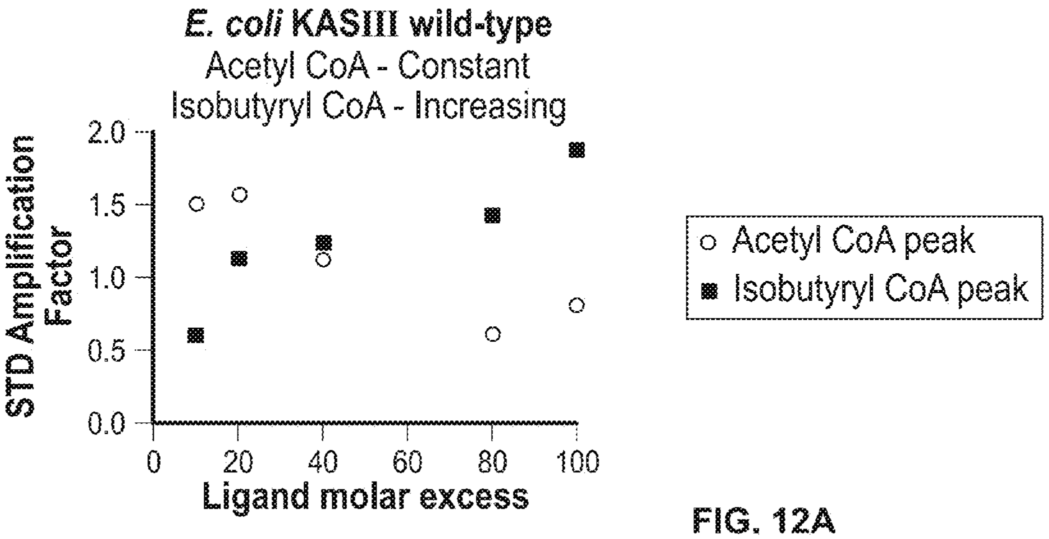
FIG. 12A is a graph of ligand molar excess vs. STD amplification factor for *E. coli* KASIII wild-type enzyme, which shows competition binding data.

For *E. coli* KASIII, a low $STD_{af}$, as seen for the $H_T$ proton of isobutyryl-CoA as compared to acetyl-CoA, could be either because isobutyryl-CoA is a poor substrate for *E. coli* KASIII and does not bind to the active site, or because it is a very tight binder with dissociation constant, $K_D$, below $10^{-10}$, resulting in an extended stay in the binding site and inefficient saturation transfer (Mayer et al., J. Am. Chem. Soc. 123: 6108-6117 (2001); and Meyer et al., Ernst Schering Res. Found. Workshop: 149-167 (2004)). To investigate which of the two scenarios is true, competition binding experiments, in which the concentration of acetyl-CoA was kept constant and isobutyryl-CoA was titrated at increasing concentrations, were performed to see if the latter ligand replaces the former ligand. Competition binding data strongly suggested that acetyl-CoA was the preferred substrate for *E. coli* KASIII, while isobutyryl-CoA competed with acetyl-CoA only when its concentration was at least four times more than that of acetyl-CoA (FIG. 12A).

Figure 12B:
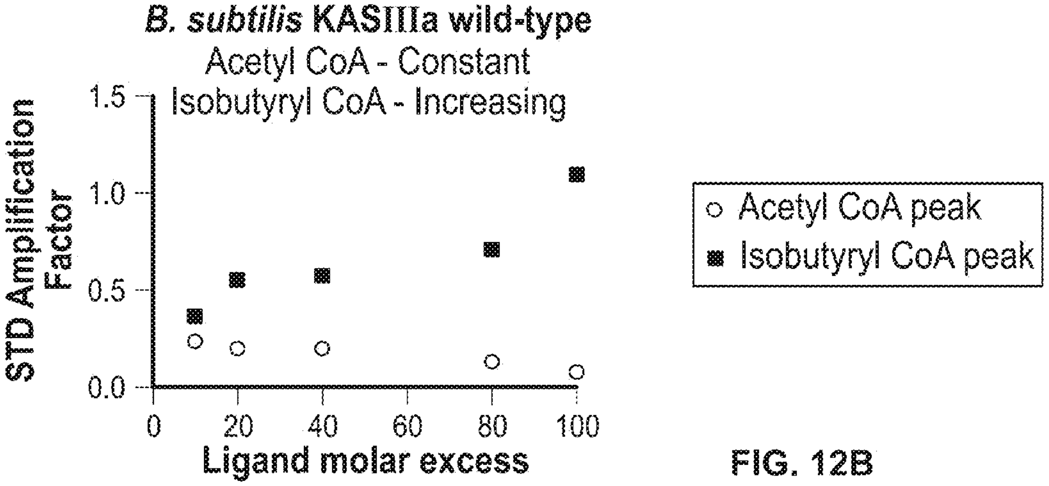
FIG. 12B is a graph of ligand molar excess vs. STD amplification factor for *B. subtilis* KASIIIA wild-type enzyme, which shows competition binding data.
Figure 12C:
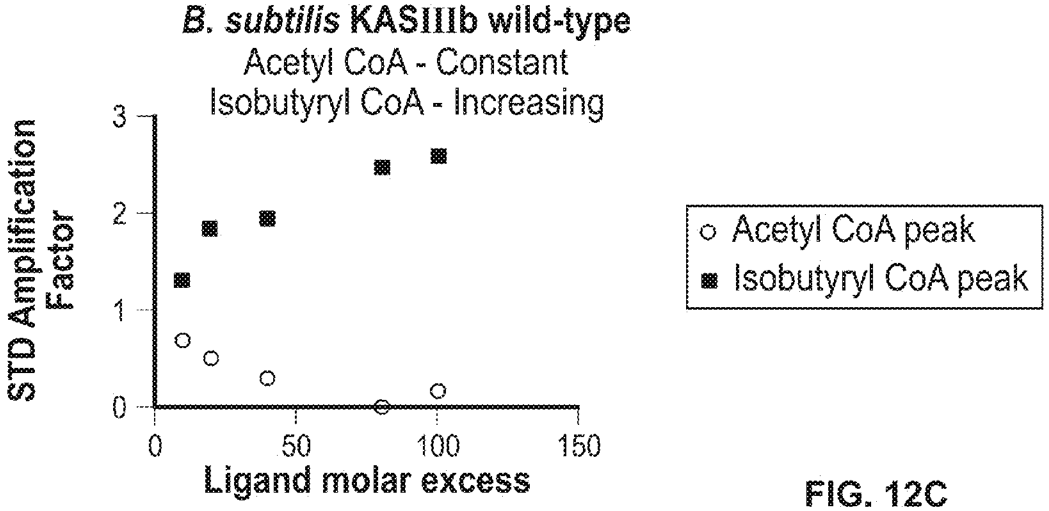
FIG. 12C is a graph of ligand molar excess vs. STD amplification factor for *B. subtilis* KASIIIB wild-type enzyme, which shows competition binding data.

For *B. subtilis* KASIIIA, to determine the competition between acetyl-CoA and isobutyryl-CoA, increasing amounts of isobutyryl-CoA were titrated, while acetyl-CoA was held at a constant concentration. The results showed that isobutyryl-CoA was the preferred substrate for *B. subtilis* KASIIIA and always had a higher STD amplification factor for the observed proton $H_T$ than that of the acetyl-CoA $H_T$ proton (FIG. 12B). Similar results were obtained for competition binding experiments with *B. subtilis* KASIIIB, where isobutyryl-CoA was found to be the preferred substrate for *B. subtilis* KASIIIB and its $STD_{af}$ increased with increasing concentration (FIG. 12C).

Example 4

This example describes the analysis of KASIII from *Alicyclobacillus acidocaldarius.*

—Expression and Purification of Recombinant *A. acidocaldarius* KASIII Protein.

The *A. acidocaldarius* KASIII gene was codon-optimized for expression in *E. coli*, chemically synthesized, and cloned into the pUC57 vector by Genscript USA (Piscataway, N.J., USA). The gene was further cloned into the pDEST-17 vector using Gateway Cloning (Invitrogen, Carlsbad, Calif.) resulting in the pDEST_AA construct. *E. coli* OverExpress™ C41 (Lucigen, Middletown, Wis.) strain was used for expression of *A. acidocaldarius* KASIII protein from the construct pDEST_AA. The C41 transformants were grown at 37° C. in 2 L Luria-Bertani medium and were supplemented with 100 μg/ml ampicillin (Research Products International Corps., Mount Prospect, Ill.). The cultures were induced by addition of IPTG (Gold Biotechnology, Olivette, Mo.) to a final concentration of 0.4 mM when the $OD_{600}$ was 0.6-0.8. After incubation for another 16-18 hours at 25° C., cells were harvested by centrifugation (10,000×g, 4° C. 10 minutes). Soluble proteins were extracted by first suspending the cell pellet in lysis buffer (0.5 M NaCl, 5 mM imidazole, 20 mM Tris-HCl, pH 8.0, 0.1 mg/ml phenylmethylsulfonyl fluoride, and 0.1% Triton-X 100), followed by sonication (10 second pulses separated by 3 second intervals for a total of 3 minutes) and centrifugation (10,000×g, 4° C., 30 minutes). The resulting supernatant (soluble protein fraction) was analyzed for its homogeneity and purity by running on SDS-PAGE gel, which showed the presence of near-homogenous, pure proteins (greater than 95% purity).

The soluble protein fraction was filtered through a 0.45 μ filter (Corning, the Netherlands) and applied to 8 ml Ni-NTA His-bind resin. After washing the unbound protein with wash buffers I and II (0.5M NaCl, 20 mM Tris-HCl, pH 8.0) supplemented with 20 mM and 40 mM imidazole, respectively, the proteins of interest were eluted with the same buffer containing 250 mM imidazole. The purified His-tagged KASIII proteins were dialyzed against sodium phosphate buffer, pH 7.2, and concentrated using 10,000 molecular weight cut-off ultrafiltration centrifugation filters (Millipore, Billerica, Mass.) at 4° C. The concentrated proteins were either supplemented with 16% glycerol and stored at −80° C. or immediately used for KASIII activity assay. Protein concentrations were determined by Bradford's assay (BioRad, Hercules. Calif.).

—Purification of Recombinant Malonyl-CoA ACP Transacylase (MCAT or FabD), β-Ketoacyl ACP Reductase (FabG), and Holo-Acyl Carrier Protein (ACP).

FabD, FabG and ACP proteins are required for the spectrophotometric assay of KASIII. Therefore, genes encoding these proteins, namely fabD, fabG and acpP, were obtained from *E. coli* Hub in pCA24N expression vectors. The acpP gene was further cloned into pETDUET vector along with acpS gene that encodes for ACP synthase. These three recombinant proteins (FabD, FabG and holo-ACP) with N-terminal His-tags were purified to near-homogeneity using the same procedure as described for the purification for *A. acidocaldarius* KASIII. Purity of these proteins was assessed by running an SDS-PAGE gel.

—Spectrophotometric Assay to Determine *A. acidocaldarius* Activity with Different Substrates.

Activity of *A. acidocaldarius* KASIII with different acyl-CoA substrates (acetyl-CoA, isobutyryl-CoA and 3-hydroxybutyryl-CoA (Sigma-Aldrich)) was ascertained by a coupled assay. The assay was performed in 96-well plate format with three replicates for each reaction condition. In a total volume of 100 μl for each reaction the reaction mix containing 100 μM holo-ACP, 200 μM malonyl-CoA, 10 mM DTT, 50 μM acyl-CoA substrate (either acetyl-CoA, isobutyryl-CoA or 3-hydroxy-butyryl-CoA) and 200 μM NADPH in 0.1 M sodium phosphate buffer (pH 7.2) was pre-incubated with 60 μg of FabD for two minutes. The reaction was started by the addition of 30 μg of FabG and varying concentrations of *A. acidocaldarius* KASIIII (0.5-15 μg). Change in absorbance of NADPH that was being converted to $NADP^+$ during reduction of 3-ketoacyl-ACP to 3-hydroxy-acyl-ACP by FabG was recorded at 340 nm using a Biotek multi-plate reader.

—Purified *A. acidocaldarius* KASIII, FabD, FabG and ACP.

Each of the recombinant proteins (*A. acidocaldarius* KASIII, FabD, FabG and holo-ACP) were purified to near-homogeneity.

—Activity of *A. acidocaldarius* KASIII with Acetyl-, Isobutyryl-, and 3-Hydroxybutyryl-CoA Substrates.

Spectrophotometric assay was used to assess the activity of *A. acidocaldarius* KASIII with various acyl-CoA substrates. The assay coupled the appearance of the KASII-product (3-ketoacyl-ACP) to the oxidation of NADPH, catalyzed by 3-ketoacyl-ACP reductase (FabG). This latter reaction resulted in a change of absorbance at 340 nm, due to the conversion of NADPH to $NADP^+$, and the rate of this change was used to directly calculate the rate of the KASIII-catalyzed reaction. Studies of *A. acidocaldarius* KASIII with different substrates using this spectrophotometric assay established that this KASIII has the ability to utilize a number of different acyl-CoA substrates, particularly with higher preference for hydroxylated acyl-CoA substrate (3-hydroxybutyryl-CoA) and branched chain substrate (i.e., isobutyryl-CoA) as compared to straight chain substrate (acetyl-CoA).

Example 5

This example describes the cloning of *A. acidocaldarius* KASIII into *Rhodospirillum rubrum*.

The *A. acidocaldarius* KASIII gene was cloned into the phaC2 locus in the *R. rubrum* genome via a double-crossover recombination event. The *R. rubrum* recipient strain for this experiment was the phaC triple mutant (ΔphaC1ΔphaC2ΔphaC3) that lacked any PhaC activity. First, the upstream flanking sequence (922 bp) of the *R. rubrum* phaC2 gene (Aru_2413) was cloned upstream of the *A. acidocaldarius* KASIII sequence, and this chimeric protein was introduced into the *E. coli* strain S17-1. The transformed S17-1 was co-incubated overnight with *R. rubrum* phaC triple mutant (ΔphaC1ΔphaC2ΔphaC3) on 0.22 μm filter for conjugation. The bacterial mixture was grown on minimal medium plate containing 25 μg/ml gentamicin for one to two weeks. The resulting colonies carry the product of a single recombination crossover event, which integrates the *A. acidocaldarius* KASIII gene at the phaC2 gene (Aru_2413) locus. These colonies were streaked out on another minimal medium plate containing 25 μg/ml gentamicin for colony purification. The resulting colonies were cultured in SMN rich medium for two to three days in the light without gentamicin selection. Finally, the culture was plated out on SMN rich medium containing 5% sucrose to screen for double-crossover events. The resulting colonies were PCR sequence-confirmed to carry the *A. acidocaldarius* KASIII gene at the phaC2 gene (Aru_2413) locus.

In order to investigate the metabolic functions of the three phaCs, single locus deletion mutants (ΔphaC1, ΔphaC2, ΔphaC3), double-loci deletion mutants (ΔphaC1ΔphaC2, ΔphaC1ΔphaC3, and ΔphaC2ΔphaC3), and a triple-loci deletion mutant (ΔphaC1ΔphaC2ΔphaC3) were created, and these mutants were characterized relative to growth, PHA yields and monomer composition of the polymer (Jin et al., J. Bacteriol. 194: 5522-5529 (2012)). Of most significance, the triple phaC mutant (ΔphaC1ΔphaC2ΔphaC3) failed to accumulate any PHA polymer, and showed only a slight impact on growth characteristics. This strain, therefore, has the capacity to generate 3-hydroxybutyryl-CoA, which could be used by a KASIII enzyme to produce o-hydroxy-branched-fatty acids. This hypothesis was tested by recombinantly expressing the *A. acidocaldarius* KASIII in the triple phaC *R. rubrum* mutant (described in Example 6), and then analyzing the fatty acids produced (described in Example 7).

Example 6

This example describes the fermentation-based production of bi-functional fatty acids.

To generate omega-hydroxy fatty acid in *R. rubrum*, the recombinant *R. rubrum* carrying the *A. acidocalcarius* KASIII was grown on RRNCO medium (but omitting ammonium chloride, hydrogen sulfide, carbon monoxide and carbon dioxide) for five days, and the bacterial pellet was used for fatty acid analysis.

*A. acidocaldarius* KASIII was cloned into triple phaC *R. rubrum* mutant to evaluate whether this KASIII enzyme has the ability to use in vivo-generated hydroxyacyl-CoA starter substrates, and produce co-hydroxy-fatty acids. After the fermentation process involving growth of recombinant *R. rubrum* cells containing *A. acidocaldarius* KASIII on RRNCO medium, fatty acids were extracted from the bacterial cells and analyzed as described in Example 7.

Example 7

This example describes the analysis of produced bi-functional fatty acids by GC-MS.

Figure 13A:
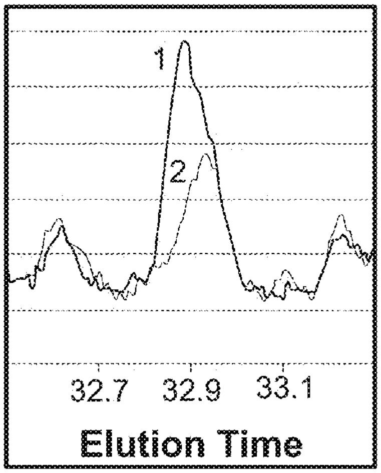
FIG. 13A is a gas chromatogram (GC) profile of the fatty acids produced by recombinant *R. rubrum* lacking phaC activity but expressing *A. acidocaldarius* KASIII (line 1) and the parallel profile of the fatty acids produced by control *R. rubrum* (line 2) lacking *A. acidocaldarius* KASIII.
Figure 13B:
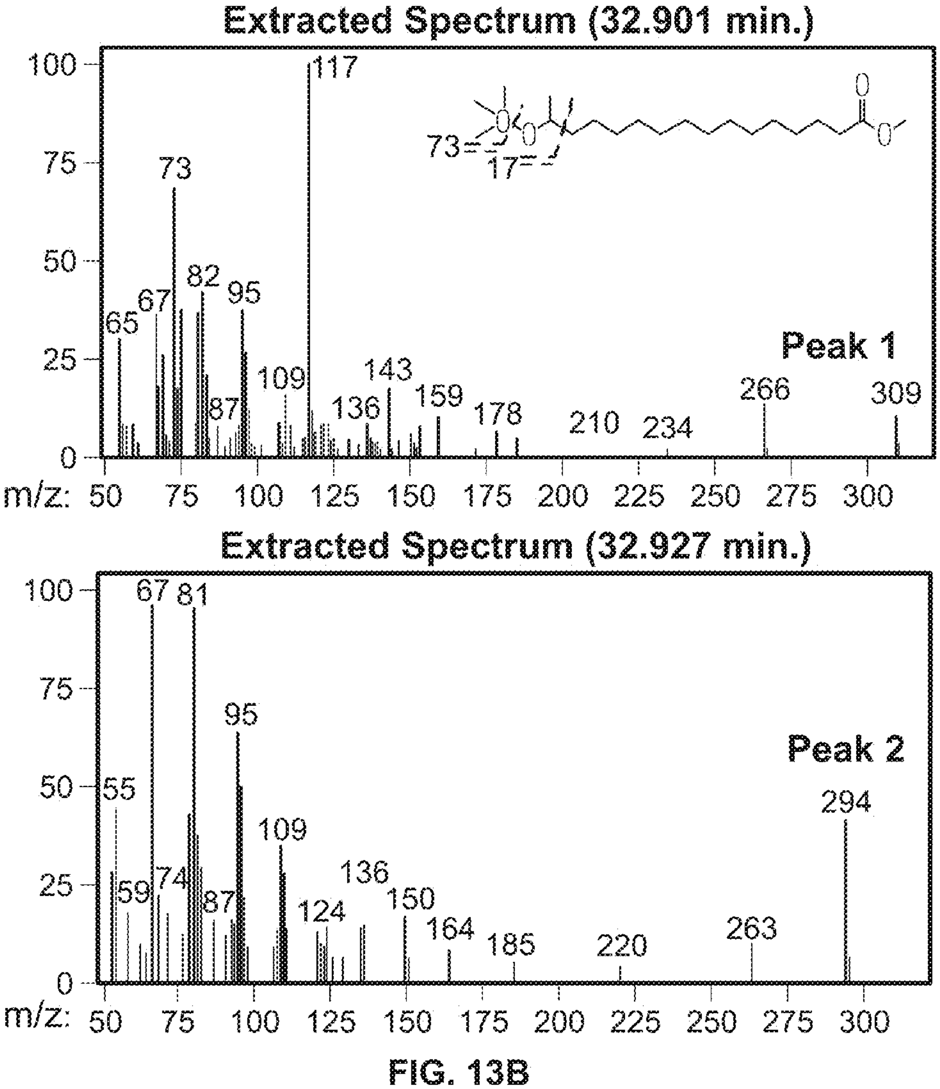
FIG. 13B is the mass spectra of the largest peaks of lines 1 and 2, wherein the peak of line 1 is the silylated form of the methyl-ester of 15-hydroxypalmitate.

The resultant fatty acids in *R. rubrum* were extracted and analyzed using GC-MS. Analysis of the fatty acids from recombinant *R. rubrum* strain containing *A. acidocaldarius* KASIII demonstrated the production of 15-hydroxypalmitate, which was identified by GC-MS analyses conducted at Iowa State University's W. M. Keck Metabolomics Research Laboratory (FIGS. 13A and 13B). Thus, this indicates that the substrate hydroxybutyryl-CoA in *R. rubrum* was being utilized by *A. acidocaldarius* KASIII and metabolized via fatty acid synthesis pathway resulting in long-chain ω-hydroxy fatty acids. This gave a proof of concept of production of bi-functional fatty acids in recombinant bacterial hosts.

Example 8

This example describes the in vitro characterization of *Bacteroides vulgatus* KASIII.

—Expression and Purification of Recombinant *B. Vulgatus* KASIII Protein.

The *B. vulgatus* KASIII gene was codon-optimized for expression in *E. coli*, chemically synthesized, and cloned into the pUC57 vector by Genscript USA (Piscataway, N.J., USA). The gene was further cloned into the pDEST-17 vector using Gateway Cloning (Invitrogen, Carlsbad, Calif.) resulting in the pDEST_BV construct. The *E. coli* OverExpress™ C41 (Lucigen, Middletown, Wis.) strain was used for expression of the *B. vulgatus* KASIII protein from the construct pDEST_BV. The *B. vulgatus* KASIII was expressed and purified using the same methods as described in Example 4.

—Spectrophotometric Assay to Determine *B. Vulgatus* KASIIIA Activity with Different Substrates.

Activity of *B. vulgatus* KASIIIA with different acyl-CoA substrates (acetyl-CoA, isobutyryl-CoA and 3-hydroxybutyryl-CoA (Sigma-Aldrich)) was ascertained by a coupled assay using the methods described in Example 4.

—Activity with Straight-, Branched-, and Hydroxy-Acyl-CoA Substrates.

Figure 14A:
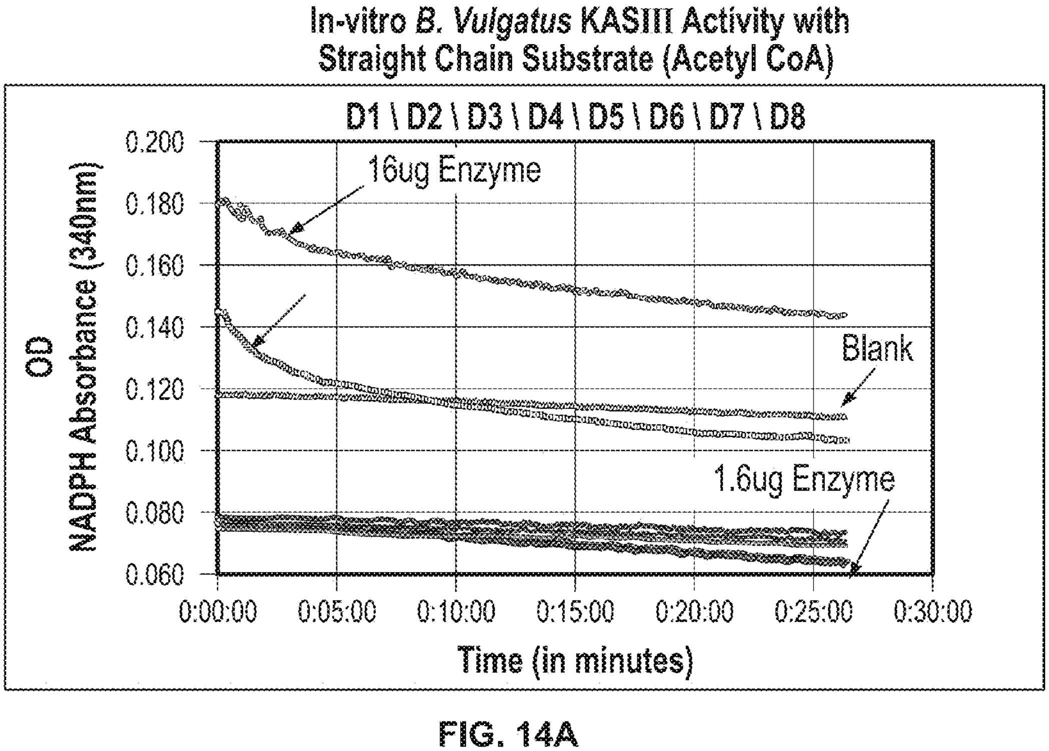
FIG. 14A is a graph of time (minutes) vs. NADPH absorbance (340 nm), which shows the in vitro activity of *B. vulgaris* KASIII with strain-chain substrate (acetyl-CoA).
Figure 14B:
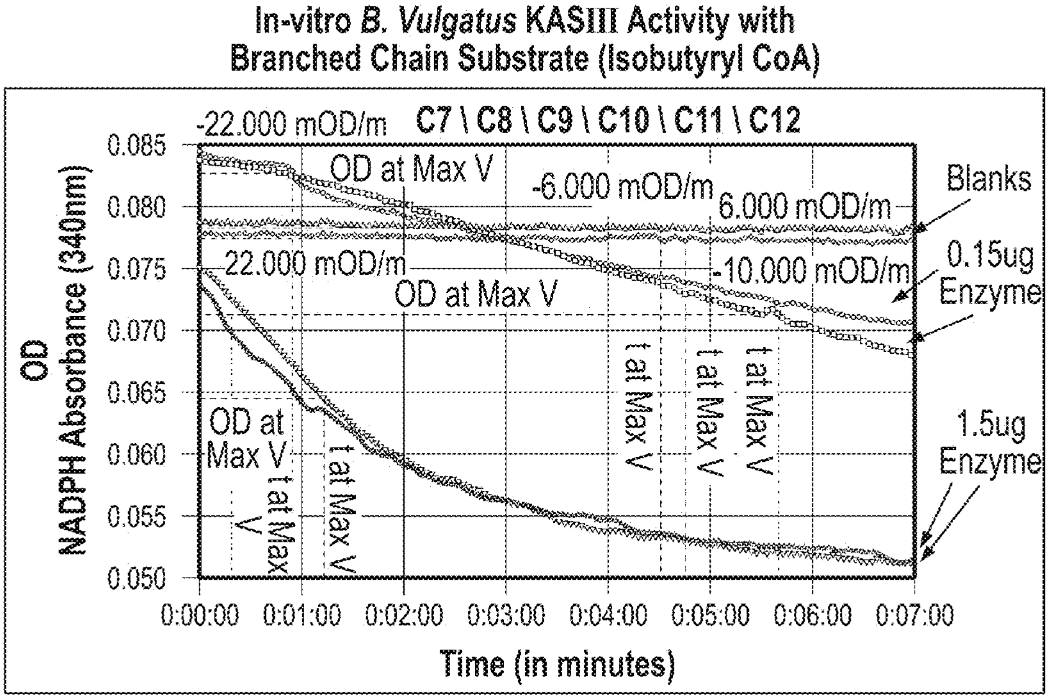
FIG. 14B is a graph of time (minutes) vs. NADPH absorbance (340 nm), which shows the in vitro activity of *B. vulgaris* KASIII with branched-chain substrate (isobutyryl-CoA).
Figure 14C:
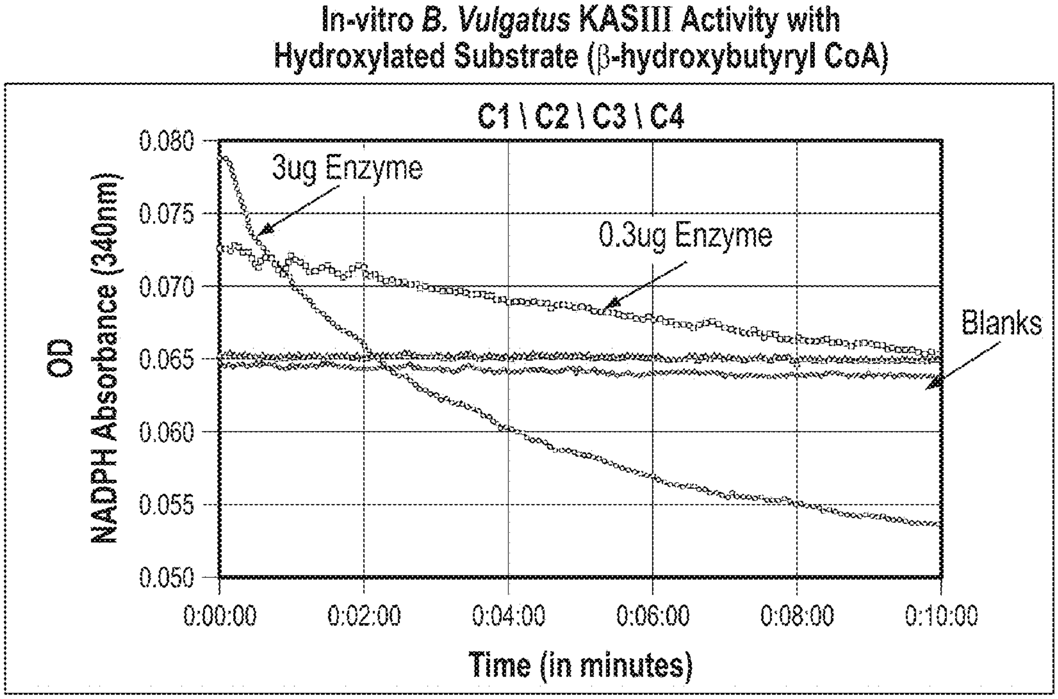
FIG. 14C is a graph of time (minutes vs. NADPH absorbance (340 nm), which shows the in vitro activity of *B. vulgaris* KAS III with hydroxylated substrate (β-hydroxybutyryl-CoA).

Results from the spectrophotometric assay established that *B. vulgatus* KASIII can utilize acetyl-CoA (straight chain substrate), isobutyryl-CoA (branched-chain substrate) and 3-hydroxybutyryl-CoA (hydroxylated substrate) with a higher preference for isobutyryl-CoA and 3-hydroxybutyryl-CoA as compared to acetyl-CoA (FIG. 14).

Example 9

This example describes the in vitro characterization of *Legionella pneumophila* KASIIIA.

—Expression and Purification of Recombinant *L. pneumophila* KASIIIA Protein.

The *L. pneumophila* KASIIIA gene was codon-optimized for expression in *E. coli*, chemically synthesized, and cloned into the pUC57 vector by Genscript USA (Piscataway, N.J., USA). The gene was further cloned into the pDEST-17 vector using Gateway Cloning (Invitrogen, Carlsbad, Calif.) resulting in the pDEST_LP1 construct. The *E. coli* OverExpress™ C41 (Lucigen, Middletown. Wis.) strain was used for expression of the *L. pneumophila* KASIIIA protein from the construct pDEST_LP1. The *L. pneumophila* KASIIIA protein was expressed and purified using the same methods as described in Example 4.

—Spectrophotometric Assay to Determine *L. pneumophila* KASIII Activity with Different Substrates.

Activity of *L. pneumophila* KASIII with different acyl-CoA substrates (acetyl-CoA, isobutyryl-CoA and 3-hydroxybutyryl-CoA (Sigma-Aldrich)) was ascertained by a coupled assay using the methods described in Example 4.

—Activity with Straight, Branched and Hydroxy-Acyl-CoA Substrates.

Figure 15A:
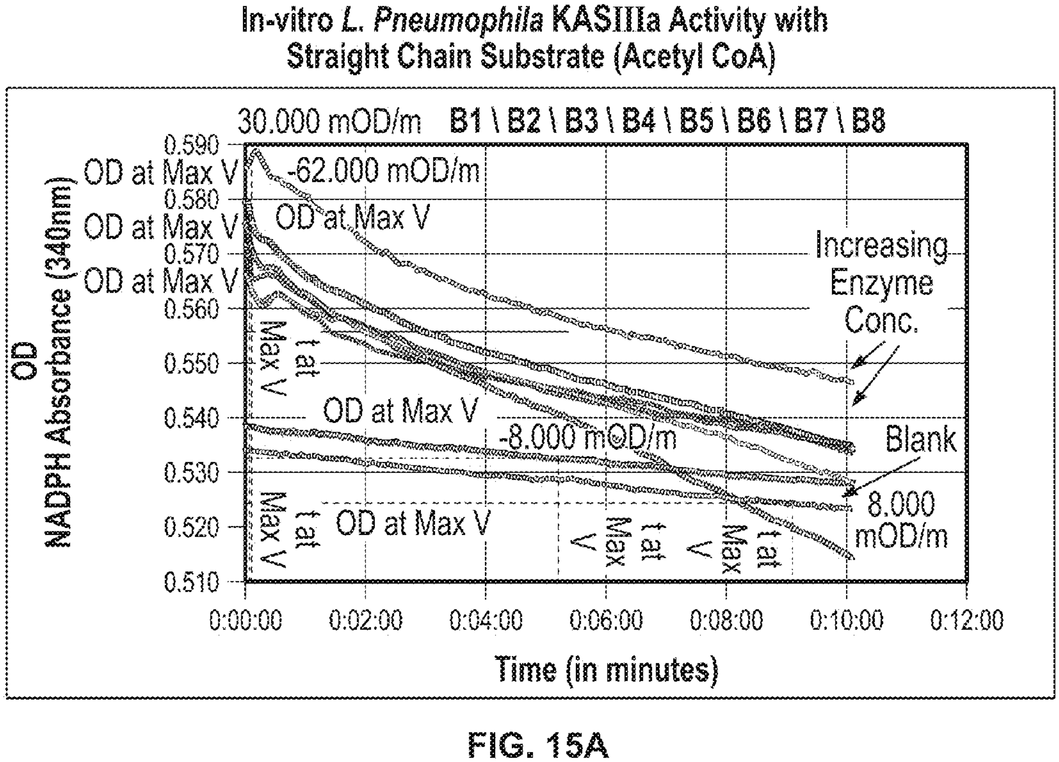
FIG. 15A is a graph of time (minutes) vs. NADPH absorbance (340 nm), which shows the in vitro activity of *L. pneumophila* KASIII with strain-chain substrate (acetyl-CoA).
Figure 15B:
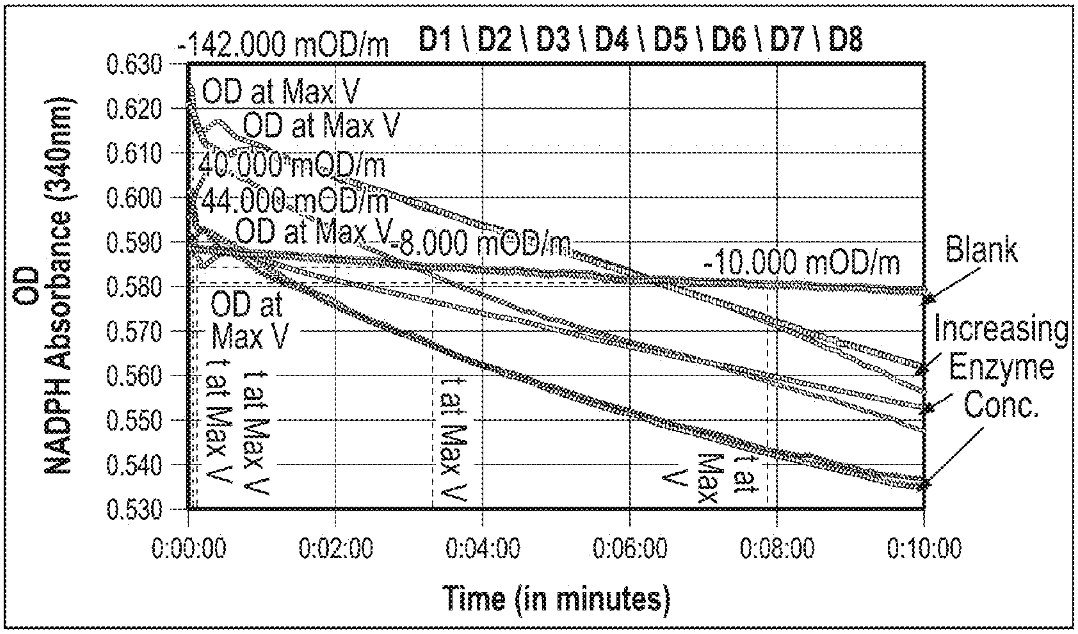
FIG. 15B is a graph of time (minutes) vs. NADPH absorbance (340 nm), which shows the in vitro activity of *L. pneumophila* KASIII with branched-chain substrate (isobutyryl-CoA).
Figure 15C:
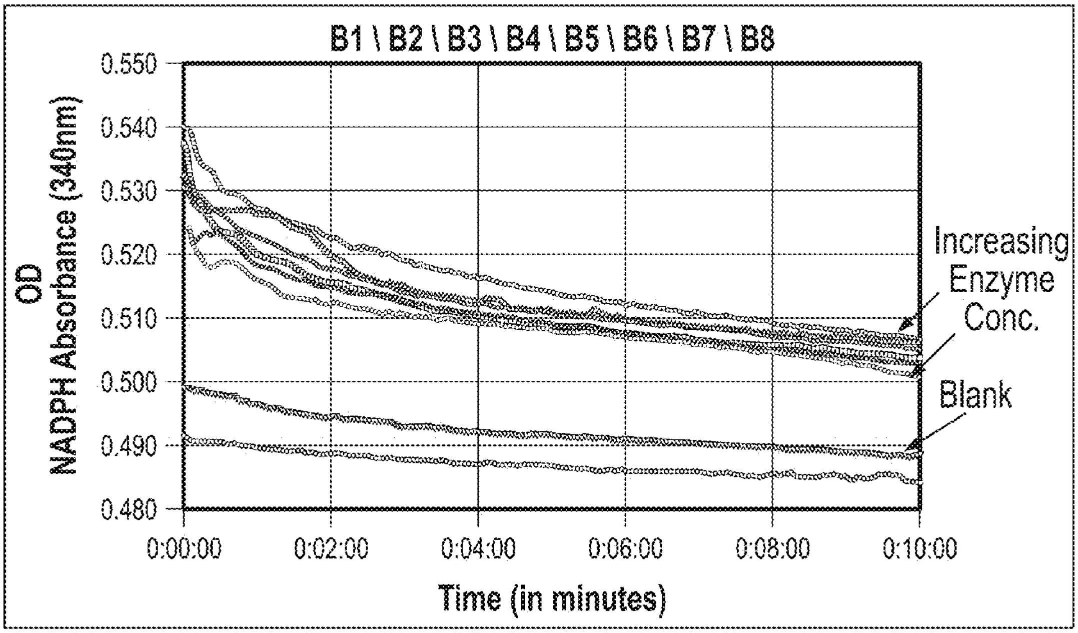
FIG. 15C is a graph of time (minutes vs. NADPH absorbance (340 nm), which shows the in vitro activity of *L. pneumophila* KAS III with hydroxylated substrate (β-hydroxybutyryl-CoA).

Results from the spectrophotometric assay established that *L. pneumophila* KASIIIA can utilize acetyl-CoA (straight-chain substrate), isobutyryl-CoA (branched-chain substrate) and 3-hydroxybutyryl-CoA (hydroxylated substrate) with a higher preference for isobutyryl-CoA and 3-hydroxybutyryl-CoA as compared to acetyl-CoA (FIG. 15).

Example 10

This example describes in vivo characterization of KASIII from various biological sources (*Aeromonas hydrophila, Bacteroides vulgatus, Brevibacterium linens, Capnocytophaga gingivalis. Thermus aquaticus. Bacillus licheniformis, Desulfovibrio vulgaris, Bacillus subtilis* subsp. *S, Haliangium ochraceum, Alicyclobacillus acidocaldarius*) using *B. subtilis* FabH deletion mutant.

—Complementation of *B. subtilis* FabH Deletion Mutant with Recombinant KASIII Genes from Various Sources.

The mutant strain ΔbfabHA ΔbfabHB::(erm-Pspac::fabH) was generated by homologous recombination via a one-step procedure, by transforming the mutant ΔbfabHA strain with plasmid pUCB-erm-fabH, followed by selection for erythromycin-resistance on LB media.

The pUCB-erm-fabH vector was constructed from plasmid pUC19. The erythromycin-resistant gene erm and the exogenous fabH gene under the control of the promoter Pspac were inserted between the downstream and upstream DNA fragments of bfabHB ORF.

—Fatty Acid Analysis of *B. subtilis* Strains Containing Recombinant KASIII Genes.

In these experiments, a 0.5 ml aliquot of an overnight *B. subtilis* culture normalized for equal cell density was collected by centrifugation at 13,200×g for 30 seconds. The cell pellet was suspended in 50 ml minimal medium or LB rich medium. Cell cultures were shaken at 250 rpm. Cells were collected at late log phase by centrifugation at 5000×g for 10 minutes. The collected cell pellets were lyophilized and stored at −20° C. until analysis. Lipids were extracted from lyophilized bacterial cell pellets using chloroform/methanol, and fatty acids were then converted to methyl esters using methanolic-HCl at 80° C. for 60 minutes. The recovered fatty acid methyl esters were concentrated as needed under a stream of nitrogen gas and analyzed with GC-MS interfaced with a Mass Detector 5973 (Agilent Technologies, Santa Clara, Calif.).

—Results.

The eleven KASIII genes from diverse biological sources (namely, *Aeromonas hydrophila, Bacteroides vulgatus, Brevibacierium linens, Capnocytophaga gingivalis, Thermus aquaticus, Bacillus licheniformis, Desulfovibrio vulgaris, Bacillus subtilis* subsp. *S, Haliangium ochraceum, Alicyclobacillus acidocaldarius*) could rescue the *B. subtilis* FabH deletion mutant that fails to grow by itself, indicating that these KASIII enzymes can synthesize branched-chain fatty acids in vivo. Fatty acid content of *B. subtilis* FabH deletion mutants rescued by recombinant KASIII genes from diverse sources is shown in Table 5.

TABLE 5

Fatty Acid Production by KASIII in *B. subtilis* FabH deletion mutant

| | Fatty acid content (mole %) | | | | |
|---|---|---|---|---|---|
| Source of KASIII | Anteiso-fatty acids | Even-number iso-fatty acids | Odd-number iso-fatty acids | Even-number normal fatty acids | Odd-number normal fatty acids |
| KASIIIB from *Aeromonas hydrophila* | 36.64 | 4.46 | 6.27 | 51.4 | 1.23 |
| KASIII from *Bacteroides vulgatus* | 70.43 | 1.73 | 18.24 | 9.51 | 0.09 |
| KASIIIA from *Capnocytophaga gingivalis* | 27.24 | 1.28 | 58.94 | 12.46 | 0.08 |
| KASIIIA from *Brevibacterium linens* | 39.96 | 0.29 | 0.5 | 59.27 | 0.04 |
| KASIII from *Thermus aquaticus* | 52.1 | 1.09 | 26.89 | 19.84 | 0.12 |
| KASIIIA from *Bacillus licheniformis* | 63.27 | 3.3 | 28.25 | 5.17 | 0.04 |

TABLE 5-continued

Fatty Acid Production by KASIII in *B. subtilis* FabH deletion mutant

| | Fatty acid content (mole %) | | | | |
|---|---|---|---|---|---|
| Source of KASIII | Anteiso-fatty acids | Even-number iso-fatty acids | Odd-number iso-fatty acids | Even-number normal fatty acids | Odd-number normal fatty acids |
| KASIIIB from *Bacillus licheniformis* | 68.83 | 8.87 | 11.59 | 10.76 | 0.07 |
| KASIII from *Desulfovibrio vulgaris* | 36.05 | 0.95 | 42.59 | 19.74 | 0.54 |
| KASIII from *Bacillus subtilis* subsp. S | 68.02 | 6.83 | 12.39 | 12.77 | 0.06 |
| KASIII from *Haliangium ochraceum* | 53.87 | 0.98 | 12.29 | 32.79 | 0.07 |
| KASIII from *Alicyclobacillus acidocaldarius* | 48.13 | 3.64 | 30.44 | 17.73 | 0.05 |

Example 11

This example identifies KASIII enzymes that can process atypical substrates.

KASIII enzymes from *Alicyclobacillus acidocaldarius* (aaKASIII), *Thermus aquaticus* (taKASIII), and *Capnocytophaga gingivalis* (cgKASIIIa), which rescued the lethal phenotype of the *B. subtilis* fabH deletion mutant were purified to homogeneity and then screened for binding with typical and atypical KASIII substrates. Also purified to homogeneity and screened for binding with KASIII substrates were *Legionella pneumophila* and *Myxococcus xanthus*. Typical substrates included straight-chain and branched-chain acyl-CoA primers, whereas atypical substrates included di-acid (malonyl-CoA and methylmalonyl-CoA), hydroxylated (3-hydroxybutyryl-CoA), unsaturated (crotonyl-CoA), and aromatic (such as benzoyl-CoA and phenylacetyl-CoA) acyl-CoAs. *E. coli* KASIII and *B. subtilis* KASIIIb were included as standards. The ability of the KASIII enzymes to bind to the substrates was measured via a fluorescence-based thermal shift assay, which measured the thermal stability of a protein in the presence and absence of a specific ligand or substrate. A positive shift in melting temperature of the protein ($T_m$) in the presence of a substrate is correlated with substrate binding and concomitant stabilization of the enzyme, whereas a negative shift in $T_m$ suggests destabilization of the protein by the substrate. Thermal shift analysis showed that the KASIIIs from *B. subtilis, A. acidocaldarius*, and *T. aquaticus* bound a broad range of substrates, whereas *C. gingivalis* KASIIIa and *E. coli* KASIII bound to a relatively narrow range of substrates. KASIIIa from *L. pneumophila* bound straight-chain (C3:0 and C4:0), branched-chain (iso-C4:0 and iso-C5:0), and dicarboxylate (malonyl and methylmalonyl) acyl-CoAs. KASIIIc from *M. xanthus* bound straight-chain acyl-CoAs (C2:0, C4:0 and C6:0) and malonyl-CoA.

Inherent $T_m$s in water without any ligand were measured for each of the KASIIIs (Table 6). These melting temperatures were used as the baseline Tins to measure the shift in $T_m$ by addition of substrate. The KASIII enzymes from *A. acidocaldarius* and *T. aquaticus* were unusually thermally stable, with baseline $T_m$s of ~73° C. and ~84° C., respectively. These melting temperatures are considerably higher than those for the other KASIIIs that were studied and can be correlated with their ability to survive at extremely high temperatures.

TABLE 6

Melting temperatures ™ of KASIII enzymes without ligand

| Organism | Enzyme | Melting temperature (° C.) |
|---|---|---|
| *C. gingivalis* | KASIIIa | 68.3 ± 0.17 |
| | KASIIIb | 67.8 ± 0.03 |
| | KASIIIc | 56.8 ± 0.62 |
| *A. acidocaldarius* | KASIII | 73.2 ± 0.05 |
| *T. aquaticus* | KASIII | 84.1 ± 0.11 |
| *B. subtilis* | KASIIIb | 48.7 ± 0.24 |
| *E. coli* | KASIII | 55.0 ± 0.18 |
| *L. pneumophila* | KASIIIa | 54.0 ± 0.36 |
| | KasIIIb | 60.2 ± 0.16 |
| | KasIIIc | 62.0 ± 0.03 |
| | KasIIId | 65.8 ± 0.18 |
| *M. xanthus* | KASIIIa | 64.6 ± 0.13 |
| | KASIIIb | 54.5 ± 0.15 |
| | KASIIIc | 61.4 ± 0.50 |

Figure 16A:
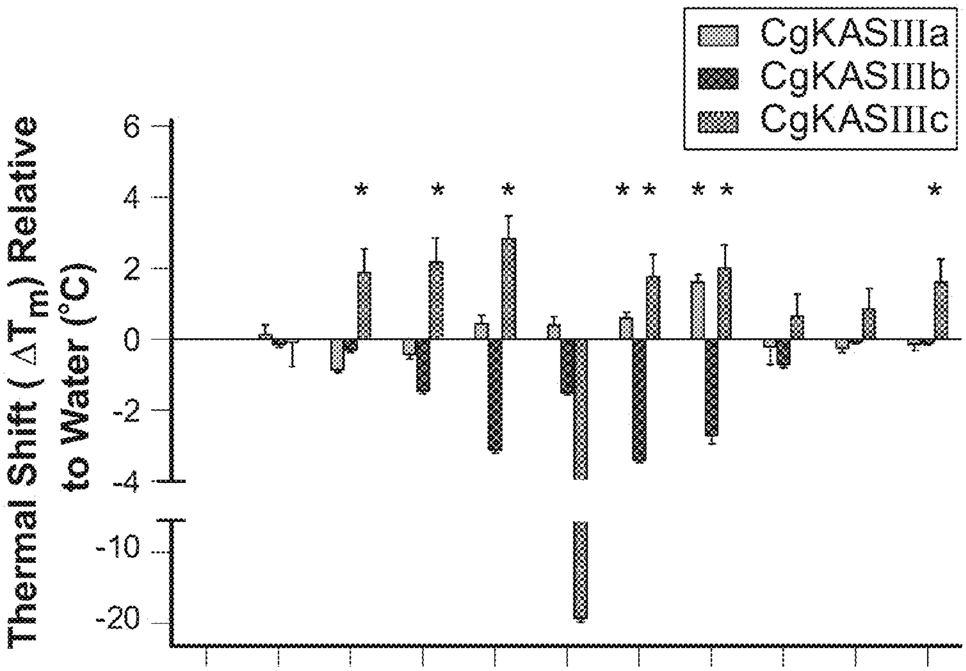
FIG. 16A is a graph of substrate vs. thermal shift ($\Delta T_m$) relative to water (° C.).

Consistent with previous reports that *E. coli* KASIII has narrow substrate specificity, ecKASIII bound only short, straight-chain acyl-CoAs (acetyl-CoA and propionyl-CoA). In contrast, *C. gingivalis* KASIIIa bound mainly branched-chain (isovaleryl-CoA and isobutyryl-CoA) and unsaturated (crotonyl-CoA; $T_m$ shift of 2° C.) substrates that resulted in statistically significant thermal shifts (see FIGS. 16A and 16D).

*B. subtilis* KASIIIb and *A. acidocaldarius* KASIII exhibited the broadest ranges of substrate specificities. In particular, *B. subtilis* KASIIIb bound the straight-chain substrates (propionyl-CoA and butyryl-CoA), the branched-chain substrates (isobutyryl-CoA and isovaleryl-CoA), and a di-acidic substrate (phenylacetyl-CoA). Each of these substrates induced at least a 6° C. increase in the $T_m$ of bsKASIIIb (see FIG. 16D). In contrast, some substrates (e.g., hexanoyl-CoA and benzoyl-CoA) apparently destabilized the protein, as evidenced by a decrease in the $T_m$ of bsKASIIIb. The binding capacity of *A. acidocaldarius* KASIII was equally broad. aaKASIII bound to the straight-chain acetyl-CoA and hexanoyl-CoA substrates, the branched-chain isobutyryl-CoA and isovaleryl-CoA, a hydroxylated substrate (3-hydroxybutyryl-CoA), an unsaturated substrate (crotonyl-CoA), and the aromatic substrate (benzoyl-CoA), each of which resulted in at least a 4° C. increase in the $T_m$ of the enzyme. Malonyl-CoA and phenylacetyl-CoA also bound to aaKASIII, inducing a 2° C. increase in $T_m$.

Figure 16B:
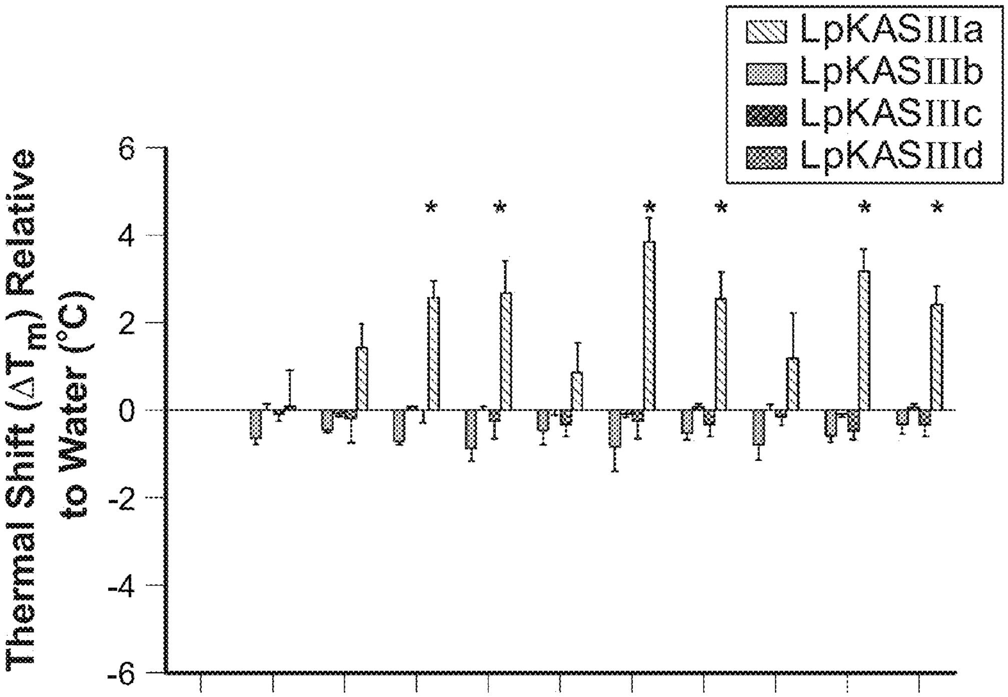
FIG. 16B is a graph of substrate vs. thermal shift ($\Delta T_m$) relative to water (° C.).
Figure 16C:
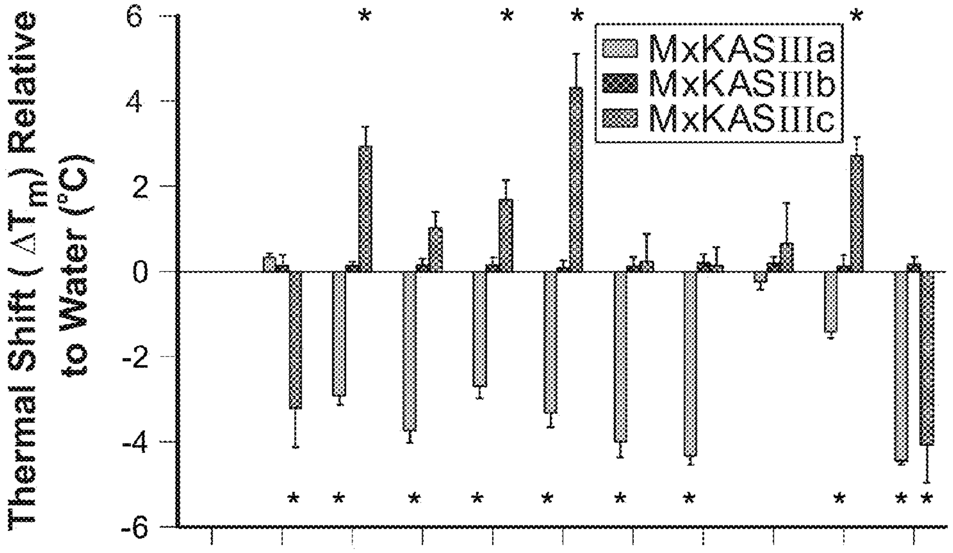
FIG. 16C is a graph of substrate vs. thermal shift ($\Delta T_m$) relative to water (° C.).
Figure 16D:
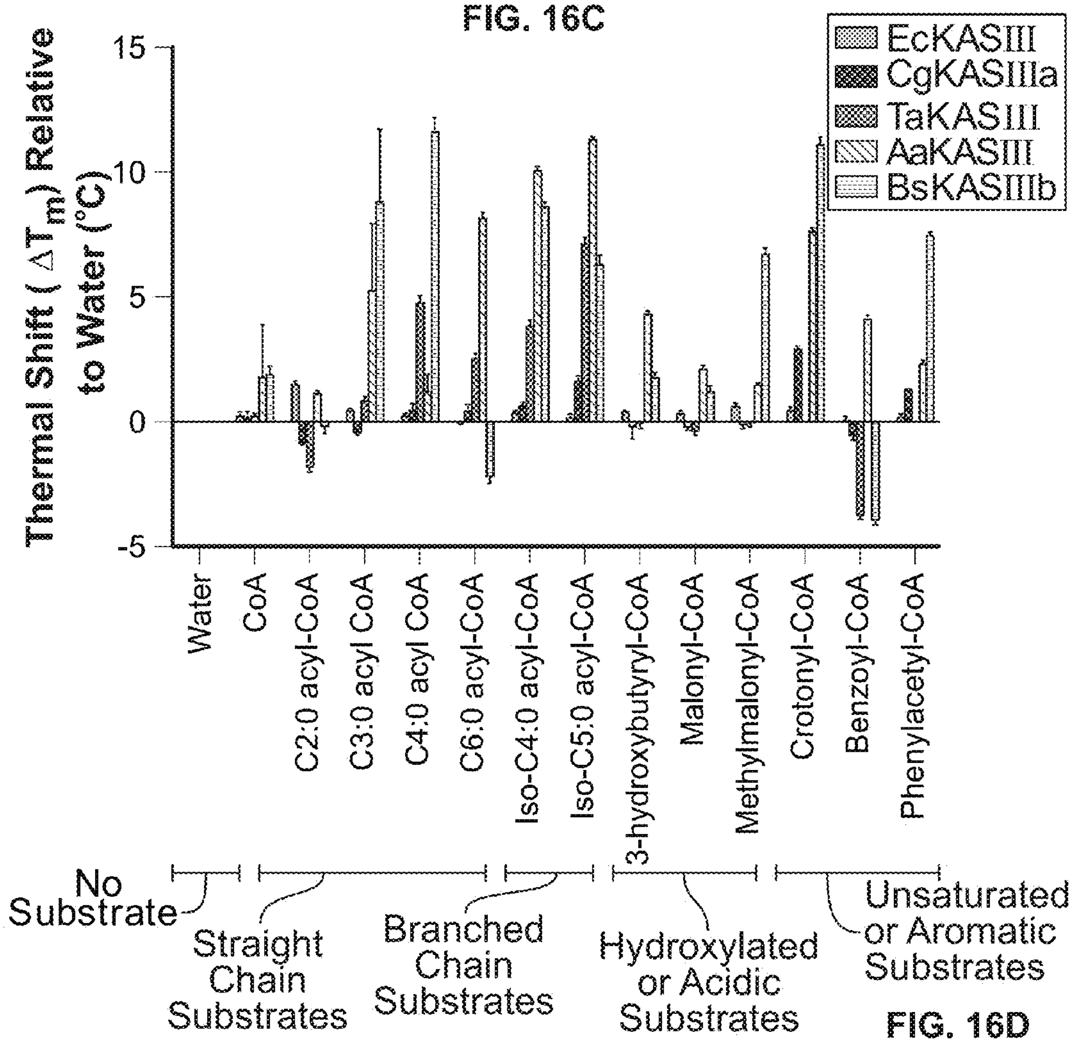
FIG. 16D is a graph of substrate vs. thermal shift ($\Delta T_m$) relative to water (° C.).
Figure 18:
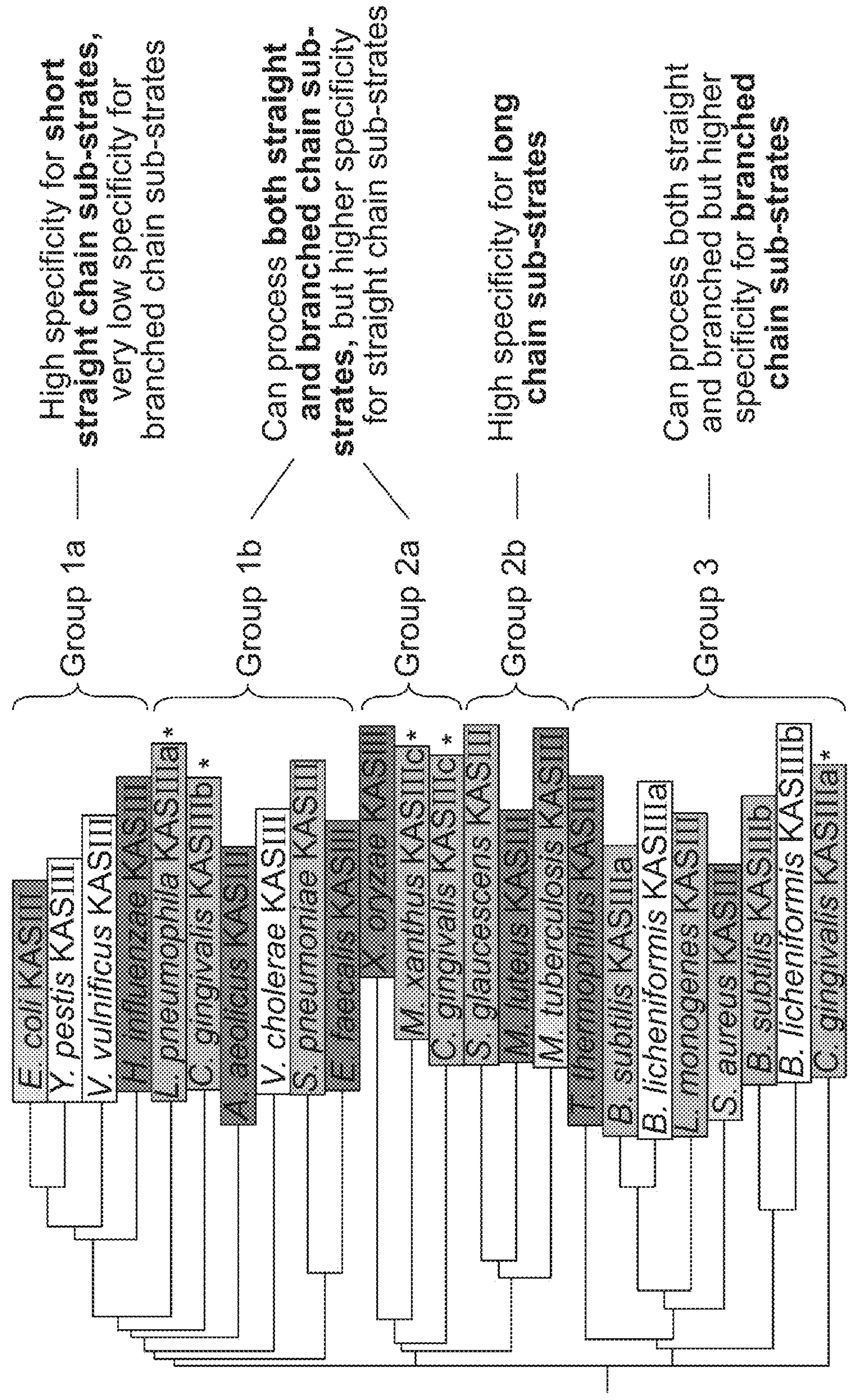
FIG. 18 shows a classification of KASIII enzymes into five distinct structure-function groups. The enzymes include those analyzed in the Examples (*), those for which structural data are available (highlighted in dark gray), those for which functional data are available (highlighted in light gray), or those for which structural and functional data are available (highlighted in gradation of light to dark gray).

*T. aquaticus* KASIII bound with rather a small range of substrates, specifically straight-chain butyryl-CoA and hexanoyl-CoA and branched-chain isobutyryl-CoA and isovaleryl-CoA substrates that resulted in 2-6° C. increases in $T_m$ as compared to the baseline $T_m$ (see FIG. 16D).

Amongst the four KASIIIs from *L. pneumophila*, LpKASIIIa was the only protein that could be thermally stabilized in the presence of potential acyl-CoA ligands (see FIG. 16B); and this protein was stabilized by straight-chain (C3:0 and C4:0), branched-chain (iso-C4:0 and iso-C5:0), and dicarboxylate (malonyl and methylmalonyl) acyl-CoAs. For each reacting ligand, the $T_m$ was increased by 2-4° C. relative to the control (p-value<0.05), suggesting that the LpKASIII enzyme has a broad substrate preference. In contrast, the observation that the remaining three LpKASIIIs are incapable of binding any acyl-CoA derivatives is consistent with the observation that these three proteins lack at least one of the conserved residues important for CoA binding (see FIG. 16B).

Of the four *M. xanthus* KASIII enzymes, MxKASIIIc was the only protein that was stabilized by binding to acyl-CoA ligands, specifically straight-chain acyl-CoAs (C2:0, C4:0 and C6:0) and malonyl-CoA, each of which increased the $T_m$ of MxKASIIIc by 2-4° C. compared to the control (p-value<0.05) (see FIG. 16C). Methylmalonyl-CoA and free CoA destabilized MxKASIIIc by 4° C. relative to the control. In contrast, MxKASIIIa was the most destabilized by most of the CoA derivatives that were tested, with the exceptions of CoA and 3-hydroxybutyryl-CoA, neither of which significantly affected the $T_m$ of the protein (see FIG. 16C). This could be explained because of lack of the catalytic triad in MxKASIIIa. In contrast to MxKASIIIa and MxKASIIIc, MxKASIIIb remained largely unaffected by each CoA-derivative, suggesting that it does not have affinity for any of the acyl-CoA ligands tested in this study. These data are supported by the fact that MxKASIIIb lacks some of the conserved CoA binding residues (see FIG. 16C).

Example 12

This example describes bioengineering of *E. coli* for the production of ω-hydroxy-branched fatty acids (HBFA).

—Disruption and Replacement of Endogenous *E. coli* KASIII Gene with Novel KASIII Genes that have Capability to Utilize Hydroxybutyryl-CoA as the Substrate.

Lambda recombinase method is used to create gene knockouts. The fabH gene in *E. coli* strain MN1655, a K12 derivative, is deleted using a kanamycin disruption cassette that is flanked by FLP recognition target sites to excise precisely the kanamycin-resistance cassette, creating an in-frame deletion. Afterwards, the PHA biosynthetic operon is overexpressed in the *E. coli* strain, but without the phaC gene, namely expressing the phaA and phaB genes in combination. This modification is coupled with introduction, and expression therein, of a recombinant KASIII gene that has the ability to utilize hydroxybutyryl-CoA as the substrate. This KASIII is introduced into the *E. coli* strain using expression cassettes that include low-copy and high-copy plasmid vectors that utilize constitutive or inducible promoters of different strengths.

—Bioengineering of *E. coli* KASIII Strain to Block Fatty Acid Degradation Pathway.

To maximize production of the targeted w-hydroxy-branched-fatty acids, the β-oxidation pathway can be blocked to result in the secretion of fatty acids into the growth medium. The lambda red recombinase method can be used to delete the *E. coli* fadD gene, which codes for acyl-CoA synthetase, the enzyme that initiates the degradation of fatty acids.

—Production of ω-Hydroxy-Branched-Fatty Acids in Bioengineered *E. coli* KASIII Strain.

The combination of phaA, phaB and an exogenous KASIII gene, such as a wild-type gene from another organism, a natural variant thereof, or a mutant thereof, which can use hydroxybutyryl-CoA as a substrate, results in the production of w-hydroxy-branched-chain fatty acids.

All references, including publications, patent applications, and patents, cited herein are hereby incorporated by reference to the same extent as if each reference were individually and specifically indicated to be incorporated by reference and were set forth in its entirety herein.

The use of the terms “a,” “an,” “the,” and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A mutant *Bacillus subtilis*, which does not express a functional 3-ketoacyl-acyl carrier protein (ACP) synthase II (KASIII) A and does not express a functional KASIIIB, and wherein the KASIIIB comprises the amino acid sequence of SEQ ID NO: 66, which further comprises a mutation of Trp221 and a mutation of Val226.

2. The mutant *Bacillus subtilis* of claim 1, wherein the mutation of Trp221 is Trp221 Val and the mutation of Val226 is Val226Leu.

3. The mutant *Bacillus subtilis* of claim 1, wherein the KASIIIA comprises the amino acid sequence of SEQ ID NO: 64, which further comprises a mutation of Met213, alone or in further combination with a mutation of Phe208.

4. The mutant *Bacillus subtilis* of claim 3, wherein the mutation of Met213 is Met213Leu and the mutation of Phe208 is Phe208Val.

5. A method of making the mutant *B. subtilis* of claim 1, which method comprises introducing into wild-type *B. subtilis* a mutation that prevents expression of a functional KASIIIA and a mutation that prevents expression of a functional KASIIIB, wherein Trp221 and Val226 are mutated in the KASIIIB comprising the amino acid sequence of SEQ ID NO:66.

6. The method of claim 5, wherein Trp221 is mutated to Val and Val226 is mutated to Leu.

7. The method of claim 5, wherein Met213is mutated or Met213 and Phe208, are mutated in the KASIIIA comprising the amino acid sequence of SEQ ID NO: 64.

8. The method of claim 7, wherein Met213 is mutated to Leu and Phe208 is mutated to Val.

* * * * *

UNITED STATES PATENT AND TRADEMARK OFFICE

CERTIFICATE OF CORRECTION

PATENT NO. : 10,233,432 B2
APPLICATION NO. : 15/721514
DATED : March 19, 2019
INVENTOR(S) : Shivani Garg et al.

It is certified that error appears in the above-identified patent and that said Letters Patent is hereby corrected as shown below:

In the Claims

In Column 183, (Line 59) Line 2 of Claim 1 should read:
--functional 3-ketoacyl-acyl carrier protein (ACP) synthase III--

In Column 183, (Line 65) Line 2 of Claim 2 should read:
--mutation of Trp221 is Trp221Val and the mutation of--

In Column 185, (Line 6) Line 1 of Claim 7 should read:
--7. The method of claim 5, wherein Met213 is mutated or--

In Column 185, (Line 7) Line 2 of Claim 7 should read:
--Met213 and Phe208 are mutated in the KASIIIA compris- --

Signed and Sealed this
Third Day of September, 2019

Andrei Iancu
*Director of the United States Patent and Trademark Office*